United States Patent
McClurken et al.

(10) Patent No.: US 10,856,935 B2
(45) Date of Patent: Dec. 8, 2020

(54) FLUID-ASSISTED MEDICAL DEVICES, SYSTEMS AND METHODS

(71) Applicant: Medtronic Advanced Energy LLC, Minneapolis, MN (US)

(72) Inventors: Michael E. McClurken, Durham, NH (US); David Lipson, North Andover, MA (US); Arnold E. Oyola, Raymond, NH (US); Jonathan E. Wilson, Amesbury, MA (US); Christopher W. Maurer, Wakefield, MA (US); Robert Luzzi, Pleasanton, CA (US); Roger D. Greeley, Portsmouth, NH (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1075 days.

(21) Appl. No.: 14/537,626

(22) Filed: Nov. 10, 2014

(65) Prior Publication Data

US 2015/0245864 A1 Sep. 3, 2015

Related U.S. Application Data

(63) Continuation of application No. 12/429,920, filed on Apr. 24, 2009, now abandoned, which is a (Continued)

(51) Int. Cl.
*A61B 18/14* (2006.01)
*A61B 17/32* (2006.01)
(Continued)

(52) U.S. Cl.
CPC ............ *A61B 18/148* (2013.01); *A61B 17/32* (2013.01); *A61B 18/1206* (2013.01);
(Continued)

(58) Field of Classification Search
CPC ............ A61B 18/1206; A61B 18/1442; A61B 18/148; A61B 2018/00011
See application file for complete search history.

(56) References Cited

U.S. PATENT DOCUMENTS 1,735,271 A 11/1929 Groff
2,888,928 A 6/1959 Seiger
(Continued)

FOREIGN PATENT DOCUMENTS

DE 1 007 960 5/1957
EP 0 175 595 3/1986
(Continued)

OTHER PUBLICATIONS

Office Action dated Jan. 27, 2010 issued in related U.S. Appl. No. 10/746,222.
(Continued)

*Primary Examiner* — Linda C Dvorak
*Assistant Examiner* — Samantha M Good
(74) *Attorney, Agent, or Firm* — Christopher & Weisberg, P.A.

(57) ABSTRACT

Surgical devices, systems and methods for treating tissue are provided. Also provided are systems for treating tissue and methods of treating tissue. An exemplary surgical device comprises a handle (20a) having a proximal end and a distal end; a shaft extending distally beyond the distal end of the handle, the shaft having a proximal end and a distal end; an electrode tip (45), at least a portion of the electrode tip extending distally beyond the distal end of the shaft, the electrode tip extending distally beyond the distal end of the shaft comprising a spherical end surface portion (25) and a cylindrical side surface portion, the spherical end surface portion located distal to the cylindrical side surface portion and comprising at least a portion of the distal end surface of
(Continued)

the surgical device; and a fluid passage directed to provide a fluid towards the cylindrical side portion of the electrode tip.

6 Claims, 76 Drawing Sheets

Related U.S. Application Data continuation of application No. 10/488,801, filed as application No. PCT/US02/28488 on Sep. 5, 2002, now Pat. No. 8,083,736, which is a continuation-in-part of application No. 09/947,658, filed on Sep. 5, 2001, now Pat. No. 7,115,139, which is a continuation-in-part of application No. 09/797,049, filed on Mar. 1, 2001, now Pat. No. 6,702,810, said application No. 10/488,801 is a continuation-in-part of application No. 10/354,643, filed on Jan. 29, 2003, now Pat. No. 7,651,494, which is a continuation of application No. 09/668,403, filed on Sep. 22, 2000, now Pat. No. 6,558,385.

(60) Provisional application No. 60/356,390, filed on Feb. 12, 2002, provisional application No. 60/368,177, filed on Mar. 27, 2002, provisional application No. 60/187,114, filed on Mar. 6, 2000.

(51) Int. Cl.
*A61B 18/12* (2006.01)
*A61B 18/00* (2006.01)
*A61B 18/18* (2006.01)

(52) U.S. Cl.
CPC . *A61B 18/1442* (2013.01); *A61B 2018/00011* (2013.01); *A61B 2018/00029* (2013.01); *A61B 2018/00035* (2013.01); *A61B 2018/0063* (2013.01); *A61B 2018/00065* (2013.01); *A61B 2018/00404* (2013.01); *A61B 2018/00589* (2013.01); *A61B 2018/00595* (2013.01); *A61B 2018/00601* (2013.01); *A61B 2018/00702* (2013.01); *A61B 2018/00744* (2013.01); *A61B 2018/00779* (2013.01); *A61B 2018/00791* (2013.01); *A61B 2018/00809* (2013.01); *A61B 2018/00875* (2013.01); *A61B 2018/126* (2013.01); *A61B 2018/1417* (2013.01); *A61B 2018/1422* (2013.01); *A61B 2018/1861* (2013.01); *A61B 2218/002* (2013.01)

(56) References Cited

U.S. PATENT DOCUMENTS

| | | |
|---|---|---|
| 3,682,130 A | 8/1972 | Jeffers |
| 3,750,650 A | 8/1973 | Ruttgers |
| 4,060,088 A | 11/1977 | Morrison, Jr. et al. |
| 4,244,371 A | 1/1981 | Farin |
| 4,276,874 A | 7/1981 | Wolvek et al. |
| 4,321,931 A | 3/1982 | Hon |
| 4,342,218 A | 8/1982 | Fox |
| 4,355,642 A | 10/1982 | Alferness |
| 4,381,007 A | 4/1983 | Doss |
| 4,671,274 A | 6/1987 | Sorochenko |
| 4,919,129 A | 4/1990 | Weber, Jr. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,013,312 A | 5/1991 | Parins et al. |
| 5,080,660 A | 1/1992 | Buelna |
| 5,190,541 A | 3/1993 | Abele et al. |
| 5,195,959 A | 3/1993 | Smith |
| 5,234,428 A | 8/1993 | Kaufman |
| 5,254,117 A | 10/1993 | Rigby |
| 5,269,782 A | 12/1993 | Sutter |
| 5,281,215 A | 1/1994 | Milder |
| 5,290,286 A | 3/1994 | Parins |
| 5,330,521 A | 7/1994 | Cohen |
| 5,336,220 A | 8/1994 | Ryan |
| 5,348,554 A | 9/1994 | Imran et al. |
| 5,383,874 A | 1/1995 | Jackson et al. |
| 5,395,312 A | 3/1995 | Desai |
| 5,401,272 A | 3/1995 | Perkins |
| 5,417,709 A | 5/1995 | Slater |
| 5,431,168 A | 7/1995 | Webster, Jr. |
| 5,441,503 A | 8/1995 | Considine et al. |
| 5,445,638 A | 8/1995 | Rydell et al. |
| 5,460,629 A | 10/1995 | Shlain et al. |
| 5,490,819 A | 2/1996 | Nicholas et al. |
| 5,540,562 A | 7/1996 | Giter |
| 5,542,945 A | 8/1996 | Fritzsch |
| 5,556,397 A | 9/1996 | Long |
| 5,562,702 A | 10/1996 | Huitema et al. |
| 5,569,243 A | 10/1996 | Kortenbach et al. |
| 5,599,346 A | 2/1997 | Edwards et al. |
| 5,605,539 A | 2/1997 | Buelna et al. |
| 5,647,869 A | 7/1997 | Goble et al. |
| 5,681,294 A | 10/1997 | Osborne et al. |
| 5,697,536 A | 12/1997 | Eggers et al. |
| 5,743,903 A | 4/1998 | Stern et al. |
| 5,766,167 A | 6/1998 | Eggers et al. |
| 5,785,706 A | 7/1998 | Bednarek |
| 5,792,140 A | 8/1998 | Tu et al. |
| 5,797,905 A | 8/1998 | Fleischman et al. |
| 5,800,432 A | 9/1998 | Swanson |
| 5,810,764 A | 9/1998 | Eggers et al. |
| 5,843,021 A | 12/1998 | Edwards et al. |
| 5,843,152 A | 12/1998 | Tu et al. |
| 5,861,021 A | 1/1999 | Thome et al. |
| 5,873,855 A | 2/1999 | Eggers |
| 5,879,348 A | 3/1999 | Owens et al. |
| 5,891,142 A | 4/1999 | Eggers et al. |
| 5,893,848 A | 4/1999 | Negus et al. |
| 5,895,355 A | 4/1999 | Schaer |
| 5,897,553 A | 4/1999 | Mulier et al. |
| 5,904,711 A | 5/1999 | Flom et al. |
| 5,913,854 A | 6/1999 | Maguire et al. |
| 5,921,982 A | 7/1999 | Lesh et al. |
| 5,925,045 A | 7/1999 | Reimels et al. |
| 5,935,123 A | 8/1999 | Edwards et al. |
| 5,944,715 A | 8/1999 | Goble et al. |
| 5,957,919 A | 9/1999 | Laufer |
| 5,971,983 A | 10/1999 | Lesh |
| 5,980,516 A | 11/1999 | Mulier |
| 5,989,248 A | 11/1999 | Tu et al. |
| 5,993,412 A | 11/1999 | Deily et al. |
| 6,004,316 A | 12/1999 | Laufer |
| 6,004,319 A | 12/1999 | Goble |
| 6,010,500 A | 1/2000 | Sherman et al. |
| 6,015,391 A | 1/2000 | Rishton et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones |
| 6,036,687 A | 3/2000 | Laufer et al. |
| 6,048,333 A | 4/2000 | Lennox et al. |
| 6,056,744 A | 5/2000 | Edwards |
| 6,056,745 A * | 5/2000 | Panescu ............. A61B 18/00 606/31 |
| 6,056,746 A | 5/2000 | Goble |
| 6,056,747 A | 5/2000 | Saadat et al. |
| 6,066,139 A | 5/2000 | Ryan et al. |
| 6,068,653 A | 5/2000 | LaFontaine |
| 6,083,237 A | 7/2000 | Huitema et al. |
| 6,086,585 A | 7/2000 | Hovda et al. |
| 6,096,037 A | 8/2000 | Mulier et al. |
| 6,113,596 A | 9/2000 | Hooven |
| 6,141,576 A | 10/2000 | Littman et al. |

(56) References Cited

U.S. PATENT DOCUMENTS

| | | |
|---|---|---|
| 6,149,620 A | 11/2000 | Baker et al. |
| 6,165,169 A | 12/2000 | Panescu et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 * | 4/2001 | Hofmann ............... A61B 18/14 606/52 |
| 6,212,426 B1 | 4/2001 | Swanson |
| 6,231,571 B1 | 5/2001 | Ellman et al. |
| 6,231,591 B1 | 5/2001 | Desai |
| 6,235,020 B1 | 5/2001 | Cheng et al. |
| 6,238,387 B1 | 5/2001 | Miller, III |
| 6,238,393 B1 | 5/2001 | Mulier et al. |
| 6,251,110 B1 | 6/2001 | Wampler |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,283,988 B1 | 9/2001 | Laufer et al. |
| 6,283,989 B1 | 9/2001 | Laufer et al. |
| 6,299,633 B1 | 10/2001 | Laufer |
| 6,322,559 B1 | 11/2001 | Daulton et al. |
| 6,328,735 B1 | 12/2001 | Curley et al. |
| 6,352,533 B1 | 3/2002 | Ellman et al. |
| 6,358,245 B1 | 3/2002 | Edwards et al. |
| 6,371,956 B1 | 4/2002 | Wilson et al. |
| 6,409,722 B1 | 6/2002 | Hoey et al. |
| 6,416,509 B1 | 7/2002 | Goble et al. |
| 6,478,793 B1 | 11/2002 | Cosman et al. |
| 6,497,704 B2 | 12/2002 | Ein-Gal |
| 6,508,815 B1 | 1/2003 | Strul et al. |
| 6,517,536 B2 | 2/2003 | Hooven et al. |
| 6,558,385 B1 | 5/2003 | McClurken et al. |
| 6,572,613 B1 | 6/2003 | Ellman et al. |
| 6,575,969 B1 | 6/2003 | Rittman, III et al. |
| 6,579,288 B1 | 6/2003 | Swanson et al. |
| 6,602,248 B1 | 8/2003 | Sharps et al. |
| 6,603,988 B2 | 8/2003 | Dowlatshahi |
| 6,610,060 B2 | 8/2003 | Mulier et al. |
| 6,635,034 B1 | 10/2003 | Cosmescu |
| 6,645,202 B1 | 11/2003 | Pless et al. |
| 6,666,862 B2 | 12/2003 | Jain et al. |
| 6,679,882 B1 | 1/2004 | Kornerup |
| 6,682,501 B1 | 1/2004 | Nelson |
| 6,702,810 B2 | 3/2004 | McClurken et al. |
| 6,723,094 B1 | 4/2004 | Desinger |
| 6,766,202 B2 | 7/2004 | Underwood et al. |
| 6,766,817 B2 | 7/2004 | da Silva |
| 6,775,575 B2 | 8/2004 | Bommannan et al. |
| 6,827,713 B2 | 12/2004 | Bek et al. |
| 6,832,996 B2 | 12/2004 | Woloszko |
| 6,915,806 B2 | 7/2005 | Pacek et al. |
| 6,918,404 B2 | 7/2005 | Dias da Silva |
| 6,942,661 B2 | 9/2005 | Swanson |
| 7,066,586 B2 | 6/2006 | da Silva |
| 7,115,139 B2 | 10/2006 | McClurken et al. |
| 7,156,845 B2 | 1/2007 | Mulier et al. |
| 7,166,106 B2 | 1/2007 | Bartel et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Muller et al. |
| 7,309,325 B2 | 12/2007 | Muller et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,645,277 B2 | 1/2010 | McClurken et al. |
| 7,651,494 B2 | 1/2010 | McClurken et al. |
| 7,811,282 B2 | 10/2010 | McClurken |
| 7,815,634 B2 | 10/2010 | McClurken et al. |
| 7,976,544 B2 | 7/2011 | McClurken |
| 7,998,140 B2 | 8/2011 | McClurken |
| 8,012,154 B2 | 9/2011 | Livneh |
| 8,038,670 B2 | 10/2011 | McClurken |
| 8,048,070 B2 | 11/2011 | O'Brien et al. |
| 8,177,783 B2 | 5/2012 | Davison et al. |
| 8,216,233 B2 | 7/2012 | McClurken et al. |
| 8,348,946 B2 | 1/2013 | McClurken et al. |
| 8,361,068 B2 | 1/2013 | McClurken |
| 8,475,455 B2 | 7/2013 | McClurken et al. |
| 8,568,409 B2 | 10/2013 | O'Brien et al. |
| 8,632,533 B2 | 1/2014 | Greeley et al. |
| 8,882,756 B2 | 11/2014 | Greeley et al. |
| 8,906,012 B2 | 12/2014 | Conley et al. |
| 8,920,417 B2 | 12/2014 | Conley et al. |
| 8,979,842 B2 | 3/2015 | McNall, III et al. |
| 2001/0007070 A1 | 7/2001 | Stewart et al. |
| 2002/0026187 A1 | 2/2002 | Swanson |
| 2002/0049483 A1 | 4/2002 | Knowlton |
| 2002/0077626 A1 | 6/2002 | Ellman et al. |
| 2003/0009164 A1 | 1/2003 | Woloszko et al. |
| 2003/0014050 A1 | 1/2003 | Sharkey et al. |
| 2003/0032954 A1 | 2/2003 | Carranza et al. |
| 2003/0073993 A1 | 4/2003 | Ciarrocca |
| 2003/0130655 A1 | 7/2003 | Woloszko et al. |
| 2003/0204185 A1 | 10/2003 | Sherman et al. |
| 2004/0024395 A1 | 2/2004 | Ellman et al. |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2005/0090816 A1 | 4/2005 | McClurken et al. |
| 2005/0171526 A1 | 8/2005 | Rioux et al. |
| 2006/0064085 A1 | 3/2006 | Baker et al. |
| 2006/0074414 A1 | 4/2006 | Mulier et al. |
| 2007/0049920 A1 | 3/2007 | McClurken et al. |
| 2007/0093808 A1 | 4/2007 | Muller et al. |
| 2007/0112343 A1 | 5/2007 | Mische et al. |
| 2007/0118114 A1 | 5/2007 | Muller et al. |
| 2007/0208332 A1 | 9/2007 | Muller et al. |
| 2008/0015563 A1 | 1/2008 | Hoey et al. |
| 2008/0071266 A1 | 3/2008 | Rioux |
| 2008/0071270 A1 | 3/2008 | Baker et al. |
| 2009/0264879 A1 | 10/2009 | McClurken et al. |
| 2010/0100095 A1 | 4/2010 | McClurken et al. |
| 2011/0028965 A1 | 2/2011 | McClurken |
| 2012/0101496 A1 | 4/2012 | McClurken et al. |
| 2012/0116397 A1 | 5/2012 | Rencher et al. |
| 2014/0188105 A1 | 7/2014 | Conley et al. |

FOREIGN PATENT DOCUMENTS

| | | |
|---|---|---|
| EP | 0 175 595 A1 | 3/1986 |
| EP | 0895755 A1 | 2/1999 |
| EP | 0895756 A1 | 2/1999 |
| EP | 1 383 438 B1 | 2/2006 |
| FR | 2 235 669 | 1/1975 |
| JP | 5-092009 | 4/1993 |
| JP | 5-092009 A | 4/1993 |
| JP | 7-124245 | 5/1995 |
| JP | 7-124245 A | 5/1995 |
| WO | WO 97/05829 A1 | 2/1997 |
| WO | WO 97/16127 A1 | 5/1997 |
| WO | WO 98/38932 A1 | 9/1998 |
| WO | WO 99/09919 A1 | 3/1999 |
| WO | WO 99/16371 A1 | 4/1999 |
| WO | WO 99/42044 A1 | 8/1999 |
| WO | WO 99/66850 A1 | 12/1999 |
| WO | 0036985 A2 | 6/2000 |
| WO | 0078240 | 12/2000 |
| WO | 0166026 | 9/2001 |
| WO | WO 01/89403 A1 | 11/2001 |
| WO | WO 2005/122938 A1 | 12/2005 |
| WO | WO 2006/062916 A2 | 6/2006 |
| WO | WO 2006/062939 A2 | 6/2006 |

OTHER PUBLICATIONS

Office Action dated Jan. 29, 2010 issued in related U.S. Appl. No. 10/488,801.

Office Action dated Jul. 17, 2009 received in related U.S. Appl. No. 11/274,908.

(56) References Cited

OTHER PUBLICATIONS

U.S. Office Action dated Jul. 16, 2009 issued in related U.S. Appl. No. 10/746,222.
Office Action dated Dec. 24, 2009 issued in related U.S. Appl. No. 10/813,736.
Nelson, Lionel M., "Radiofrequency Treatment for Obstructive Tonsillar Hypertrophy," Arch Otolaryngol Head Neck Surg., vol. 126, Jun. 2000, downloaded from www.archoto.com on Mar. 31, 2010, pp. 736-740.
Supplementary European Search Report dated Aug. 28, 2007 and completed on Aug. 22, 2007, for European Application No. 02798936.7-1265, 5 pages.
International Preliminary Examination Report from the International Preliminary Examining Authority, completed on May 5, 2003 and dated Nov. 21, 2003, for International Application No. PCT/US02/28488, 4 pages.
Communication pursuant to Article 94(3) EPC, dated May 6, 2009, issued in the examination of related European Patent Application No. 05851938.0-2305, 4 pages.
Non-Final Office Action, dated Jan. 12, 2009, issued in the examination of related U.S. Appl. No. 10/365,170, 13 pages.
English Abstract of European Patent Publication No. EP 0 175 595 A1, published on Mar. 26, 1986, provided by http://worldwide.espacenet.com, downloaded on Jun. 13, 2012, 2 pages.
English Abstract of Japanese Patent Publication No. JP 5-092009 A, published on Apr. 16, 1993, provided by http://worldwide.espacenet.com, downloaded on Jun. 13, 2012, 2 pages.
English Abstract of Japanese Patent Publication No. JP 7-124245 A, published on May 16, 1995, provided by http://worldwide.espacenet.com, downloaded on Jun. 13, 2012, 2 pages.
Office Action dated Apr. 26, 2010 issued in related U.S. Appl. No. 11/537,852.
Office Action dated Mar. 18, 2010 issued in related U.S. Appl. No. 10/365,170.
Notice of Allowance dated Apr. 2, 2010 issued in related U.S. Appl. No. 11/274,908.
Supplemental Notice of Allowance dated May 27, 2010 issued in related U.S. Appl. No. 11/274,908.
Office Action dated Apr. 5, 2010 issued in related U.S. Appl. No. 11/318,207.
Office Action dated Apr. 14, 2009 issued in related U.S. Appl. No. 10/547,881.
Office Action dated Sep. 17, 2009 issued in related U.S. Appl. No. 11/318,207.
Office Action dated Jun. 22, 2009 issued in related U.S. Appl. No. 10/486,807.
U.S. Office Action issued in related U.S. Appl. No. 11/318,207 dated Dec. 30, 2008.
U.S. Office Action issued in related U.S. Appl. No. 10/488,801 dated Dec. 2, 2008.
European Office Action dated May 6, 2009 issued in related European Patent Application No. 05851938.0.
European Office Action dated Nov. 25, 2008 issued in related European Patent Application No. 05851938.0.
European Office Action dated Feb. 20, 2009 issued in related European Patent Application No. 02798936.7.
U.S. Office Action issued in related Patent Application No. 10265170 dated Jan. 12, 2009.
Office Action dated Jul. 2, 2009 issued in related U.S. Appl. No. 10/813,736.
Office Action dated Sep. 8, 2009 issued in related U.S. Appl. No. 10/488,801.
Office Action dated Sep. 15, 2009 issued in related U.S. Appl. No. 10/365,170.
Nelson, L.M., "Radiofrequency Treatment for Obstructive Tonsillar Hypertrophy," *Arch Otolaryngol Head Neck Surg*, vol. 126, pp. 736-740, American Medical Association (Jun. 2000).
Sun, W., "Ablation Pathway Currents of a Linear Phased Multi-Electrode System," *Proceedings of the 20th Annual International Conference of the IEEE Engineering in Medicine and Biology Society*, vol. 20, No. 1, pp. 248-251 (1998).
European Search Report dated Aug. 28, 2007, for European Patent Application No. EP 02798936.7, 5 pages.
International Search Report dated Dec. 13, 2002, issued in PCT Patent Application No. PCT/US02/28488, 4 pages.
International Preliminary Examination Report dated May 5, 2003, issued in PCT Patent Application No. PCT/US02/28488, 3 pages.
United States Office Action dated Aug. 4, 2009 issued in related U.S. Appl. No. 11/537,852.

\* cited by examiner

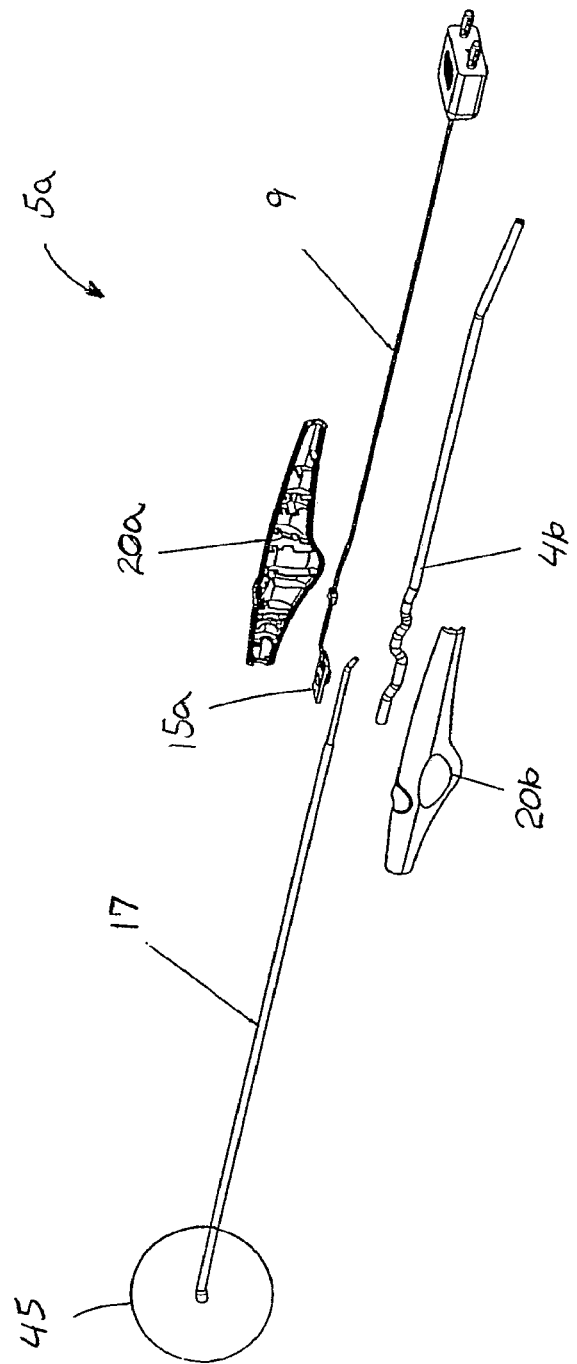

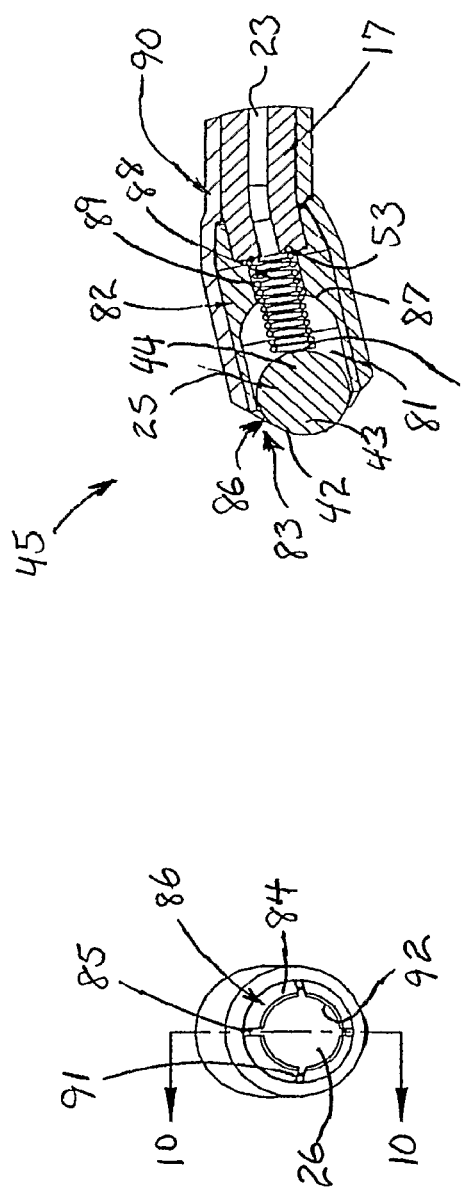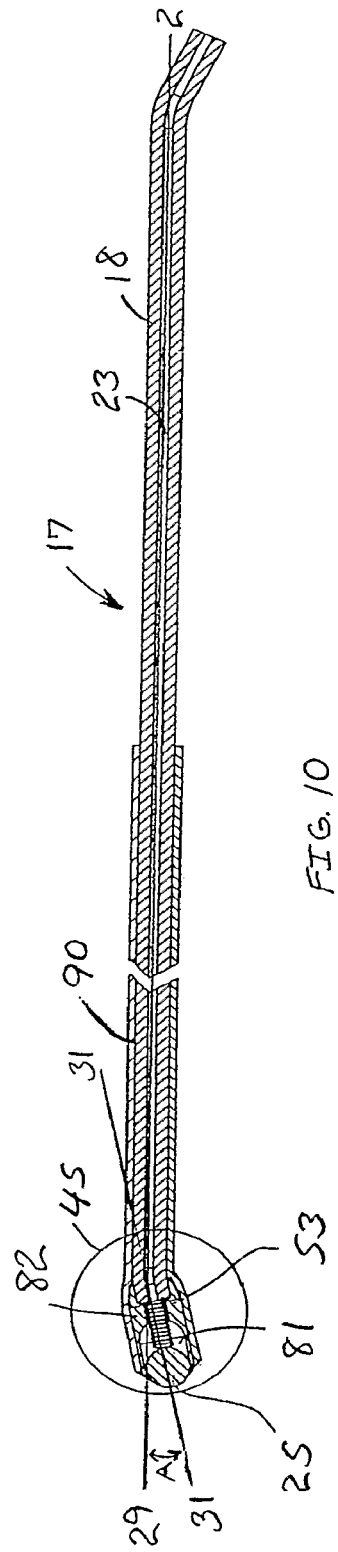

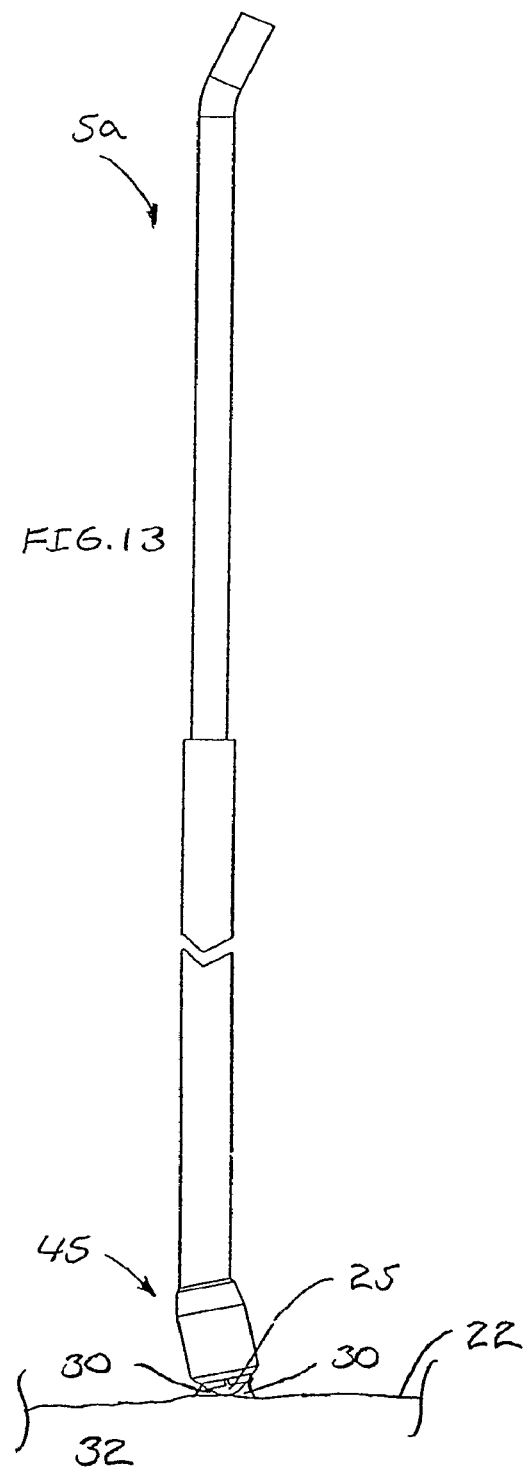

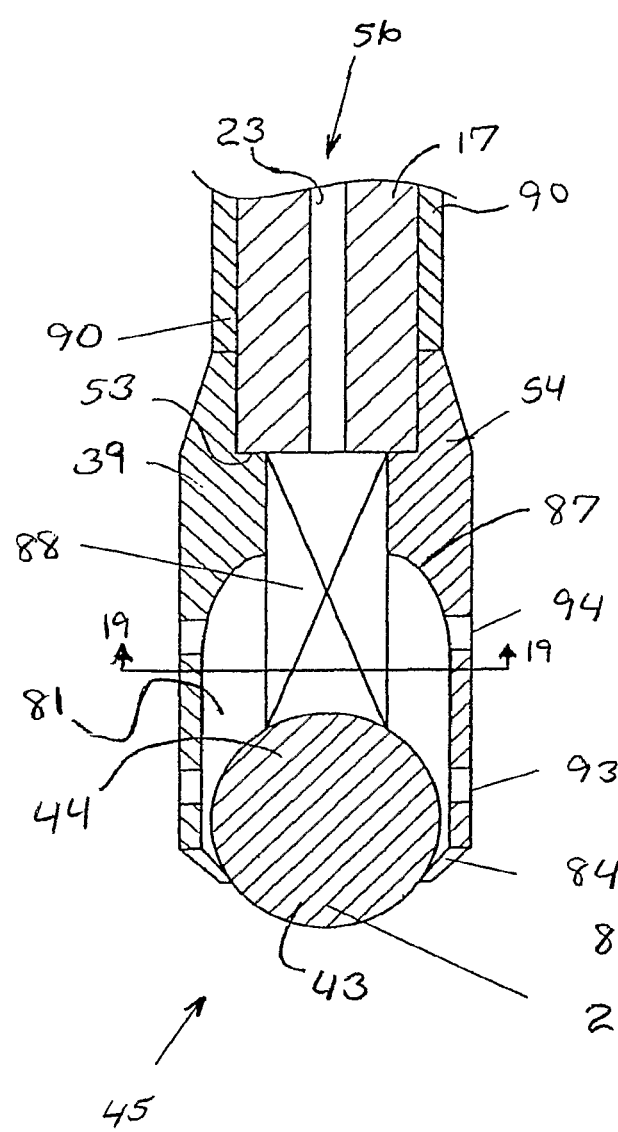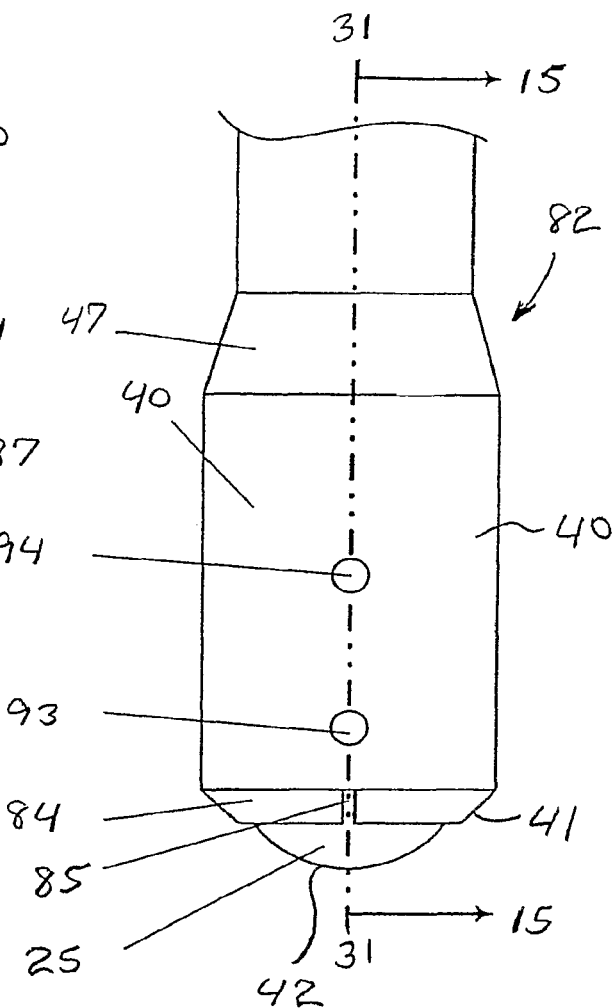

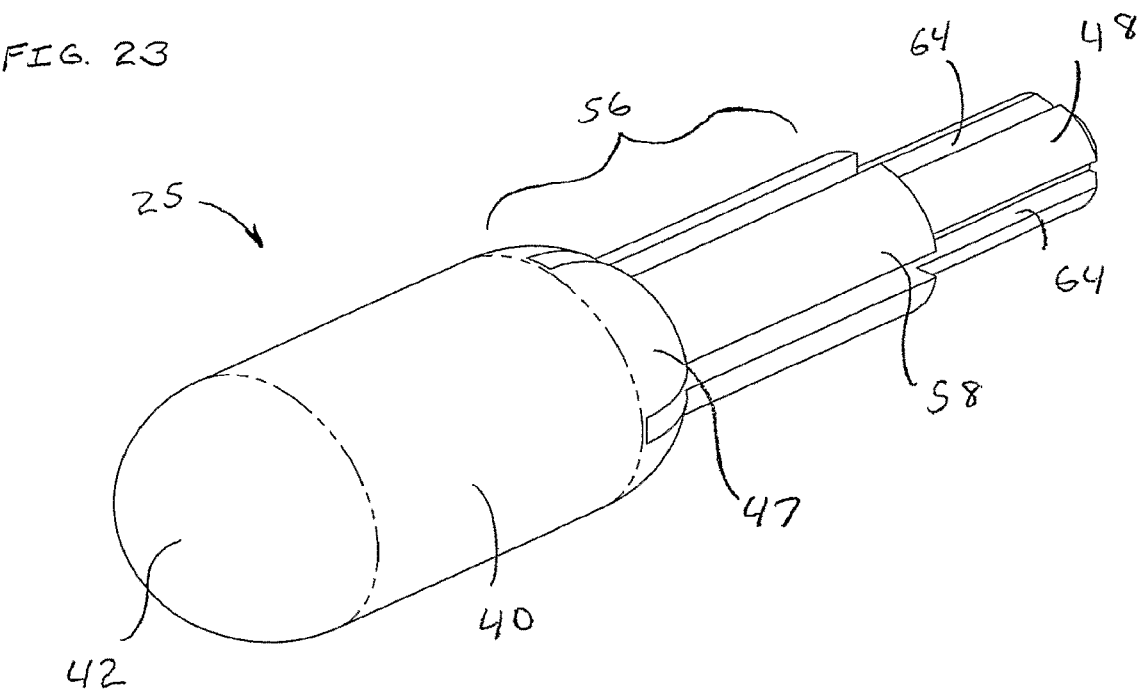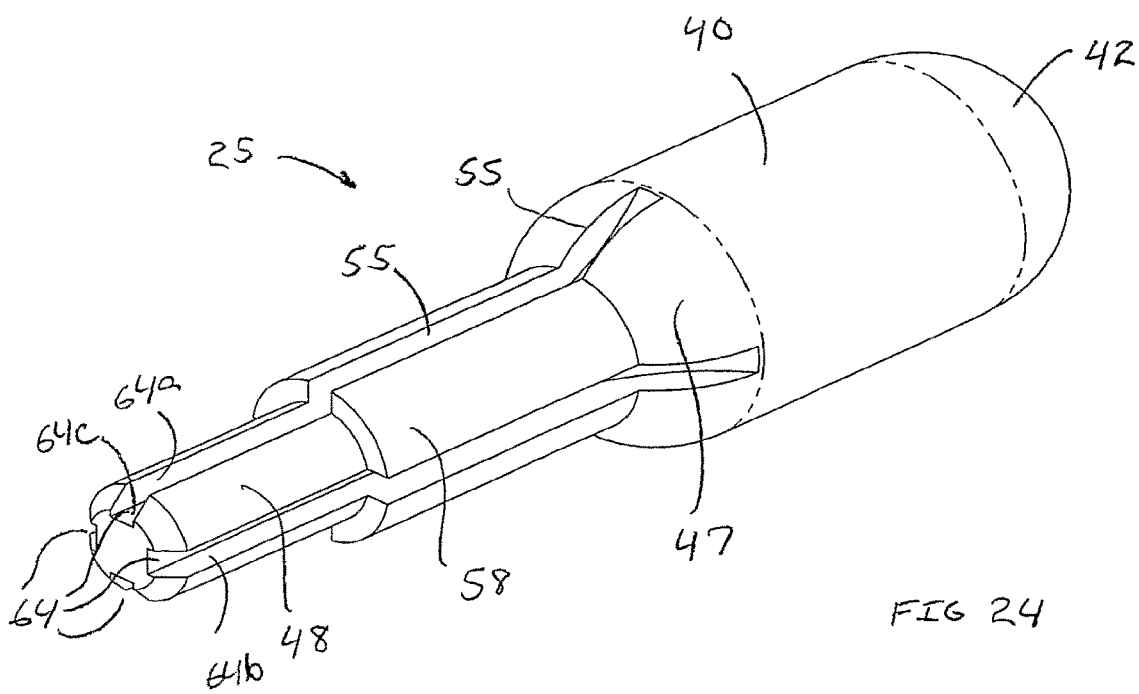

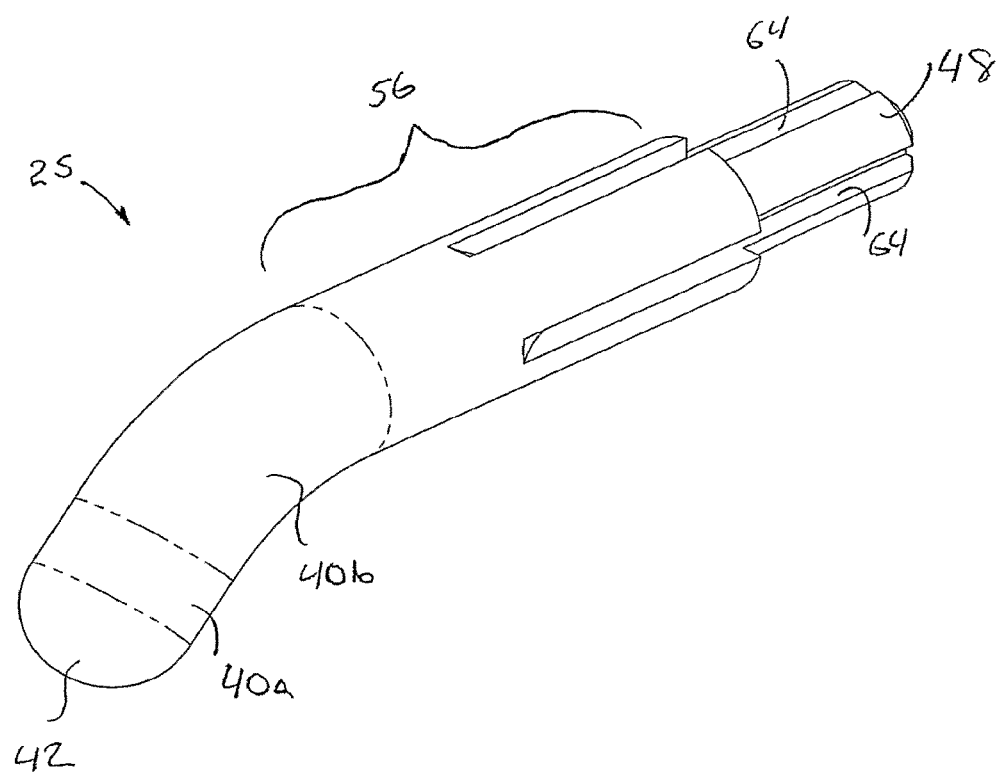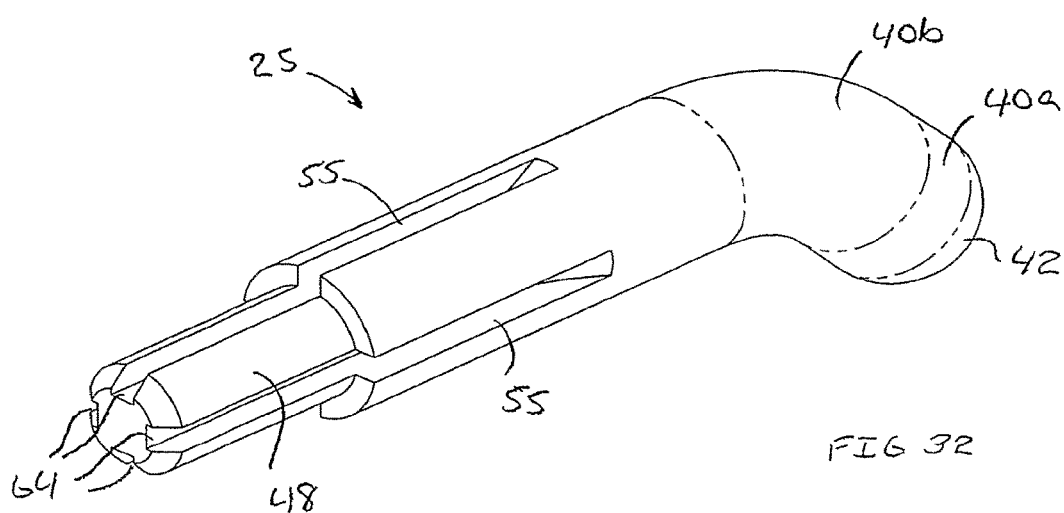

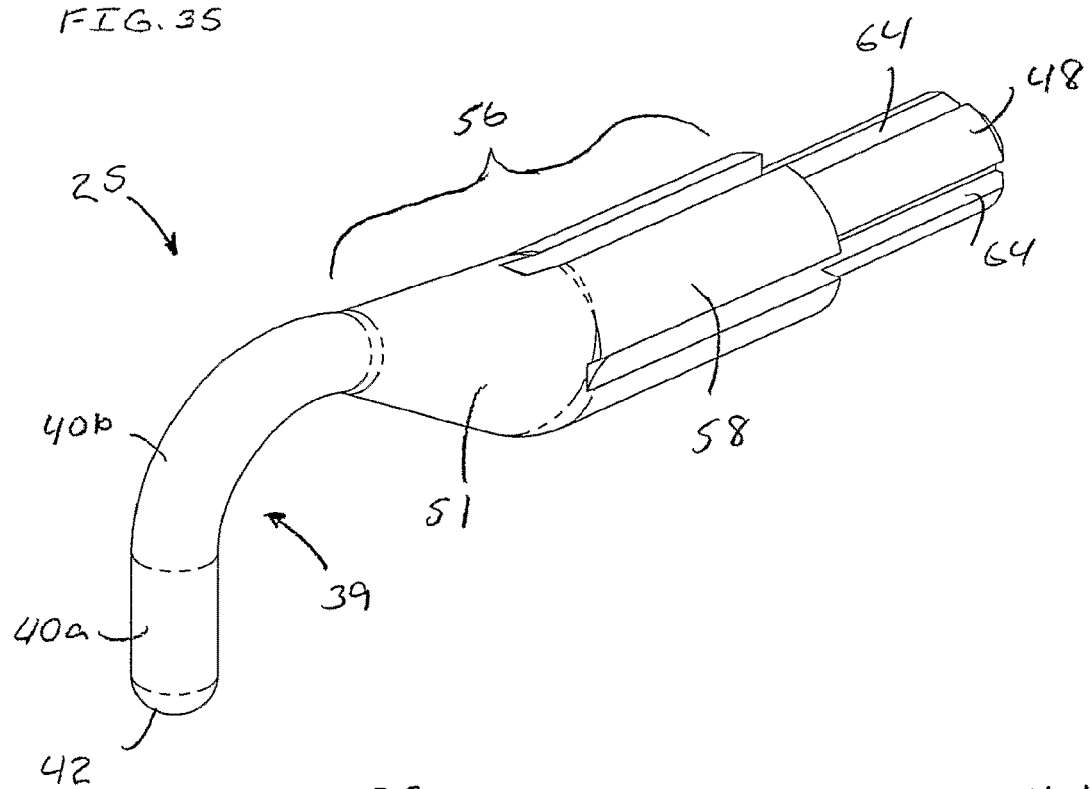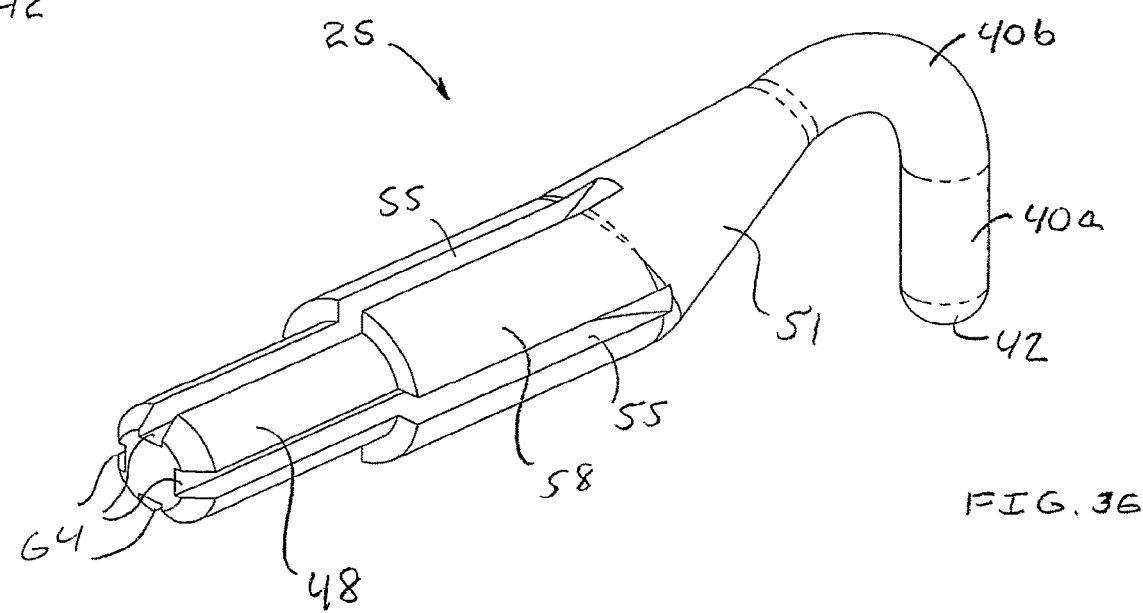

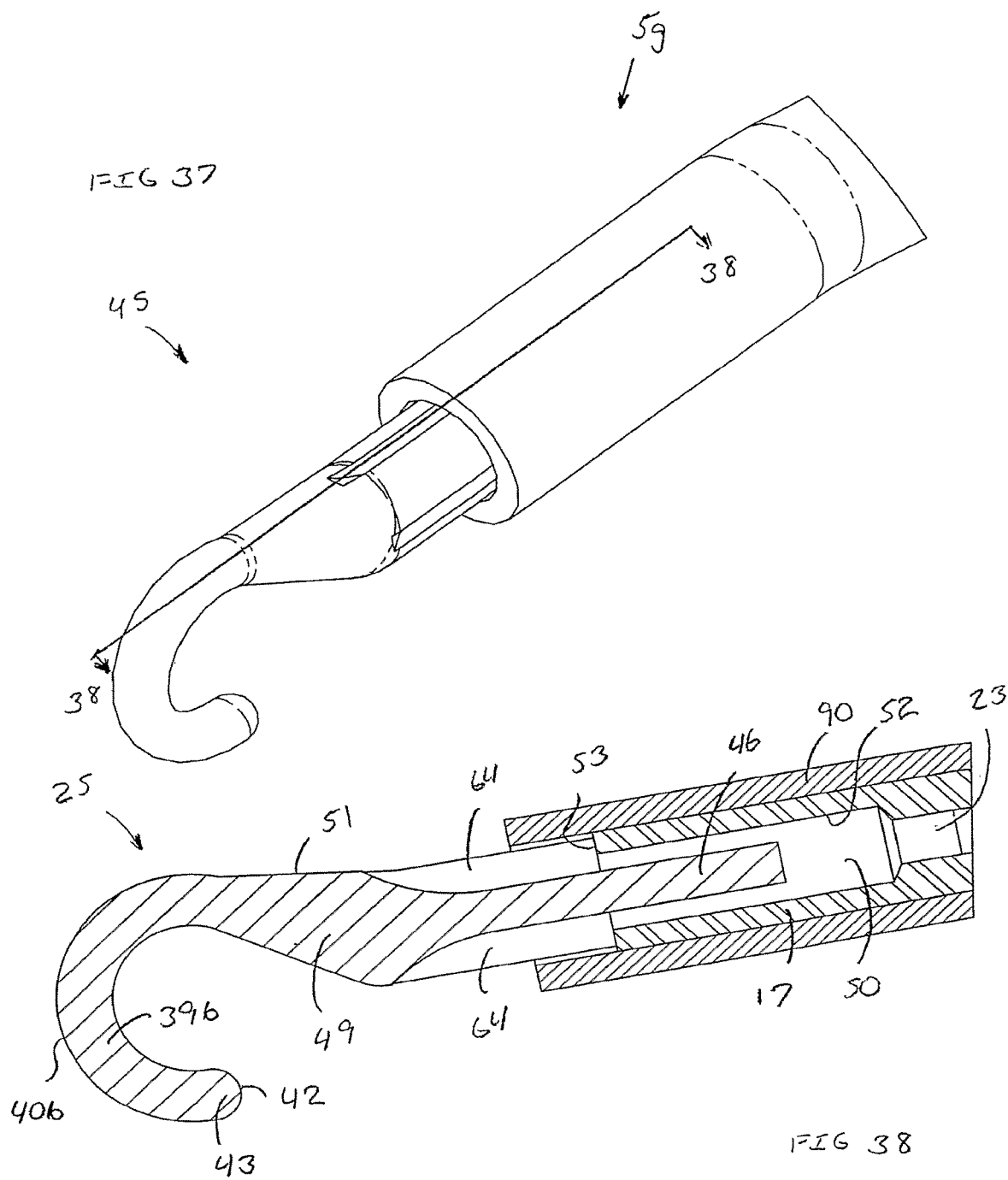

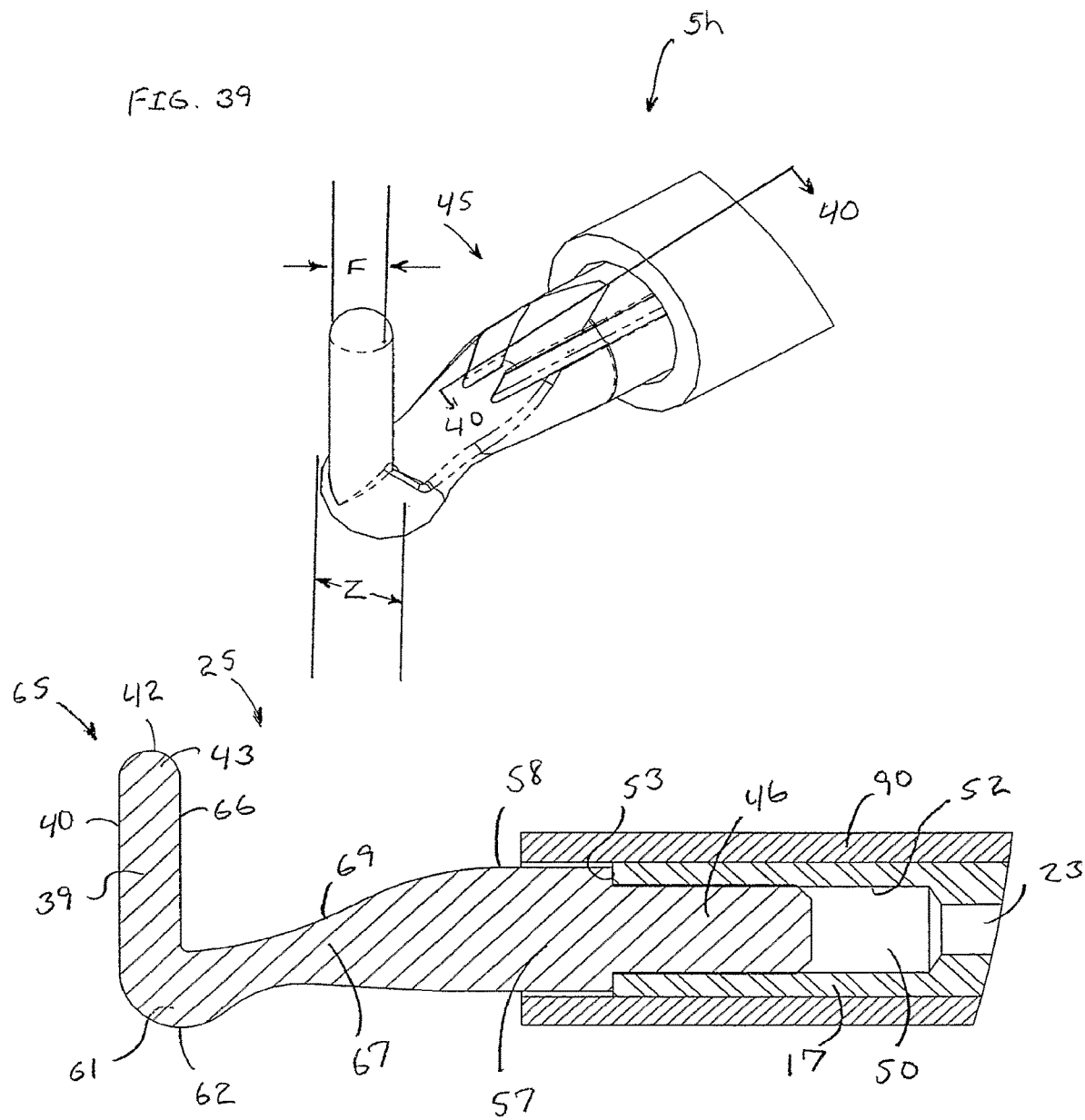

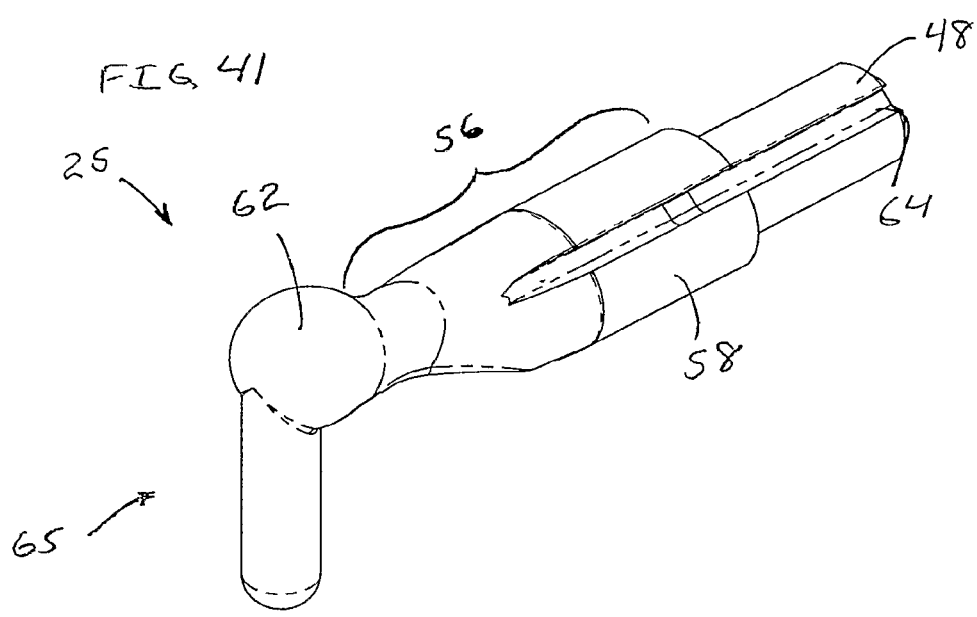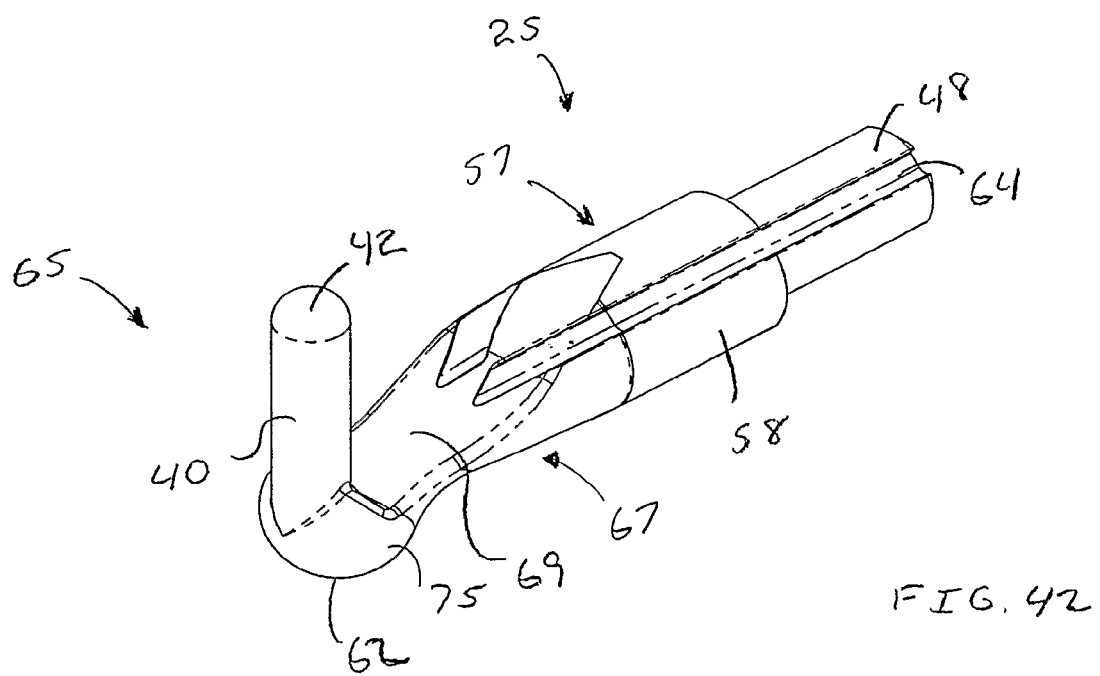

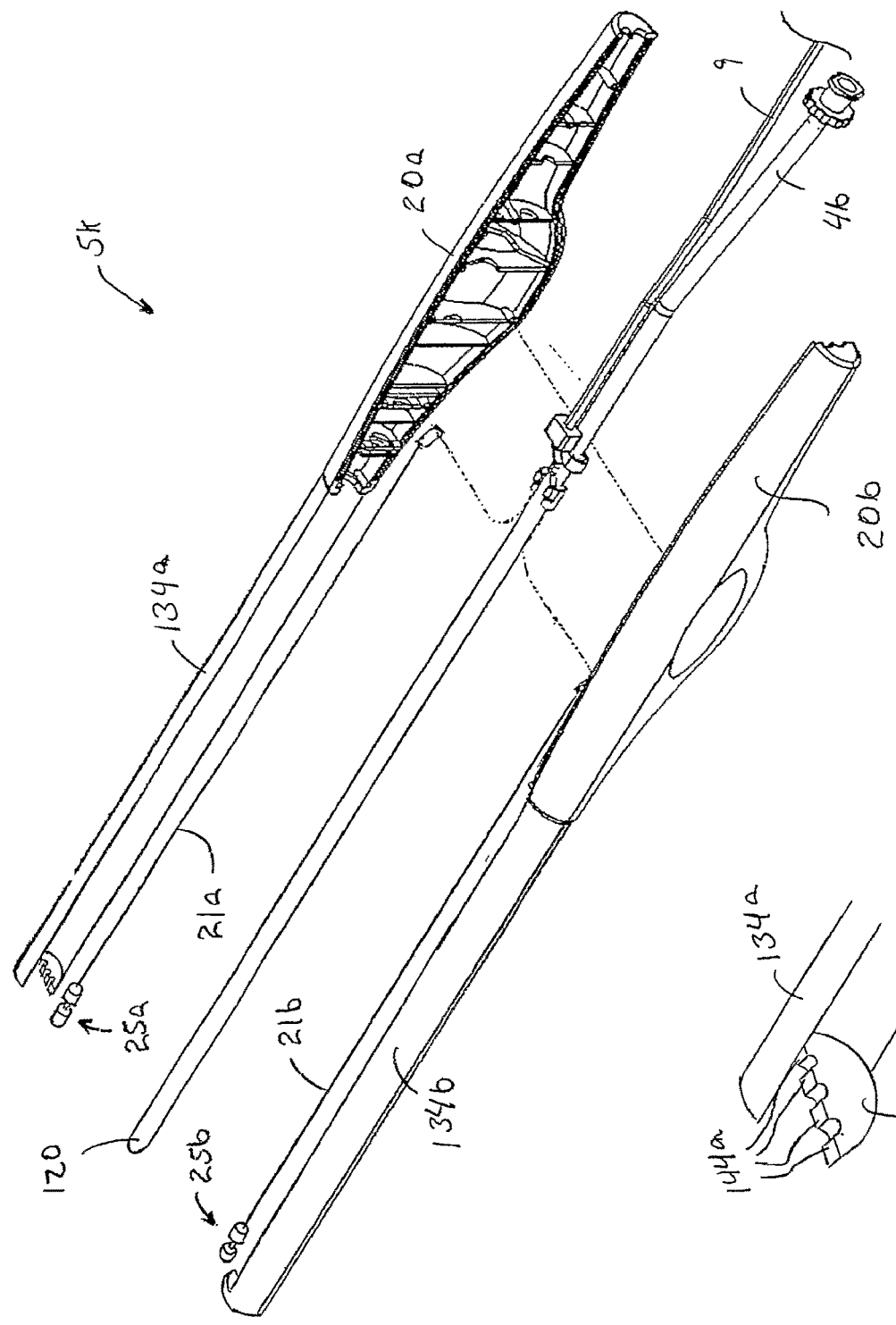

FLUID-ASSISTED MEDICAL DEVICES, SYSTEMS AND METHODS

CROSS REFERENCE TO RELATED APPLICATIONS

This application is a continuation of U.S. patent application Ser. No. 12/429,920, filed Apr. 29, 2009, entitled "FLUID-ASSISTED MEDICAL DEVICES, SYSTEMS AND METHODS, now abandoned, which is a continuation of application Ser. No. 10/488,801 filed Dec. 16, 2004, now U.S. Pat. No. 8,083,736, which is the National Stage Entry of PCT Application No. PCT/US02/28488, filed Sep. 6, 2002, which claims priority to Provisional Application No. 60/356,390, filed on Feb. 12, 2002, and Provisional Application No. 60/368,177, filed on Mar. 27, 2002; PCT Application No. PCT/US02/28488 application is also a continuation-in-part of application Ser. No. 09/947,658, filed Sep. 5, 2001, now U.S. Pat. No. 7,115,139 issued Oct. 3, 2006, which is a continuation-in-part of application Ser. No. 09/797,049, filed on Mar. 1, 2001 now U.S. Pat. No. 6,702,810, which claims priority to Provisional Application No. 60/187,114, filed on Mar. 6, 2000 the entirety of all of which are incorporated herein by reference.

U.S. patent application Ser. No. 10/488,801 is also a continuation-in-part of application Ser. No. 10/345,643, filed on Jan. 29, 2003, now U.S. Pat. No. 7,651,494, which is a continuation of application Ser. No. 09/668,403, filed on Sep. 22, 2000, now U.S. Pat. No. 6,558,385, the entirety of which is incorporated herein by reference.

This application is being filed as a PCT International Patent application in the name of TissueLink Medical, Inc. (a U.S. national corporation), for the designation of all countries except the US, and Michael E. McClurken, David Lipson, Robert Luzzi, Arnold E. Oyola, Jonathan E. Wilson, Christopher W. Maurer, and Roger D. Greeley (all US citizens), for the designation of the United States only, on 5 Sep. 2002.

FIELD

This invention relates generally to the field of medical devices, systems and methods for use upon a body during surgery. More particularly, the invention relates to electrosurgical devices, systems and methods for use upon tissues of a human body during surgery, particularly open surgery and minimally invasive surgery such as laparoscopic surgery.

BACKGROUND

Electrosurgical devices configured for use with a dry tip use electrical energy, most commonly radio frequency (RF) energy, to cut tissue or to cauterize blood vessels. During use, a voltage gradient is created at the tip of the device, thereby inducing current flow and related heat generation in the tissue. With sufficiently high levels of electrical energy, the heat generated is sufficient to cut the tissue and, advantageously, to stop the bleeding from severed blood vessels.

Current dry tip electrosurgical devices can cause the temperature of tissue being treated to rise significantly higher than 100° C., resulting in tissue desiccation, tissue sticking to the electrodes, tissue perforation, char formation and smoke generation. Peak tissue temperatures as a result of RF treatment of target tissue can be as high as 320° C., and such high temperatures can be transmitted to adjacent tissue via thermal diffusion. Undesirable results of such transmission to adjacent tissue include unintended thermal damage to the tissue.

Using saline according to the present invention to couple RF electrical energy to tissue inhibits such undesirable effects as sticking, desiccation, smoke production and char formation. One key factor is inhibiting tissue desiccation, which occurs when tissue temperature exceeds 100° C. and all of the intracellular water boils away, leaving the tissue extremely dry and much less electrically conductive. However, an uncontrolled or abundant flow rate of saline can provide too much cooling at the electrode/tissue interface. This cooling reduces the temperature of the target tissue being treated, and the rate at which tissue thermal coagulation occurs is determined by tissue temperature. This, in turn, can result in longer treatment time to achieve the desired tissue temperature for treatment of the tissue. Long treatment times are undesirable for surgeons since it is in the best interest of the patient, physician and hospital, to perform surgical procedures as quickly as possible.

RF energy delivered to tissue can be unpredictable and often not optimal when using general-purpose generators. Most general-purpose RF generators have modes for different waveforms (e.g. cut, coagulation, or a blend of these two) and device types (e.g. monopolar, bipolar), as well as power levels that can be set in watts. However, once these settings are chosen, the actual power delivered to tissue and associated heat generated can vary dramatically over time as tissue impedance changes over the course of RF treatment. This is because the power delivered by most generators is a function of tissue impedance, with the power ramping down as impedance either decreases toward zero or increases significantly to several thousand ohms. Current dry tip electrosurgical devices are not configured to address a change in power provided by the generator as tissue impedance changes or the associated effect on tissue and rely on the surgeon's expertise to overcome this limitation.

SUMMARY OF THE INVENTION

In certain embodiments, a system for treating tissue is provided. The system comprises radio frequency power provided from a power source at a power level; an electrically conductive fluid provided from a fluid source at a fluid flow rate; and an electrosurgical device configured to provide the radio frequency power and the electrically conductive fluid to the tissue.

In certain embodiments the conductive fluid is an indicator of tissue temperature. The conductive fluid can relate the tissue temperature to boiling, an amount of boiling, or an onset of boiling of the conductive fluid.

The conductive fluid can cool the tissue or dissipate heat from the tissue. Alternately or additionally, the conductive fluid dissipates heat from at least one of the tissue and the conductive fluid by a boiling of at least a portion of the fluid.

For other embodiments, at least one of the radio frequency power level and the flow rate of the conductive fluid is used to effect a boiling of the electrically conductive fluid. Furthermore, in some embodiments, the effect on boiling may comprise at least one of initiating, increasing, decreasing and eliminating boiling of the electrically conductive fluid.

For other embodiments, the electrically conductive fluid functions to limit the temperature of the tissue at the tissue surface to about a boiling temperature of the electrically conductive fluid.

Generally, the electrically conductive fluid protects the tissue from desiccation. In some embodiments, the conductive fluid protects the tissue from desiccation by boiling at least a portion of the electrically conductive fluid. In other embodiments, the electrically conductive fluid protects the tissue from desiccation by boiling at least a portion of the conductive fluid at a temperature below the temperature of tissue desiccation.

For some embodiments, the electrically conductive fluid is provided to the tissue at the tissue surface and the radio frequency power is also provided to the tissue at the tissue surface. The radio frequency power reaches below the tissue surface into the tissue via (through) the electrically conductive fluid at the tissue surface.

At least one of the radio frequency power level and the conductive fluid flow rate can be adjusted based on a boiling of the conductive fluid. Furthermore, for other embodiments, adjusting at least one of the radio frequency power level and the conductive fluid flow rate based on a boiling of the conductive fluid comprises one of initiating, increasing, decreasing and eliminating boiling of the electrically conductive fluid.

In certain embodiments, a method for treating tissue is provided comprising providing radio frequency power at a power level; providing an electrically conductive fluid at a fluid, flow rate; and providing an electrosurgical device configured to provide the radio frequency power with the electrically conductive fluid to the tissue.

Still further, a system for treating tissue is provided, the system comprising radio frequency power provided from a power source at a power level; an electrically conductive fluid provided from a fluid source at a fluid flow rate; an electrosurgical device configured to provide the radio frequency power and the conductive fluid to the tissue; and a fluid coupling which couples the tissue and the electrosurgical device, the coupling comprising the conductive fluid.

In certain embodiments the fluid coupling is an indicator of tissue temperature. The fluid coupling can function as an indicator of tissue temperature by using boiling; an amount of boiling; or an onset of boiling of the fluid coupling.

For other embodiments, the fluid coupling cools the tissue or dissipates heat from the tissue. The fluid coupling can dissipate heat from at least one of the tissue and the fluid coupling by a boiling of at least a portion of the fluid coupling. For other embodiments, the fluid coupling can limit the temperature of the tissue at the tissue surface to close to a boiling temperature of the fluid coupling.

The fluid coupling can protect the tissue from desiccation. In some embodiments, the fluid coupling protects the tissue from desiccation by boiling at least a portion of the fluid coupling. In other embodiments, the fluid coupling protects the tissue from desiccation by boiling at least a portion of the fluid coupling at a temperature which protects the tissue from desiccation.

For other embodiments, at least one of the radio frequency power level and the conductive fluid flow rate is used to effect a boiling of the fluid coupling. Furthermore, in some embodiments, the effect on boiling may be at least one of initiating, increasing, decreasing and eliminating boiling of the fluid coupling.

The conductive fluid can be provided to the tissue at the tissue surface, and the radio frequency power can also be provided to the tissue at the tissue surface. The radio frequency power can be provided to an area below the tissue surface via (through) the fluid coupling at the tissue surface.

In certain embodiments, a method for treating tissue is provided, the method comprising providing radio frequency power at a power level; providing an electrically conductive fluid at a fluid flow rate; providing an electrosurgical device configured to provide the radio frequency power and the electrically conductive fluid to the tissue; and forming a fluid coupling which couples the tissue and the electrosurgical device. The fluid coupling comprises conductive fluid.

The fluid coupling can be used as an indicator of tissue temperature. This can be done by boiling; an amount of boiling of the fluid coupling; or an onset of boiling of the fluid coupling.

For some embodiments, the fluid coupling is used to cool the tissue or dissipate heat from the tissue by transferring heat to the fluid coupling. The fluid coupling can dissipate heat from at least one of the tissue and the fluid coupling by a boiling of at least a portion of the fluid coupling.

For other embodiments, at least one of the radio frequency power level and the conductive fluid flow rate is adjusted based on a boiling of the fluid coupling. Furthermore, for other embodiments, adjusting at least one of the radio frequency power level and the conductive fluid flow rate based on a boiling of the fluid coupling comprises one of initiating, increasing, decreasing and eliminating boiling of the fluid coupling.

For other embodiments, the temperature of the tissue at the tissue surface is limited to about a boiling temperature of the fluid coupling.

For other embodiments, the tissue is protected from desiccation with the fluid coupling. Furthermore, for other embodiments, the tissue is protected from desiccation with the fluid coupling by a boiling of at least a portion of the fluid coupling. Furthermore, for other embodiments, the tissue is protected from desiccation with the fluid coupling by a boiling of at least a portion of the fluid coupling at a temperature which protects the tissue from desiccation.

The method for treating tissue can further comprise providing the conductive fluid to the tissue at the tissue surface; and providing the radio frequency power to the tissue at the tissue surface and below the tissue surface into the tissue through the fluid coupling.

With regards to specific devices, in certain embodiments a surgical device for treating tissue is provided comprising a handle having a proximal end and a distal end; a shaft extending distally beyond the distal end of the handle, the shaft having a proximal end and a distal end; an electrode tip, at least a portion of the electrode tip extending distally beyond the distal end of the shaft, the electrode tip extending distally beyond the distal end of the shaft comprising a spherical end surface portion and a cylindrical side surface portion, the spherical end surface portion located distal to the cylindrical side surface portion and comprising at least a portion of the distal end surface of the surgical device; and a fluid passage directed to provide a fluid towards the cylindrical side portion of the electrode tip.

In other embodiments, a surgical device for treating tissue is provided comprising a handle having a proximal end and a distal end; a shaft extending distally beyond the distal end of the handle, the shaft having a proximal end and a distal end; an electrode tip, at least a portion of the electrode tip extending distally beyond the distal end of the shaft, the electrode tip extending distally beyond the distal end of the shaft comprising a neck portion and an enlarged head portion, the enlarged head portion located distal to the neck portion and comprising at least a portion of a distal end surface of the surgical device; and a fluid passage directed to provide a fluid towards the enlarged head portion of the electrode tip.

In still other embodiments, a device for treating tissue is provided comprising a handle having a proximal end and a distal end; a shaft extending distally beyond the distal end of the handle, the shaft having a proximal end and a distal end; an electrode tip, the electrode tip comprising a spherical end surface portion and a cylindrical side surface portion, the spherical end surface portion located distal to the cylindrical side surface portion and comprising at least a portion of the distal end surface of the device; a fluid passage connectable to a fluid source; and a plurality of fluid outlet openings in fluid communication with the fluid passage, the fluid outlet openings positioned to provide a fluid from the fluid source around the cylindrical side surface portion of the electrode tip.

In still other embodiments, a device for treating tissue is provided comprising a handle having a proximal end and a distal end; a shaft extending distally beyond the distal end of the handle, the shaft having a proximal end and a distal end; an electrode tip comprising a rounded distal end surface portion configured to blunt dissect tissue and a side surface portion configured to seal tissue from at least one of the flow of bodily fluids and air, the side surface portion having a surface area greater than the surface area of the distal end surface portion; a fluid passage connectable to a fluid source; and at least one fluid outlet opening in fluid communication with the fluid passage, the fluid outlet opening positioned to provide a fluid from the fluid source to the side surface portion of the electrode tip and proximal the distal end surface portion.

In other embodiments, a device for treating tissue is provided comprising a first electrode tip spaced from a second electrode tip, the first and second electrode tips being connectable to different terminals of a radio frequency generator to generate electrical current flow therebetween; at least one fluid passage connectable to a fluid source; at least one fluid outlet opening in fluid communication with the fluid passage, the fluid outlet opening configured to provide a fluid from the fluid source to at least one of a tissue surface and at least one of the first and second electrode tips; and the first and second electrode tips configured to slide over and seal tissue in the presence of a fluid provided from the fluid outlet opening and an electrical current provided from the electrode tips.

Additional methods for treating tissue may also comprise providing tissue having a tissue surface; providing radio frequency power at a power level; providing an electrically conductive fluid at a fluid flow rate; providing an surgical device configured to simultaneously provide the radio frequency power and the electrically conductive fluid to tissue; providing the electrically conductive fluid to the tissue at the tissue surface; forming a fluid coupling comprising the electrically conductive fluid which couples the tissue and the surgical device; providing the radio frequency power to the tissue at the tissue surface and below the tissue surface into the tissue through the fluid coupling; sealing the tissue against at least one of the flow of bodily fluids and air by at least one of shrinking collagen and coagulating blood in the tissue; and blunt dissecting the tissue.

In other embodiments, methods for treating tissue may also comprise providing tissue having a tissue surface; providing radio frequency power at a power level; providing an electrically conductive fluid at a fluid flow rate; providing an surgical device configured to simultaneously provide the radio frequency power and the electrically conductive fluid to tissue, the surgical device comprising a first electrode tip and a second electrode tip; providing the electrically conductive fluid to the tissue at the tissue surface; forming a fluid coupling comprising the electrically conductive fluid which couples the tissue and the surgical device; providing the radio frequency power to the tissue at the tissue surface and below the tissue surface into the tissue through the fluid coupling; sliding the first electrode tip and the second electrode tip over the tissue surface; and sealing the tissue against at least one of the flow of bodily fluids and air by at least one of shrinking collagen and coagulating blood in the tissue.

BRIEF DESCRIPTION OF THE DRAWINGS

To better understand and appreciate the invention, refer to the following detailed description in connection with the accompanying drawings, hand and computer generated:

FIG. 9 is a schematic exploded perspective view of an assembly of an electrosurgical device according to the present invention;

FIG. 10 is a schematic longitudinal cross-sectional side view of the tip and shaft of the device of FIG. 9 taken along line 10-10 of FIG. 12;

FIG. 11 is a schematic close-up longitudinal cross-sectional side view of the tip portion of the device bounded by circle 45 shown in FIG. 10 taken along line 10-10 of FIG. 12;

FIG. 12 is a schematic distal end view of the tip portion of the device bounded by circle 45 shown in FIG. 10;

FIG. 13 is a schematic side view of the of the tip and shaft of the device of FIG. 9 with a fluid coupling to a tissue surface of tissue;

FIG. 14 is a schematic close-up cross-sectional side view of an alternative tip portion;

FIG. 15 is a schematic close-up section side view of the tip portion of FIG. 14 taken along line 15-15 of FIG. 14;

FIG. 23 is a schematic close-up front perspective view of the electrode for the tip portion of FIG. 20;

FIG. 24 is a schematic close-up rear perspective view of the electrode for the tip portion of FIG. 20;

FIG. 31 is a schematic close-up front perspective view of the electrode for the tip portion of FIG. 29;

FIG. 32 is a schematic close-up rear perspective view of the electrode for the tip portion of FIG. 29;

FIG. 35 is a schematic close-up front perspective view of the electrode for the tip portion of FIG. 33;

FIG. 36 is a schematic close-up rear perspective view of the electrode for the tip portion of FIG. 33;

FIG. 37 is a schematic close-up perspective view of an alternative tip portion;

FIG. 38 is a schematic close-up section side view of the tip portion of FIG. 37 taken along line 38-38 of FIG. 37;

FIG. 39 is a schematic close-up perspective view of an alternative tip portion;

FIG. 40 is a schematic close-up section side view of the tip portion of FIG. 39 taken along line 40-40 of FIG. 39;

FIG. 41 is a schematic close-up front posterior perspective view of the electrode for the tip portion of FIG. 39;

FIG. 42 is a schematic close-up front anterior perspective view of the electrode for the tip portion of FIG. 39;

FIG. 51 is a schematic exploded perspective view of an assembly of an alternative electrosurgical device according to the present invention;

FIG. 52 is a schematic close-up perspective side view of a distal end portion of the device of FIG. 51;

DETAILED DESCRIPTION

Figure 1:
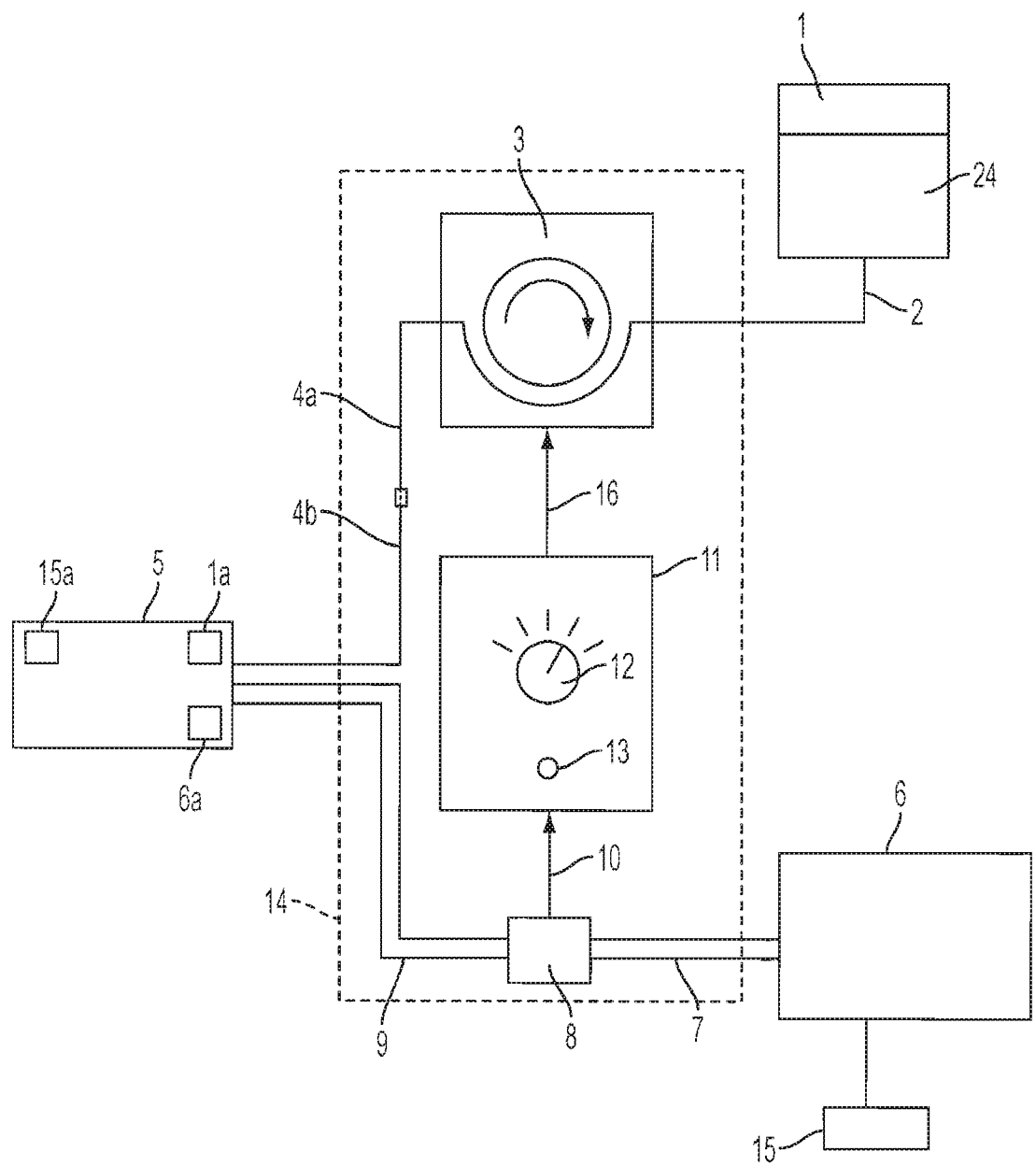
FIG. 1 is a block diagram showing one embodiment of a control system of the invention, and an electrosurgical device.

Throughout the present description, like reference numerals and letters indicate corresponding structure throughout the several views, and such corresponding structure need not be separately discussed. Furthermore, any particular feature(s) of a particular exemplary embodiment may be equally applied to any other exemplary embodiment(s) of this specification as suitable. In other words, features between the various exemplary embodiments described herein are interchangeable as suitable, and not exclusive.

The invention provides devices, systems and methods that preferably improve control of tissue temperature at a tissue treatment site during a medical procedure. The invention is particularly useful during surgical procedures upon tissues of the body, where it is desirable to coagulate and shrink tissue, to occlude lumens of blood vessels (e.g. arteries, veins), airways (e.g. bronchi, bronchioles), bile ducts and lymphatic ducts.

The invention includes electrosurgical procedures, which preferably utilize RF power and electrically conductive fluid, to treat tissue. Preferably, a desired tissue temperature range is achieved by adjusting parameters, such as conductive fluid flow rate, that affect the temperature at the tissue/electrode interface. Preferably, the device achieves a desired tissue temperature by utilizing a desired percentage boiling of the conductive solution at the tissue/electrode interface.

In one embodiment, the invention provides a control device, the device comprising a flow rate controller that receives a signal indicating power applied to the system, and adjusts the flow rate of conductive fluid from a fluid source to an electrosurgical device. The invention also contemplates a control system comprising a flow rate controller, a measurement device that measures power applied to the system, and a pump that provides fluid at a selected flow rate.

The invention will be discussed generally with reference to FIG. 1. FIG. 1 shows a block diagram of one exemplary embodiment of a system of the invention. Preferably, as shown in FIG. 1, an electrically conductive fluid 24 is provided from a fluid source 1 through a fluid line 2 to a pump 3, which has an outlet fluid line 4a that is connected as an input fluid line 4b, to electrosurgical device 5. In a preferred embodiment, the outlet fluid line 4a and the input fluid line 4b are flexible and are made from a polymeric material, such as polyvinylchloride (PVC) or polyolefin (e.g. polypropylene, polyethylene) and the conductive fluid comprises a saline solution. More preferably, the saline comprises sterile, and even more preferably, normal saline. Although the description herein will specifically describe the use of saline as the fluid 24, other electrically conductive fluids, as well as non-conductive fluids, can be used in accordance with the invention.

For example, in addition to the conductive fluid comprising physiologic saline (also known as "normal" saline, isotonic saline or 0.9% sodium chloride (NaCl) solution), the conductive fluid may comprise hypertonic saline solution, hypotonic saline solution, Ringers solution (a physiologic solution of distilled water containing specified amounts of sodium chloride, calcium chloride, and potassium chloride), lactated Ringer's solution (a crystalloid electrolyte sterile solution of distilled water containing specified amounts of calcium chloride, potassium chloride, sodium chloride, and sodium lactate), Locke-Ringer's solution (a buffered isotonic solution of distilled water containing specified amounts of sodium chloride, potassium chloride, calcium chloride, sodium bicarbonate, magnesium chloride, and dextrose), or any other electrolyte solution. In other words, a solution that conducts electricity via an electrolyte, a substance (salt, acid or base) that dissociates into electrically charged ions when dissolved in a solvent, such as water, resulting solution comprising an ionic conductor.

While a conductive fluid is preferred, as will become more apparent with further reading of this specification, the fluid 24 may also comprise an electrically non-conductive fluid. The use of a non-conductive fluid is less preferred to that of a conductive fluid as the non-conductive fluid does not conduct electricity. However, the use of a non-conductive fluid still provides certain advantages over the use of a dry electrode including, for example, reduced occurrence of tissue sticking to the electrode of the device 5 and cooling of the electrode and/or tissue. Therefore, it is also within the scope of the invention to include the use of a non-conducting fluid, such as, for example, dionized water.

Returning to FIG. 1, energy to heat tissue is provided from energy source, such as an electrical generator 6 which preferably provides RF alternating current energy via a cable 7 to energy source output measurement device, such as a power measurement device 8 that measures the RF alternating current electrical power. In one exemplary embodiment, preferably the power measurement device 8 does not turn the power off or on, or alter the power in any way. A power switch 15 connected to the generator 6 is preferably provided by the generator manufacturer and is used to turn the generator 6 on and off. The power switch 15 can comprise any switch to turn the power on and off, and is commonly provided in the form of a footswitch or other easily operated switch, such as a switch 15a mounted on the electrosurgical device 5. The power switch 15 or 15a may also function as a manually activated device for increasing or decreasing the rate of energy provided from the surgical device 5. Alternatively, internal circuitry and other components of the generator 6 may be used for automatically increasing or decreasing the rate of energy provided from the surgical device 5. A cable 9 preferably carries RF energy from the power measurement device 8 to the electrosurgical device 5. Power, or any other energy source output, is preferably measured before it reaches the electrosurgical device 5.

For the situation where capacitation and induction effects are negligibly small, from Ohm's law, power P, or the rate of energy delivery (e.g. joules/sec), may be expressed by the product of current times voltage (i.e. I×V), the current squared times resistance (i.e. $I^2 \times R$), or the voltage squared divided by the resistance (i.e. $V^2/R$); where the current I may be measured in amperes, the voltage V may be measured in volts, the electrical resistance R may be measured in ohms, and the power P may be measured in watts (joules/sec). Given that power P is a function of current I, voltage V, and resistance R as indicated above, it should be understood, that a change in power P is reflective of a change in at least one of the input variables. Thus, one may alternatively measure changes in such input variables themselves, rather than power P directly, with such changes in the input variables mathematically corresponding to a changes in power P as indicated above.

As to the frequency of the RF electrical energy, it is preferably provided within a frequency band (i.e. a continuous range of frequencies extending between two limiting frequencies) in the range between and including about 9 kHz (kilohertz) to 300 GHz (gigahertz). More preferably, the RF energy is provided within a frequency band in the range between and including about 50 kHz (kilohertz) to 50 MHz (megahertz). Even more preferably, the RF energy is provided within a frequency band in the range between and including about 200 kHz (kilohertz) to 2 MHz (megahertz). Most preferably, RF energy is provided within a frequency band in the range between and including about 400 kHz (kilohertz) to 600 kHz (kilohertz). Further, it should also be understood that, for any frequency band identified above, the range of frequencies may be further narrowed in increments of 1 (one) hertz anywhere between the lower and upper limiting frequencies.

While RF electrical energy is preferred, it should be understood that the electrical energy (i.e., energy made available by the flow of electric charge, typically through a conductor or by self-propagating waves) may comprise any frequency of the electromagnetic spectrum (i.e. the entire range of radiation extending in frequency from $10^{23}$ hertz to 0 hertz) and including, but not limited to, gamma rays, x-rays, ultraviolet radiation, visible light, infrared radiation, microwaves, and any combinations thereof.

With respect to the use of electrical energy, heating of the tissue is preferably performed by means of resistance heating. In other words, increasing the temperature of the tissue as a result of electric current flow through the tissue, with the electrical energy being absorbed from the voltage and transformed into thermal energy (i.e. heat) via accelerated movement of ions as a function of the tissue's electrical resistance.

Heating with electrical energy may also be performed by means of dielectric heating (capacitation). In other words, increasing the temperature of the tissue through the dissipation of electrical energy as a result of internal dielectric loss when the tissue is placed in a varying electric field, such as a high-frequency (e.g. microwave), alternating electromagnetic field. Dielectric loss is the electrical energy lost as heat in the polarization process in the presence of the applied electric field. In the case of an alternating current field, the energy is absorbed from the alternating current voltage and converted to heat during the polarization of the molecules.

However, it should be understood that energy provided to heat the tissue may comprise surgical devices other than electrosurgical devices, energy sources other than generators, energy forms other than electrical energy and mechanisms other than resistance heating. For example, providing thermal energy to the tissue from energy source with a difference (e.g. higher) in temperature. Such may be provided, for example, to the tissue from a heated device, which heats tissue through direct contact with the energy source (conduction), heats through contact with a flowing fluid (convection), or from a remote heat source (radiation).

Also, for example, providing energy to the tissue may be provided via mechanical energy which is transformed into thermal energy via accelerated movement of the molecules, such as by mechanical vibration provided, for example, by energy source such as a transducer containing a piezoelectric substance (e.g., a quartz-crystal oscillator) that converts high-frequency electric current into vibrating ultrasonic waves which may be used by, for example, an ultrasonic surgical device.

Also, for example, providing energy to the tissue may be provided via radiant energy (i.e. energy which is transmitted by radiation/waves) which is transformed into thermal energy via absorption of the radiant energy by the tissue. Preferably the radiation/waves comprise electromagnetic radiation/waves which include, but is not limited to, radio waves, microwaves, infrared radiation, visible light radiation, ultraviolet radiation, x-rays and gamma rays. More preferably, such radiant energy comprises energy with a frequency of $3 \times 10^{11}$ hertz to $3 \times 10^{16}$ hertz (i.e. the infrared, visible, and ultraviolet frequency bands of the electromagnetic spectrum). Also preferably the electromagnetic waves are coherent and the electromagnetic radiation is emitted from energy source such as a laser device.

A flow rate controller 11 preferably includes a selection switch 12 that can be set to achieve desired levels of percentage fluid boiling (for example, 100%, 98%, 80% boiling). Preferably, the flow rate controller 11 receives an input signal 10 from the power measurement device 8 and calculates an appropriate mathematically predetermined fluid flow rate based on percentage boiling indicated by the selection switch 12. In a preferred embodiment, a fluid switch 13 is provided so that the fluid system can be primed (e.g. air eliminated) before turning the generator 6 on. The output signal 16 of the flow rate controller 11 is preferably sent to the pump 3 motor to regulate the flow rate of conductive fluid, and thereby provide an appropriate fluid flow rate which corresponds to the amount of power being delivered.

In one exemplary embodiment, the invention comprises a flow rate controller 11 that is configured and arranged to be connected to a source of RF power (e.g. generator 6), and a source of fluid (e.g. fluid source 1), for example, a source of conductive fluid. The device of the invention receives information about the level of RF power applied to an electrosurgical device 5, and adjusts the flow rate of the fluid 24 to the electrosurgical device 5, thereby controlling temperature at the tissue treatment site.

In another exemplary embodiment, elements of the system are physically included together in one electronic enclosure. One such embodiment is shown by enclosure within the outline box 14 of FIG. 1. In the illustrated embodiment, the pump 3, flow rate controller 11, and power measurement device 8 are enclosed within an enclosure, and these elements are connected through electrical connections to allow signal 10 to pass from the power measurement device 8 to the flow rate controller 11, and signal 16 to pass from the flow rate controller 11 to the pump 3. Other elements of a system can also be included within one enclosure, depending upon such factors as the desired application of the system, and the requirements of the user.

The pump 3 can be any suitable pump used in surgical procedures to provide saline or other fluid at a desired flow rate. Preferably, the pump 3 comprises a peristaltic pump. With a rotary peristaltic pump, typically a fluid 24 is conveyed within the confines of a flexible tube (e.g. 4a) by waves of contraction placed externally on the tube which are produced mechanically, typically by rotating rollers which squeeze the flexible tubing against a support intermittently. Alternatively, with a linear peristaltic pump, typically a fluid 24 is conveyed within the confines of a flexible tube by waves of contraction placed externally on the tube which are produced mechanically, typically by a series of compression fingers or pads which squeeze the flexible tubing against a support sequentially. Peristaltic pumps are generally preferred for use as the electro-mechanical force mechanism (e.g. rollers driven by electric motor) does not make contact the fluid 24, thus reducing the likelihood of inadvertent contamination.

Alternatively, pump 3 can be a "syringe pump", with a built-in fluid supply. With such a pump, typically a filled syringe is located on an electro-mechanical force mechanism (e.g. rain driven by electric motor) which acts on the plunger of the syringe to force delivery of the fluid 24 contained therein. Alternatively, the syringe pump may comprise a double-acting syringe pump with two syringes such that they can draw saline from a reservoir (e.g. of fluid source 1), either simultaneously or intermittently. With a double acting syringe pump, the pumping mechanism is generally capable of both infusion and withdrawal. Typically, while fluid 24 is being expelled from one syringe, the other syringe is receiving fluid 24 therein from a separate reservoir. In this manner, the delivery of fluid 24 remains continuous and uninterrupted as the syringes function in series. Alternatively, it should be understood that a multiple syringe pump with two syringes, or any number of syringes, may be used in accordance with the invention.

Furthermore, fluid 24, such as conductive fluid, can also be provided from an intravenous (IV) bag full of saline (e.g. of fluid source 1) that flows under the influence (i.e. force) of gravity. In such a manner, the fluid 24 may flow directly to the electrosurgical device 5, or first to the pump 3 located there between. Alternatively, fluid 24 from a fluid source 1 such as an IV bag can be provided through an IV flow controller that may provide a desired flow rate by adjusting the cross sectional area of a flow orifice (e.g. lumen of the connective tubing with the electrosurgical device 5) while sensing the flow rate with a sensor such as an optical drop counter. Furthermore, fluid 24 from a fluid source 1 such as an IV bag an be provided through a manually or automatically activated device such as a flow controller, such as a roller clamp, which also adjusts the cross sectional area of a flow orifice and may be adjusted manually by, for example, the user of the device in response to their visual observation (e.g. fluid boiling) at the tissue treatment site or a pump.

Similar pumps can be used in connection with the invention, and the illustrated embodiments are exemplary only. The precise configuration of the pump 3 is not critical to the invention. For example, pump 3 may include other types of infusion and withdrawal pumps. Furthermore, pump 3 may comprise pumps which may be categorized as piston pumps, rotary vane pumps (e.g. axial impeller, centrifugal impeller), cartridge pumps and diaphragm pumps. In some embodiments, the pump 3 can be substituted with any type of flow controller, such as a manual roller clamp used in conjunction with an IV bag, or combined with the flow controller to allow the user to control the flow rate of conductive fluid to the device. Alternatively, a valve configuration can be substituted for pump 3.

Furthermore, similar configurations of the system can be used in connection with the invention, and the illustrated embodiments are exemplary only. For example, the fluid source 1 pump 3, generator 6, power measurement device 8 or flow rate controller 11, or any other components of the system not expressly recited above, may comprise a portion of the electrosurgical device 5. For example, in one exemplary embodiment the fluid source 1 may comprise a compartment of the electrosurgical device 5 which contains fluid 24, as indicated at reference character 1a. In another exemplary embodiment, the compartment may be detachably connected to the electrosurgical device 5, such as a canister which may be attached via threaded engagement with the device 5. In yet another exemplary embodiment, the compartment may be configured to hold a pre-filled cartridge of fluid 24, rather than the fluid directly.

Also for example, with regards to alternative for the generator 6, an energy source, such as a direct current (DC) battery used in conjunction with inverter circuitry and a transformer to produce alternating current at a particular frequency, may comprise a portion of the electrosurgical device 5, as indicated at reference character 6a. In one embodiment the battery element of the energy source may comprise a rechargeable battery. In yet another exemplary embodiment, the battery element may be detachably connected to the electrosurgical device 5, such as for recharging. The components of the system will now be described in further detail. From the specification, it should be clear that any use of the terms "distal" and "proximal" are made in reference from the user of the device, and not the patient.

Figure 2:
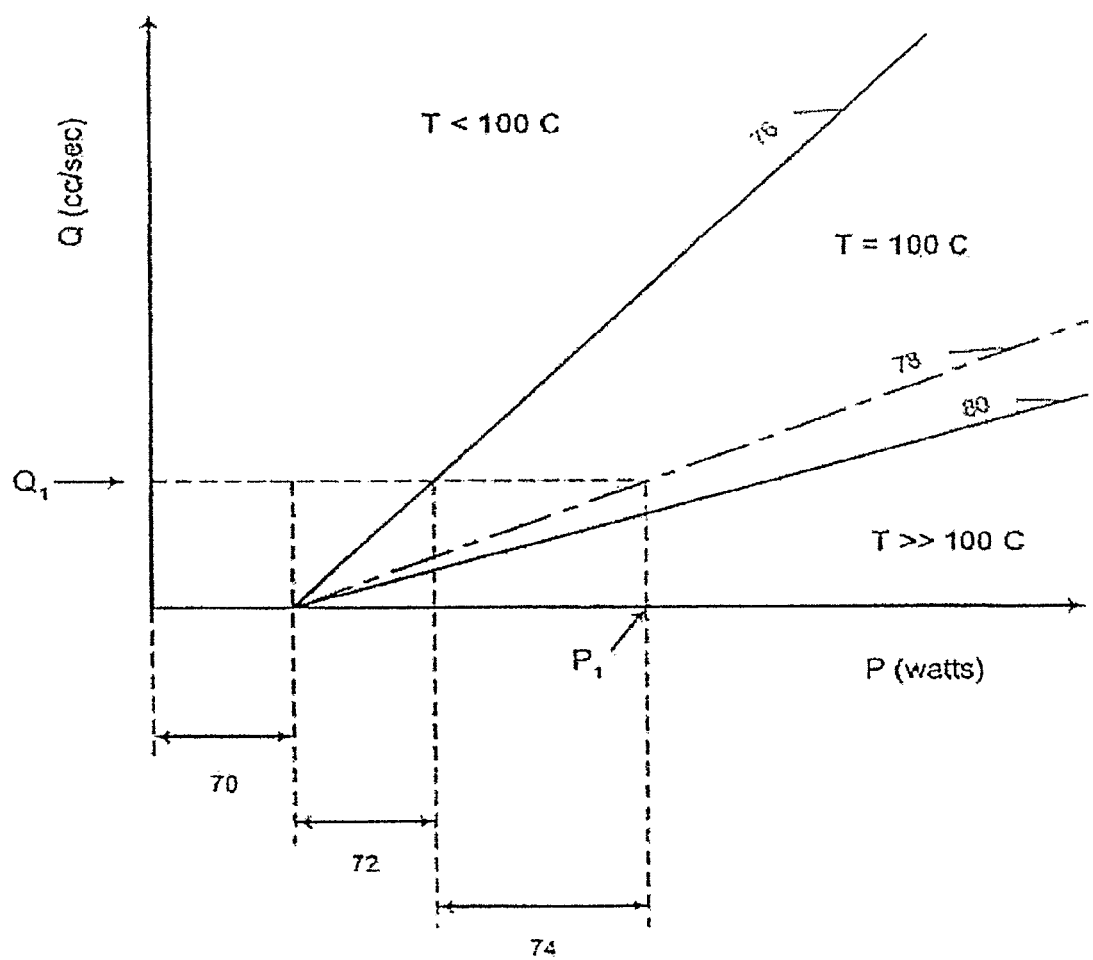
FIG. 2 is a schematic graph that describes the relationship between RF power to tissue (P), flow rate of saline (Q), and tissue temperature (T) when heat conduction to adjacent tissue is considered.

The flow rate controller 11 controls the rate of flow from the fluid source 1. Preferably, the rate of fluid flow from the fluid source 1 is based upon the amount of RF power provided from the generator 6 to the electrosurgical device 5. In other words, as shown in FIG. 2, preferably there is a relationship between the rate of fluid flow Q and the RF power P indicated by the Y- and X-axes of the schematic graph, respectively. More precisely, as shown in FIG. 2, the relationship between the rate of fluid flow Q and RF power P may be expressed as a direct, linear relationship. The flow rate Q of conductive fluid 24, such as saline, interacts with the RF power P and various modes of heat transfer away from the target tissue, as described herein.

Throughout this disclosure, when the terms "boiling point of saline", "vaporization point of saline", and variations thereof are used, what is actually referenced for explanation purposes, is the boiling point of the water (i.e. 100° C.) in the saline solution given that the difference between the boiling point of normal saline (about 100.16° C.) and the boiling point of water is negligible.

FIG. 2 shows a schematic graph that describes the relationship between the flow rate of saline, RF power to tissue, and regimes of boiling as detailed below. Based on a simple one-dimensional lumped parameter model of the heat transfer, the peak tissue temperature can be estimated, and once tissue temperature is estimated, it follows directly whether it is hot enough to boil saline. The total RF electrical power P that is converted into heat can be defined as:

$$P = \Delta T/R + \rho c_p Q_1 \Delta T + \rho Q_b h_v \quad (1)$$

where P=the total RF electrical power that is converted into heat.

Conduction.

The term [$\Delta T/R$] in equation (1) is heat conducted to adjacent tissue, represented as 70 in FIG. 2, where:

$\Delta T=(T-T_\infty)$ the difference in temperature between the peak tissue temperature (T) and the normal temperature ($T_\infty$) of the body tissue (° C.). Normal temperature of the body tissue is generally 37° C.; and R=Thermal resistance of surrounding tissue, the ratio of the temperature difference to the heat flow (° C./watt).

This thermal resistance can be estimated from published data gathered in experiments on human tissue (see for example, Phipps, J. H., "Thermometry studies with bipolar diathermy during hysterectomy," *Gynaecological Endoscopy*, 3:5-7 (1994)). As described by Phipps, Kleppinger bipolar forceps were used with an RF power of 50 watts, and the peak tissue temperature reached 320° C. For example, using the energy balance of equation (1), and assuming all the RF heat put into tissue is conducted away, then R can be estimated:

$$R = \Delta T/P = (320-37)/50 = 5.7 \approx 6° C./watt$$

However, it is undesirable to allow the tissue temperature to reach 320° C., since tissue will become desiccated. At a temperature of 320° C., the fluid contained in the tissue is typically boiled away, resulting in the undesirable tissue effects described herein. Rather, it is preferred to keep the peak tissue temperature at no more than about 100° C. to inhibit desiccation of the tissue. Assuming that saline boils at about 100° C., the first term in equation (1) ($\Delta T/R$) is equal to (100−37)/6=10.5 watts. Thus, based on this example, the maximum amount of heat conducted to adjacent tissue without any significant risk of tissue desiccation is 10.5 watts.

Referring to FIG. 2, RF power to tissue is represented on the X-axis as P (watts) and flow rate of saline (cc/min) is represented on the Y-axis as Q. When the flow rate of saline equals zero (Q=0), there is an "offset" RF power that shifts the origin of the sloped lines 76, 78, and 80 to the right. This offset is the heat conducted to adjacent tissue. For example, using the calculation above for bipolar forceps, this offset RF power is about 10.5 watts. If the power is increased above this level with no saline flow, the peak tissue temperature can rise well above 100° C., resulting in tissue desiccation from the boiling off of water in the cells of the tissue.

Convection.

The second term [$\rho c_p Q_1 \Delta T$] in equation (1) is heat used to warm up the flow of saline without boiling the saline, represented as 72 in FIG. 2, where:

$\rho$=Density of the saline fluid that gets hot but does not boil (approximately 1.0 gm/cm$^3$);

$c_p$=Specific heat of the saline (approximately 4.1 watt-sec/gm-° C.);

$Q_1$=Flow rate of the saline that is heated (cm$^3$/sec); and $\Delta T$=Temperature rise of the saline. Assuming that the saline is heated to body temperature before it gets to the electrode, and that the peak saline temperature is similar to the peak tissue temperature, this is the same $\Delta T$ as for the conduction calculation above.

The onset of boiling can be predicted using equation (1) with the last term on the right set to zero (no boiling) ($\rho Q_b h_v = 0$), and solving equation (1) for $Q_1$ leads to:

$$Q_1 = [P - \Delta T/R]/\rho c_p \Delta T \quad (2)$$

This equation defines the line shown in FIG. 2 as the line of onset of boiling 76.

Boiling.

The third term [$\rho Q_b h_v$] in equation (1) relates to heat that goes into converting the water in liquid saline to water vapor, and is represented as 74 in FIG. 2, where:

$Q_b$=Flow rate of saline that boils (cm$^3$/sec); and $h_v$=Heat of vaporization of saline (approximately 2,000 watt-sec/gm).

A flow rate of only 1 cc/min will absorb a significant amount of heat if it is completely boiled, or about $\rho Q_b h_v=(1)(1/60)(2,000)=33.3$ watts. The heat needed to warm this flow rate from body temperature to 100° C. is much less, or $\rho c_p Q_1 \Delta T=(1)(4.1)(1/60)(100-37)=4.3$ watts. In other words, the most significant factor contributing to heat transfer from a wet electrode device can be fractional boiling. The present invention recognizes this fact and exploits it.

Fractional boiling can be described by equation (3) below:

$$Q_1 = \frac{\{P - \Delta T/R\}}{\{\rho c_p \Delta T + \rho h_v Q_b / Q_1\}} \quad (3)$$

If the ratio of $Q_b/Q_1$ is 0.50 this is the 50% boiling line 78 shown in FIG. 2. If the ratio is 1.0 this is the 100% boiling line 80 shown in FIG. 2.

As indicated previously in the specification, using a fluid to couple energy to tissue inhibits such undesirable effects as sticking, desiccation, smoke production and char formation, and that one key factor is inhibiting tissue desiccation, which occur if the tissue temperature exceeds 100° C. and all the intracellular water boils away, leaving the tissue extremely dry and much less electrically conductive.

As shown in FIG. 2, one control strategy or mechanism which can be employed for the electrosurgical device 5 is to adjust the power P and flow rate Q such that the power P used at a corresponding flow rate Q is equal to or less than the power P required to boil 100% of the fluid and does not exceed the power P required to boil 100% of the fluid. In other words, this control strategy targets using the electrosurgical device 5 in the regions of FIG. 2 identified as T<100° C. and T=100° C., and includes the 100% boiling line 80. Stated another way, this control strategy targets not using the electrosurgical device 5 only in the region of FIG. 2 identified as T>>100° C.

Another control strategy that can be used for the electrosurgical device 5 is to operate the device 5 in the region T<100° C., but at high enough temperature to shrink tissue containing Type I collagen (e.g., walls of blood vessels, bronchi, bile ducts, etc.), which shrinks when exposed to about 85° C. for an exposure time of 0.01 seconds, or when exposed to about 65° C. for an exposure time of 15 minutes. An exemplary target temperature/time for tissue shrinkage is about 75° C. with an exposure time of about 1 second. As discussed herein, a determination of the high end of the scale (i.e., when the fluid reaches 100° C.) can be made by the phase change in the fluid from liquid to vapor. However, a determination at the low end of the scale (e.g., when the fluid reaches, for example, 75° C. for 1 second) requires a different mechanism as the temperature of the fluid is below the boiling temperature and no such phase change is apparent. In order to determine when the fluid reaches a temperature that will facilitate tissue shrinkage, for example 75° C., a thermochromic material, such as a thermochromic dye (e.g., leuco dye), may be added to the fluid. The dye can be formulated to provide a first predetermined color to the fluid at temperatures below a threshold temperature, such as 75° C., then, upon heating above 75° C., the dye provides a second color, such as clear, thus turning the fluid clear (i.e. no color or reduction in color). This color change may be gradual, incremental, or instant. Thus, a change in the color of the fluid, from a first color to a second color (or lack thereof) provides a visual indication to the user of the electrosurgical device 5 as to when a threshold fluid temperature below boiling has been achieved. Thermochromic dyes are available, for example, from Color Change Corporation, 1740 Cortland Court, Unit A, Addison, Ill. 60101.

It is also noted that the above mechanism (i.e., a change in the color of the fluid due to a dye) may also be used to detect when the fluid reaches a temperature which will facilitate tissue necrosis; this generally varies from about 60° C. for an exposure time of 0.01 seconds and decreasing to about 45° C. for an exposure time of 15 minutes. An exemplary target temperature/time for tissue necrosis is about 55° C. for an exposure time of about 1 second.

In order to reduce coagulation time, use of the electrosurgical device 5 in the region T=100° C. of FIG. 2 is preferable to use of the electrosurgical device 5 in the region T<100° C. Consequently, as shown in FIG. 2, another control strategy which may be employed for the electrosurgical device 5 is to adjust the power P and flow rate Q such that the power P used at a corresponding flow rate Q is equal to or more than the power P required to initiate boiling of the fluid, but still less than the power P required to boil 100% of the fluid. In other words, this control strategy targets using the electrosurgical device 5 in the region of FIG. 2 identified as T=100° C., and includes the lines of the onset of boiling 76 and 100% boiling line 80. Stated another way, this control strategy targets use using the electrosurgical device 5 on or between the lines of the onset of boiling 76 and 100% boiling line 80, and not using the electrosurgical device 5 in the regions of FIG. 2 identified as T<100° C. and T>>100° C.

For consistent tissue effect, it is desirable to control the saline flow rate so that it is always on a "line of constant % boiling" as, for example, the line of the onset of boiling 76 or the 100% boiling line 80 or any line of constant % boiling located in between (e.g. 50% boiling line 78) as shown in FIG. 2. Consequently, another control strategy that can be used for the electrosurgical device 5 is to adjust power P and flow rate Q such that the power P used at a corresponding flow rate Q targets a line of constant % boiling.

It should be noted, from the preceding equations, that the slope of any line of constant % boiling is known. For example, for the line of the onset of boiling 76, the slope of the line is given by $(\rho c_p \Delta T)$, while the slope of the 100% boiling line 80 is given by $1/(\rho c_p \Delta T + \rho h_v)$. As for the 50% boiling line 78, for example, the slope is given by $1/(\rho c_p \Delta T + \rho h_v 0.5)$.

If, upon application of the electrosurgical device 5 to the tissue, boiling of the fluid is not detected, such indicates that the temperature is less than 100° C. as indicated in the area of FIG. 2, and the flow rate Q must be decreased to initiate boiling. The flow rate Q may then decreased until boiling of the fluid is first detected, at which time the line of the onset of boiling 76 is transgressed and the point of transgression on the line 76 is determined. From the determination of a point on the line of the onset of boiling 76 for a particular power P and flow rate Q, and the known slope of the line 76 as outlined above (i.e. $1/\rho c_p \Delta T$), it is also possible to determine the heat conducted to adjacent tissue 70.

Conversely, if upon application of the electrosurgical device 5 to the tissue, boiling of the fluid is detected, such indicates that the temperature is approximately equal to 100° C. as indicated in the areas of FIG. 2, and the flow rate Q must be increased to reduce boiling until boiling stops, at which time the line of the onset of boiling 76 is transgressed and the point of transgression on the line 76 determined. As with above, from the determination of a point on the line of the onset of boiling 76 for a particular power P and flow rate Q, and the known slope of the line 76, it is also possible to determine the heat conducted to adjacent tissue 70.

With regards to the detection of boiling of the fluid, such may be physically detected by the user (e.g. visually by the naked eye) of the electrosurgical device 5 in the form of either bubbles or steam evolving from the fluid coupling at the electrode/tissue interface. Alternatively, such a phase change (i.e. from liquid to vapor or vice-versa) may be measured by a sensor which preferably senses either an absolute change (e.g. existence or non-existence of boiling with binary response such as yes or no) or a change in a physical quantity or intensity and converts the change into a useful input signal for an information-gathering system. For example, the phase change associated with the onset of boiling may be detected by a pressure sensor, such as a pressure transducer, located on the electrosurgical device 5. Alternatively, the phase change associated with the onset of boiling may be detected by a temperature sensor, such as a thermistor or thermocouple, located on the electrosurgical device 5, such as adjacent to the electrode. Also alternatively, the phase change associated with the onset of boiling may be detected by a change in the electric properties of the fluid itself. For example, a change in the electrical resistance of the fluid may be detected by an ohm meter; a change in the amperage may be measured by an amp meter; as change in the voltage may be detected by a volt meter; and a change in the power may be determined by a power meter.

Figure 3:
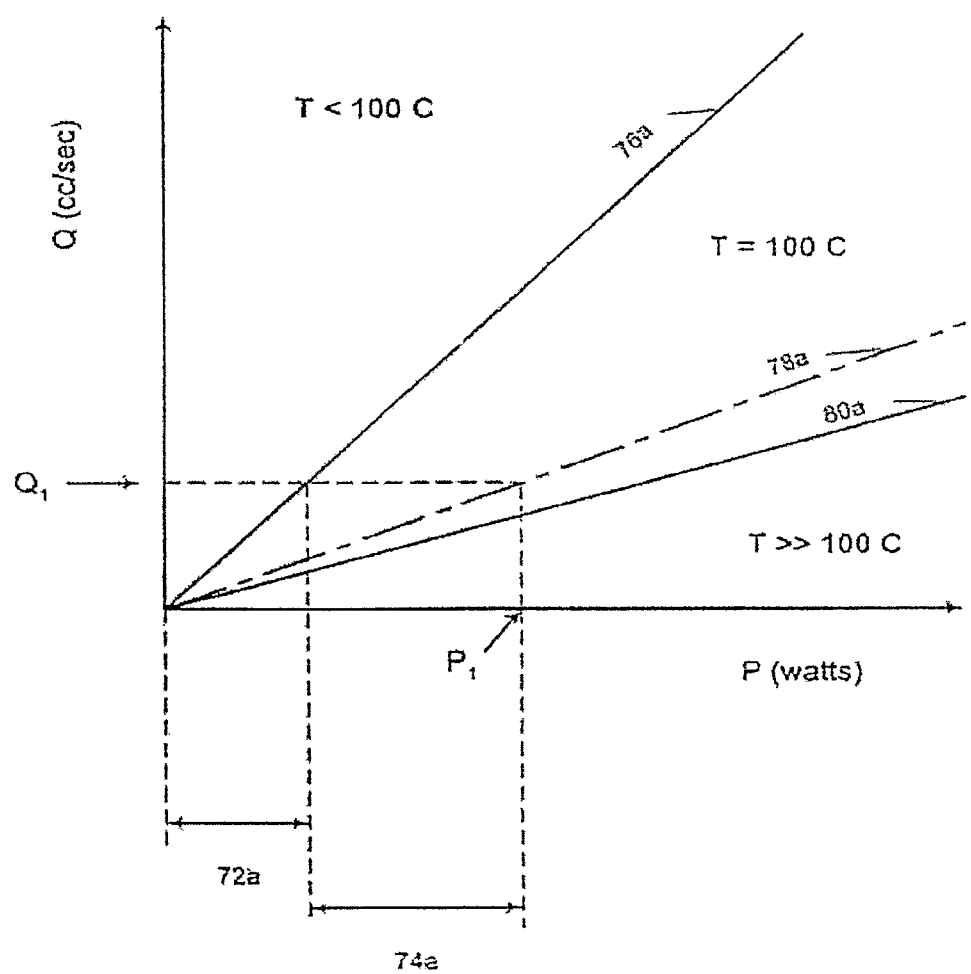
FIG. 3 is schematic graph that describes the relationship between RF power to tissue (P), flow rate of saline (Q), and tissue temperature (T) when heat conduction to adjacent tissue is neglected.

Yet another control strategy which may be employed for the electrosurgical device 5 is to eliminate the heat conduction term of equation (1) (i.e. $\Delta T/R$). Since the amount of heat conducted away to adjacent tissue can be difficult to precisely predict, as it may vary, for example, by tissue type, it may be preferable, from a control point of view, to assume the worst case situation of zero heat conduction, and provide enough saline so that if necessary, all the RF power could be used to heat up and boil the saline, thus providing that the peak tissue temperature will not go over 100° C. a significant amount. This situation is shown in the schematic graph of FIG. 3.

Stated another way, if the heat conducted to adjacent tissue 70 is overestimated, the power P required to intersect the 100% boiling line 80 will, in turn, be overestimated and the 100% boiling line 80 will be transgressed into the T>>100° C. region of FIG. 2, which is undesirable as established above. Thus, assuming the worse case situation of zero heat conduction provides a "safety factor" to avoid transgressing the 100% boiling line 80. Assuming heat conduction to adjacent tissue 70 to be zero also provides the advantage of eliminating the only term from equation (1) which is tissue dependent, i.e., depends on tissue type. Thus, provided ρ, $c_p$, ΔT, and $h_v$ are known as indicated above, the equation of the line for any line of constant % boiling is known. Thus, for example, the 98% boiling line, 80% boiling line, etc. can be determined in response to a corresponding input from the selection switch 12. In order to promote flexibility, it should be understood that the input from the selection switch preferably may comprise any percentage of boiling. Preferably the percentage of boiling may be selected in single percent increments (i.e. 100%, 99%, 98%, etc.).

Upon determination of the line of the onset of boiling 76, the 100% boiling line 80 or any line of constant % boiling there between, it is generally desirable to control the flow rate Q so that it is always on a particular line of constant % boiling for consistent tissue effect. In such a situation, the flow rate controller 11 will adjust the flow rate Q of the fluid 24 to reflect changes in power P provided by the generator 6, as discussed in greater detail below. For such a use the flow rate controller 11 may be set in a line of constant boiling mode, upon which the % boiling is then correspondingly selected.

As indicated above, it is desirable to control the saline flow rate Q so that it is always on a line of constant % boiling for consistent tissue effect. However, the preferred line of constant % boiling may vary based on the type of electrosurgical device 5. For example, if with use of the device 5, shunting through saline is not an issue, then it can be preferable to operate close to or directly on, but not over the line of the onset of boiling, such as 76a in FIG. 3. This preferably keeps tissue as hot as possible without causing desiccation. Alternatively, if with use of the device 5 shunting of electrical energy (e.g. from one jaw to an opposing jaw of certain copative bipolar devices) through excess saline is an issue, then it can be preferable to operate along a line of constant boiling, such as line 78a in FIG. 3, the 50% line. This simple proportional control will have the flow rate determined by equation (4), where K is the proportionality constant:

$$Q_1 = K \times P \quad (4)$$

In essence, when power P goes up, the flow rate Q will be proportionately increased. Conversely, when power P goes down, the flow rate Q will be proportionately decreased.

The proportionality constant K is primarily dependent on the fraction of saline that boils, as shown in equation (5), which is equation (3) solved for K after eliminating P using equation (4), and neglecting the conduction term (ΔT/R):

$$K = \frac{1}{\{\rho c_p \Delta T + \rho h_v Q_b / Q_1\}} \quad (5)$$

Thus, the present invention provides a method of controlling boiling of fluid, such as a conductive fluid, at the tissue/electrode interface. In a preferred embodiment, this provides a method of treating tissue without use of tissue sensors, such as temperature or impedance sensors. Preferably, the invention can control boiling of conductive fluid at the tissue/electrode interface and thereby control tissue temperature without the use of feedback loops.

In describing the control strategy of the present invention described thus far, focus has been drawn to a steady state condition. However, the heat required to warm the tissue to the peak temperature (T) may be incorporated into equation (1) as follows:

$$P = \Delta T/R + \rho c_p Q_1 \Delta T + \rho Q_b h_v + \rho c_p V \Delta T/\Delta t \quad (6)$$

where $\rho c_p V \Delta T/\Delta t$ represents the heat required to warm the tissue to the peak temperature (T) 68 and where:
 ρ=Density of the saline fluid that gets hot but does not boil (approximately 1.0 gm/cm$^3$);
 $c_p$=Specific heat of the saline (approximately 4.1 watt-sec/gm-° C.);
 V=Volume of treated tissue
 ΔT=(T−T$_\infty$) the difference in temperature between the peak tissue temperature (T) and the normal temperature (T$_\infty$) of the body tissue (° C.). Normal temperature of the body tissue is generally 37° C.; and
 Δt=(t−t$_\infty$) the difference in time to achieve peak tissue temperature (T) and the normal temperature (T$_\infty$) of the body tissue (° C.).

Figure 4:
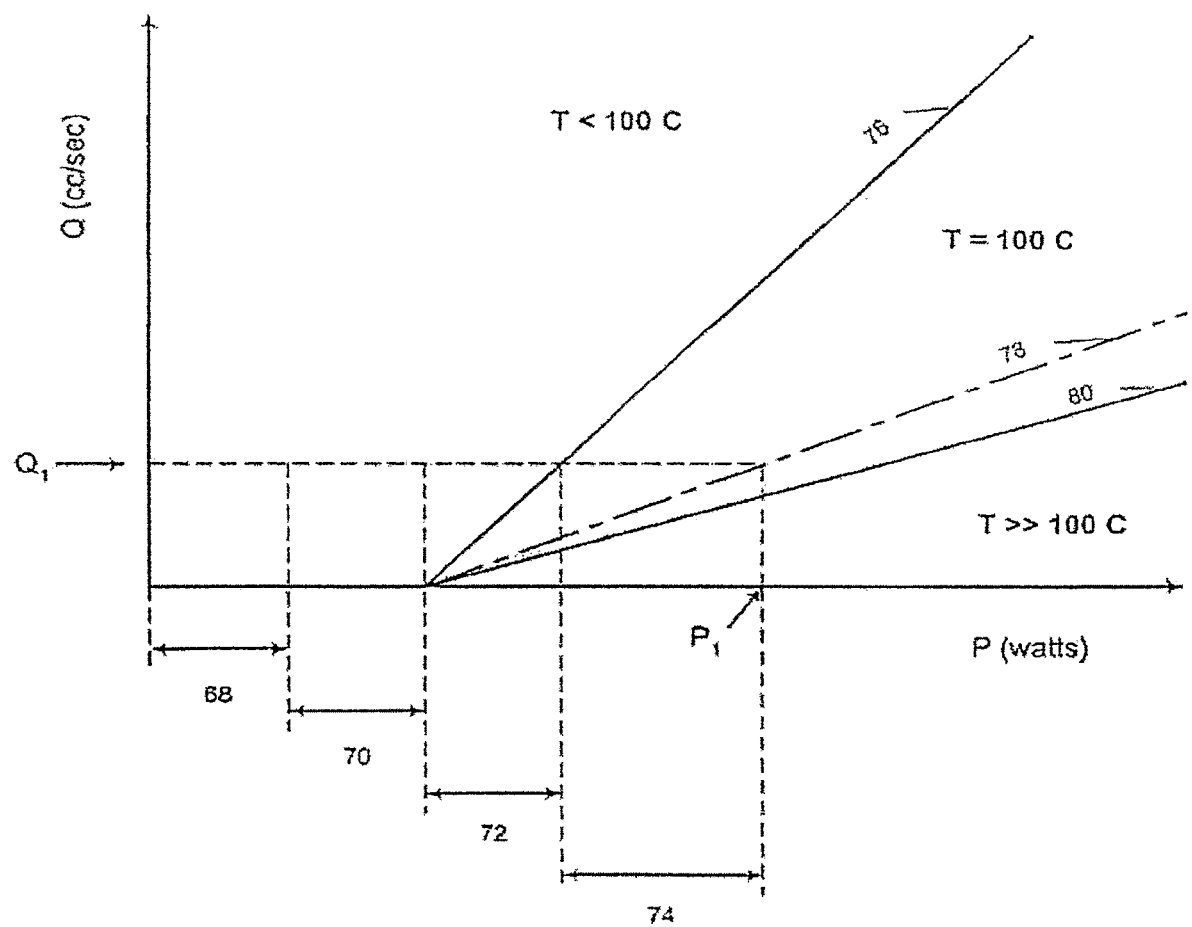
FIG. 4 is a schematic graph that describes the relationship between RF power to tissue (P), flow rate of saline (Q), and tissue temperature (T) when the heat required to warm the tissue to the peak temperature (T) 68 is considered.

The inclusion of the heat required to warm the tissue to the peak temperature (T) in the control strategy is graphically represented at 68 in FIG. 4. With respect to the control strategy, the effects of the heat required to warm the tissue to the peak temperature (T) 68 should be taken into account before flow rate Q adjustment being undertaken to detect the location of the line of onset of boiling 76. In other words, the flow rate Q should not be decreased in response to a lack of boiling before at least a quasi-steady state has been achieved as the location of the line of onset of boiling 76 will continue to move during the transitory period. Otherwise, if the flow rate Q is decreased during the transitory period, it may be possible to decrease the flow Q to a point past the line of onset of boiling 76 and continue past the 100% boiling line 80 which is undesirable. In other words, as temperature (T) is approached the heat 68 diminishes towards zero such that the lines of constant boiling shift to the left towards the Y-axis.

Figure 5:
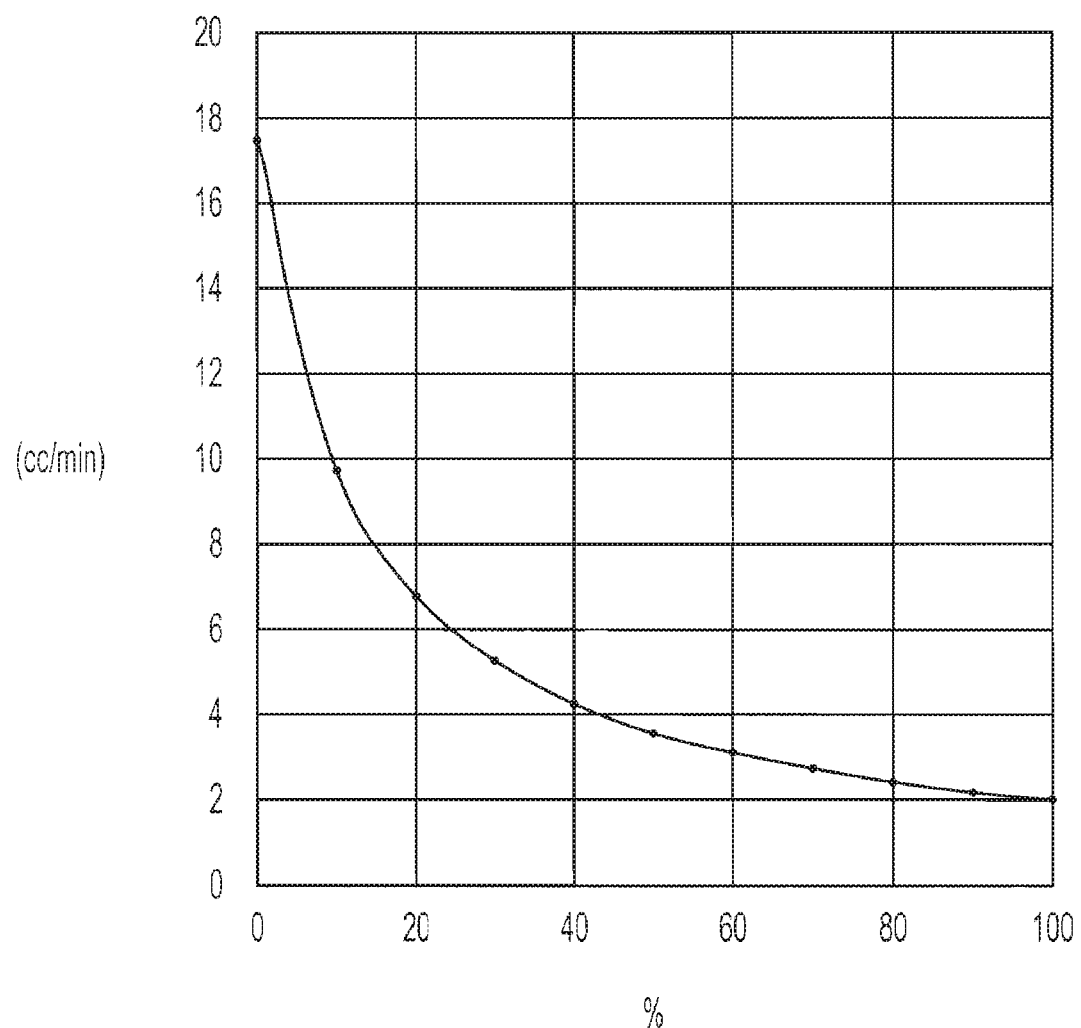
FIG. 5 is a graph showing the relationship of percentage saline boiling and saline flow rate (cc/min) for an exemplary RF generator output of 75 watts.

FIG. 5 is an exemplary graph of flow rate Q versus % boiling for a situation where the RF power P is 75 watts. The percent boiling % is represented on the X-axis, and the saline flow rate Q (cc/min) is represented on the Y-axis. According to this example, at 100% boiling the most desirable predetermined saline flow rate Q is 2 cc/min. Also according to this example, flow rate Q versus % boiling at the remaining points of the graft illustrates a non-linear relationship as follows:

TABLE 1

| % Boiling and Flow Rate Q (cc/min) at RF Power P of 75 watts | |
|---|---|
| 0% | 17.4 |
| 10% | 9.8 |
| 20% | 6.8 |
| 30% | 5.2 |
| 40% | 4.3 |
| 50% | 3.6 |
| 60% | 3.1 |
| 70% | 2.7 |
| 80% | 2.4 |
| 90% | 2.2 |
| 100% | 2.0 |

Typical RF generators used in the field have a power selector switch to 300 watts of power, and on occasion some have been found to be selectable up to 400 watts of power. In conformance with the above methodology, at 0% boiling with a corresponding power of 300 watts, the calculated flow rate Q is 69.7 cc/min and with a corresponding power of 400 watts the calculated flow rate Q is 92.9 cc/min. Thus, when used with typical RF generators in the field, a fluid flow rate Q of about 100 cc/min or less with the present invention is expected to suffice for the vast majority of applications.

Figure 6:
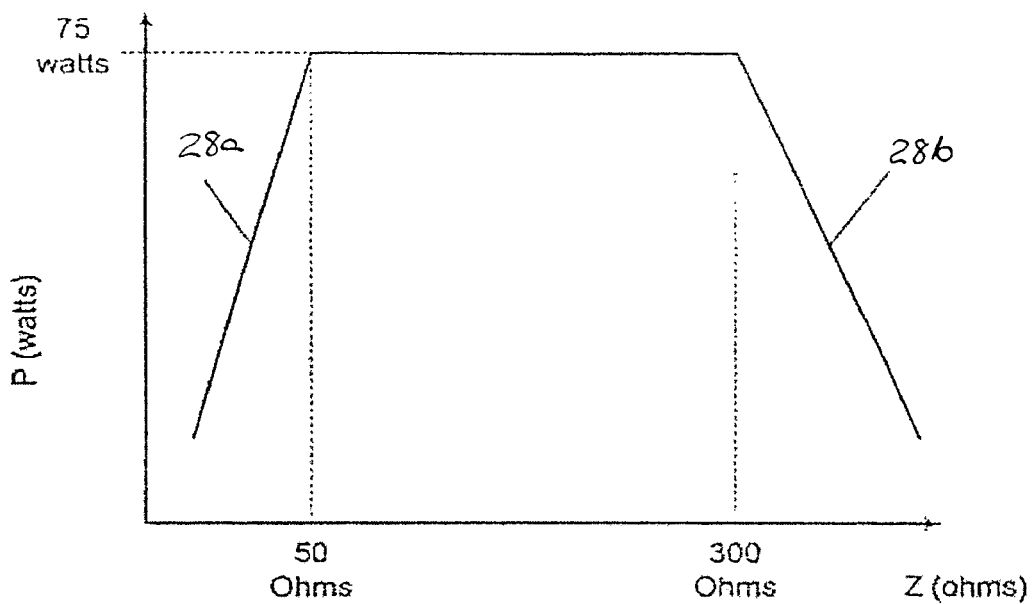
FIG. 6 is a schematic graph that describes the relationship of load impedance (Z, in ohms) and generator output power (P, in watts), for an exemplary generator output of 75 watts in a bipolar mode.

As discussed herein, RF energy delivery to tissue can be unpredictable and vary with time, even though the generator has been "set" to a fixed wattage. The schematic graph of FIG. 6 shows the general trends of the output curve of a typical general-purpose generator, with the output power changing as load (tissue plus cables) impedance Z changes. Load impedance Z (in ohms) is represented on the X-axis, and generator output power P (in watts) is represented on the Y-axis. In the illustrated embodiment, the electrosurgical power (RF) is set to 75 watts in a bipolar mode. As shown in the figure, the power will remain constant as it was set as long as the impedance Z stays between two cut-offs, low and high, of impedance, that is, for example, between 50 ohms and 300 ohms in the illustrated embodiment. Below load impedance Z of 50 ohms, the power P will decrease, as shown by the low impedance ramp 28a. Above load impedance Z of 300 ohms, the power P will decrease, as shown by the high impedance ramp 28b. Of particular interest to saline-enhanced electrosurgery is the low impedance cut-off (low impedance ramp 28a), where power starts to ramp down as impedance Z drops further. This change in output is invisible to the user of the generator and not evident when the generator is in use, such as in an operating room.

Figure 7:
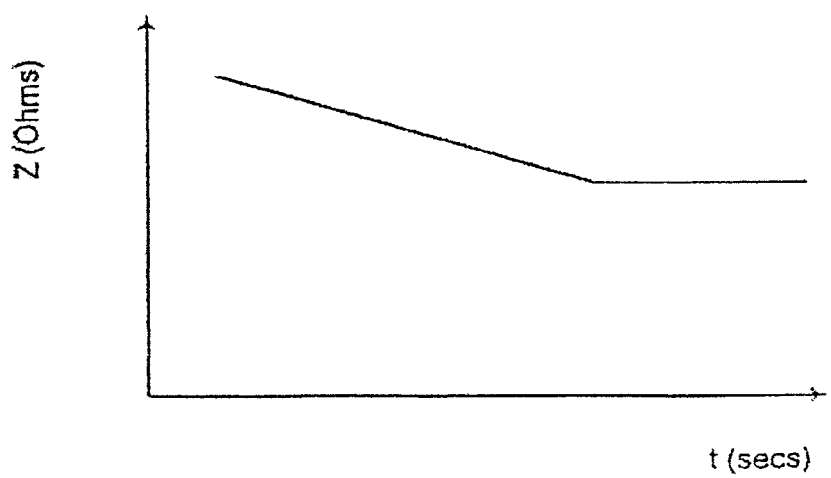
FIG. 7 is a schematic graph that describes the relationship of time (t, in seconds) and tissue impedance (Z, in ohms) after RF activation.

FIG. 7 shows the general trend of how tissue impedance generally changes with time for saline-enhanced electrosurgery. As tissue heats up, the temperature coefficient of the tissue and saline in the cells is such that the tissue impedance decreases until a steady-state temperature is reached upon which time the impedance remains constant. Thus, as tissue heats up, the load impedance Z decreases, potentially approaching the impedance Z cut-off of 50 ohms. If tissue is sufficiently heated, such that the low impedance cut-off is passed, the power P decreases along the lines of the low impedance ramp 28a of FIG. 6.

Combining the effects shown in FIG. 6 and FIG. 7, it becomes clear that when using a general-purpose generator set to a "fixed" power, the actual power delivered can change dramatically over time as tissue heats up and impedance drops. Looking at FIG. 6, if the impedance Z drops from 100 to 75 ohms over time, the power output would not change because the curve is "flat" in that region of impedances. If, however, the impedance Z drops from 75 to 30 ohms one would transgress the low impedance cut-off and "turn the corner" onto the low impedance ramp 28a portion of the curve and the power output would decrease dramatically.

According to one exemplary embodiment of the invention, the control device, such as flow rate controller 11, receives a signal indicating the drop in actual power delivered to the tissue and adjusts the flow rate Q of saline to maintain the tissue/electrode interface at a desired temperature. In a preferred embodiment, the drop in actual power P delivered is sensed by the power measurement device 8 (shown in FIG. 1), and the flow rate Q of saline is decreased by the flow rate controller 11 (also shown in FIG. 1). Preferably, this reduction in saline flow rate Q allows the tissue temperature to stay as hot as possible without desiccation. If the control device was not in operation and the flow rate Q allowed to remain higher, the tissue would be over-cooled at the lower power input. This would result in decreasing the temperature of the tissue at the treatment site.

The flow rate controller 11 of FIG. 1 can be a simple "hard-wired" analog or digital device that requires no programming by the user or the manufacturer. The flow rate controller 11 can alternatively include a processor, with or without a storage medium, in which the determination procedure is performed by software, hardware, or a combination thereof. In another embodiment, the flow rate controller 11 can include semi-programmable hardware configured, for example, using a hardware descriptive language, such as Verilog. In another embodiment, the flow rate controller 11 of FIG. 1 is a computer, microprocessor-driven controller with software embedded. In yet another embodiment, the flow rate controller 11 can include additional features, such as a delay mechanism, such as a timer, to automatically keep the saline flow on for several seconds after the RF is turned off to provide a post-coagulation cooling of the tissue or "quench," which can increase the strength of the tissue seal. Also, in another embodiment, the flow rate controller 11 can include a delay mechanism, such as a timer, to automatically turn on the saline flow several seconds before the RF is turned on to inhibit the possibility of undesirable effects as sticking, desiccation, smoke production and char formation. Also in another embodiment, the flow rate controller 11 can include a low level flow standby mechanism, such as a valve, which continues the saline flow at a standby flow level (which prevents the flow rate from going to zero when the RF power is turned off) below the surgical flow level ordinarily encountered during use of the electrosurgical device 5.

An exemplary electrosurgical device of the present invention which may be used in conjunction with the system of the present invention is shown at reference character 5a in FIG. 9, and more particularly in FIGS. 9-13. While various electrosurgical devices of the present invention are described with reference to use with the remainder of the system of the invention, it should be understood that the description of the combination is for purposes of illustrating the remainder of the system of the invention only. Consequently, it should be understood that the electrosurgical devices of the present invention can be used alone, or in conjuction with the remainder of the system of the invention, or that a wide variety of electrosurgical devices can be used in connection with the remainder of the system of the invention. The electrosurgical devices disclosed herein are preferably further configured for both open and laparoscopic surgery. For laparoscopic surgery, the devices are preferably configured to fit through either a 5 mm or 12 mm trocar cannula.

Figure 8:
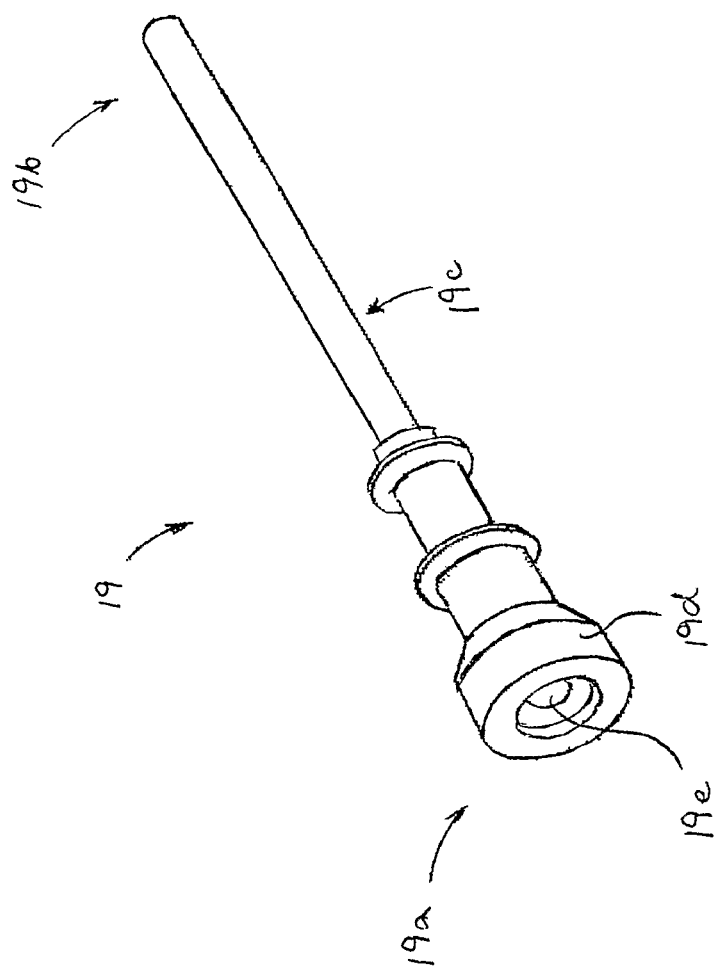
FIG. 8 is a schematic perspective view of a cannula which may be used with an electrosurgical device according to the present invention.

As shown in FIG. 8, electrosurgical device 5a may be used in conjunction with a cannula as illustrated at reference character 19, during laparoscopic surgery such as, for example, a laparoscopic cholecystectomy. Cannula 19 comprises a proximal portion 19a separated from a distal portion 19b by an elongated rigid shaft portion 19c. Proximal portion 19a of cannula 19 preferably comprises a head portion 19d connected to rigid shaft portion 19e, preferably by threaded engagement. Most importantly, cannula 19 has a working channel 19e which extends through head portion 19d and shaft portion 19c from proximal portion 19a to distal portion 19b of cannula 19. In one particular embodiment, during insertion into cannula 19, electrosurgical device 5a is configured to enter the proximal end of working channel 19e, move along the channel 19e distally, and then be extended from the distal end of the working channel 19e. In the same embodiment, during retraction from cannula 19, electrosurgical device 5a is configured to enter the distal end of working channel 19e, move along the channel 19e proximally, and then be removed from the proximal end of working channel 19e.

Referring back to FIG. 9, as shown electrosurgical device 5a comprises a monopolar electrosurgical device. As shown in FIG. 9, electrosurgical device 5a preferably includes a rigid, self-supporting, hollow shaft 17, a proximal handle comprising mating handle portions 20a, 20b and a tip portion as shown by circle 45. Handle 20a, 20b is preferably made of a sterilizable, rigid, non-conductive material, such as a polymer (e.g. polycarbonate). As shown in FIGS. 10 and 11, tip portion 45 includes a contact element preferably comprising an electrode 25 which, as shown, comprises a solid ball having a smooth, uninterrupted surface. Also as shown in FIGS. 10 and 11, tip portion 45 also comprises a sleeve 82 having a uniform diameter along its longitudinal length, a spring 88 and a distal portion of shaft 17. As shown in FIG. 10, the longitudinal axis 31 of the tip portion 45 may be configured at an angle A relative to the longitudinal axis 29 of the proximal remainder of shaft 17. Preferably the longitudinal axis 31 of the tip portion 45 is configured at an angle A of about 5 degrees to 90 degrees relative to the longitudinal axis 29 of the proximal remainder of shaft 17. More preferably, the longitudinal axis 31 of tip portion 45 is configured at an angle A of about 8 degrees to 45 degrees relative to the longitudinal axis of 29 of the proximal remainder of shaft 17.

As shown in FIGS. 10 and 11, for electrosurgical device 5a, electrode 25 generally has a spherical shape with a corresponding spherical surface, a portion 42 of which is exposed to tissue 32 (less than 180 degrees and more specifically about 100-120 degrees) at the distal end of device 5a. When electrode 25 is in the form of a sphere, the sphere may have any suitable diameter. However, the sphere preferably has a diameter in the range between and including about 1 mm to about 7 mm. Although, it has been found that when a sphere is larger than about 4 mm and less than about 2 mm tissue treatment can be adversely effected (particularly tissue treatment time) due to an electrode surface that is respectively either to large or to small. Thus, more preferably the sphere has a diameter in the range between and including about 2.5 mm to about 3.5 mm. Even more preferably, the sphere has a diameter of about 3 mm.

It is understood that shapes other than a sphere can be used for the contact element. Examples of such shapes include oblong or elongated shapes. However, as shown in FIGS. 10 and 11, preferably a distal end surface of electrosurgical device 5a always provides a blunt, rounded surface which is non-pointed and non-sharp as shown by electrode 25.

As shown in FIGS. 10 and 11, electrode 25, is preferably located in a cavity 81 of a cylindrical sleeve 82 providing a receptacle for electrode 25. Among other things, sleeve 82 guides movement of the electrode 25. Among other things, sleeve 82 also functions as a housing for retaining the electrode 25.

Also as shown in FIG. 11, a portion 44 of the electrode 25, is retained within the cavity 81 while another portion 43 extends distally through the fluid outlet opening provided by circular fluid exit hole 26. Also as shown, sleeve 82 is connected, preferably via welding with silver solder, to the distal end 53 of shaft 17. For device 5a, electrode 25, sleeve 82 and shaft 17 preferably comprise, and more preferably at least essentially consists of, an electrically conductive metal, which is also preferably non-corrosive; and more particularly stainless steel. Other metals include copper, titanium, gold, silver and platinum. Furthermore, shaft 17 preferably comprises thick walled stainless steel hypo-tubing.

As for cavity 81, the internal diameter of cavity 81 surrounding the electrode 25, is preferably slightly larger than the diameter of the sphere, typically by about 0.25 mm. This permits the sphere to freely rotate within the cavity 81. Consequently, cavity 81 of sleeve 82 also preferably has a diameter in the range of about 1 mm to about 7 mm.

As best shown in FIGS. 11 and 12, in order to retain the electrode 25, within the cavity 81 of sleeve 82, preferably the fluid exit hole 26, which ultimately provides a fluid outlet opening, of cavity 81 at its distal end 83 comprises a distal pinched region 86 which is reduced to a size smaller than the diameter of the electrode 25, to inhibit escape of the electrode 25 from the sleeve 82. More preferably, the fluid exit hole 26 comprises a diameter smaller than the diameter of the electrode 25.

As best shown in FIG. 12, the fluid exit hole 26 preferably has a diameter smaller than the diameter of the electrode 25, which can be accomplished by at least one crimp 84 located at the distal end 83 of the sleeve 82 which is directed towards the interior of the sleeve 82 and distal to the portion 44 of the electrode 25 confined in cavity 81. Where one crimp 84 is employed, the crimp 84 may comprise a single continuous circular rim pattern. In this manner, the contact element portion extending distally through the fluid outlet opening (i.e. electrode portion 43) provided by fluid exit hole 26 has a complementary shape to the fluid outlet opening provided by fluid exit hole 26, here both circular.

However, as shown in FIG. 12, the crimp 84 may also comprise a discontinuous circular rim pattern where the crimp 84 is interrupted by at least one rectangular hole slot 85 formed at the distal end 83 of the sleeve 82. Thus, the fluid outlet opening located at the distal end of the device 5a may comprise a first portion (e.g. the circular fluid exit hole portion 26) and a second portion (e.g. the slot fluid exit hole portion 85). As shown in FIG. 12, preferably, crimp 84 comprises at least four crimp sections forming a circular rim pattern separated by four discrete slots 85 radially located there between at 90 degrees relative to one another and equally positioned around the fluid outlet opening first portion. Slots 85 are preferably used to provide a fluid outlet opening or exit adjacent the electrode 25, when the electrode 25 is fully seated (as discussed below) and/or when the electrode 25 is not in use (i.e. not electrically charged) to keep surface portion 42 of the electrode surface of electrode 25 wet. Preferably, slots 85 have a width in the range between and including about 0.1 mm to 1 mm, and more preferably have a width in the range between and including about 0.2 mm to 0.3 mm. As for length, slots 85 preferably have a length in the range between and including about 0.1 mm to 1 mm, and more preferably have a length in the range between and including about 0.4 mm to 0.6 mm.

As shown in FIG. 12, the contact element portion extending distally through the fluid outlet opening (i.e. electrode portion 43) extends distally through the fluid outlet opening first portion (e.g. the circular fluid exit hole portion 26) and does not extend distally through the fluid outlet opening second portion (e.g. the slot fluid exit hole portion 85). In this manner an edge 91 of the slot 85 remains exposed to tissue 32 to provide a tissue separating edge as discussed below.

It should be understood that the particular geometry of fluid outlet opening provided by the fluid exit hole located at the distal end of the device 5a to the electrode, is not critical to the invention, and all that is required is the presence of a fluid exit hole which provides fluid 24 as required. For example, the fluid exit hole 26 may comprise an oval shape while electrode 25, comprises a different shape, such as a round shape.

As shown in FIG. 12, in addition to slot 85 providing a fluid exit, at least one edge 91 of slot 85 may provide a tissue separating edge adjacent a blunt surface (e.g. surface portion 42 of the electrode 25) which may be used for blunt dissection when the electrosurgical device 5a is manipulated, particularly by rotating (e.g. twirling), abrading or impacting. When edge 91 is used in such regard, it is preferred that the edge comprise a sharp edge with a sharp angle which has not been rounded by, for example, a fillet.

Turning to the proximal end of the tip (comprising the electrode 25, spring 88 and sleeve 82) of the device 5a and electrode 25, as shown in FIG. 11, preferably the portion of the sleeve 82 proximal to the electrode 25, also has a proximal pinched region 87 which retains the electrode 25 in the cavity 81 of the sleeve 82 and inhibits escape of the electrode 25 from the cavity 81 of the sleeve 82, such as a diameter smaller than the diameter of the electrode 25.

While distal pinched region 86 and proximal pinched region 87 may be used solely to support the electrode 25, in its position of use, the electrode may be further supported by a compression spring 88 as shown in FIG. 11. The use of spring 88 is preferred to provide a variable length support within the working length of the spring 88 for overcoming manufacturing tolerances (e.g. length) between the fixed supports (i.e. pinched regions 86 and 87) of the sleeve 82. As for maintaining proper location of the spring 88, sleeve 82 also comprises a lumen 89 as shown in FIG. 11 (i.e. the cavity of an elongated hollow structure, such as a tube or tube like structure; typically cylindrical) which, in addition to providing a direct passage for fluid, provides a guide tube for spring 88. Furthermore, the surface portion 60 of electrode 25, which contacts the spring 88 may comprise a flat surface rather than a curvilinear surface to better seat the spring against the electrode 25.

In addition to the above, spring 88 provides a multitude of functions and advantages. For example, the configuration of the distal pinched region 86, proximal pinched region 87 and spring 88 offers the ability to move the electrode 25, distally and proximally within sleeve 82. As shown in FIG. 11, spring 88 is located proximal to the electrode 25 between a first load bearing surface comprising the electrode surface 60 and a second load bearing surface comprising the distal end 53 of shaft 17. In this manner, spring 88 can be configured to provide a decompression force to seat the electrode 25 against the distal pinched region 86, in this case the perimeter edge 92 of crimp 84, prior to use of the electrosurgical device 5a.

Conversely, upon application of the electrode 25, of the device 5a against the surface 22 of tissue 32 with sufficient force to overcome the compression force of the spring 88, spring 88 compresses and the electrode 25 retracts proximally away from distal pinched region 86, in this case perimeter edge 92 of crimp 84, changing the position thereof. In the above manner, the contact element comprising electrode 25 is retractable into the cavity 81 of the housing provided by sleeve 82 upon the application of a proximally directed force against surface 42 of the portion 43 of the electrode 25 extending distally beyond the distal opening 26 located at the distal end 83 of the housing and spring 88 functions as a retraction biasing member.

By making the electrode 25, positionable in the above manner via spring 88, in various embodiments the electrosurgical device 5a can be provided with a damper mechanism which dampens the force of the electrode 25 on tissue 32 being treated.

Furthermore, in various embodiments the electrosurgical device 5a, an electrode 25 which can be positioned as outlined above can comprise a fluid flow rate adjustment mechanism which incrementally increases the area of the fluid exit hole 26 and the corresponding fluid flow rate in response to the incremental proximal retraction of the electrode 25. In such an instance the electrode 25 functions as a valve in regulating flow of the fluid 24 through fluid exit hole 26.

In various embodiments, spring 88 may be used in conjunction with the distal pinched region 86 (e.g. crimp 84 comprising a single continuous circular pattern) to provide a fluid seal between the electrode 25 and the distal pinched region 86 which stops fluid flow from the electrosurgical device 5a. In this manner, the electrosurgical 5a device may be used to provide both a wet electrode and dry electrode (i.e. when the fluid flow is on and off, respectively) with the energy and fluid provided sequentially in addition to simultaneously. The incorporation of a dry electrode function into the device of the current invention may be desirable to provide a mechanism for electrosurgical cutting.

Furthermore, in various embodiments of electrosurgical device 5a, an electrode 25 which can be positioned as outlined above can comprise a declogging mechanism which retracts to provide access for unclogging fluid exit holes, such as fluid exit holes 26 and 85, which may become flow restricted as a result of loose debris (e.g. tissue, blood) becoming lodged therein. For example, when a biasing force, such as from a handheld cleaning device (e.g. brush) or from pushing the distal tip against a hard surface such as a retractor, is applied to surface 42 of electrode 25 which overcomes the compression force of the spring 88 causing the spring 88 to compress and the electrode 25 to retract, the tip of the handheld cleaning device may by extended into the fluid exit hole 26 for cleaning the fluid exit hole 26, perimeter edge 92, slot 85 and edge 91. Stated another way, an electrode 25, which can be positioned as outlined, provides a method for declogging a fluid exit hole by increasing the cross-sectional area of the fluid exit hole to provide access thereto.

Also, in various embodiments of the electrosurgical device 5a, the spring 88 comprises an electrical conductor, particularly when the electrode 25, is retracted to a non-contact position (i.e. not in contact) with the sleeve 82.

In other embodiments, proximal pinched region 87 may comprise one or more crimps similar to distal pinched region 86, such that electrode 25 is retained in sleeve 82 both distally and proximally by crimps. Also, in other embodiments, sleeve 82 may be disposed within shaft 17 rather than being connected to the distal end 53 of shaft 17. Also, in still other embodiments, sleeve 82 may be formed unitarily (i.e. as a single piece or unit) with shaft 17 as a unitary piece.

As best shown in FIGS. 10 and 11, the electrode 25 is retained in the sleeve 82 such that a portion 43 of the electrode 25 extends distally beyond distal end 83 of the sleeve 82. As shown, preferably the surface 42 of this exposed portion 43 of the electrode 25 is blunt and does not comprise any sharp corners. Also, the portion 43 of the electrode 25 which extends distally beyond the distal end 83 of the sleeve 82 is controlled by the shape of the fluid exit hole 26 in sleeve 82 in relation to the shape of the electrode 25. In other words, the portion 43 of the electrode 25 which extends distally beyond the distal end 83 of the sleeve 82 is controlled by the contact of the electrode surface with the edge 92.

As shown in FIGS. 10 and 11, in locations where shaft 17 and sleeve 82 are electrically conductive (for device 5a, preferably shaft 17 and sleeve 82 are completely electrically conductive and do not comprise non-conductive portions), preferably an electrical insulator 90 (i.e. comprising non-conductive or insulating material) preferably surrounds shaft 17 and sleeve 82 along substantially its entire exposed length (e.g. the portion outside the confines of the handle 20), terminating a short distance (e.g. at the proximal onset of the crimp 84 or less than about 3 mm) from distal end 83 of the sleeve 82. Insulator 90 preferably comprises a shrink wrap polymer tubing.

As with the other electrosurgical devices described within, a input fluid line 4b and a power source, preferably comprising generator 6 preferably providing RF power via cable 9, are preferably fluidly and electrically coupled, respectively, to the tip portion 45 of the electrosurgical device 5a.

As indicated above, device 5a comprises a monopolar device. In other words, a first electrode, often referred to as the active electrode, comprises an electrode of the electrosurgical device 5a (e.g. electrode 25) while a second electrode, often referred to as the indifferent or return electrode, comprises a ground pad dispersive electrode located on the patient, typically on the back or other suitable anatomical location. Preferably, both electrodes are electrically coupled to the generator 6 to form an electrical circuit. Preferably the active electrode is coupled to the generator 6 via a wire conductor from insulated wire cable 9 to the outer surface 18 of the shaft 17 within the confines of the handle 20a, 20b, typically through a switch 15a.

In other embodiments, the shaft 17 may be made of an electrical non-conducting material except for a portion at its distal end 53 that comes in contact with sleeve 82. This portion of shaft 17 that contacts the sleeve 82 should be electrically conducting. In this embodiment, the wire conductor from insulated wire cable 9 extends to this electrically conducting portion of shaft 17. In still other embodiments, the shaft 17 may completely comprise a non-conducting material as where the wire conductor from insulated wire cable 9 extends directly to the sleeve 82.

With respect to the fluid coupling, fluid 24 from the fluid source 1 for use with electrosurgical device 5a preferably is communicated from fluid source 1 through a flexible, polyvinylchloride (PVC) outlet fluid line 4a to a flexible, polyvinylchloride (PVC) inlet fluid line 4b connected to the electrosurgical device 5a. The outlet fluid line 4a and the inlet fluid line 4b are preferably connected via a male and female mechanical fastener configuration, preferably comprising a Luer-Lok® connection from Becton, Dickinson and Company. The lumen of the inlet line is then preferably interference fit over the outside diameter of the shaft 17 to provide a press fit seal there between. Additionally an adhesive may be disposed there between to strengthen the seal. Fluid 24 is then communicated down the lumen 23 of the shaft 17 through the lumen 89 and cavity 81 of the sleeve 82 where it is expelled from around and on the exposed surface 42 of the electrode 25. This provides a wet electrode for performing electrosurgery.

As shown in FIG. 13, during use of electrosurgical device 5a, typically a fluid coupling 30 preferably comprising a discrete, localized web and more preferably comprising a triangular shaped web or bead portion providing a film of fluid 24 is provided between the surface 22 of the tissue 32 and electrode 25. When the user of electrosurgical device 5a places the electrode 25 at a tissue treatment site and moves the electrode 25 across the surface 22 of the tissue 32, fluid 24 is expelled around and on the surface 42 of the electrode 25 at the distal end 83 of the sleeve 82 and onto the surface 22 of the tissue 32 via coupling 30. The fluid 24, in addition to providing an electrical coupling between the electrosurgical device 5a and the tissue 32, lubricates the surface 22 of the tissue 32 and facilitates the movement of electrode 25 across the surface 22 of the tissue 32. During movement of the electrode 25, the electrode 25 typically slides across the surface 22 of the tissue 32, but also may rotate as the electrode 25 moves across the surface 22 of the tissue 32. Typically the user of the electrosurgical device 5a slides the electrode across the surface 22 of the tissue 32 back and forth with a painting motion while using the fluid 24 as, among other things, a lubricating coating. Preferably the thickness of the fluid 24 between the distal end surface of the electrode 25 and the surface 22 of the tissue 32 at the outer edge of the coupling 30 is in the range between and including about 0.05 mm to 1.5 mm. More preferably, the fluid 24 between the distal end surface of the electrode 25 and the surface 22 of the tissue 32 at the outer edge of the coupling 30 is in the range between and including about 0.1 mm to 0.3 mm. Also preferably, in certain embodiments, the distal end tip of the electrode 25 contacts the surface 22 of tissue 32 without any fluid 24 in between.

Figure 16:
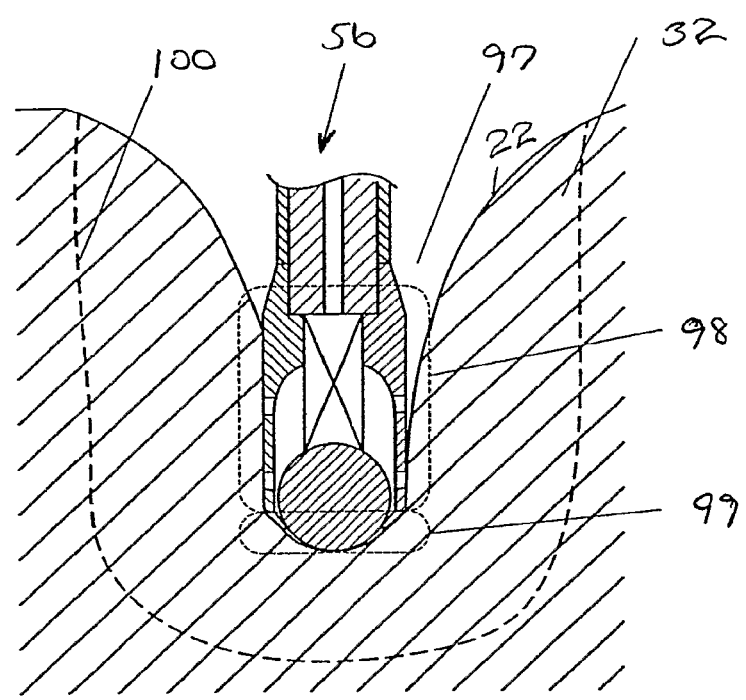
FIG. 16 is a schematic close-up cross-sectional side view of the tip portion of FIG. 14 disposed in a tissue crevice.

Another exemplary electrosurgical device of the present invention which may be used in conjunction with the system of the present invention is shown at reference character 5b in FIGS. 14-16. In this embodiment, electrical insulator 90 preferably terminates proximally to the sleeve 82 where sleeve 82 is connected to the distal end 53 of shaft 17. In certain embodiments where the sleeve 82 is formed unitary with the shaft 17, the electrical insulator 90 preferably terminates proximally to proximal pinched region 87. In this manner, in addition to the spherical surface portion 42 of the electrode 25 and the narrowing surface portion 41, here conical, of the sleeve 82 being used for treating tissue 32 when exposed thereto, a cylindrical surface 40 of a cylindrical portion 39 of the sleeve 82 and a broadening surface portion 47 of broadening portion 54, here both conical, of the sleeve 82 also function as electrode surfaces for treating tissue. Thus, the electrode exposed to tissue 32 now comprises a cylindrical surface portion 40 and a broadening surface portion 47 in addition to the spherical surface portion 42 and the narrowing surface portion 41, with the cylindrical surface portion 40 substantially increasing the surface area of the electrode. As a result, the electrode 25 now also comprises surfaces which are parallel and perpendicular to the longitudinal axis 31 of the tip portion 45, and more particularly sleeve 82, of the electrosurgical device 5b. In the above manner, front end use (e.g. surfaces 41 and 42), sideways use (e.g. surface 40 and 47) or oblique use (e.g. surfaces 40, 41 and 42) of the electrosurgical device 5b is facilitated.

In the above manner, the tip portion 45 now comprises a first tissue treating surface (e.g. distal end spherical surface 42) and a second tissue treating surface (e.g. side surface 40). As discussed above, preferably the first tissue treating surface is configured for blunt dissection while the second tissue treating surface is configured for coagulation. Additionally, tip portion 45 also comprises a third tissue treating surface (e.g. surface 41) located between the first tissue treating surface (e.g. surface 42) and a second tissue treating surface (e.g. surface 40). Furthermore, tip portion 45 also comprises a fourth tissue treating surface (e.g. surface 47) located proximal and adjacent to surface 40.

With device 5a, when the electrode 25, is placed directly in contact with surface 22 of tissue 32, it may be possible for the tissue 32 to occlude fluid flow from the fluid exit holes 26, 85 located at the distal end of the device 5a. Consequently, for device 5b fluid exit holes 93, 94 may be located in the cylindrical side portion 39 of the sleeve 82, either proximal or adjacent to the electrode 25, and either in addition to or as an alternative to fluid exit holes 26, 85.

As shown in FIGS. 14 and 15, at least one fluid exit hole 93 is preferably formed in the cylindrical longitudinal side surface 40 and through the wall of side portion 39 of the sleeve 82 adjacent to electrode 25 when electrode 25 is fully seated. Furthermore, preferably at least one fluid exit hole 94 is formed in the cylindrical side portion 39 of the sleeve 82 proximal to electrode 25 when electrode 25 is fully seated.

Preferably, holes 93, 94 each comprise more than one hole which are equally spaced radially in a circular pattern around the longitudinal axis 31 of the tip portion 45, and more particularly sleeve 82. More preferably, holes 93, 94 each comprise four discrete holes equally spaced 90 degrees around the cylindrical side portion 39 of the sleeve 82. Preferably holes 93, 94 have a diameter in the range between and including about 0.1 mm to 1.0 mm, and more preferably have a length in the range between and including about 0.2 mm to 0.6 mm. Electrode 25 which can be positioned as outlined above can comprise not only a valve for regulating fluid flow from the fluid exit holes, such as fluid exit hole 26, but also comprise a valve which while opening one fluid flow exit simultaneously closes another fluid flow exit. For example, as electrode 25 retracts proximally, fluid exit hole 26 is opened while fluid exit hole 93 is closed. Stated another way, an electrode 25 which can be positioned as outlined above can provide a mechanism for altering the size and/or location of the fluid exit holes during use of the electrosurgical device 5b which may be necessary, for example, to direct fluid to a particular tissue location or balance fluid flow among the fluid exit outlets.

Thus, as shown in FIGS. 14 and 15, surfaces 40, 41 and 47 of the sleeve 82, and surface 42 of electrode 25 are all active electrode surfaces and can provide electrical energy to tissue 32. Portions of this combined electrode surface can be wet by fluid flow from holes 26, 94 or 93, as well as from the hole slots 85 in the crimp 84 adjacent the electrode 25.

The holes 94, 93 in the cylindrical sleeve 82 of the overall electrode surface are intended to assure that fluid 24 is provided to the smooth, less rough, atraumatic sides of the electrode that are used to produce tissue coagulation and hemostasis (e.g. surfaces 40 and 47) rather than blunt dissection (e.g. surfaces 41 and 42). The most distal portion of the device may have a more rough, but also wetted, electrode surface that can blunt dissect as well as coagulate tissue.

The electrode configuration shown in FIGS. 14 and 15 is particularly useful to a surgeon performing a liver resection. Once the outer capsule of the liver is scored with a dry bovie blade along the planned line of resection the distal tip of tip portion 45 is painted back and forth along the line, resulting in coagulation of the liver parenchyma. As the tissue is coagulated under and around the electrode surfaces 40, 41 and 42, the electrode is used to blunt dissect into the coagulated parenchyma, with the edge 91 of the slots 85 around the crimp 84 providing roughness elements that aid in disrupting the tissue 32 and enabling the parting of the tissue 32.

As shown in FIG. 16, the device 5b can be used deeply in a crevice 97 of tissue 32 to blunt dissect the tissue 32 and coagulate it at the same time. Blunt dissection is preferred over sharp dissection, such as with a blade or scissors, since blunt dissection is less likely to tear or damage the larger blood vessels or other vessels. Once identified by blunt dissection, larger vessels can be safely clipped, tied with suture or sealed with some other device. If the larger vessels are not thus first "skeletonized" without being damaged by blunt dissection, they may bleed profusely and require much more time to stop the bleeding. The device can also be used to coagulate first without simultaneous blunt dissection, and then blunt dissect in a separate step.

This technique can also be used on other parenchymal organs such as the pancreas, the kidney, and the lung. In addition, it may also be useful on muscle tissue and subcutaneous fat. Its use can also extend to benign tumors, cysts or other tissue masses found in the urological or gynecological areas. It would also enable the removal of highly vascularized tumors such as hemangiomas.

In FIG. 16 the zone 99 identifies the part of the electrode that has the ability to blunt dissect and coagulate, and the zone 98 identifies the part that is intended primarily for coagulation and hemostasis. The line 100 indicates the depth of the zone of tissue that is coagulated, typically from 3 mm to 5 mm deep.

Figure 17:
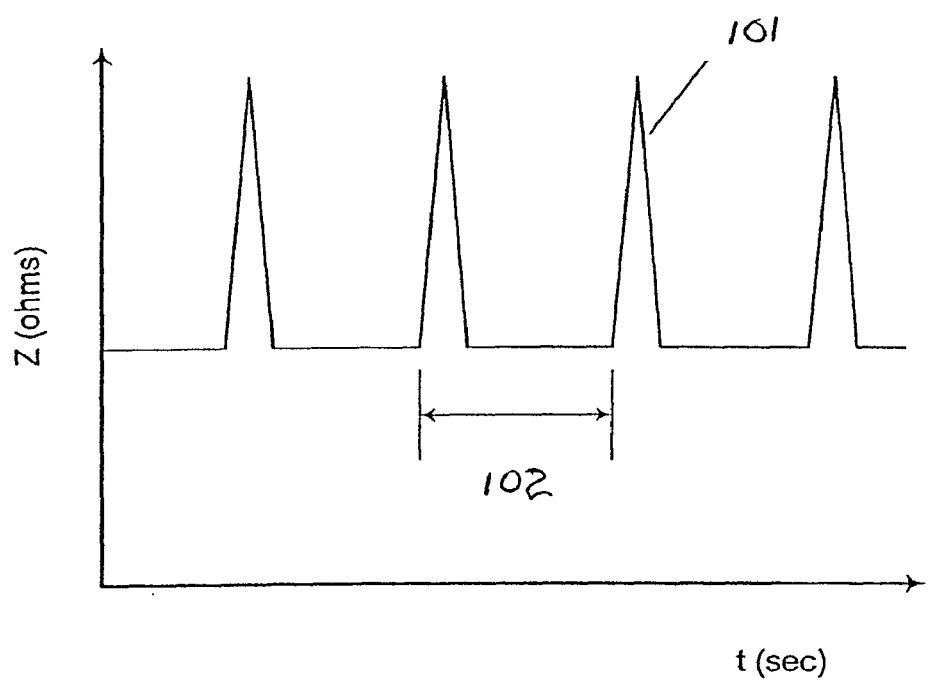
FIG. 17 is a schematic graph of impedance Z versus time t showing changes in impedance represented by impedance spikes.

For the devices disclosed herein, the presence of various fractions of boiling can be visually estimated by the naked eye, or by detecting changes in electrical impedance. FIG. 17 shows a plot of electrical impedance Z versus time t. The impedance spikes 101 shown in FIG. 17 occur at a frequency of about 1 cycle per second and with an amplitude that is on the same order as the baseline impedance. This frequency is shown in FIG. 17 as the interval 102 between successive impedance spikes. Impedance is directly measurable by dividing the voltage by the current as previously described. The use of electrical impedance to detect the onset of tissue dessication when impedance rises dramatically as a result of being heated to the point of smoking and charring, but not to detect the presence of boiling, is described above. As shown in FIG. 17, the impedance Z may change from a level of about 100 ohms with no boiling, to a level of about 400 ohms or more with a large fraction of the conductive fluid boiling. The percentages of boiling shown are exemplary as are the levels of impedance.

Figure 18:
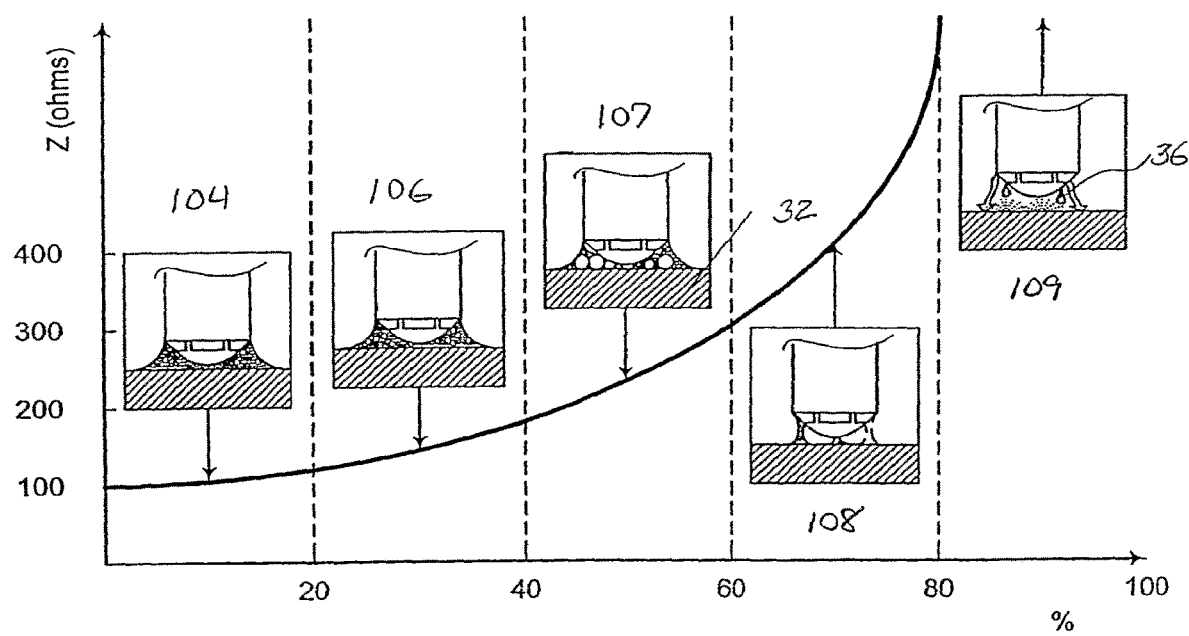
FIG. 18 is a schematic graph of the impedance Z versus boiling of fluid %.

Shown in FIG. 18 is the qualitative nature of the boiling as the % boiling increases, indicated by the small figures for each of five exemplary "regimes" of boiling. In each small figure a portion of the tip of the tip portion 45 of the device 5a is shown in close proximity to tissue 32. As boiling begins in regime 104, there are few small bubbles 37 of vapor in the conductive fluid 24, here saline, of coupling 30. As the percentage of boiling increases at regime 106 there are a larger number of small bubbles 37. As the percentage boiling increases further at regime 107, the bubbles 37 become much larger. At even higher percentage boiling at regime 108 intermittent threads of saline form and are quickly boiled off. Finally, at the highest level of regime 109, drops 36 of saline are instantly boiled upon contacting the hot surface 22 of the tissue 32 and arcing occurs from the metal to the tissue 32.

Figure 19:
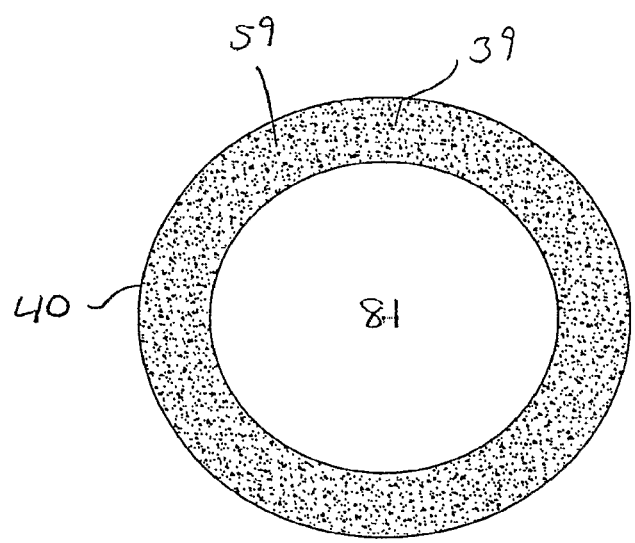
FIG. 19 is schematic close-up cross-sectional view of the sleeve taken along line 19-19 of FIG. 15.

Returning to FIGS. 14 and 15, fluid outlet openings are provided by substantially linear through holes 93, 94 which provide conductive fluid 24 to the treatment site. However, in an alternative embodiment, as shown in FIG. 19, fluid outlet openings in the sleeve 82 may be provided by holes in the form of tortuous and interconnected pathways 59, which are formed in a material pervious to the passage of fluid 24, therethrough, such as a porous material. The discrete, linear through holes 93, 94 may be either supplemented with or replaced by a plurality of tortuous, interconnected pathways 59 formed in the porous material which, among other things, provides porous surfaces 40, 41 and 47 to more evenly distribute fluid flow and provide the conductive fluid 24 to tissue 32 at the treatment site. According to the invention, all or a portion of the sleeve 82 may comprise a material pervious to the passage of fluid 24 therethrough as disclosed herein.

In certain embodiments, the contact element, here electrode 25 may also comprise a material pervious to the passage of fluid 24, therethrough, such as a porous material (e.g. metal, polymer or ceramic) to provide the tortuous pathways 59. In these embodiments, the porous structure of the electrode 25 allows fluid 24 to not only pass around electrode 25 on the outer porous surface 42 to be expelled, but also allows fluid 24 to pass through the electrode 25, to be expelled. According to the invention, all or a portion of the electrodes or any particular electrodes for treating tissue 32 may comprise a material pervious to the passage of fluid 24 therethrough as disclosed herein.

Where the contact element and sleeve provide electrodes for treating tissue and compromise a porous material, preferably the porous material further comprises porous metal. Porous sintered metal is available in many materials (such as, for example, 316L stainless steel, titanium, Ni-Chrome) and shapes (such as cylinders, discs, plugs) from companies such as Porvair, located in Henderson, N.C.

Porous metal components can be formed by a sintered metal powder process or by injection molding a two-part combination of metal and a material that can be burned off to form pores that connect (open cell) to each other. With sintering, for example, typically solid particles of material are placed in a mold under heat and pressure such that the outer surface of the particles soften and bond to one another with the pores comprising the interstices between the particles. Alternatively, when porosity is formed by burning off material, it is not the interstice between the particles which provides the porosity as with sintering, but rather a partial evisceration of the material generally provided by the removal of a component with a lower melt temperature than the burn off temperature.

While the electrode provided by contact element and/or sleeve preferably comprises an electrically conductive material such as metal, a non-electrically conductive porous contact element and/or sleeve, such as porous polymers and ceramics, can be used to replace an electrically conductive contact element and/or sleeve. While the porous polymers and ceramics are generally non-conductive, they may also be used to conduct the RF energy through the porous polymer and ceramic thickness and porous surface to the tissue to be treated by virtue of conductive fluid 24 contained within the plurality of interconnected tortuous pathways 59.

Preferably the tortuous passages in the porous materials have a pore size (cross-sectional dimension) in the range between and including about 2.5 micrometers (0.0025 mm) to 500 micrometers (0.5 mm) and more preferably has pore size in the range between and including about 10 micrometers (0.01 mm) to 120 micrometers (0.12 mm). Even more preferably, the porous material has a pore size in the range between and including about 20 micrometers (0.02 mm) to 80 micrometers (0.08 mm).

In addition to possibly providing a more uniform distribution of fluid 24, the porous materials also may provide other advantages. For example, when the electrode surfaces, such as surfaces 40, 41, 42 and 47, in contact with the surface 22 of tissue 32 are porous and dissipate fluid 24, the tissue 32 is less apt to stick to the surfaces 40, 41, 42 and 47 of the electrode as compared to the situation where the surfaces 40, 41, 42 and 47 are not porous. In addition, by providing fluid 24 to surfaces 40, 41, 42 and 47 through tortuous pathways 59, heated and/or electrified fluid 24 can now be provided more uniformly to surfaces 40, 41, 42 and 47, which may result in a wider tissue treatment region as compared to when the surfaces are not porous.

Preferably the porous material provides for the wicking (i.e. drawing in of fluid by capillary action or capillarity) of the fluid 24 into the pores of the porous material. In order to promote wicking of the fluid 24 into the pores of the porous material, preferably the porous material, and in particular the surface of the tortuous pathways, is hydrophilic. The porous material may be hydrophilic with or without post treating (e.g. plasma surface treatment such as hypercleaning, etching or micro-roughening, plasma surface modification of the molecular structure, surface chemical activation or cross-linking), or made hydrophilic by a coating provided thereto, such as a surfactant.

Though not preferable, it is not necessary that fluid coupling 30 of fluid 24 be present in between the metal electrode surfaces (e.g. 40, 41, 42) and tissue 32 at all locations of tissue treatment and there may be points of direct tissue contact by the electrode surfaces without any fluid coupling 30 therebetween. In such an instance, the convective cooling of the metal electrode by flowing saline is often sufficient to keep the metal electrode and tissue contacting the metal electrode at or below a temperature of 100° C. In other words, heat may be also first dissipated from the tissue 32 to the electrodes by conduction, then dissipated from the electrodes to the fluid 24 by convection.

Preferably the relationship between the material for electrodes particularly their surfaces (e.g. 40, 41, 42, 47), and fluid 24 throughout the various embodiments should be such that the fluid 24 wets the surface of the electrodes to form a continuous thin film coating thereon (for example, see FIG. 19A) and does not form isolated rivulets or circular beads (e.g. with a contact angle, θ greater than 90 degrees) which freely run off the surface of the electrode. Contact angle, θ, is a quantitative measure of the wetting of a solid by a liquid. It is defined geometrically as the angle formed by a liquid at the three phase boundary where a liquid, gas and solid intersect. In terms of the thermodynamics of the materials involved, contact angle θ involves the interfacial free energies between the three phases given by the equation $\gamma_{LV} \cos\theta = \gamma_{SV} - \gamma_{SL}$ where $\gamma_{LV}$, $\gamma_{SV}$ and $\gamma_{SL}$ refer to the interfacial energies of the liquid/vapor, solid/vapor and solid/liquid interfaces, respectively. If the contact angle θ is less than 90 degrees the liquid is said to wet the solid. If the contact angle is greater than 90 degrees the liquid is non-wetting. A zero contact angle θ represents complete wetting. Thus, preferably the contact angle is less than 90 degrees.

For clarification, while it is known that the contact angle θ may be defined by the preceding equation, in reality contact angle θ is determined by a various models to an approximation. According to publication entitled "Surface Energy Calculations" (dated Sep. 13, 2001) from First Ten Angstroms (465 Dinwiddie Street, Portsmouth, Va. 23704), there are five models which are widely used to approximate contact angle θ and a number of others which have small followings. The five predominate models and their synonyms are: (1) Zisman critical wetting tension; (2) Girifalco, Good, Fowkes, Young combining rule; (3) Owens, Wendt geometric mean; (4) Wu harmonic mean; and (5) Lewis acid/base theory. Also according to the First Ten Angstroms publication, for well-known, well characterized surfaces, there can be a 25% difference in the answers provided for the contact angle θ by the models. Also for clarification, any one of the five predominate models above which calculates a contact angle θ within a particular range of contact angles θ or the contact angle θ required of a particular embodiment of the invention should be considered as fulfilling the requirements of the embodiment, even if the remaining four models calculate a contact angle θ which does not fulfill the requirements of the embodiment.

The effects of gravity and surface tension tend to wick the fluid 24, here saline, around the circumference of the cylindrical sleeve 82 to preferably cover the entire active electrode surface. More specifically, the effects of gravity and surface tension on fluid 24 which is located on the electrode surfaces may be modeled by the Bond number $N_{BO}$. Bond number $N_{BO}$ measures the relationship of gravitational forces to surface tension forces and may be expressed as:

$N_{BO}$=gravitational force/surface tension force $N_{BO}=\rho L^2 g/\sigma$ where:
ρ=Density of the saline fluid (approximately 1.0 gm/cm$^3$);
L=droplet diameter (cm)
g=Gravitational acceleration (980 cm/s$^2$)
σ=Surface tension (approximately 72.8 dynes/cm @ 20° C.)

For a Bond number $N_{BO}$=1, the droplet diameter is equal to about 0.273 cm or about 2.7 mm, which is in the same order of magnitude as the preferred size of the electrode. For the purposes of the present invention, preferably Bond number $N_{BO}$ for a droplet of fluid 24 on a surface of the electrode 25 is preferably less than 1.

Figure 20:
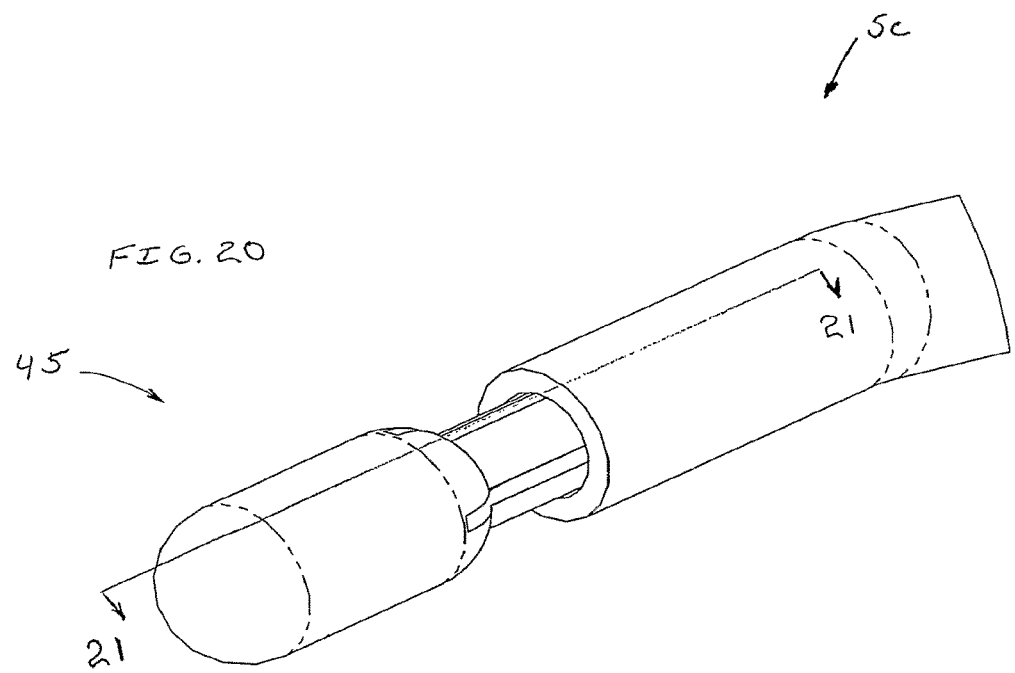
FIG. 20 is a schematic close-up perspective view of an alternative tip portion.
Figure 21:
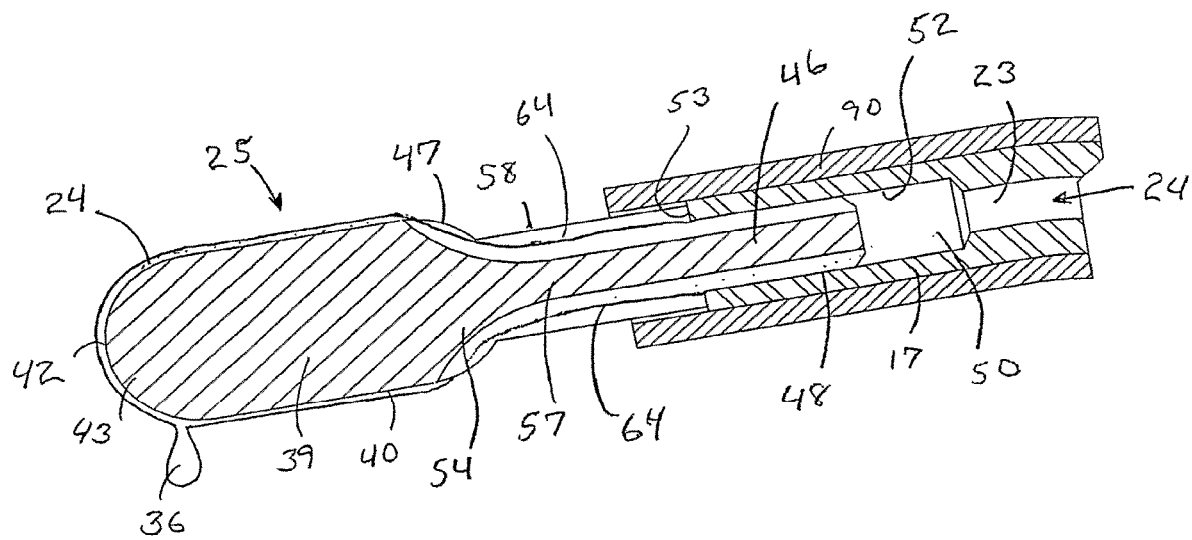
FIG. 21 is a schematic close-up section side view of the tip portion of FIG. 20 taken along line 21-21 of FIG. 20.
Figure 22:
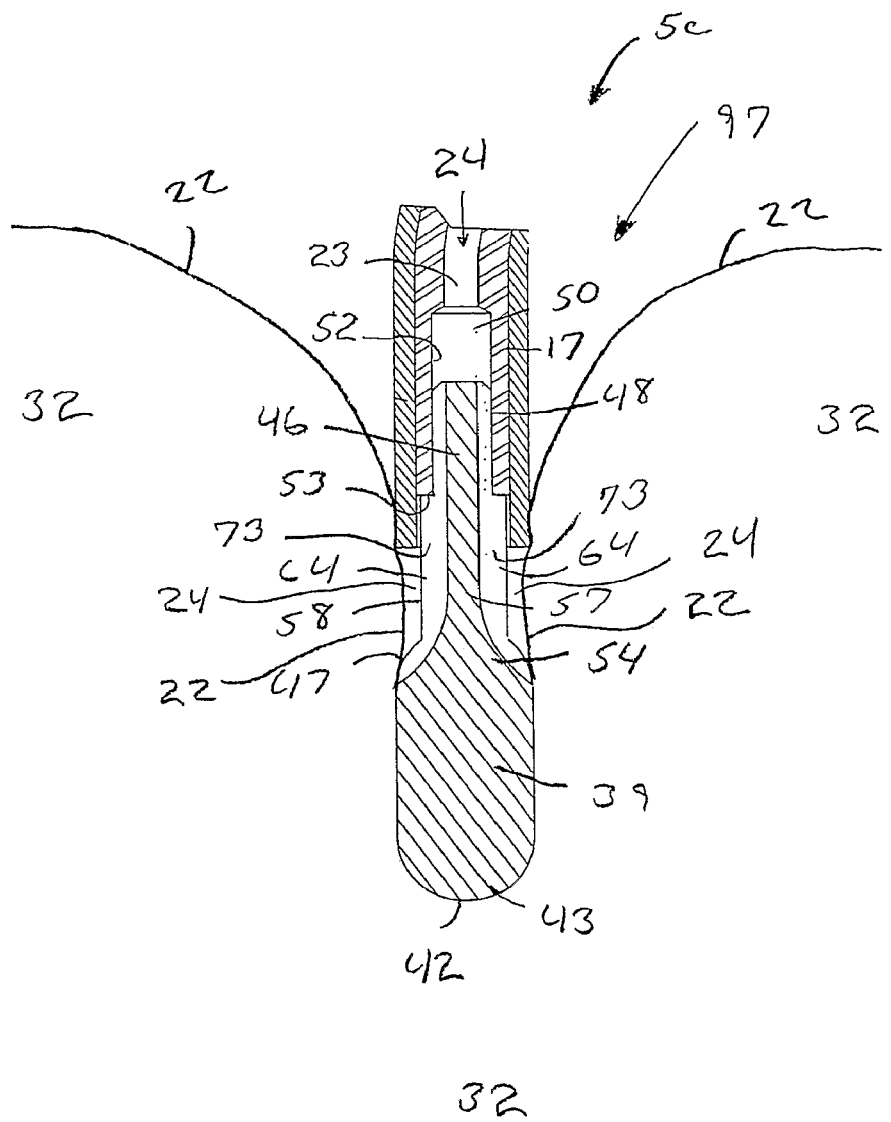
FIG. 22 is a schematic close-up cross-sectional side view of the tip portion of FIG. 20 disposed in a tissue crevice.

Another tip portion of an exemplary electrosurgical device 5c of the present invention which may be used in conjunction with the system of the present invention is shown at reference character 45 in FIGS. 20-24. As best shown in FIGS. 20 and 21, the separate sleeve 82 of embodiments 5a and 5b has been eliminated from tip portion 45 of device 5c. Consequently, the contact element, still preferably comprising an electrode 25, is assembled directly with the shaft 17. Electrode 25 is preferably assembled (e.g. mechanically connected via press fit, mechanical connector, threaded, welded, adhesively bonded) adjacent the distal end 53 of shaft 17. In certain embodiments, the electrode 25 preferably is detachably assembled to the shaft 17 such that it may be removed from the shaft 17, preferably manually by human hand, so that the shaft 17 may be used with multiple different contact elements/electrodes, or the shaft 17 may be reuseable and used with disposable contact elements/electrodes.

As shown in FIGS. 20-24, electrode 25 preferably comprises an enlarged head portion comprising a spherical portion 43 and a corresponding spherical surface portion 42 located at the distal end of the device 5c which provided a smooth, blunt contour outer surface. More specifically, as shown, the spherical portion 43 and spherical surface portion 42 further provide a domed, hemisphere (i.e. less than a full sphere) and hemispherical surface portion comprising preferably about 180 degrees.

Also as shown in FIGS. 20-24, the enlarged head portion of electrode 25 preferably also comprises a cylindrical portion 39 and a corresponding cylindrical surface portion 40 located proximal and adjacent to the spherical portion 43 and spherical surface portion 42, respectively.

Further continuing with FIGS. 20-24, electrode 25 preferably comprises a connector portion, preferably comprising a shank 46, which connects the remainder of the electrode 25 to the shaft 17. Among other things, the connector portion of the electrode 25 is preferably configured to form a connection with a mating connector portion of the shaft 17. As shown, preferably the shank portion 46 is configured to extend into cavity 50 of shaft 17 which comprises a cylindrical receptacle and provides the mating connector portion for shank 46. More preferably, surface 48 of the shank portion 46 is configured to mate against and form an interference fit with surface 52 of cavity 50 to provide the connection.

Continuing with FIGS. 20-24, shank portion 46 is preferably cylindrical and located proximal and adjacent to a neck portion 56. As shown, here neck portion 56 also comprises a cylindrical portion 57 (having a corresponding cylindrical surface portion 58) located proximal and adjacent to a broadening portion 54 (having a corresponding broadening surface portion 47). Here broadening portion 54 and corresponding broadening surface portion 47 are both spherical, and more specifically comprise a domed, hemisphere and hemispherical surface portion comprising preferably about 180 degrees, located proximal and adjacent to the cylindrical portion 39 and cylindrical surface portion 40.

As shown in FIGS. 20-24, the cylindrical portion 57 of neck portion 56 preferably has a cross-sectional dimension, here diameter, greater than the cross-sectional dimension, here also diameter, of the shank 46. In this manner, in certain embodiments, the proximal end of the neck portion 56 may be located adjacent and in contact with the distal end 53 of shaft 17.

Also as shown in FIGS. 20-24, electrode 25 comprises at least one recess 64 which provides an elongated fluid flow channel for the distribution of fluid 24. The use of device 5c, and in particular recesses 64, for the distribution of fluid 24 is generally preferred to the fluid exit holes 93, 94 of device 5b in particularly deep tissue crevices 97 where tissue 32 can occlude fluid flow from the fluid exit holes located in the cylindrical portion 39 of the electrode 25.

As shown, electrode 25 preferably comprises a plurality of longitudinally directed recesses 64 and, more specifically, four recesses 64 equally spaced 90 degrees around the shank 46 and/or neck portion 56, both proximal of cylindrical portion 39. As best shown in FIG. 24, in certain embodiments, the recess 64 may comprise a first side wall 64a, a second opposing side wall 64b, and a bottom wall 64c.

In use, when tissue 32 overlies and occludes the fluid outlet opening 55 of recess 64 for a portion of its longitudinal length, thus inhibiting fluid 24 from exiting therefrom, fluid 24 from recess 64 may still be expelled from the electrosurgical device 5c after flowing longitudinally in the channel 64 to a remote location where the channel 64 is unoccluded and uninhibited to fluid flow exiting therefrom.

However, in certain instances, it may be possible that the recess 64 may be occluded by tissue 32 completely along its longitudinal length, thus completely inhibiting fluid flow from exiting through opening 55. In order to overcome this problem, at least a portion of the electrode 25 may comprise a material pervious to the passage of fluid 24, therethrough, such as a porous material described above.

Figure 25:
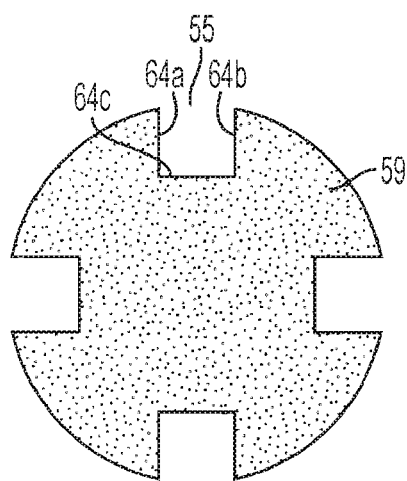
FIG. 25 is a schematic close up cross-sectional view of a porous electrode with recesses.

As shown in FIG. 25, in another embodiment of the electrosurgical device of the present invention, as shown at reference character 5d in FIG. 25, the walls 64a, 64b of recess 64, surface 48 of the shank portion 46, and/or the surfaces of the neck portion 56 of electrode 25 may be porous and connected by a plurality of tortuous pathways 59 in the porous material. Consequently, rather than flowing out of recess 64 from a direct fluid outlet opening 55, which may be occluded by tissue 32, the fluid 24 may exit indirectly from recess 64 by first flowing through tortuous pathways 59 of the electrode 25 from side walls 64a, 64b of the recess 64 and then exit the electrode 25 from surface 58, which may be in unoccluded by tissue 32. Alternatively, if adjacent surface 58 of the electrode 25 is also occluded by tissue 32, the fluid 24 may continue to flow through tortuous pathways 59 of electrode 25 and exit electrode 25 from a surface 64a, 64b of a recess 64 or surface such as 40, 42, 47 or 58 which may be in unoccluded by tissue 32.

Where the electrode 25 comprises a porous material, recess 64 may be either supplemented with or replaced by the plurality of tortuous, interconnected passages 59 formed in the porous material as shown in FIG. 25, with porous surfaces such as 40, 42, 47 or 58 to more evenly distribute fluid flow and provide conductive fluid 24 to the tissue treatment site. All or a portion of the electrodes can be porous according to the invention.

Figure 27:
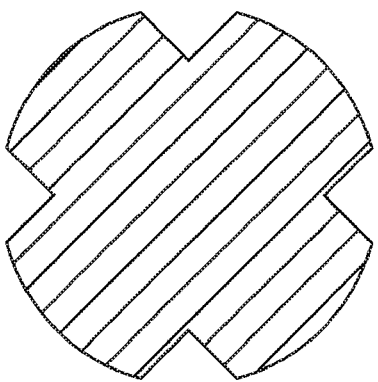
FIG. 27 is schematic close up cross-sectional view of an electrode with V-shaped recesses.
Figure 26:
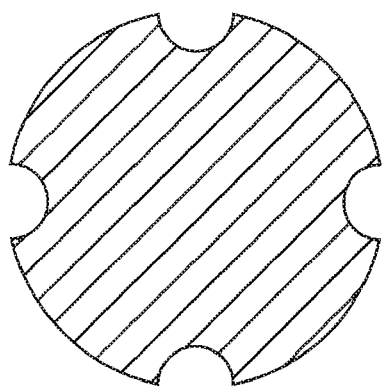
FIG. 26 is schematic close up cross-sectional view of an electrode with semi-circular recesses.
Figure 28:
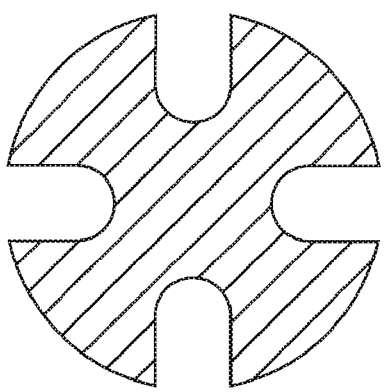
FIG. 28 is schematic close up cross-sectional view of an electrode with U-shaped recesses.
Figure 29:
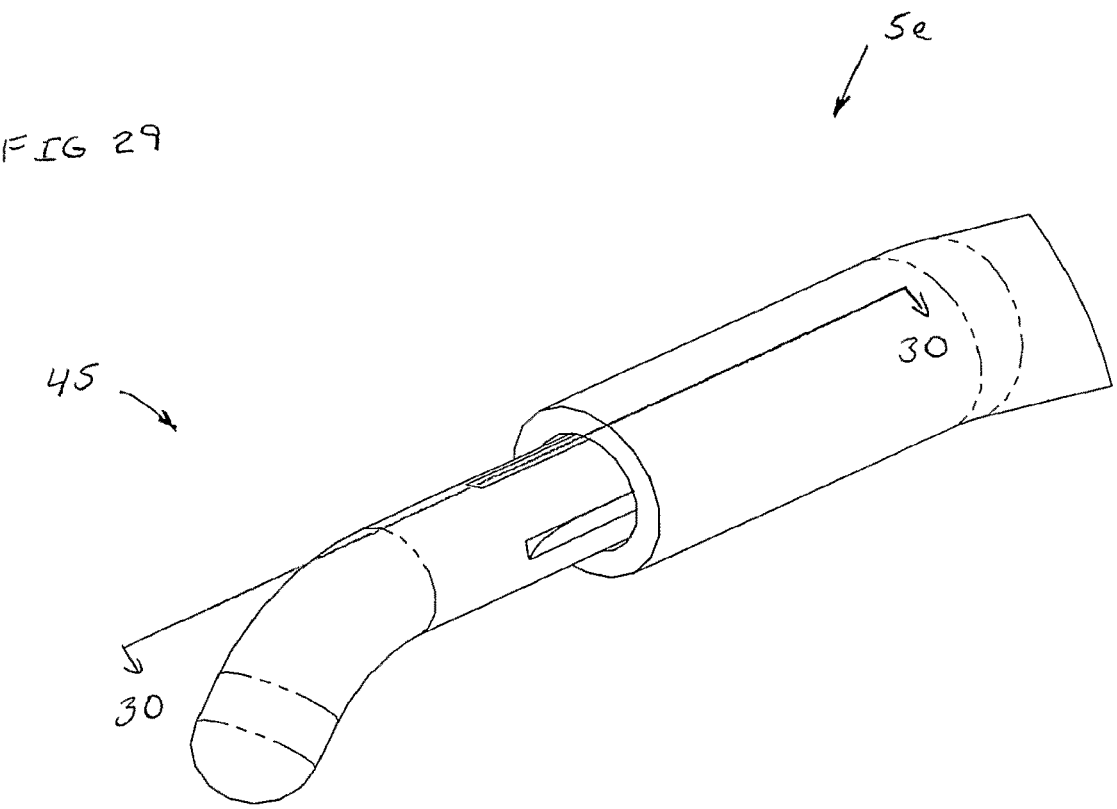
FIG. 29 is a schematic close-up perspective view of an alternative tip portion.
Figure 30:
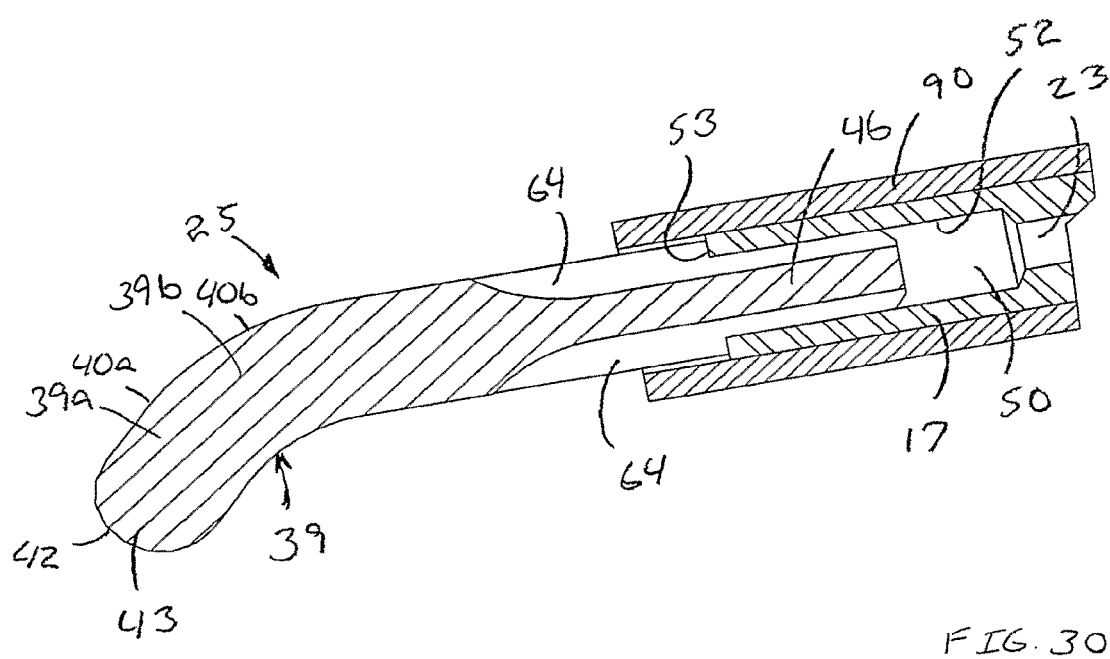
FIG. 30 is a schematic close-up section side view of the tip portion of FIG. 29 taken along line 30-30 of FIG. 29.
Figure 33:
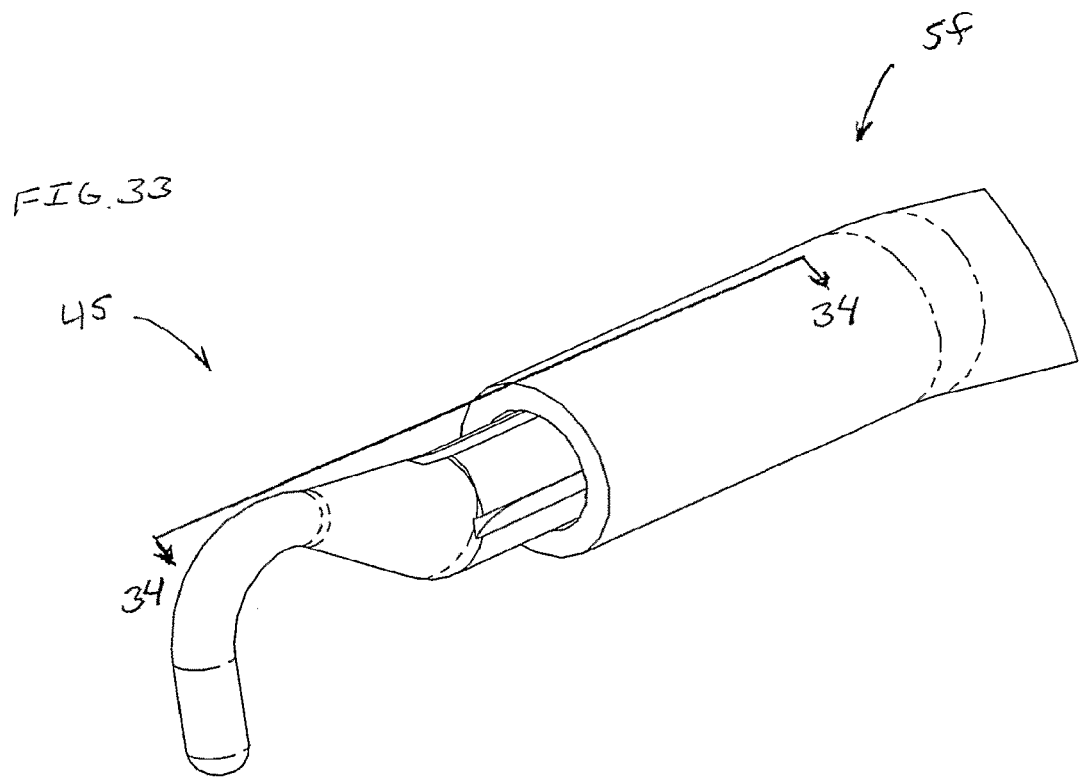
FIG. 33 is a schematic close-up perspective view of an alternative tip portion.

In other embodiments of the invention, recess 64 may comprise cross-sectional shapes other than rectangular shapes. For example, as shown in FIGS. 26-28 recess 64 comprises a semi-circular shape, a V-shape, or a U-shape respectively, or any combination thereof.

Returning to FIG. 21, in order to facilitate direct fluid communication of recess 64 with lumen 23 of shaft 17, preferably recesses 64 of device 5c are initiated within the confines of shaft 17. In other words, within the cavity 50 of shaft 17 proximal to distal end 53. Preferably the configuration of the recesses 64 as provided by geometry (e.g. width, depth) and/or the material and/or surface treatment of the electrode 25 may be arranged such that surface tension will act to retain fluid collected in the recess 64 where the force of gravity is acting to remove the fluid from the recess 64. However, while it is desirable that a certain predetermined amount of surface tension act to retain fluid collected in the recess 64 in the presence of gravity, the surface tension must be balanced against the inhibition of fluid flow from the recess 64.

As indicated above, the use of device 5c, and in particular recesses 64, for the distribution of fluid 24 is generally preferred to the fluid exit holes 93, 94 of device 5b in particularly deep tissue crevices 97 where tissue 32 can occlude fluid flow from the fluid exit holes 93, 94 located in the cylindrical portion 39 of the electrode 25. Also, since holes 93, 94 are not presented with a declogging mechanism, such as provided for such as fluid exit holes 26 and 85, holes such as 93, 94 that can be simply occluded by ordinary tissue/electrode contact will sooner or later become irreversibly clogged.

As shown in FIG. 21, with device 5c fluid outlet openings 73 are provided by the structure of the electrode 25 (i.e. recesses 64) at the distal end 53 of the shaft 17 which are protected and sheltered from contact and occlusion from surface 22 of tissue 32. Fluid outlet openings 73 of device 5c are protected from occlusion from surface 22 of tissue 32 as the structure of device 5c defining the openings 73 is at least partially configured for non-contact with surface 22 of tissue 32. More specifically, here the structure of the device defining the openings 73 is completely configured for non-contact with surface 22 of tissue 32. Stated another way, the openings 73 are provided on the device 5c at a location removed from the tissue surface 22. Also, as shown, openings 73 are particularly sheltered from occlusion from surface by 22 of tissue 32 by a portion of the shaft 17. Also as shown, when openings 73 are formed substantially perpendicular to the surface 22 of tissue 32 and thus turned away from direct contact with surface 22 of tissue 32.

Another tip portion of an exemplary electrosurgical device 5e of the present invention which may be used in conjunction with the system of the present invention is shown at reference character 45 in FIGS. 29-32. As best shown in FIGS. 31 and 32, the broadening portion 54 has been eliminated and the cylindrical portion 39 has an equal cross-sectional dimension, here diameter, with the neck portion 56. Conversely, for device 5c, the cylindrical portion 39 has a cross-sectional dimension, there also diameter, greater than the cross-sectional dimension, there also diameter, of the neck portion 56.

Also as shown in FIGS. 31 and 32, the cylindrical portion 39 further comprises a rectilinear (straight) cylindrical portion 39a having a rectilinear cylindrical surface portion 40a and a curvilinear cylindrical portion 39b having a curvilinear cylindrical surface portion 40b. As shown, device 5e comprises the shape of a hockey stick. The cylindrical portion 39 for device 5c may be similarly arranged.

Another tip portion of an exemplary electrosurgical device 5f of the present invention which may be used in conjunction with the system of the present invention is shown at reference character 45 in FIGS. 33-36. As best shown in FIGS. 35 and 36, the cylindrical portion 39 has a cross-sectional dimension, here diameter, less than the cross-sectional dimension, here also diameter, of the neck portion 56. As shown the neck portion 56 is located proximal and adjacent to a narrowing portion 49 with a corresponding narrowing surface portion 51, here both conical.

Figure 34:
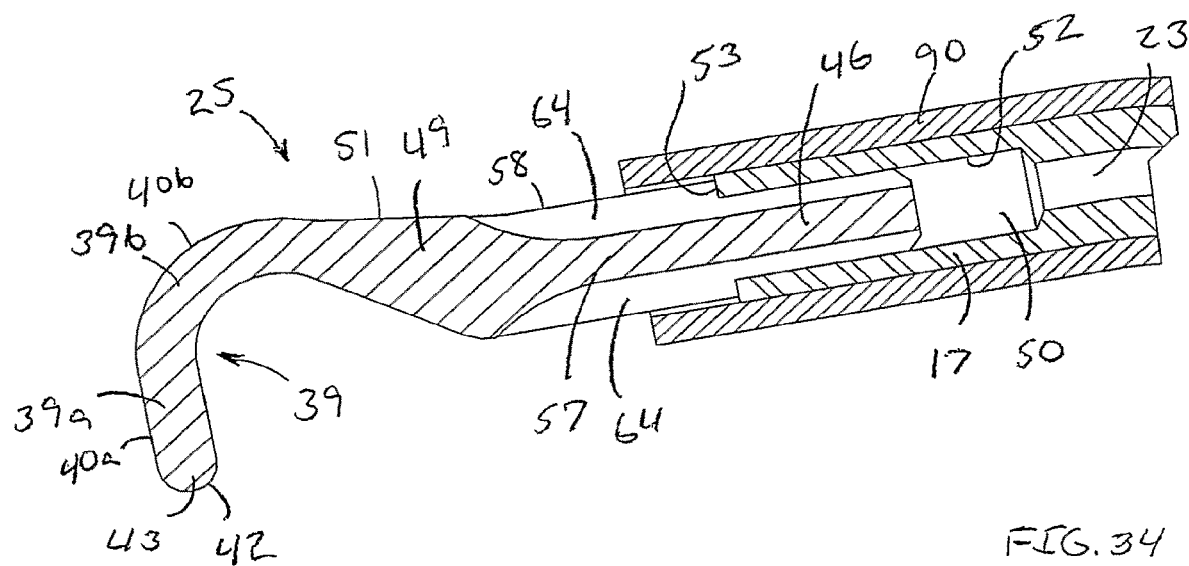
FIG. 34 is a schematic close-up section side view of the tip portion of FIG. 33 taken along line 34-34 of FIG. 33.

Also as shown in FIG. 34, the cylindrical portion 39 further comprises a rectilinear cylindrical portion 39a having a rectilinear cylindrical surface portion 40a and a curvilinear cylindrical portion 39b having a curvilinear cylindrical surface portion 40b. Furthermore, as shown, the cylindrical portion 39, and more specifically at least one of the rectilinear cylindrical portion 39a and the curvilinear cylindrical portion 39b, comprises a portion of a hook. Preferably, as shown both the rectilinear cylindrical portion 39a and the curvilinear cylindrical portion 39b comprise portions of a hook. As shown in FIGS. 35 and 36, the hook further comprises an L-hook.

Another tip portion of an exemplary electrosurgical device 5g of the present invention which may be used in conjunction with the system of the present invention is shown at reference character 45 in FIGS. 37-38. As shown, for device 5g the cylindrical portion 39, and more specifically both the rectilinear cylindrical portion 39a and the curvilinear cylindrical portion 39b comprise portions of a hook. Also as shown in FIGS. 37 and 38, the hook further comprises an J-hook.

Another tip portion of an exemplary electrosurgical device 5h of the present invention which may be used in conjunction with the system of the present invention is shown at reference character 45 in FIGS. 39-42. As shown in FIGS. 39 and 40, electrode 25 preferably comprises a finger portion 65 (preferably comprising cylindrical portion 39 and cylindrical surface portion 40) having a distal end (preferably comprising a spherical portion 43 and spherical surface portion 42) which, among other things, is configured for blunt dissection or electrosurgical dissection of tissue 32. Electrosurgical dissection occurs when tension or force is applied to tissue while also applying RF energy. The RF energy heats the tissue, thereby weakening it, and the tissue yields or breaks where desired. Surgeons may refer to this type of dissection with a hook-type electrode as "hook and cook". Furthermore, finger portion 65 is also preferably configured to function as a hook, particularly the anterior (i.e. front) surface portion 66 of finger portion 65 which is configured, among other things, to engage and restrain tissue 32.

As shown, finger portion 65 is rectilinear and forms an L-hook with an angle of about 90 degrees relative to the longitudinal axis 31 of the tip portion 45, particularly shank 45. However, finger portion may be formed at angles other than 90 degrees. For example, finger portion 65 may be formed at any angle in the range between and including about 60 degrees relative to the tip portion 45 to about 180 degrees relative to the tip portion 45, or any other range of angles or particular angle inclusive therein (e.g. 75°, 105°, 120°, 135°, 180°, 90°-135°, 90°-180°).

Among other things, electrode 25 preferably comprises a knuckle portion 61 comprising a rounded protuberance having a raised prominence on the posterior (back) surface portion 62 of the electrode 25. Also as shown, knuckle portion 61 also comprises a rounded protuberance having a raised prominence on the lateral surface portion 75 of the electrode 25. Among other things, posterior knuckle surface portion 62 and lateral knuckle surface portion 75 formed by knuckle portion 61 are configured for coagulation and stasis (e.g. hemostasis, aerostasis) of tissue 32.

Key to device 5g is the cross-sectional dimension of the knuckle Z to the cross-section dimension of the finger F. When comparing the functions of blunt or electrosurgical dissection and coagulation/hemostasis, the coagulation/hemostasis portion of the electrode 25 preferably comprises a greater surface area than the blunt or electrosurgical dissection portion of the electrode 25.

As shown in FIG. 36, preferably the cross-sectional dimension Z, of the knuckle portion 61 is greater than cross-section dimension F of the finger portion 65. Here, as shown, the cross-sectional dimensions Z and F comprise diameters. However, in other embodiments where the cross-sectional dimension Z and/or F could not properly be considered to comprise a diameter, the cross-sectional dimension Z and/or F could comprise a width or thickness.

Preferably, the cross-sectional dimension Z of the knuckle portion 61 is in the range between and including about 1.6 to 3.3 times greater than the cross-section dimension F of the finger portion 65, with typical dimensions comprising the ratios of 2.5 mm to 1.5 mm (1.6 times) and 2.5 mm to 0.75 mm (3.3 times). Even more preferably, the cross-sectional dimension Z of the knuckle portion 61 is in the range between and including about 2 to 2.5 times greater than the cross-section dimension F of the finger portion 65, with typical dimensions comprising the ratios of 2.5 mm to 1.25 mm (2 times) and 2.5 mm to 1 mm (2.5 times).

From the above dimensions, the ratio of the surface area of the knuckle portion 61 to the surface area of the distal end (e.g. surface 42) of the finger portion 65 may be determined to an approximation using a formula for half the area of a sphere. For the above dimensions, preferably the surface area of the knuckle portion 61 is in the range between and including about 2.8 times to 11 times greater than the surface area the distal end of the finger portion 65. More preferably, the surface area of the knuckle portion 61 is in the range between and including about 4 times to 6.2 times greater than the surface area the distal end of the finger portion 65.

Also as shown in FIGS. 39 and 40, neck portion 56 preferably comprises a cylindrical portion 57 located proximal and adjacent to a spatula portion 67. As shown, spatula portion 67 comprises a substantially flat anterior surface portion 69 of electrode 25. In certain embodiments, electrode 25 may comprise one, any combination of, or all of the features of finger portion 65, knuckle portion 61 and spatula portion 67.

Turning to use of the devices, similar to device 5b, device 5c is particularly useful to a surgeon performing a liver resection. Once the outer capsule of the liver is scored with a dry bovie blade along the planned line of resection with distal tip of tip portion 45 is painted back and forth along the line, with radio frequency power and the flow of fluid 24 on, resulting in coagulation of the liver parenchyma. Once the tissue is coagulated under and around the electrode surface 42 and, as the device 5c enters a crevice 97, surface 40, surface 42 of electrode 25 is used to blunt dissect the coagulated parenchyma. Blunt dissection of the coagulated parenchyma is performed by continuous abrading or splitting apart of the parenchyma with the substantially the same back and forth motion as coagulation and with the device 5c being held substantially in the same orientation as for coagulation of the liver parenchyma. However, with blunt dissection, the surgeon typically applies more force to the tissue. In various embodiments, once the liver parenchyma is coagulated, blunt dissection may be performed with or without the radio frequency power (i.e. on or off) and/or with or without the presence of fluid 24.

In addition to liver resections, device 5h are particularly useful to a surgeon performing a laparoscopic cholecystectomy (abbr. "lap chole") for the case of, for instance, either acute cholecystitis or an intrahepatic gallbladder in that the device provides multi-functional uses. More particularly, device 5h is useful to the surgeon for coagulation and dissection of an inflamed serosal layer of tissue 32 between the liver and gallbladder, which may include tough, fibrous, highly vascular connecting tissue between the organs.

Figure 43:
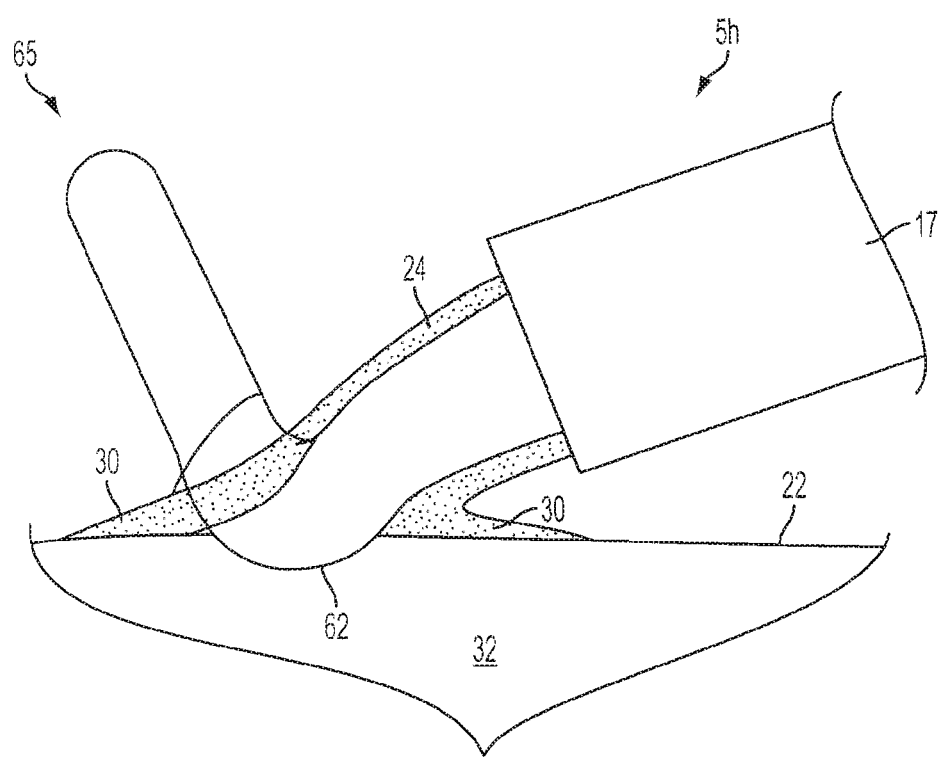
FIG. 43 is a schematic side view of the tip portion of FIG. 39 with a fluid coupling to a tissue surface of tissue.

For coagulation, device 5h may be positioned in at least three different orientations. For the first orientation, as shown in FIG. 43, coagulation may be performed with posterior knuckle surface portion 62 formed by knuckle portion 61. Similar to device 5c, coagulation with device 5h is performed with radio frequency power and the flow of fluid 24 on. Preferably power is applied in the coagulation mode of the generator and at a power level in the range between and including about 10 watts to 60 watts. More preferably, the power level is in the range between and including about 20 watts to 50 watts. Even more preferably, the power level is in the range between and including about 30 watts to 40 watts. With respect to motion of surface portion 62 during coagulation, coagulation may be performed with surface portion 62 stationary, or with a painting motion by moving surface portion 62 back and forth substantially along the longitudinal axis 29 or laterally side to side.

Figure 44:
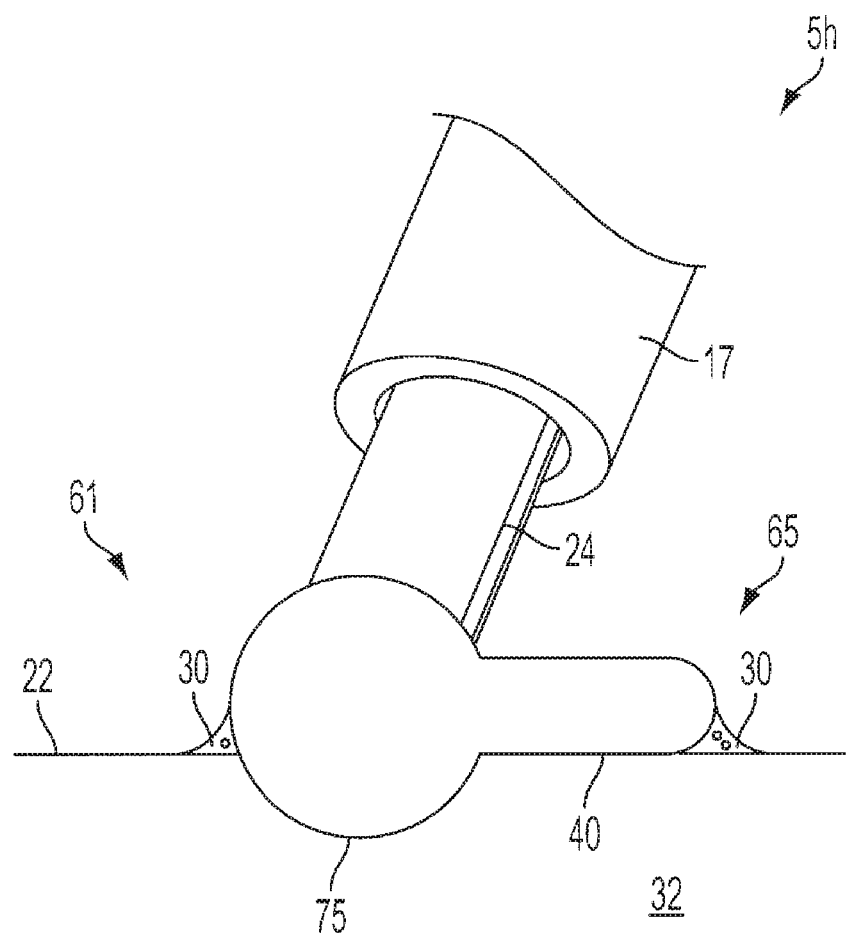
FIG. 44 is a schematic front view of the tip portion of FIG. 39 with a fluid coupling to a tissue surface of tissue.
Figure 45:
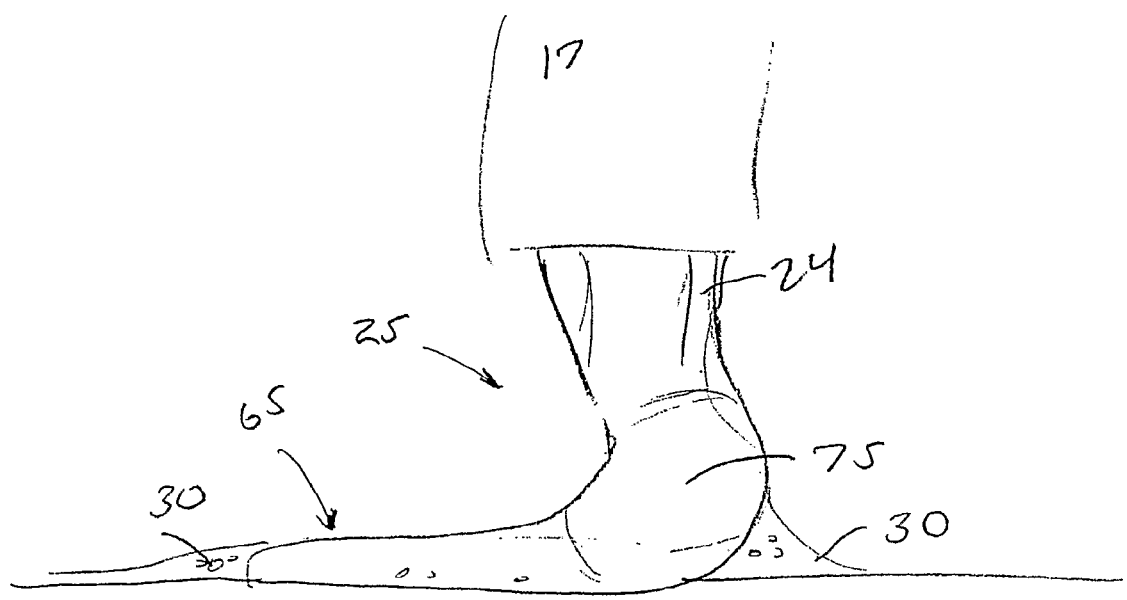
FIG. 45 is a schematic side view of the tip portion of FIG. 39 with a fluid coupling to a tissue surface of tissue.

For the second orientation, as shown in FIG. 44, coagulation may be performed with a combination of lateral knuckle surface portion 75 formed by knuckle portion 61 and cylindrical surface portion 40, and more specifically a lateral cylindrical surface portion of cylindrical surface portion, of finger portion 65. For the third orientation, as shown in FIG. 45, coagulation may be performed also with another combination of knuckle portion 61 and finger portion 65. As shown in FIG. 45, coagulation may be performed with a posterior cylindrical surface portion of cylindrical surface portion 40 and a posterior surface of knuckle portion 61. In the various orientations, coagulation may be used to stop active bleeding (e.g. such as a spleen injury comprising a splenic capsule tear) or pre-coagulation of tissue before dissection for bloodless surgery.

Where the surgeon has pre-coagulated the tissue 32, the surgeon may dissect the tissue 32 with simultaneous mechanical fraction (i.e. the process of drawing or pulling of the tissue 32 with a mechanical device) with anterior (i.e. front) surface portion 66 of finger portion 65 which is configured, among other things, to engage and restrain tissue 32. More specifically, the surgeon may hook the tissue 32 for dissection against the surface portion 66 of finger portion 65 and apply fraction to the tissue 32, then dissect the tissue 32.

Since the tissue 32 has been coagulated, dissection may be performed with or without the radio frequency power (i.e. on or off) and/or with or without the presence of fluid 24. Where the tissue 32 is dissected without fluid 24, but with the radio frequency power on and with the generator set to the coagulation mode, the process of dissecting may be referred to as "hook and cook" in the art. While dissecting in this manner is fast, it suffers from the problems of significant arcing, the production of smoke and char, and the possibility of inadvertent perforation of the gall bladder wall. Alternatively, dissecting without the radio frequency power on may eliminate the problems of arcing, the production of smoke and char, and the possibility of inadvertent perforation, but may result in bleeding if the tissue 32 is not sufficiently coagulated. In order to overcome the aforementioned issues, dissection of the tissue 32 with traction may be performed similar to coagulation (i.e. in the presence of both radio frequency power and fluid 24). However, this alternative typically requires more time than "hook and cook".

With regards to the sequence of events for dissect the tissue 32 with fraction and using the "hook and cook" technique (i.e. without fluid 24), the surgeon first engages the tissue 32 on the surface portion 66 of finger portion 65. The surgeon then applies traction to the engaged tissue 32. Once complete, the surgeon checks for proper position then applies the radio frequency power. Upon application of the radio frequency power, the tissue 32 yields, separates and breaks. The surgeon then turns the radio frequency power off. This process may then be repeated numerous times as the surgeon incrementally dissects tissue 32 along a length in step-wise fashion.

Certain embodiments of the invention may be particularly configured for bipolar devices. For example, an exemplary bipolar electrosurgical device of the present invention which may be used in conjunction with the system of the present invention is shown at reference character 5i in FIGS. 46-48. With a bipolar device, the ground pad electrode located on the patient is eliminated and replaced with a second electrical pole as part of the device. An alternating current electrical circuit is then created between the first and second electrical poles of the device. Consequently, alternating current no longer flows through the patient's body to the ground pad electrode, but rather through a localized portion of tissue preferably between the poles of the bipolar device.

Figure 46:
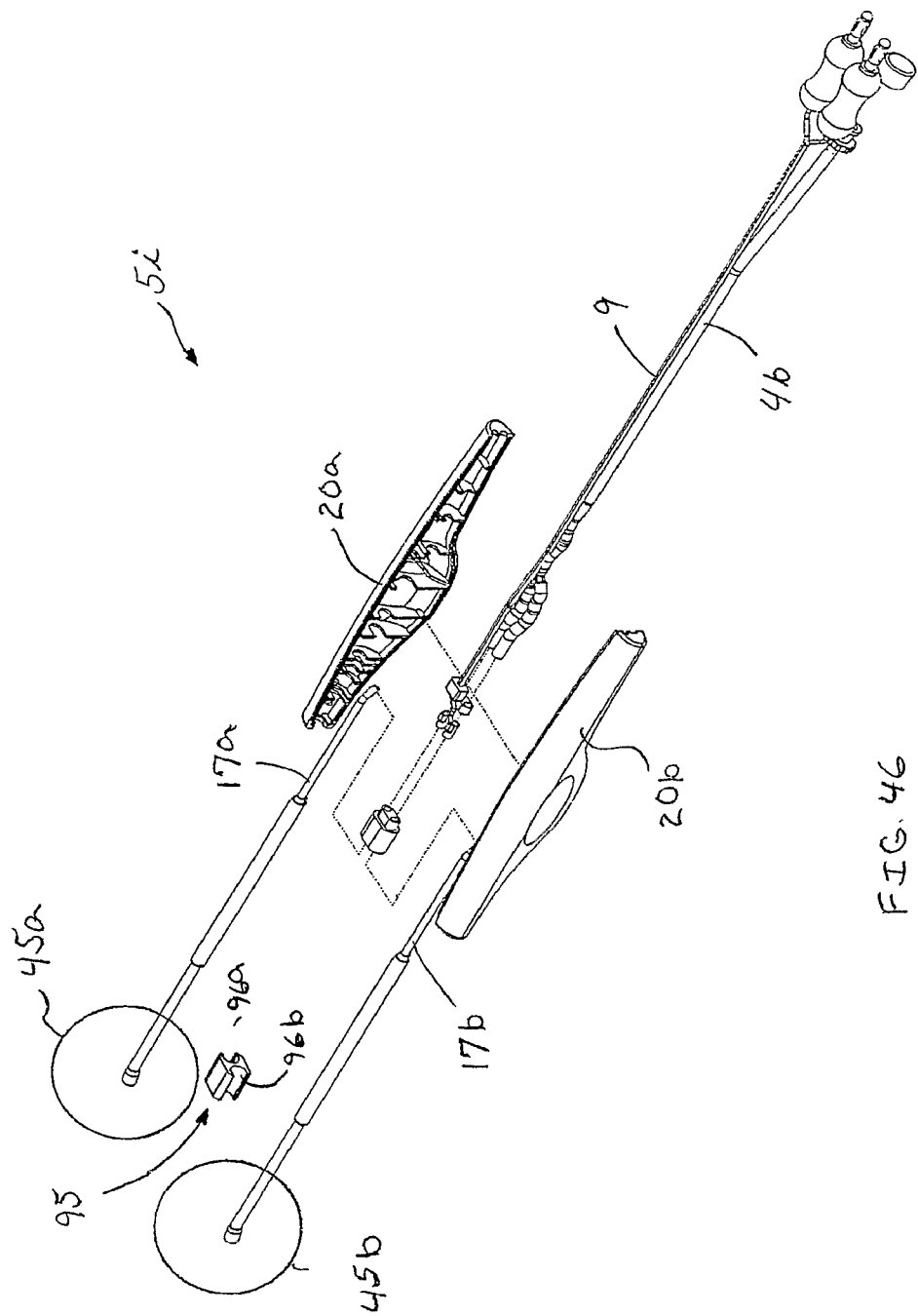
FIG. 46 is a schematic exploded perspective view of an assembly of an alternative electrosurgical device according to the present invention.

In certain embodiments, an exemplary bipolar surgical device of the present invention may comprise, among other things, multiple, substantially parallel, arms. As shown in FIG. 46, electrosurgical device 5i preferably includes two arms comprising rigid, self-supporting, hollow shafts 17a, 17b, a proximal handle comprising mating handle portions 20a, 20b and arm tip portions as shown by circles 45a, 45b. In this embodiment, shafts 17a, 17b preferably comprise thick walled hypo-tubing. In this manner, the shafts 17a, 17b have sufficient rigidity to maintain their form during use of the device without kinking or significant bending.

Preferably the arms of device 5i (comprising shafts 17a, 17b) are retained in position relative to each other by a mechanical coupling device comprising a collar 95 and inhibited from separating and/or rotating relative to each other. Collar 95 preferably comprises a polymer (e.g. acrylonitrile-butadiene-styrene or polycarbonate) and is preferably located on the distal portion of the arms. More preferably, the collar 95 is located proximal the distal ends 53a, 53b of the shafts 17a, 17b. Preferably the collar 95 comprises two apertures 96a, 96b, preferably comprising opposing C-shapes, configured to receive a portion of the shafts 17a, 17b which are preferably snap-fit therein. Once the collar 95 is connected to the shafts 17a, 17b, preferably by a snap-fit connection, the collar 95 may be configured to slide along the length of the shafts 17a, 17b as to adjust or vary the location of the collar 95 on the shafts 17a, 17b. Alternatively, the location of the collar 95 may be fixed relative to the shafts 17a, 17b by welding, for example.

Device 5i comprises a first arm tip portion 45a and a second arm tip portion 45b. As shown, preferably both first arm tip portion 45a and second arm tip portion 45b are each individually configured identical to tip portion 45 of device 5a. As a result, device 5i has two separate, spatially separated (by empty space) contact elements preferably comprising electrodes 25a, 25b.

Figure 47:
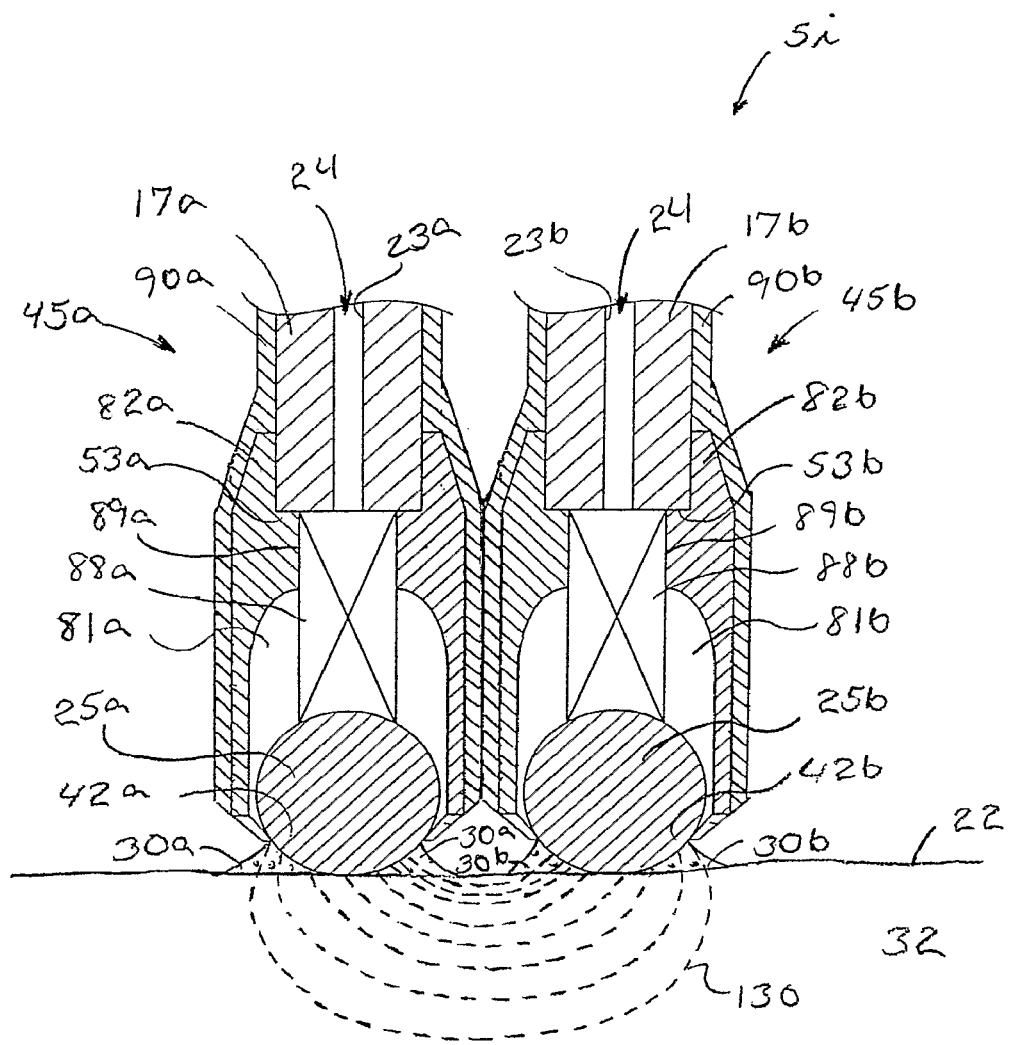
FIG. 47 is a schematic close-up cross-sectional side view of the tip portions of FIG. 46 assembled with a fluid coupling to a tissue surface of tissue.

As shown in FIG. 47, when device 5i is in use electrodes 25a, 25b are laterally spaced adjacent tissue surface 22 of tissue 32. Electrodes 25a, 25b are connected to a source of alternating electrical current and alternating current electrical field is created between electrodes 25a and 25b. In the presence of alternating current, the electrodes alternate polarity between positive and negative charges with current flow from the positive to negative charge.

Similar to device 5a, for device 5i fluid 24 is communicated from a fluid source 1 within the lumens 23a, 23b of the shafts 17a, 17b through the lumens 89a, 89b and cavities 81a, 81b of the sleeves 82a, 82b where it is expelled from around and on the surface 42a, 42b of the electrodes 25a, 25b.

As with use of device 5a, with use of device 5i fluid couplings 30a, 30b preferably comprising discrete, localized webs and more preferably comprising a triangular shaped web or bead portion providing a film of fluid 24 is provided between the surface 22 of the tissue 32 and the electrodes 25a, 25a. When the user of electrosurgical device 5i places the electrodes 25a, 25b at a tissue treatment site and moves the electrodes 25a, 25b across the surface 22 of the tissue 32, fluid 24 is expelled around and on the surfaces 42a, 42b of the electrodes 25a, 25b at the distal ends 83a, 83b of the sleeves 82a, 82b and onto the surface 22 of the tissue 32 via couplings 30a, 30b. At the same time, RF electrical energy, shown by electrical field lines 130, is provided to the tissue 32 at the tissue surface 22 and below the tissue surface 22 into the tissue 32 through the fluid couplings 25a, 25b.

As with device 5a, the fluid 24, in addition to providing an electrical coupling between the electrosurgical device 5i and the tissue 32, lubricates the surface 22 of the tissue 32 and facilitates the movement of electrodes 25a, 25b across the surface 22 of the tissue 32. During movement of the electrodes 25a, 25b the electrodes 25a, 25b typically slide across the surface 22 of the tissue 32, but also may rotate as the electrodes 25a, 25b move across the surface 22 of the tissue 32. Typically the user of the electrosurgical device 5i slides the electrodes 25a, 25b across the surface 22 of the tissue 32 back and forth with a painting motion while using the fluid 24 as, among other things, a lubricating coating. Preferably the thickness of the fluid 24 between the distal end surface of the electrodes 25a, 25b and the surface 22 of the tissue 32 at the outer edge of the couplings 30a, 30b is in the range between and including about 0.05 mm to 1.5 mm. More preferably, the fluid 24 between the distal end surface of the electrodes 25a, 25b and the surface 22 of the tissue 32 at the outer edge of the coupling 30a, 30b is in the range between and including about 0.1 mm to 0.3 mm. Also preferably, in certain embodiments, the distal end tip of the electrode 25 contacts the surface 22 of tissue 32 without any fluid 24 in between.

Figure 48:
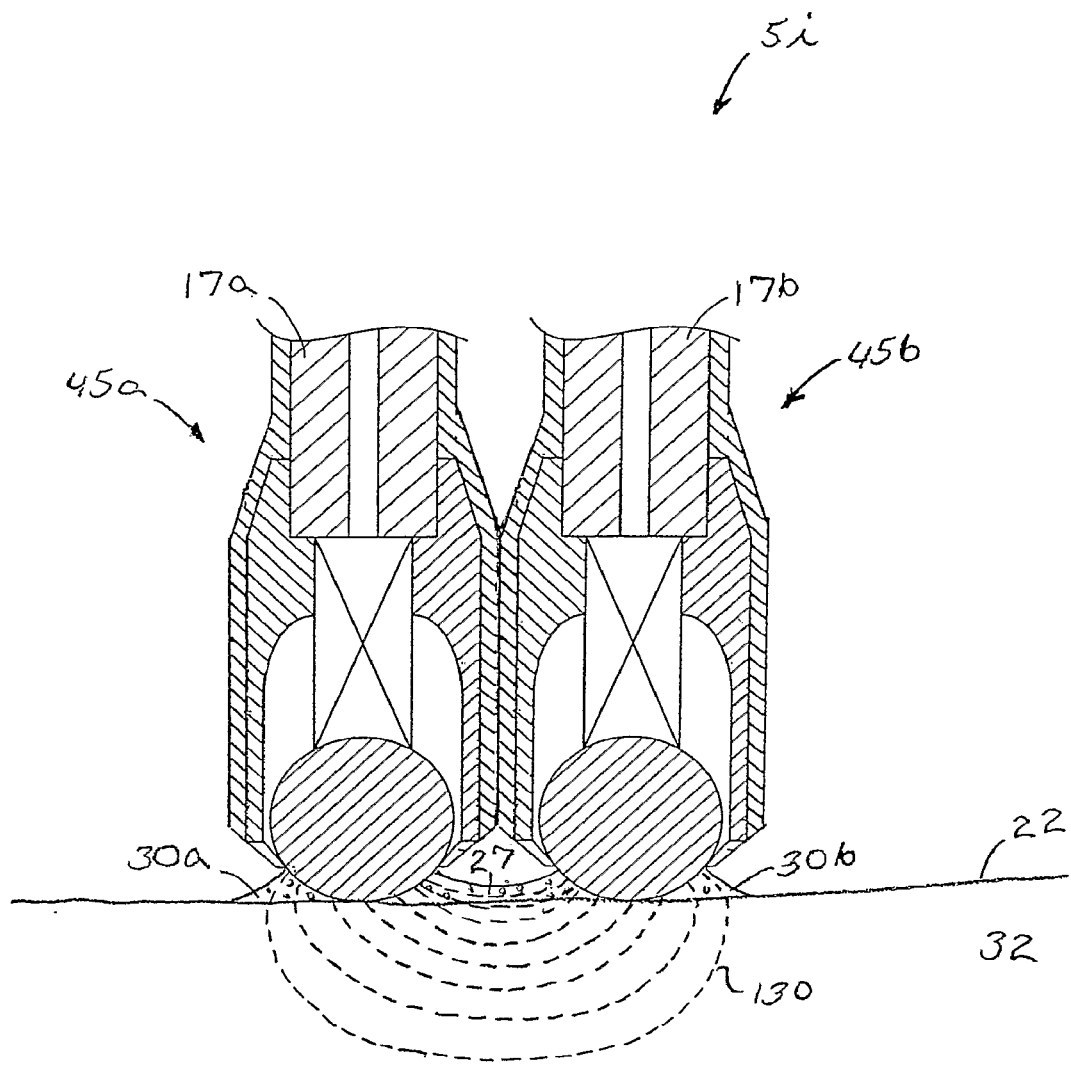
FIG. 48 is a schematic close-up cross-sectional side view of the tip portions of FIG. 46 assembled with an alternative fluid coupling to a tissue surface of tissue.

As shown in FIG. 48, the fluid coupling for device 5i may comprise a conductive fluid bridge 27 between electrodes 25a, 25b which rests on the surface 22 of the tissue 32 and forms a shunt between the electrodes 25a, 25b. Given this scenario, a certain amount of RF energy may be diverted from going into the tissue 32 and actually pass between the electrodes 25a, 25b via the conductive fluid bridge 27. This loss of RF energy may slow down the process of coagulating tissue and producing the desired hemostasis or aerostasis of the tissue.

In order to counteract the loss of energy through bridge 27, once enough energy has entered the bridge 27 to boil the fluid 24 of bridge 27, the loss of RF energy correspondingly decreases with the loss of the bridge 27. Preferably energy is provided into the fluid 24 of the bridge 27 by means of heat dissipating from tissue 32.

Thus, where a high % boiling of the conductive fluid 24 of the bridge 24 is created, the loss of RF energy through the bridge 27 may either be reduced or eliminated because all the fluid 24 of bridge 27 boils off or a large fraction of boiling creates enough disruption in the continuity of the bridge 27 to disrupt the electrical circuit through the bridge 27. Thus, one control strategy of the present invention is to reduce the presence of a conductive fluid shunt by increasing the % boiling of the conductive fluid.

Figure 49:
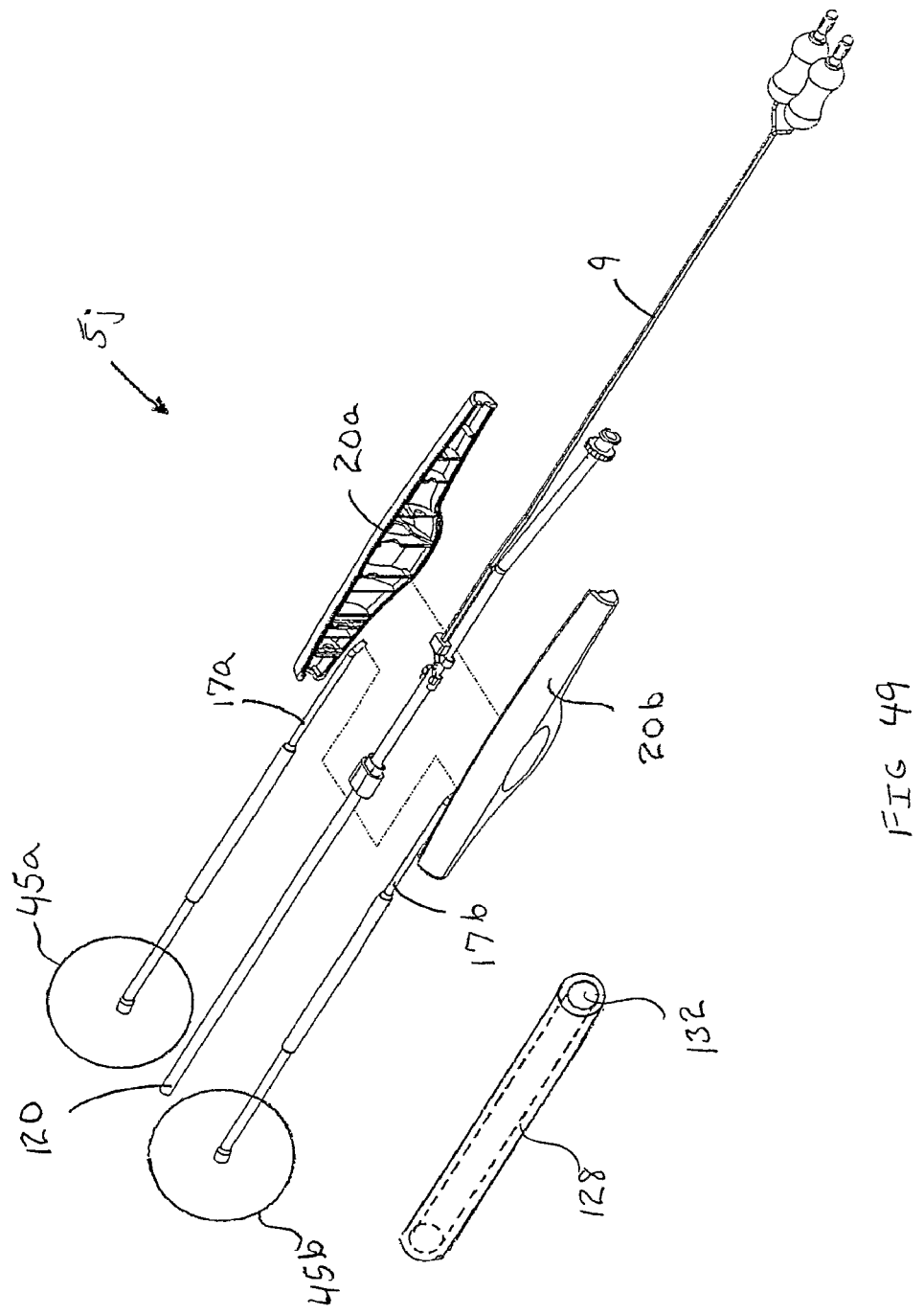
FIG. 49 is a schematic exploded perspective view of an assembly of an alternative electrosurgical device according to the present invention.
Figure 50:
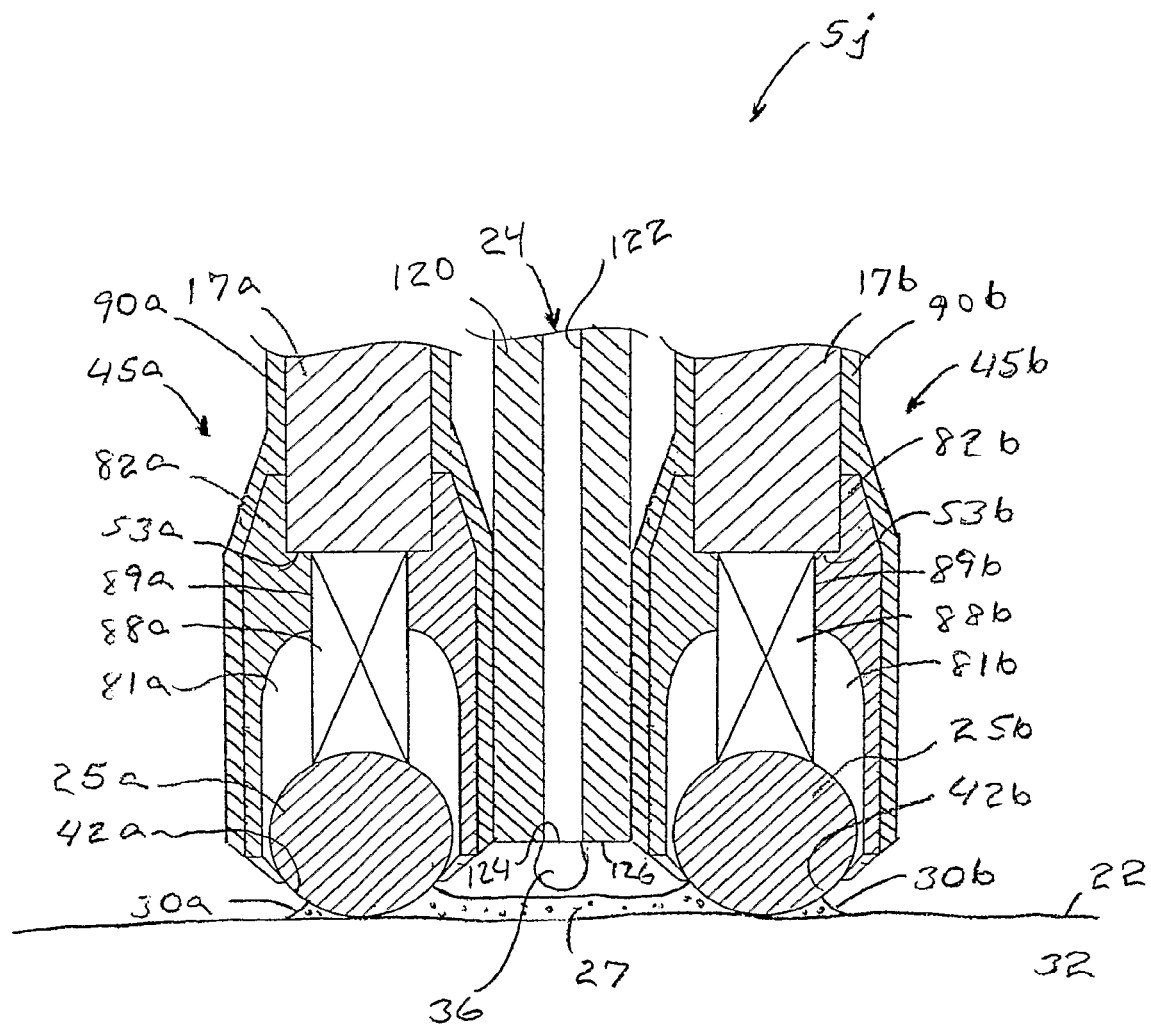
FIG. 50 is a schematic close-up cross-sectional side view of the tip portions of FIG. 49 assembled with a fluid coupling to a tissue surface of tissue.

Another embodiment of a bipolar device is shown at 5j in FIGS. 49 and 50. Similar to device 5i, electrosurgical device 5j preferably includes two arms comprising rigid, self-supporting, shafts 17a, 17b, a proximal handle comprising mating handle portions 20a, 20b and first and second arm tip portions as shown by circles 45a, 45b. However, as shown in FIG. 50, unlike device 5i, for device 5j the shafts 17a, 17b may comprise solid rods (i.e. do not have lumens) which provide for electrical connection to a power source but do not have lumens for providing conductive fluid through the sleeves 82a, 82b. Rather conductive fluid 24 is preferably provided by means of a lumen 122 of a separate fluid line 120, preferably comprising either a metal (e.g. stainless steel hypo-tubing) or polymer (e.g. PVC tubing) material, extending distally and substantially parallel to the arms along side shafts 17a, 17b. In order to minimize the risk of clogging of the lumen 122 at the distal end outlet opening 124 of the fluid line 120, as shown, preferably the distal end 126 of the fluid line 120 is located proximal and adjacent to the distal end of the device 5j and more preferably, proximal to spherical surface portions 42a, 42b of electrodes 25a, 25b, or other tissue treating surfaces of electrodes as the electrode configurations vary.

Also as shown for device 5j, the outlet opening 124 for the fluid line 120 is preferably spaced uniformly between electrodes 25a, 25b such that conductive fluid 24 expelled from the outlet opening 124 may form a fluid coupling comprising the a bridge 27 between the tissue surface 22 and the surface 42a, 42b of each of the electrodes 25a, 25b. If a collar 95 is used with device 5j preferably the collar contains a third C-shaped aperture to accommodate fluid line 120 there through.

In certain embodiments, at least a portion of the length of the two arms (comprising the shafts 17a, 17b and sleeves 82a, 82b) or the two arms and fluid line 120 of device 5j may be located and housed within the cavity 132, typically a lumen, of an elongated hollow tubular enclosure 128 as shown in FIG. 49. The elongated tubular enclosure 128 may or may not be connected to the handle portions 20a, 20b. Where the tubular enclosure is not connected to the handle portions 20a, 20b, similar to collar 95, the tubular enclosure 128 may be configured to slide along the length of the shafts 17b, 17c as to adjust or vary the location of the enclosure 128 on the shafts 17a, 17b or, alternatively, may be fixed relative to the shafts 17a, 17b by welding, for example.

The elongated tubular enclosure 128 may comprise, for example a wrapping, such as shrink wrap polymer film or shrink wrap polymer tubing, which may be formed and located with the surface of cavity 132 against insulators 90a, 90b upon the application of heat thereto. In this manner, the elongated members shafts 17a, 17b or the shafts 17a, 17b and fluid line 120, are retained in position relative to each other and inhibited from separating relative to each other.

Figure 53:
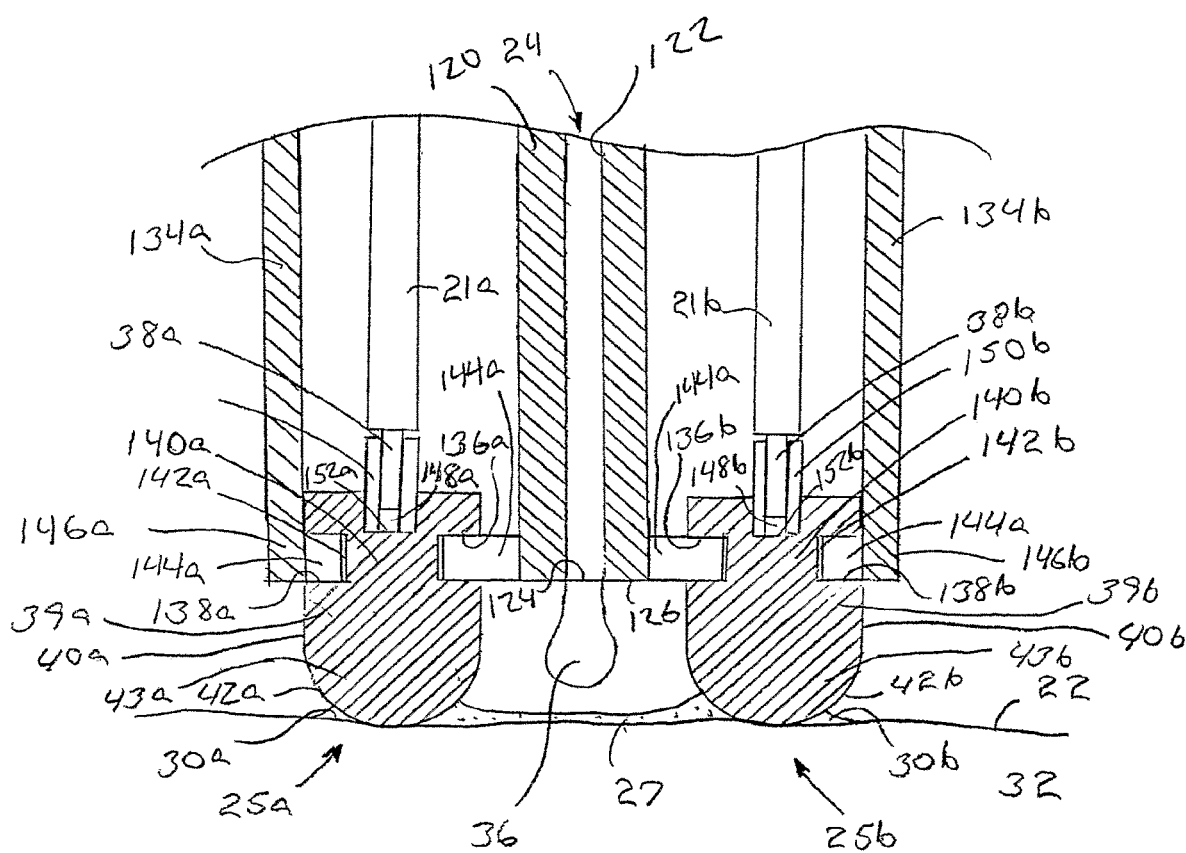
FIG. 53 is a schematic close-up cross-sectional side view of a distal end portion of the device of FIG. 51 assembled with a fluid coupling to a tissue surface of tissue.

Another embodiment of a bipolar device is shown at 5k in FIGS. 51-53. As shown in FIGS. 51 and 53, electrosurgical device 5k preferably includes a housing comprising mating handle portions 20a, 20b and mating elongated shaft portions 134a, 134b forming a hollow shaft. As best shown in FIG. 51, shaft portions 134a, 134b, preferably comprise two semi-circular elongated portions which are connected to handle portions 20a, 20b, respectively, preferably as part of a unitary (i.e. single piece) polymer molding.

As best shown in FIG. 53, electrodes 25a, 25b are preferably assembled directly with shaft portions 134a, 134b adjacent the distal end of shaft portions 134a, 134b. As shown, preferably electrodes 25a, 25b are mechanically assembled adjacent the distal end of shaft portions 134a, 134b via a spool configuration. More specifically, preferably electrodes 25a, 25b comprise locking portions comprising proximal circular flange portions 136a, 136b and distal circular flange portions 138a, 138b separated and connected by circular spindles 140a, 140b there between which form the respective spool configurations.

The circular recesses 142a, 142b formed between the proximal circular flange portions 136a, 136b and distal circular flange portions 138a, 138b provides a receptacle for receiving semi-circular interlocking tab portions 144a, 144b of distal end portions 146a, 146b of shaft portions 134a, 134b.

During assembly, the interlocking tab portions of one of the shaft portions are first located in a portion of the recesses 142a, 142b of electrodes 25a, 25b. In other words, for example, electrodes 25a, 25b may be first assembled with semi-circular interlocking tab portions 144a of distal end portion 146a of shaft portion 134a which then occupy a first semi-circular portion of circular recesses 142a, 142b. Then, once the electrodes 25a, 25b have been properly seated with respect to the first shaft portion, here 134a, the interlocking tab portions of the second shaft portion, here 144b of shaft 134b, are located in the remaining semi-circular portion of circular recesses 142a, 142b. After the electrodes 25a, 25b have been properly seated with respect to both shaft portions 134a, 134b and all remaining components are properly located, the shaft portions 134a, 134b and handle portions 20a, 20b may be assembled to one another by use of, for example an adhesive (e.g. cyanoacrylate) or welding.

As best shown in FIG. 53, electrodes 25a, 25b of device 5k preferably comprise spherical portions 43a, 43b and a corresponding spherical surface portions 42a, 42b located at the distal end of the device which provided a smooth, blunt contour outer surface. More specifically, as shown, the spherical portions 43a, 43b and spherical surface portion 42a, 42b further provide a domed, hemisphere (i.e. less than a full sphere) and hemispherical surface portion comprising preferably about 180 degrees. Also as shown in FIG. 53, electrodes 25a, 25b preferably also comprise cylindrical portions 39a, 39b and a corresponding cylindrical surface portions 40a, 40b located proximal and adjacent to the spherical portions 43a, 43b and spherical surface portions 42a, 42b, respectively.

Electrodes 25a, 25b of device 5k are preferably coupled to the generator 6 via wire conductors 38a, 38b of insulated wires 21a, 21b. At their distal ends, conductors 38a, 38b may be coupled to electrodes 25a, 25b by means of first being inserted into the lumens 148a, 148b of hollow metal tubes 150a, 150b, such as hypo-tubes, then crimping the tubes 150a, 150b. The tubes 150a, 150b are then preferably inserted and retained in proximal end receptacles 152a, 152b of electrodes 25a, 25b by an interference fit. Alternatively, tubes 150a, 150b may be eliminated and wire conductors 38a, 38b may be coupled to electrodes 25a, 25b by welding, soldering, mechanical fasteners or other suitable methods.

For device 5k conductive fluid 24 is preferably provided by means of a lumen 122 of a separate fluid line 120, preferably comprising either a metal (e.g. stainless steel hypo-tubing) or polymer (e.g. PVC tubing) material, extending distally and substantially parallel within the lumen of the shaft comprising shaft portions 134a, 134b.

Similar to device 5j, in order to minimize the risk of clogging of the lumen 122 at the distal end outlet opening 124 of the fluid line 120, as shown, preferably the distal end 126 of the fluid line 120 is located proximal to the distal end of the device 5k and more preferably, proximal to spherical surface portions 42a, 42b and cylindrical surface portions 40a, 40b of electrodes 25a, 25b, or other tissue treating surfaces of electrodes as the electrode configurations vary.

Also similar to device 5j, for device 5k the outlet opening 124 for the fluid line 120 is preferably spaced uniformly between electrodes 25a, 25b such that conductive fluid 24 expelled from the outlet opening 124 may form a fluid coupling comprising the a bridge 27 between the tissue surface 22 and the surface 42a, 42b of each of the electrodes 25a, 25b.

Figure 54:
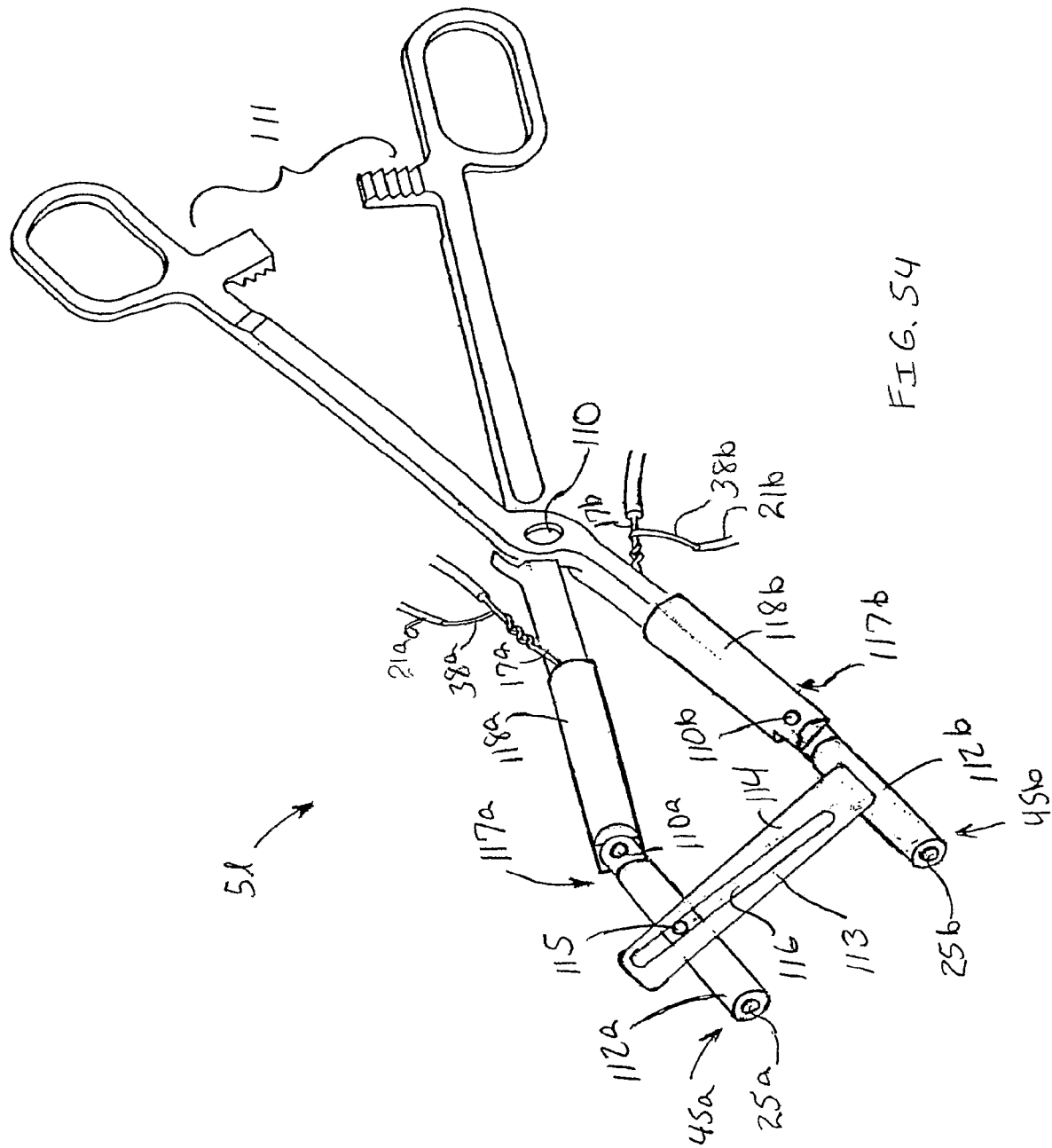
FIG. 54 is a schematic perspective view of an alternative electrosurgical device according to the present invention.

The effect of the bipolar devices of the present invention on tissue may be varied by changing the separation distance between the contact elements. Consequently, as shown in FIG. 54, in contrast to certain other embodiments which the separation distance is unadjustable, bipolar device 5i provides an adjustment mechanism for changing the separation distance (either increasing or decreasing) between the electrodes 25a, 25b. As shown in FIG. 54, the changing of the separation distance between the electrodes 25a, 25b is provided by a scissors type adjustment mechanism with two arms 117a, 117b hinged relative to one another in the middle on a pivot 110 preferably comprising a pin. Device 5l may also comprise a latching mechanism 111 which incrementally fixes the position of the electrodes 25a, 25b relative to one another during tissue treatment by increasing or decreasing the separation distance.

Furthermore, as shown, the arms 117a, 117b themselves are preferably hinged on pivots 110a and 110b, also preferably comprising pins, which divide the arms 117a, 117b into proximal arm portions 118a, 118b and distal arm portions 112a, 112b. Distal arm portions 112a, 112b are preferably connected by a linkage 113 which keeps distal arm portions 112a, 112b and electrodes 25a, 25b substantially parallel to one another with use of the device 5l. As shown, linkage 113 comprises a bar 114 fixed to distal arm portion 112b and having an elongated opening 116 therein. Linkage also comprises a pin 115 fixed to distal arm portion 112a which moves along and within the opening 116 during use of the device 5l with the changing of the separation distance between electrodes 25a, 25b. For device 5l, tip portions 45a, 45b may particularly comprise the configuration disclosed with device 5i.

Figure 55:
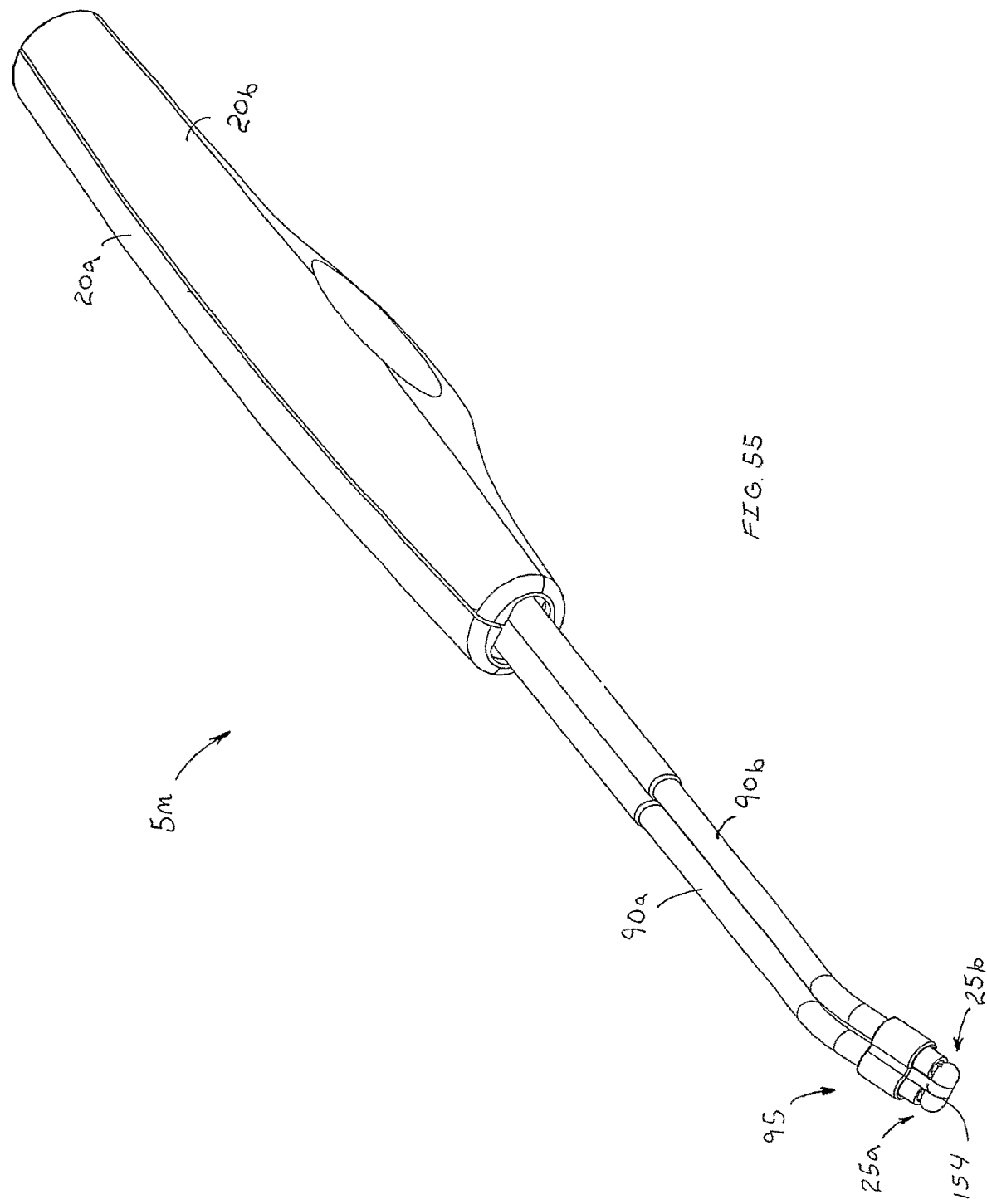
FIG. 55 is a schematic perspective view of an alternative electrosurgical device according to the present invention.
Figure 56:
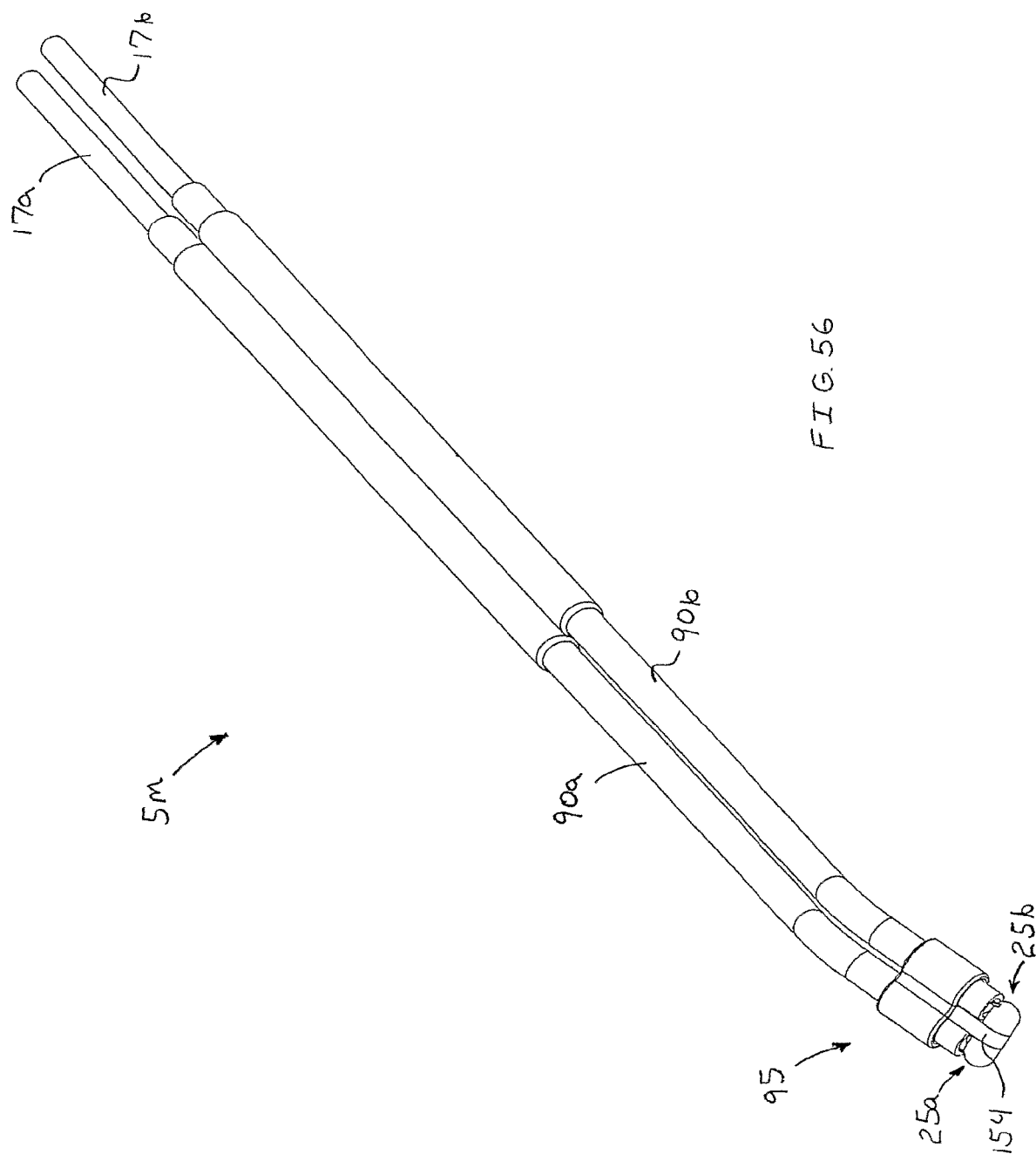
FIG. 56 is a schematic close-up perspective view of the arms of the device of FIG. 55.

Another embodiment of a bipolar device is shown at 5m in FIGS. 55-58. As best shown in FIGS. 55 and 56 and similar to device 5i, electrosurgical device 5m preferably includes two stationary, immobile arms comprising rigid, self-supporting, hollow shafts 17a, 17b. Shafts 17a, 17b for device 5m preferably comprise thick walled hypo-tubing providing sufficient rigidity to maintain their form during use of the device without kinking or significant bending. In certain embodiments, shafts 17a, 17b may be hand malleable.

Figure 57:
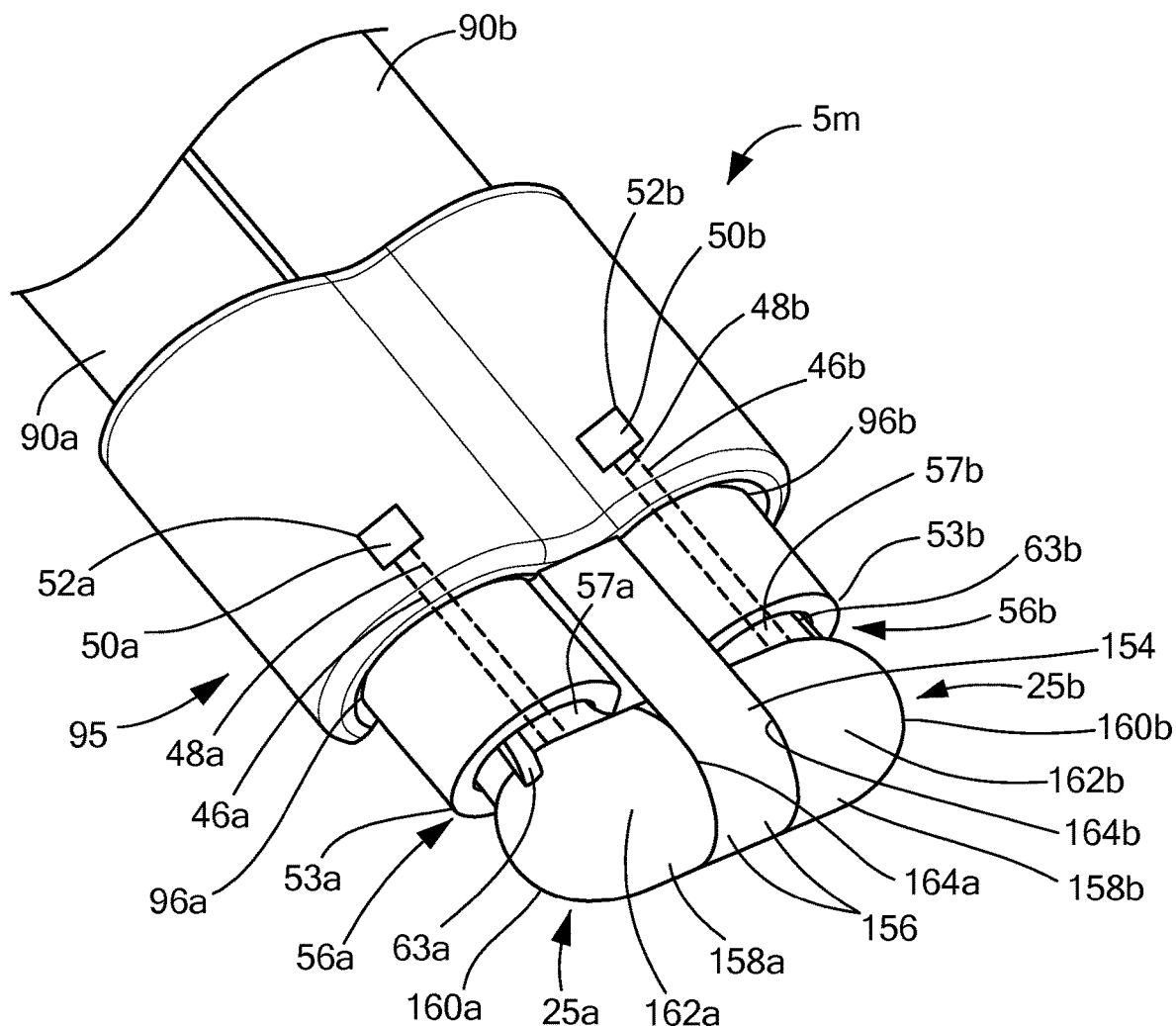
FIG. 57 is a schematic close-up perspective view of a distal end portion of the device of FIG. 55.
Figure 58:
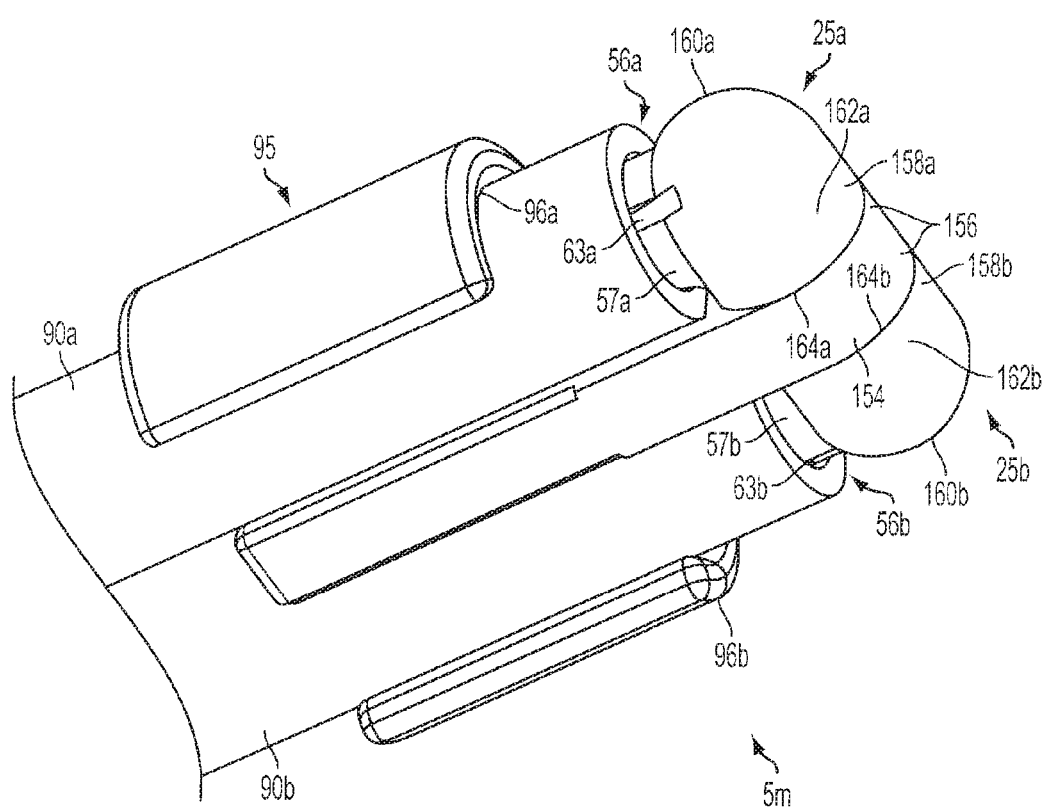
FIG. 58 is a schematic close-up perspective view of a distal end portion of the device of FIG. 55.
Figure 59:
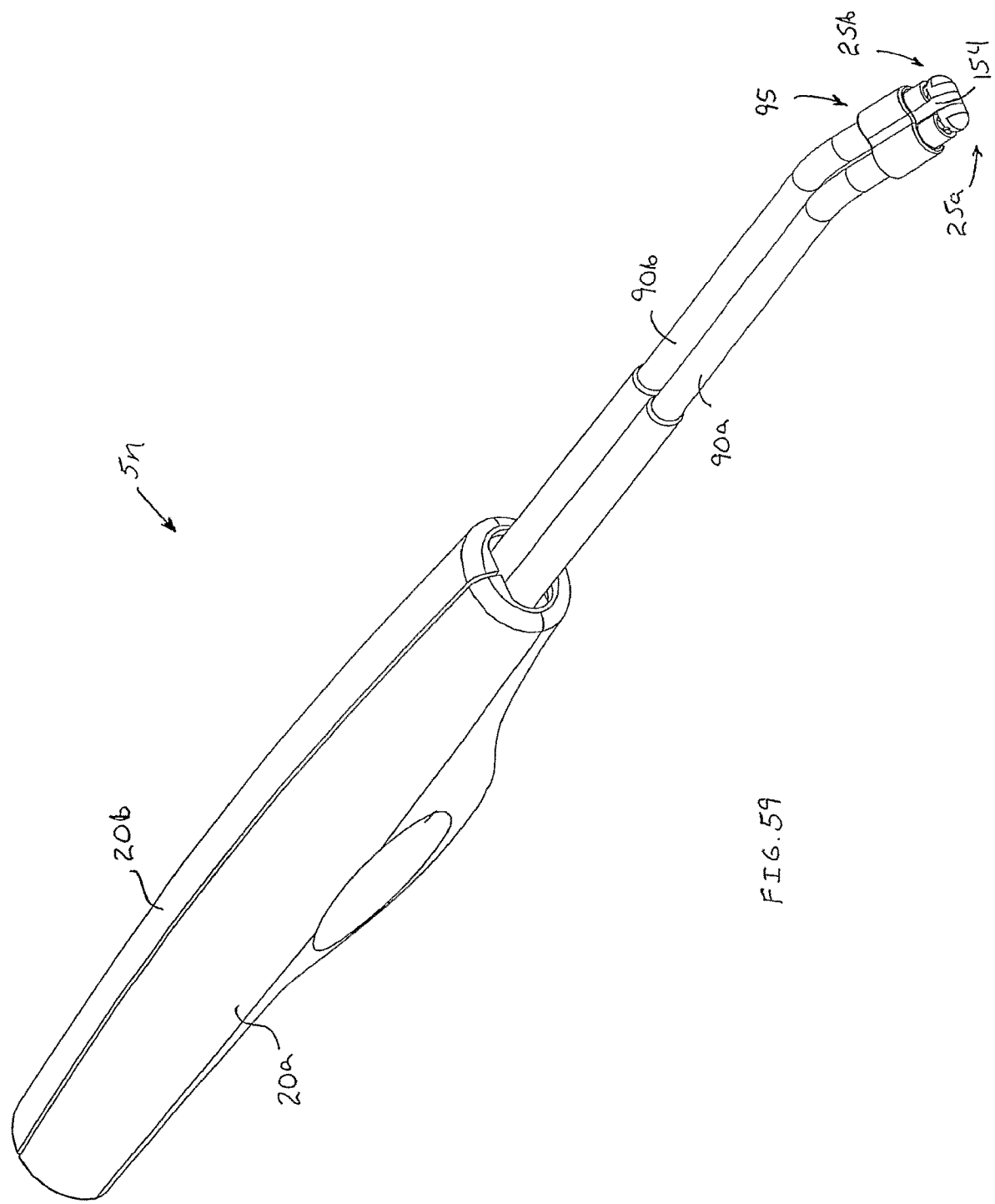
FIG. 59 is a schematic perspective view of an alternative electrosurgical device according to the present invention.
Figure 60:
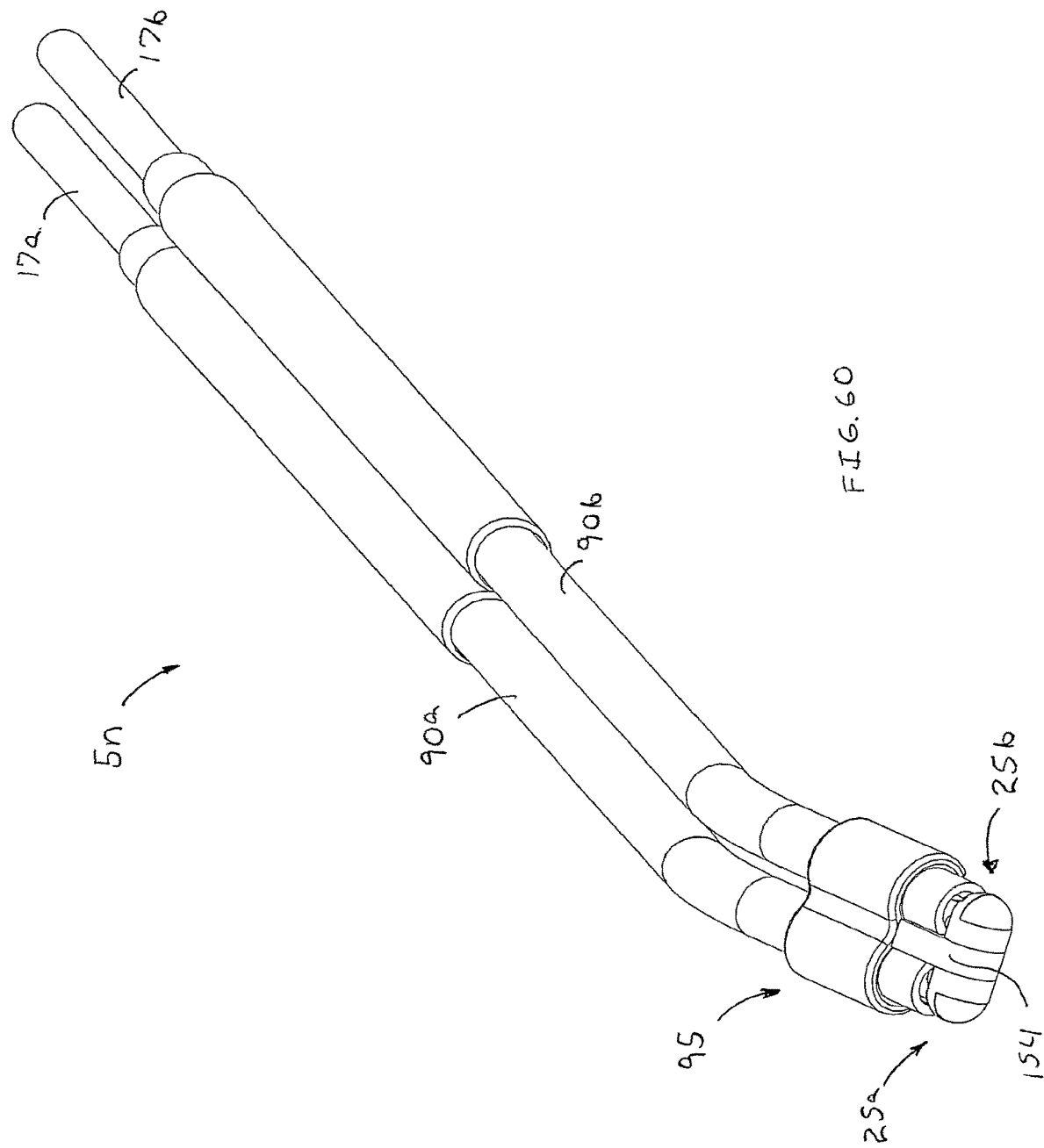
FIG. 60 is a schematic close-up perspective view of the arms of the device of FIG. 59.
Figure 61:
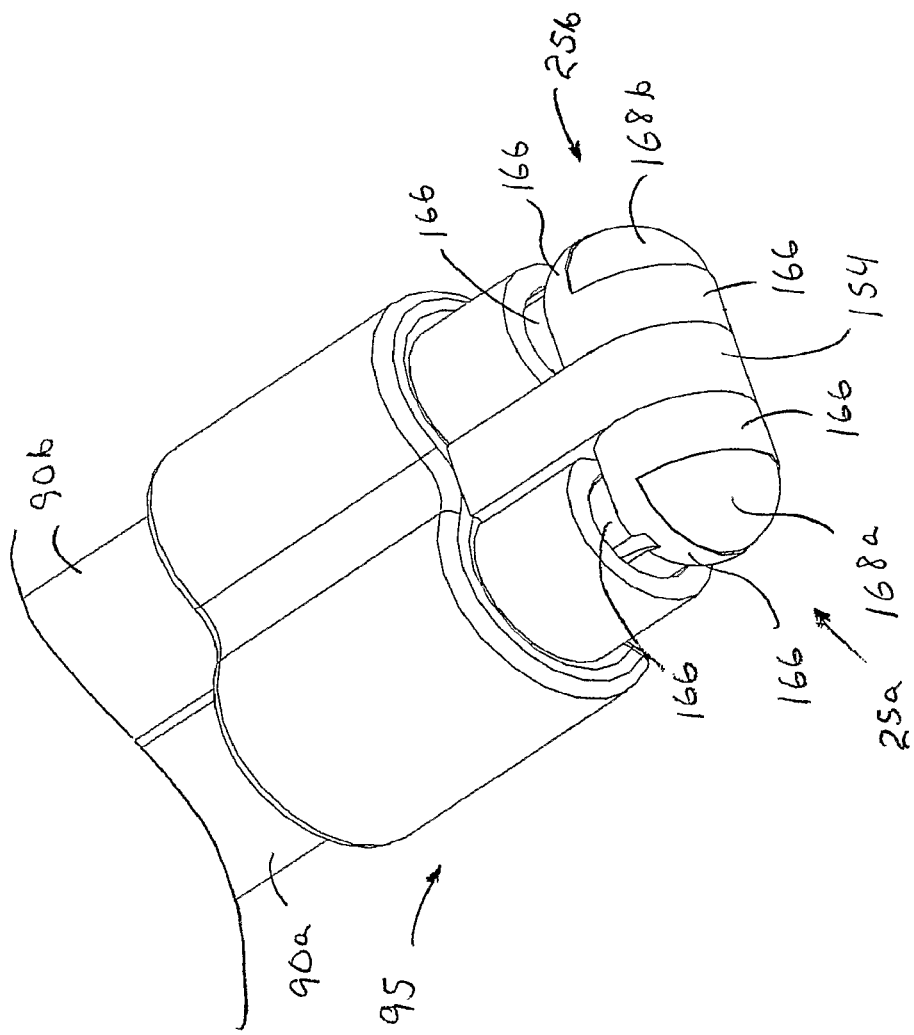
FIG. 61 is a schematic close-up perspective view of a distal end portion of the device of FIG. 59.
Figure 62:
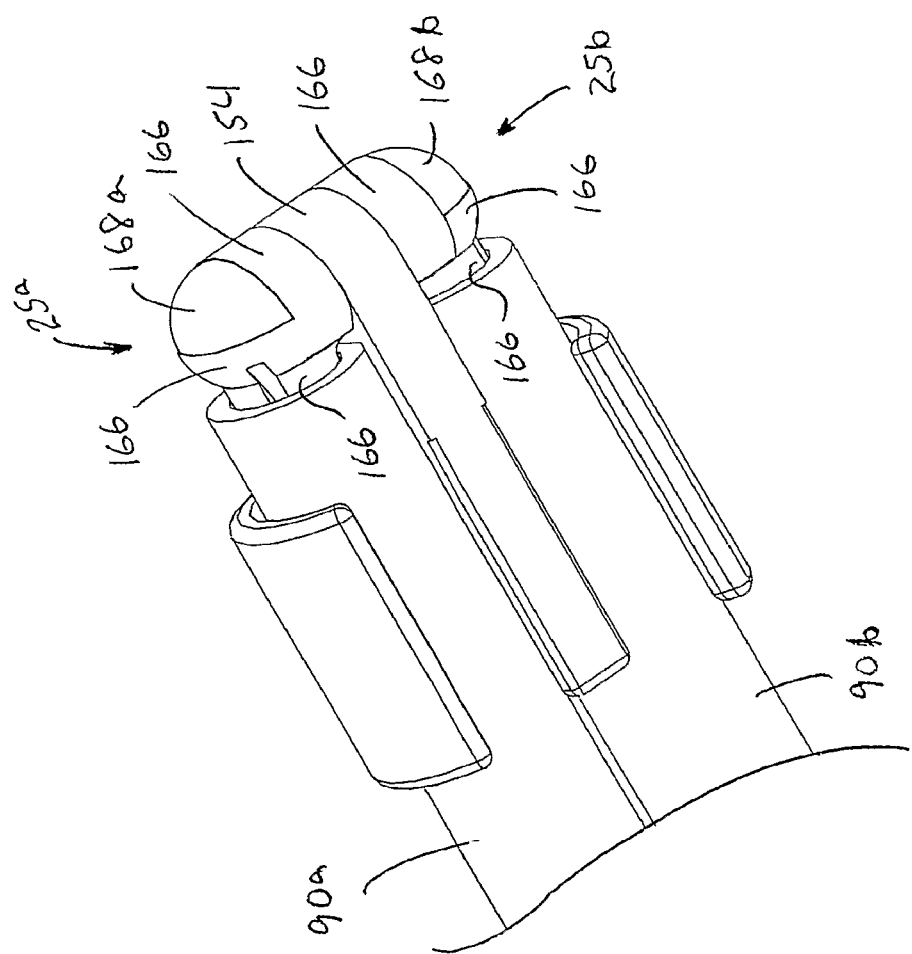
FIG. 62 is a schematic close-up perspective view of a distal end portion of the device of FIG. 59.

As shown throughout FIGS. 55-58 and similar to device 5i, preferably the arms of device 5m (comprising shafts 17a, 17b) are retained in position relative to each other by a mechanical coupling device comprising a collar 95 and inhibited from separating relative to each other. Also as shown throughout FIGS. 55-58, collar 95 is preferably located on a distal portion of the arms. More preferably, the collar 95 is located adjacent the distal ends 53a, 53b of the shafts 17a, 17b. As best shown in FIGS. 57 and 58, preferably the collar 95 comprises two apertures 96a, 96b, shown as comprising C-shapes, configured to receive a distal end portion of the shafts arms. Once the collar 95 is mechanically connected to the shafts 17a, 17b, preferably by a snap-fit or slide-through connection, the location of the collar 95 may be further fixed relative to the shafts 17a, 17b by, for example, adhesive bonding the collar 95 to shaft insulators 90a, 90b. Such adhesive bonding may be accomplished, for example, either by use of a separate adhesive or autogenic bonding of the collar 95 to the insulators 90a, 90b by, for example, welding such as ultrasonic welding.

Collar 95 comprises an electrically insulating (dielectric) material. In some embodiments, the electrically insulating material for collar 95 may comprise a polymer, either thermoplastic or thermoset, reinforced or unreinforced, filled or unfilled. Exemplary polymer materials include, but are not limited to, polyacetal (POM), polyamide (PA), polyamideimide (PAI), polyetheretherketone (PEEK), polyetherimide (PEI), polyethersulfone (PES), polyimide (PI), polyphenylenesulfide (PPS), polyphthalamide (PPA), polysulfone (PSO), polytetrafluoroethylene (PTFE) and syndiotactic polystyrene (SPS). More preferably, the electrically insulating polymer comprises either a liquid crystal polymer and, more particularly, an aromatic liquid crystal polyester which is reinforced with glass fiber, such as Vectra® A130 from Ticona, or Ultern® 10% glass filled polyetherimide from the General Electric Company. Exemplary reinforcement materials for polymers include, but are not limited to, glass fibers and boron fibers. Exemplary filler materials for polymers include mica, calcium carbonate and boron nitride. Reinforcement materials for the polymer material may be preferable for increased strength while filler materials may be preferable for increased heat resistance and/or thermal conductivity. Still other electrically insulating materials for collar 95 may a ceramic such as boron nitride.

As discussed above with reference to device 5i and FIG. 48, the fluid coupling to tissue for device 5i may comprise a conductive fluid bridge 27 between electrodes 25a, 25b which rests on the surface 22 of the tissue 32 and forms a shunt between the electrodes 25a, 25b. As discussed above, a certain amount of RF energy may be diverted from going into the tissue 32 and actually pass between the electrodes 25a, 25b, via the conductive fluid bridge 27. This loss of RF energy may slow down the process of coagulating tissue and producing the desired hemostasis or aerostasis of the tissue. Also as discussed above, the loss of RF energy through the bridge 27 may either be reduced or eliminated because all the fluid 24 of bridge 27 boils off or a large fraction of boiling creates enough disruption in the continuity of the bridge 27 to disrupt the electrical circuit through the bridge 27. Thus, as indicated above one control strategy of the present invention is to reduce the presence of a conductive fluid shunt by increasing the % boiling of the conductive fluid.

Rather than increasing the % boiling of the conductive fluid bridge 27 to reduce the presence of a fluid shunt between the electrodes 25a, 25b, in certain applications it may be advantageous to provide the electrosurgical device with a dam between the electrodes 25a, 25b which reduces, and preferably prevents, the formation of the conductive fluid bridge 27 between the electrodes 25a, 25b.

As best shown in FIGS. 57 and 58, collar 95 of device 5m preferably further includes a substantially flat, blade-shaped electrical insulator spacer portion 154 located laterally between the electrodes 25a, 25b. In addition to keeping the electrodes 25a, 25b separated at a predetermined minimum separation distance (as dictated by the thickness of spacer portion 154), spacer portion 154 also provides a dam between electrodes 25a, 25b which reduces, and preferably prevents, the formation of the conductive fluid bridge 27 between the electrodes 25a, 25b.

Also as best shown in FIGS. 57 and 58, the distal end surface 156 of spacer portion 154 preferably follows the contour of the adjacent distal end surfaces 158a, 158b of the electrodes 25a, 25b such that the distal end surface 156 of spacer portion 154 is substantially flush, and preferably flush, with the adjacent distal end surfaces 158a, 158b of electrodes 25a, 25b. In this manner, the spacer portion 156 and the electrodes 25a, 25b are better configured to slide along the surface of tissue given there are no raised or recessed edges created between the distal end surface 156 of spacer portion 154 and the adjacent distal end surfaces 158a, 158b of the electrodes 25a, 25b which could impair sliding movement.

Similar to device 5c, electrodes 25a, 25b of device 5m are preferably assembled adjacent the distal ends 53a, 53b of shafts 17a, 17b by connector portions, preferably comprising shank portions 46a, 46b which connect the remainder of the electrodes 25a, 25b to shafts 17a, 17b. Among other things, the connector portion of the electrodes 25a, 25b are preferably configured to form a connection with a mating connector portion of the shafts 17a, 17b. Also similar to device 5c, preferably shank portions 46a, 46b of device 5m are configured to extend into cavities 50a, 50b of shafts 17a, 17b which comprise cylindrical receptacles and provide the mating connector portions for shank portions 46a, 46b. Also similar to device 5c, preferably surfaces 48a, 48b of shank portions 46a, 46b of device 5m are configured to mate against and form an interference fit with surfaces 52a, 52b of cavities 50a, 50b to provide the connection.

Similar to device 5c, shank portions 46a, 46b of device 5m are preferably cylindrical and located proximal and adjacent to neck portions 56a, 56b. As best shown in FIGS. 57 and 58, neck portions 56a, 56b comprise cylindrical portions 57a, 57b preferably having a cross-sectional dimension, here diameter, greater than the cross-sectional dimension, here also diameter, of shank portions 46a, 46b. In this manner, similar to device 5c, in certain embodiments, the proximal end of neck portions 56a, 56b of device 5m may be located adjacent and in contact with distal ends 53a, 53b of shafts 17a, 17b.

As best shown in FIGS. 57 and 58, similar to recess 64 of device 5c, electrodes 25a, 25b of device 5m preferably comprises at least one recess 63a, 63b which provides an elongated fluid flow channel and outlet for the distribution of fluid 24.

Electrodes 25a, 25b of device 5m preferably comprise an enlarged head portion. Each enlarged head portion preferably comprises a side hemispherical portion 160a, 160b with a hemispherical surface comprising preferably about 180 degrees. As best shown in FIGS. 57 and 58, preferably the hemisphere portions 160a, 160b are arranged facing away from one another in outwardly facing opposing relation on opposite sides of the device. The hemispherical portions 160a, 160b are preferably located laterally of transversely orientated cylindrical medial transition portions 162a, 162b which preferably provide the smooth transition between the hemispherical portions 160a, 160b and spacer portion 154 of collar 95. As shown electrodes 25a, 26b and spacer portion 154 may comprise abutting flat surfaces 164a, 164b which are arranged facing towards and opposing one another. In alternative embodiments, medial transition portions 162a, 162b of electrodes 25a, 25b may be eliminated resulting in the head portion of electrodes 25a, 25b comprising just hemispherical portions 160a, 160b with a hemispherical surfaces comprising preferably about 180 degrees.

In certain embodiments spacer portion 154 may comprise a thickness in the range between and including about 0.5 mm to 10 mm, or in any 0.1 mm increment or range therebetween, to provide a separation distance between the electrodes 25a, 25b of such. For example, spacer portion 154 comprises a thickness in the range between and including about 1.5 mm to 4 mm.

As an alternative to adjusting the separation distance between the electrodes 25a, 25b by changing the thickness of the spacer portion 154, portions of electrodes 25a, 25b may be coated with an thin (e.g. 0.01 to 0.5 mm) electrically insulating coating comprising, for example, a polymer or ceramic material. As shown in FIGS. 59-62, a portion of the electrodes 25a, 25b for device 5n, here the neck portions 56a, 56b, medial transition portions 162a, 162b and approximately half of each hemisphere portion 160a, 160b of the enlarged head portion are shown with an electrically insulating coating 166 thereon. As a result, the active tissue treating electrode surface is now limited to about quarter-sphere surfaces 168a, 168b and the separation distance between the tissue treating electrode surfaces has been increased by the thickness of the medial transition portions 162a, 162b of electrodes 25a, 25b.

Figure 63:
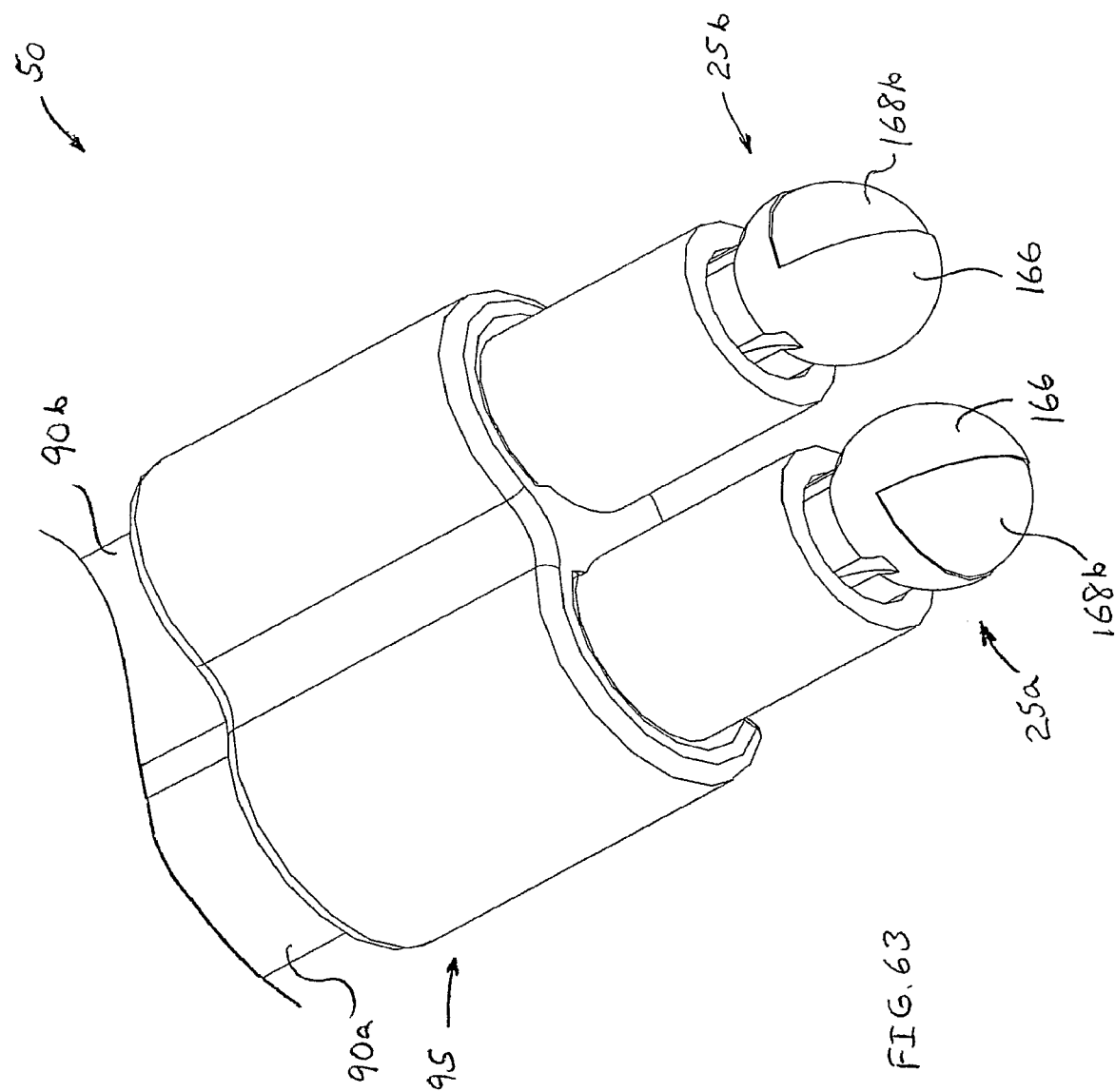
FIG. 63 is a schematic close-up perspective view of a distal end portion of an alternative electrosurgical device according to the present invention.
Figure 64:
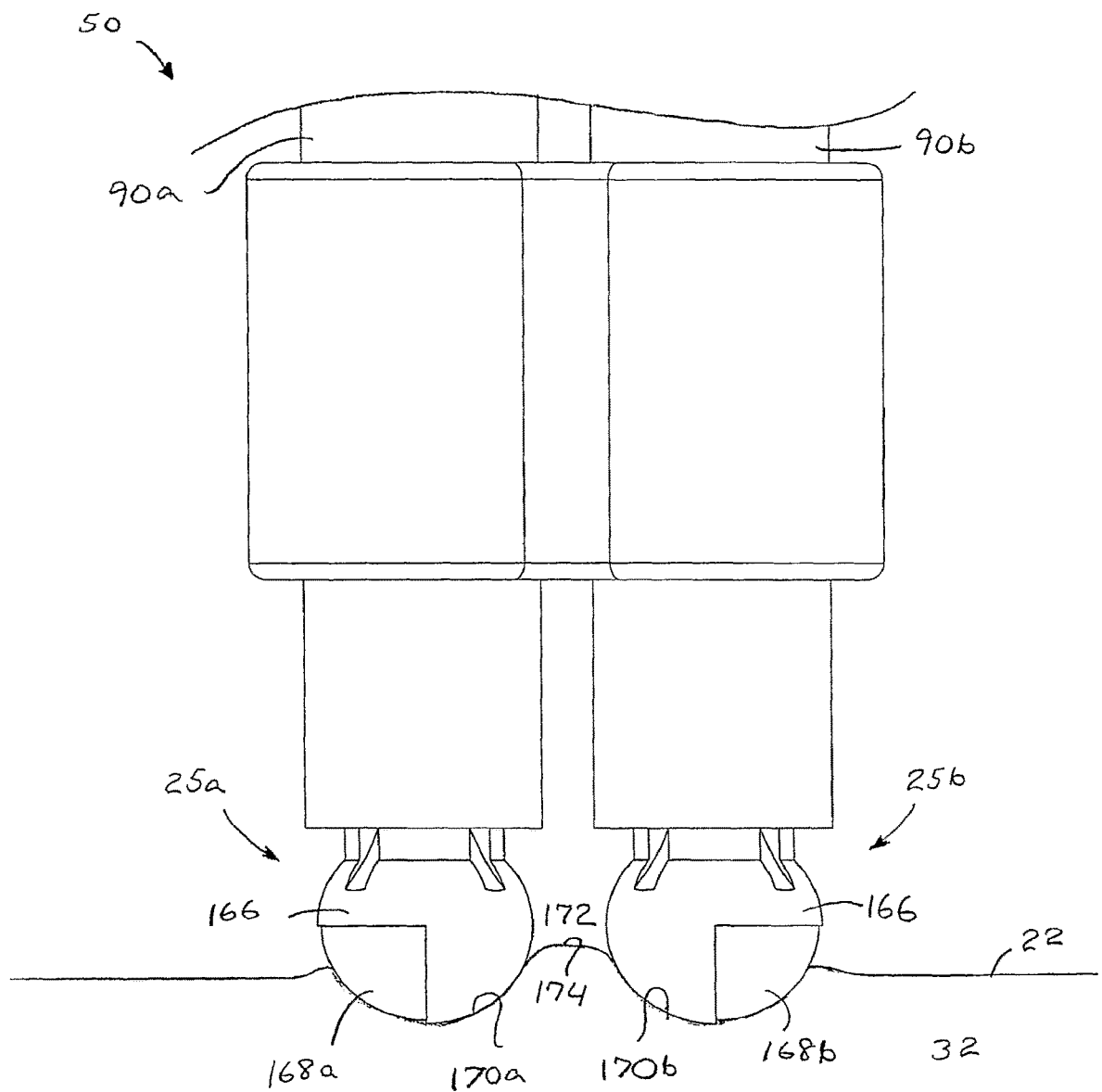
FIG. 64 is a schematic close-up perspective view of a distal end portion of the device of FIG. 63 with tissue.
Figure 65:
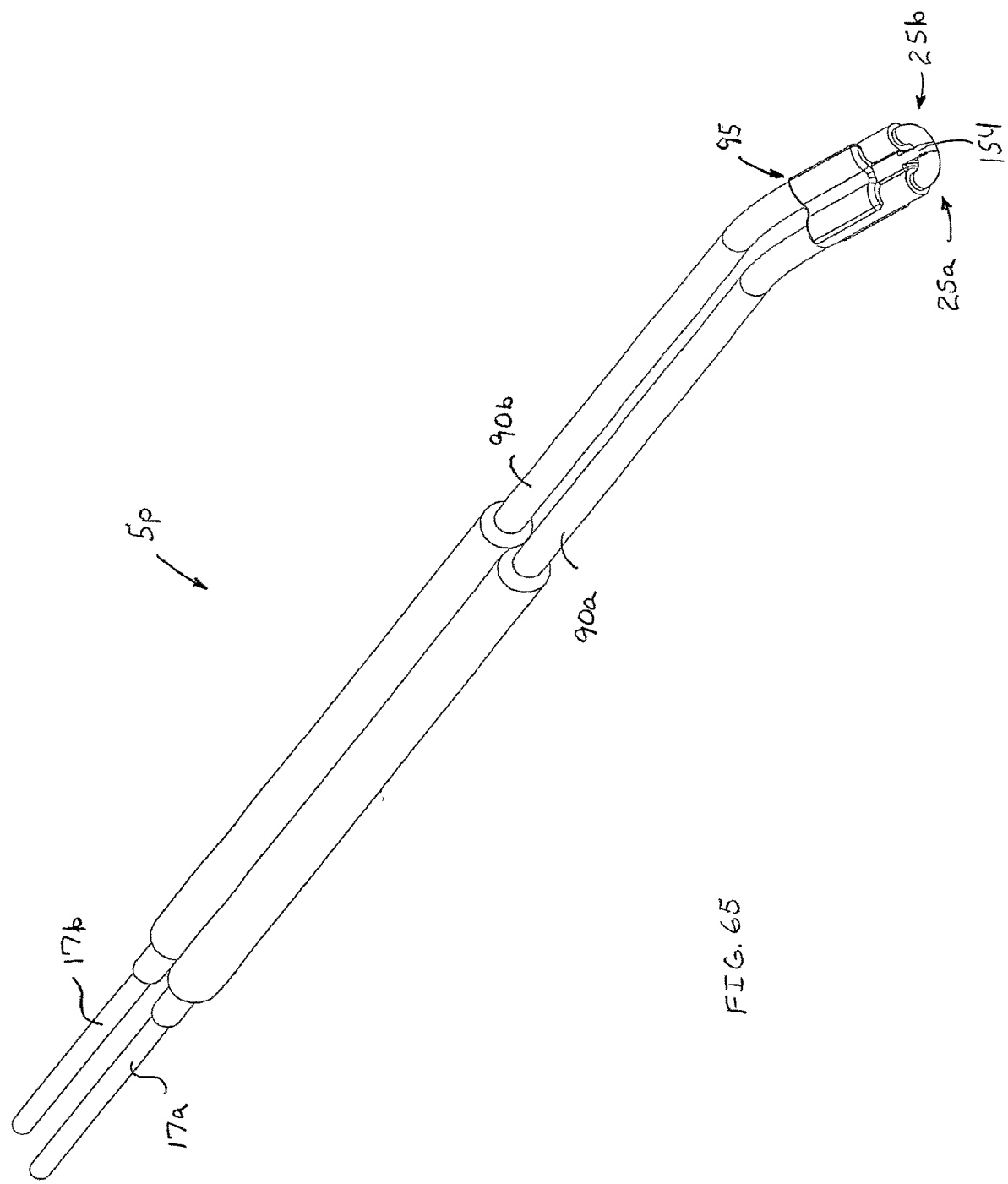
FIG. 65 is a schematic close-up perspective view of the arms of an alternative electrosurgical device according to the present invention.

Another embodiment of a bipolar device is shown at 5o in FIGS. 63-64. Similar to device 5n, the active tissue treating electrode surface of electrodes 25a, 25b may be limited to about quarter-sphere surfaces 168a, 168b (about 90 degrees) with the other surfaces of the electrode extending from the distal end of shaft insulators 90a, 90b having electrically insulating coating 166 thereon. However, different from device 5n, the enlarged head portion of the electrodes 25a, 25b of device 5o comprise two substantially circular spheres (i.e. except where they join to neck portions 56a, 56b). The spheres may have any suitable diameter. However, the spheres preferably have a diameter in the range between and including about 0.5 mm to about 7 mm. More preferably the spheres have a diameter in the range between and including about 1.0 mm to about 4 mm. Even more preferably, the spheres have a diameter in the range between and including about 1.5 mm to about 3 mm. Where coating 166 is not located thereon, the active electrical surface of the spheres is about 260 degrees.

Also different from device 5n, collar 95 of device 5o does not include spacer portion 154. With device 5o, electrodes 25a, 25b are separated by an air gap therebetween. As a result, as shown in FIG. 64, when electrodes 25a, 25b of device 5o are pressed against the surface 22 of tissue 32 and the tissue 32 against electrodes 25a, 25b compresses and forms recesses 170a, 170b, device 5o is configured to allow tissue 32 located adjacent the gap 172 between the electrodes 25a, 25b to form a tissue protuberance 174 there into with downward slopes into the recess 170a, 170b. Since fluid 24 which may exist between the electrodes 25a, 25b will tend to flow with gravity down the slopes of the tissue protuberance 174 and into the adjoining recesses 170a, 170b, the possibility of formation of a conductive fluid bridge 27 between electrodes 25a, 25b is reduced. Furthermore, even if a conductive fluid bridge 27 where to form between the electrodes 25a, 25b (e.g. where electrodes 25a, 25b of device 5o are not pressed against tissue 32 significantly enough to form recesses 170a, 170, the coating 166 on the inner facing surfaces of the electrodes 25a, 25b reduces the possibility such a bridge would be electrified by electrodes 25a, 25b directly.

Figure 66:
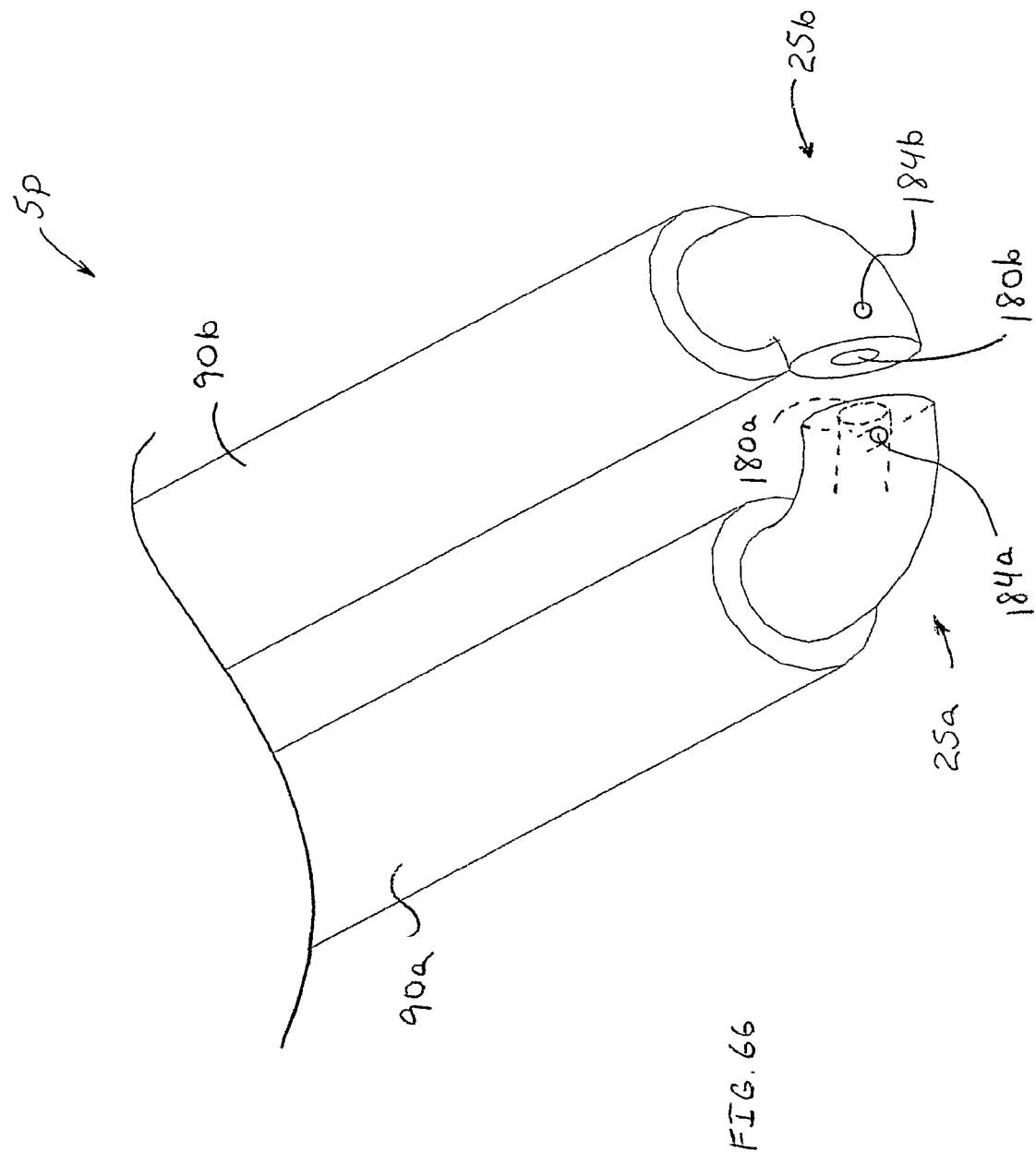
FIG. 66 is a schematic close-up perspective view of a distal end portion of the arms of the device of FIG. 65 with the collar removed.

Another embodiment of a bipolar device is shown at 5p in FIGS. 65-69. As best shown in FIG. 66, the electrodes 25a, 25b now comprise a hollow metal tubes. More specifically, the distal end portion of the tubes comprise about a 90 degree bend (within about ±5 degrees) forming two right angle elbows and which curves the distal end portions towards each other as they extend distally. Furthermore, the distal ends of the tubes are arranged facing towards and opposing one another. Consequently, the electrodes 25a, 25b are substantially mirror images of each other.

As shown in FIG. 66, collar 95 has been removed to better show that preferably the electrodes 25a, 25b comprise circular, stainless steel hypo-tubing. Where the electrodes 25a, 25b comprise separate pieces from shafts 17a, 17b, electrodes 25a, 25b of device 5p are preferably connected to shafts 17a, 17b by interference fit of the inner diameter of the shafts 17a, 17b with the inner diameter of the electrodes 25a, 25b. However, in order to minimize the number of components and assembly thereof, preferably a single piece of continuous tubing provides both the shaft and the electrode. In other words, as shown, preferably the electrodes 25a, 26b are provided by the same piece of tubing used for shafts 17a, 17b.

Figure 67:
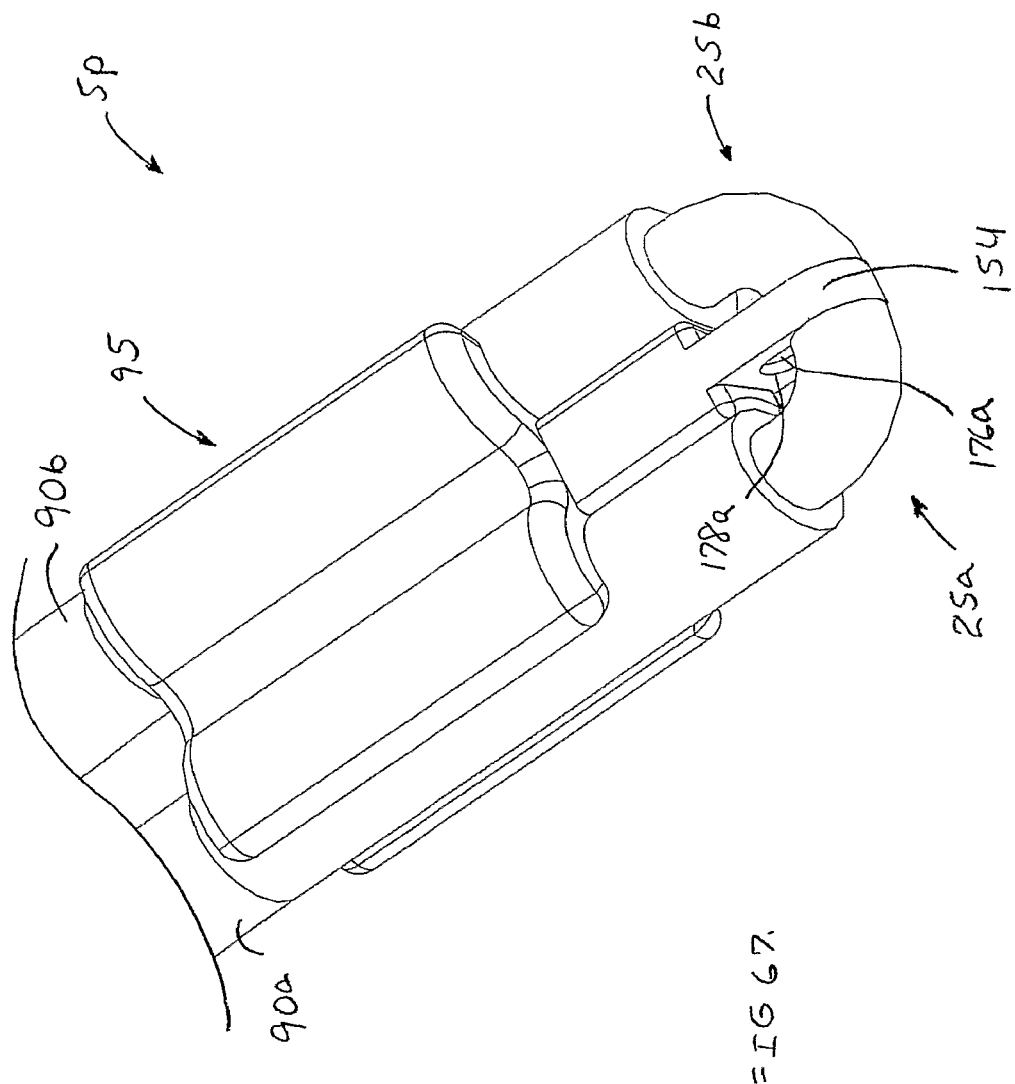
FIG. 67 is a schematic close-up perspective view of a distal end portion of the device of FIG. 65.
Figure 68:
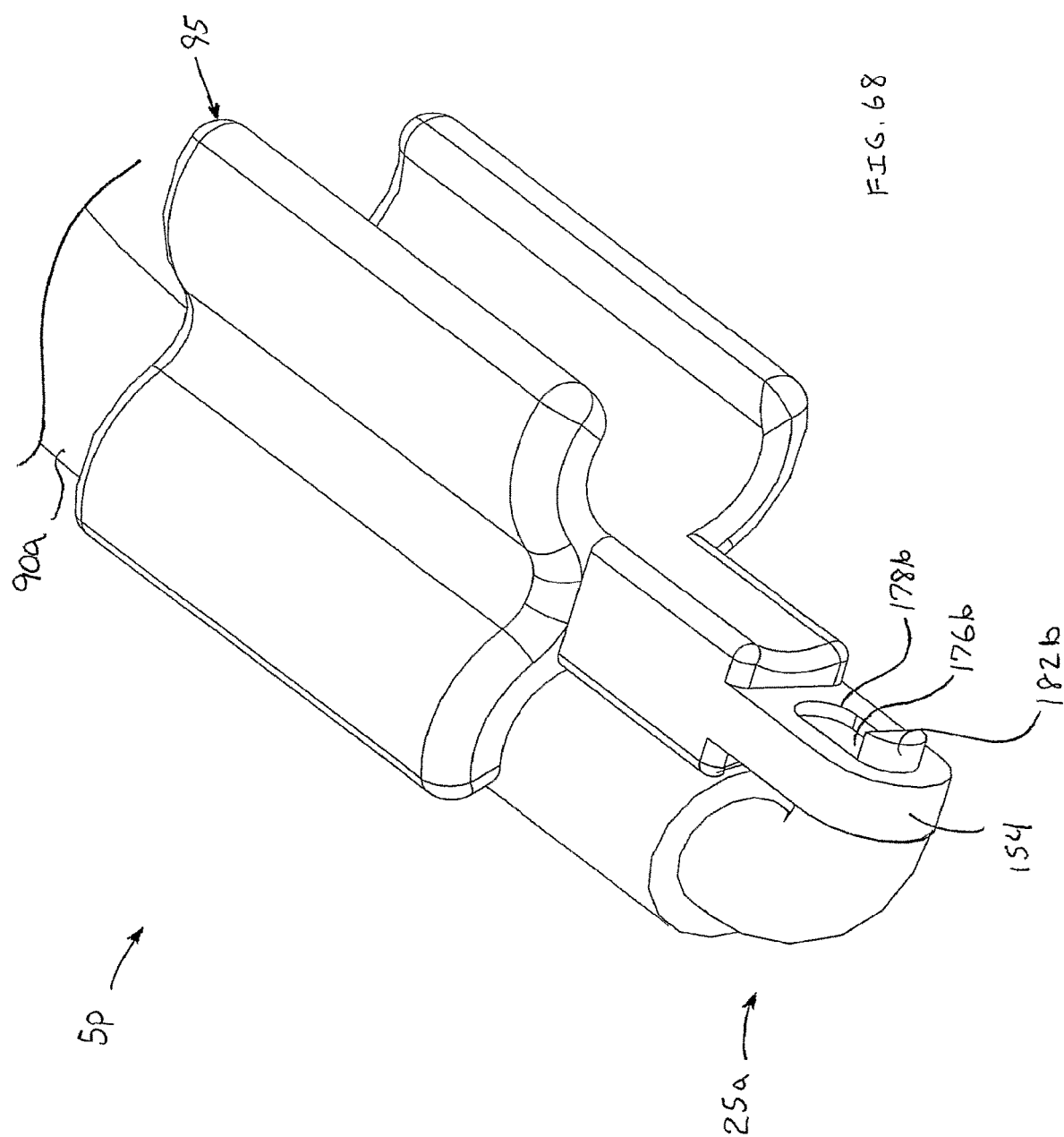
FIG. 68 is a schematic close-up perspective view of a distal end portion of the device of FIG. 65 with one arm removed.
Figure 69:
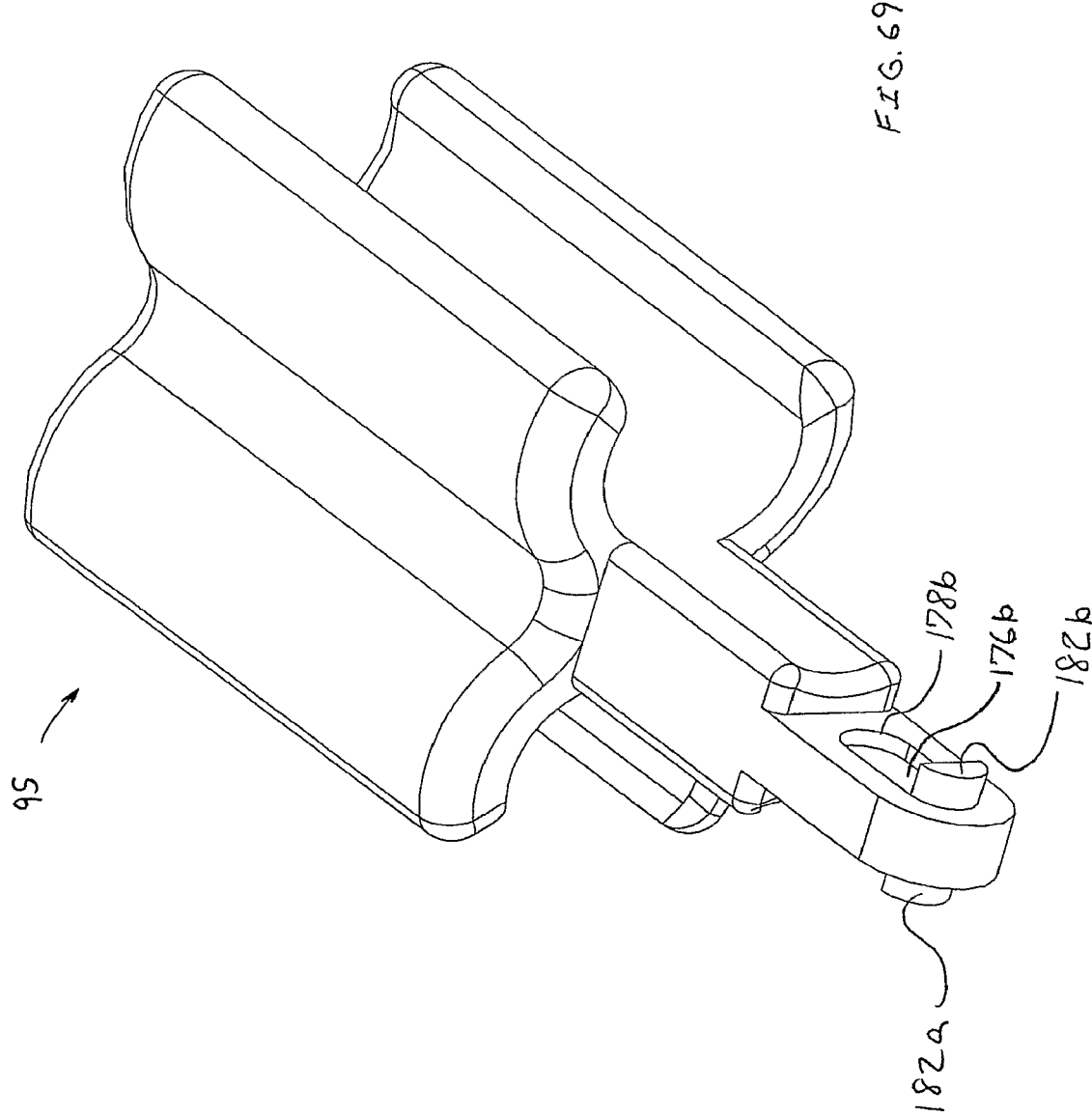
FIG. 69 is a schematic close-up perspective view of the collar of the device of FIG. 65.

As best shown in FIGS. 67-69, preferably device 5p includes a collar 95 which includes an electrical insulator spacer portion 154 located laterally between the electrodes 25a, 25b. Furthermore, spacer portion 154 preferably includes at least one recess 176a, 176b which provides an elongated fluid flow channel and a portion of the fluid passage for the distribution of fluid 24 from openings 178a, 178b. As shown, both the distal end openings 180a, 180b of the tubes and openings 178a, 178b of recesses 176a, 176b are positioned at a location substantially inaccessible to direct contact with tissue or otherwise configured away from direct contact with tissue as to not become occluded by tissue with use of device 5p.

Preferably spacer portion 154 includes protrusions 182a, 182b, and more specifically semi-circular protrusions configured to fit into distal end openings 180a, 180b and at least partially occlude openings 180a, 180b. In this manner electrodes 25a, 25b are retained from movement relative to spacer 154, as well as the rest of collar 95.

In certain embodiments, in order that heat may be transferred away from electrodes 25a, 25b by spacer portion 154, preferably the material for collar 95 has a thermal conductivity $k_{tc}$ at 300° K (Kelvin) equal or greater than about 0.01 watt/cm° K. More preferably, the material for collar 95 has a thermal conductivity $k_{tc}$ at 300° K (Kelvin) equal or greater than about 0.16 watt/cm° K. Even more preferably, the material for collar 95 has a thermal conductivity $k_{tc}$ at 300° K (Kelvin) equal or greater than about 0.35 watt/cm° K.

The use of openings 178a, 178b of recesses 176a, 176b for the distribution of fluid 24 may be preferred to at least one fluid exit opening 184a, 184b which may be provided on the distal end side of electrodes 25a, 25b proximal to the distal end (see FIG. 66), particularly in deep tissue crevices where tissue can occlude fluid flow from openings 184a, 184b. However, as shown in FIGS. 70-71 for device 5q, where fluid exit openings 184a, 184b are positioned at a location substantially inaccessible to direct contact with tissue or otherwise configured away from direct contact with tissue as to not become occluded by tissue (such as slots shown on the inner side wall of the electrodes 25a, 25b adjacent the inner radius of the elbow bend and distal end of the electrode), the openings 184a, 184b may be equally effective as openings 178a, 178b.

Figure 70:
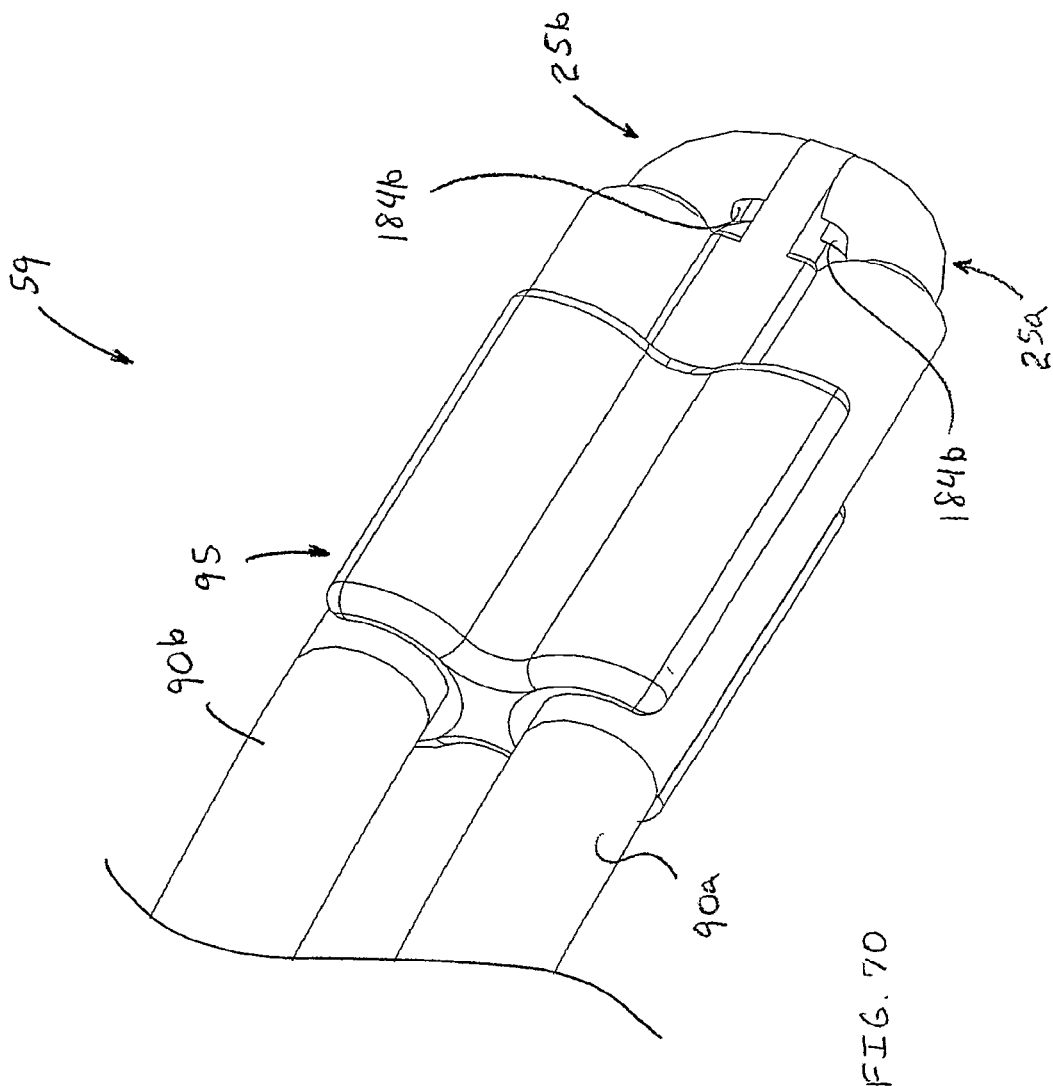
FIG. 70 is a schematic close-up perspective view of a distal end portion of an alternative electrosurgical device according to the present invention.
Figure 71:
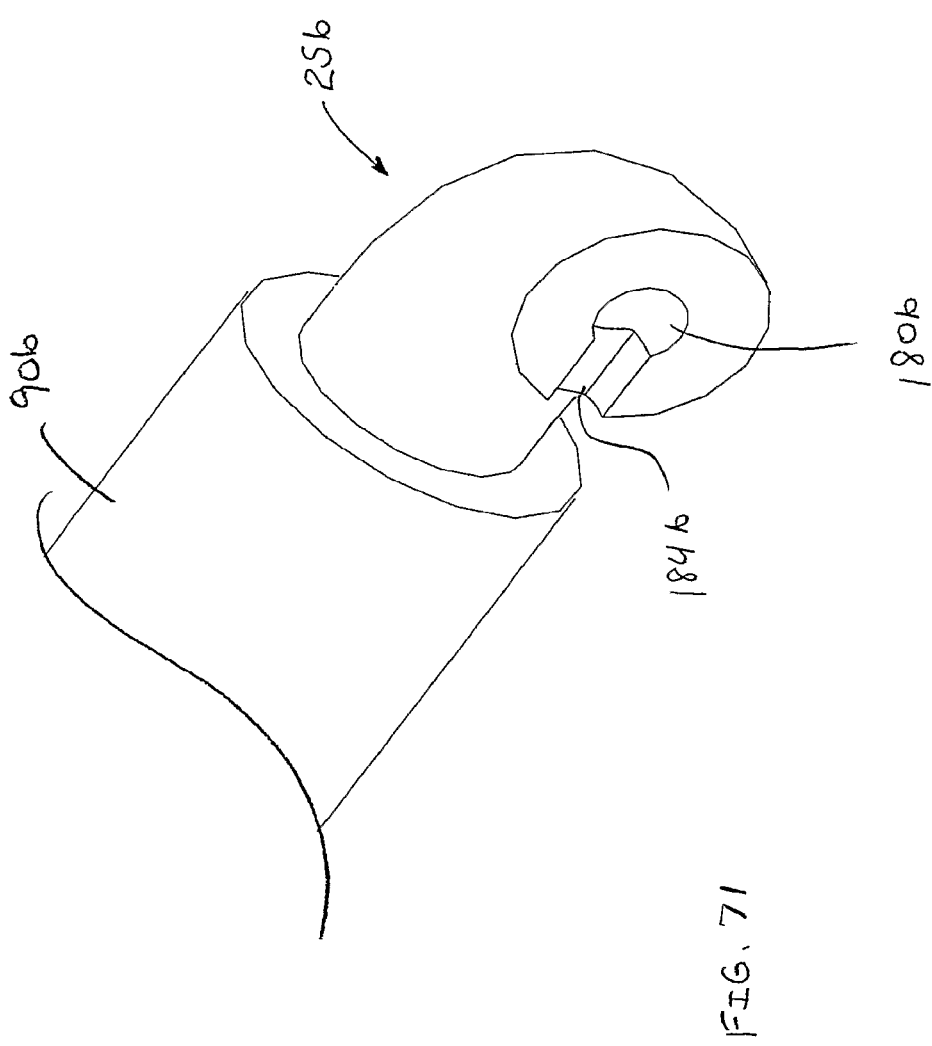
FIG. 71 is a schematic close-up perspective view of a distal end portion of one of the arms of the device of FIG. 70.

More particularly, as shown, openings 184a, 184b in FIG. 70-71, for example, are closer to the inner radius of elbow bend than the other radius of the elbow bend, which aids in reducing occlusion by tissue. However, in other embodiments, the fluid exit openings 184a, 186a may be closer to the outer radius of elbow bend than the inner radius of the elbow bend, as shown in FIG. 66. Still, in other embodiments, the fluid exit openings 184a, 186a may be equidistant the outer radius of elbow bend and the inner radius of the elbow bend, as shown in FIG. 73.

Figure 72:
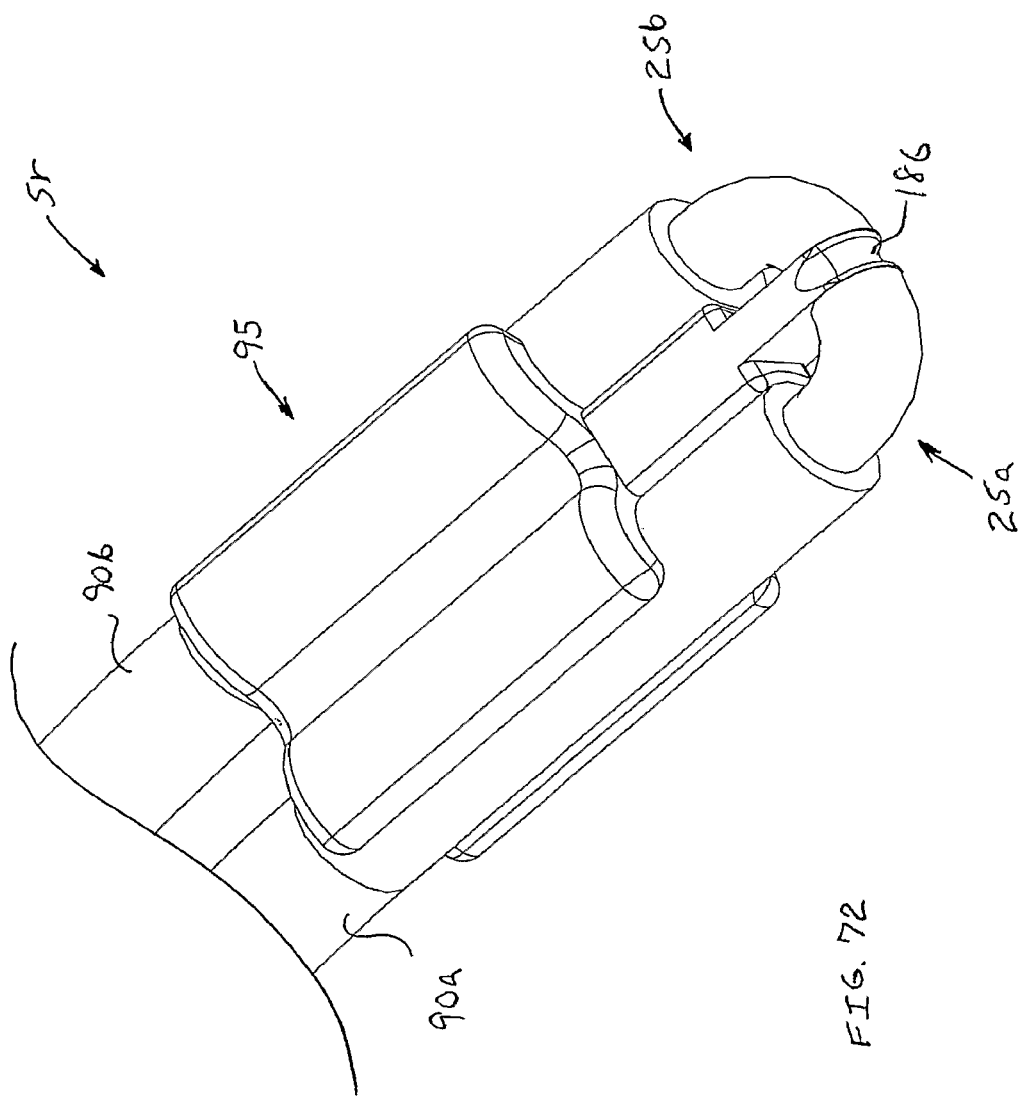
FIG. 72 is a schematic close-up perspective view of a distal end portion of an alternative electrosurgical device according to the present invention.
Figure 73:
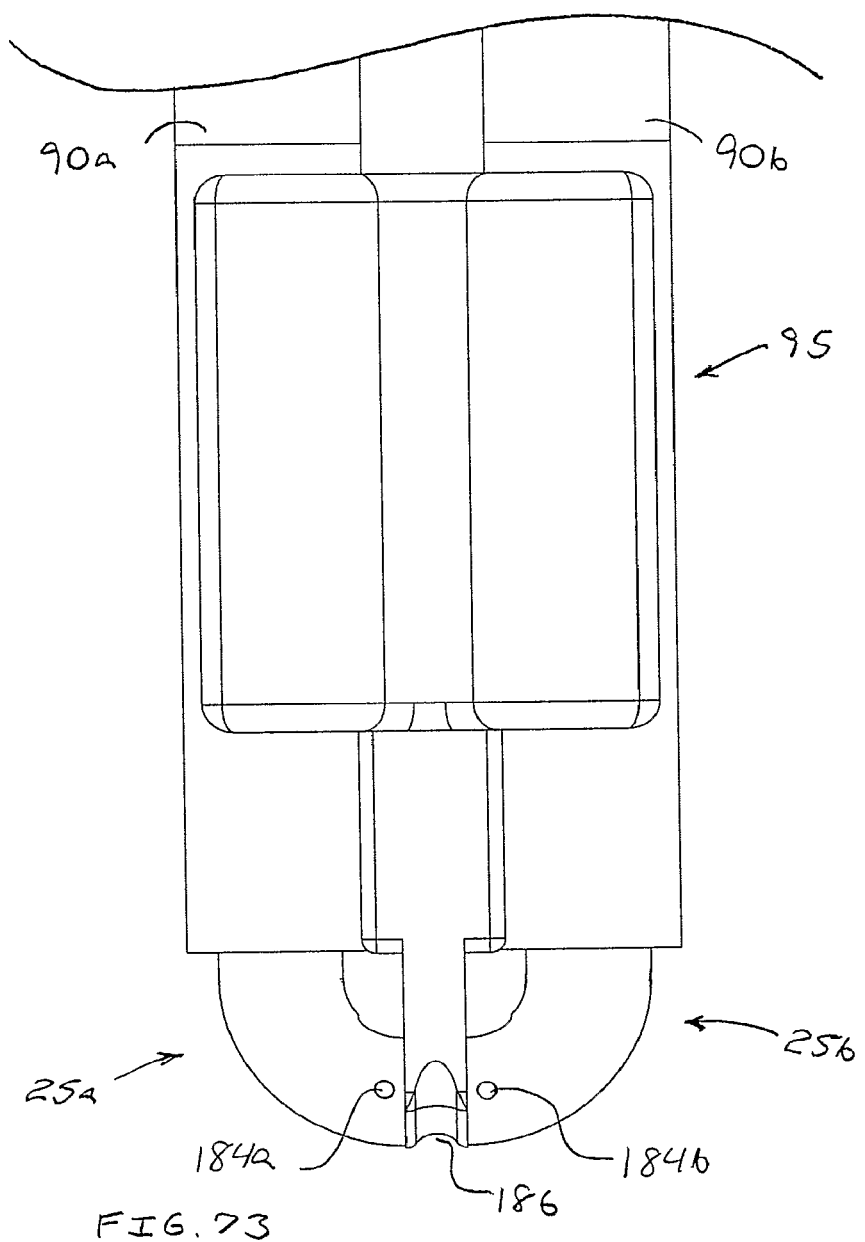
FIG. 73 is a schematic close-up side view of a distal end portion of the device of FIG. 72.
Figure 74:
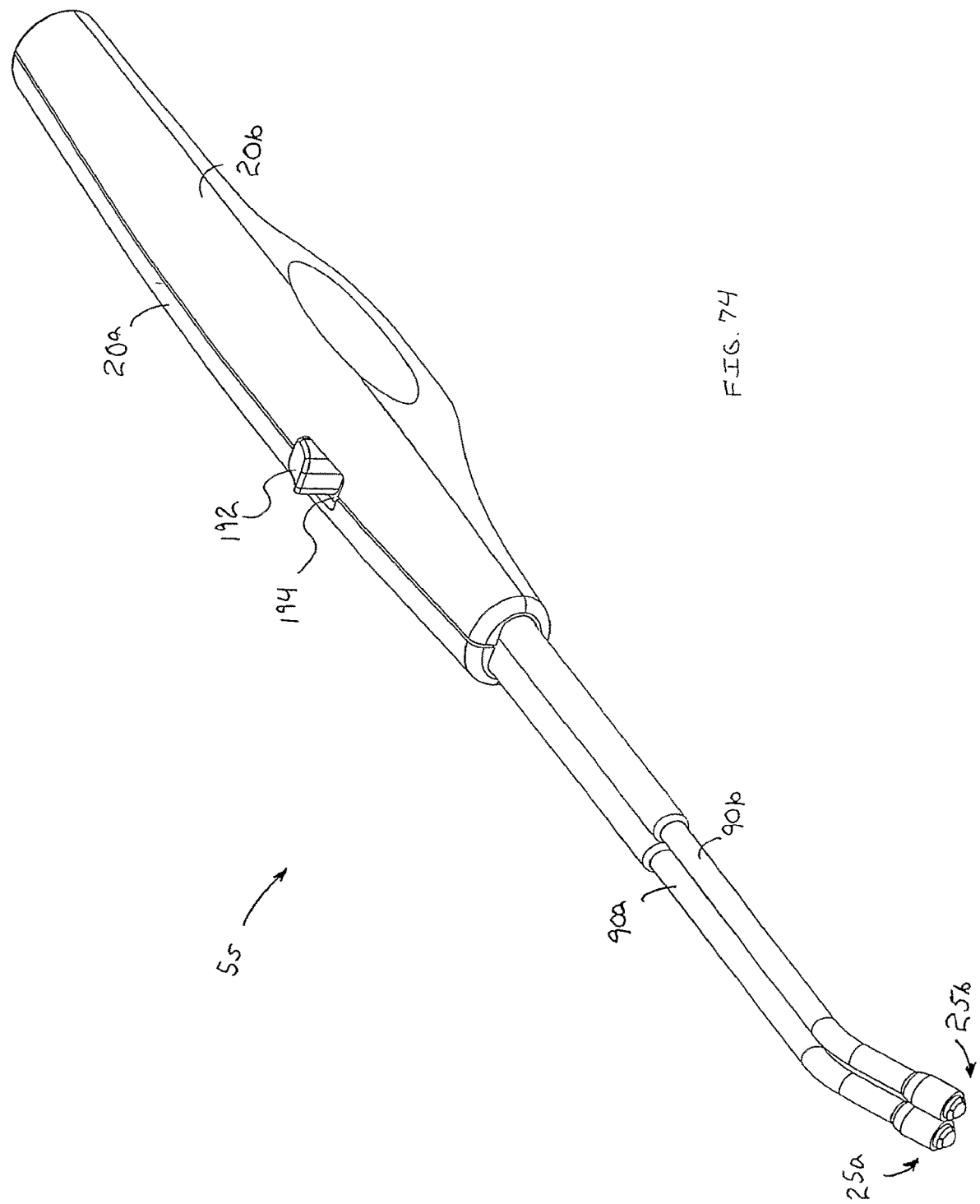
FIG. 74 is a schematic perspective view of an alternative electrosurgical device according to the present invention.
Figure 75:
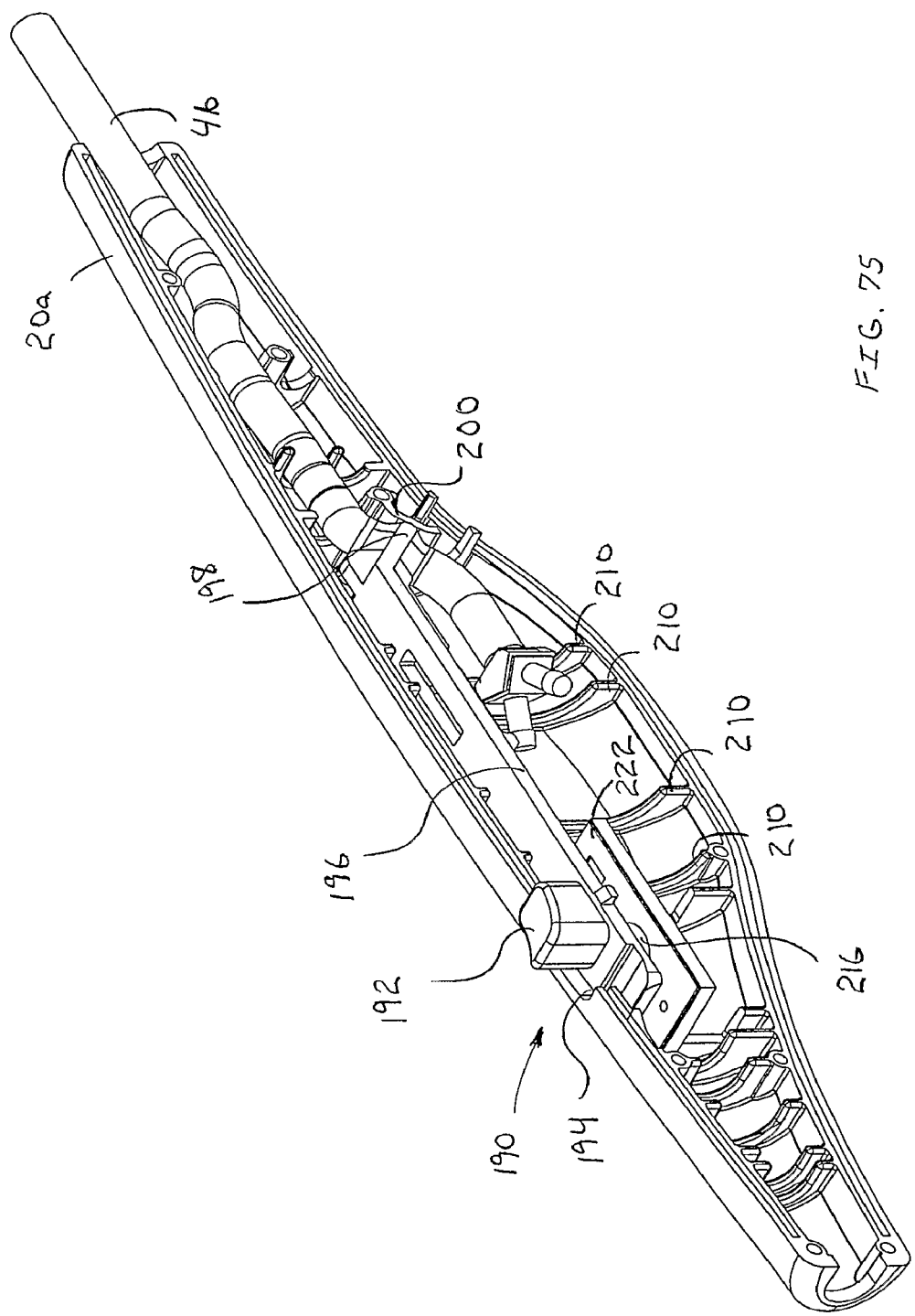
FIG. 75 is a schematic perspective view of a handle portion of the device of FIG. 74 assembled with various components.

Another embodiment of a bipolar device is shown at 5r in FIGS. 72-73. As shown the distal end of spacer portion 154 includes a recess 186 configured to allow tissue 32 to form a tissue protuberance 174 there into to reduce the possibility of formation of a conductive fluid bridge 27 between electrodes 25a, 25b as discussed above.

One or more of the devices of the present invention may include assemblies which control power and/or fluid flow to the tissue treating portion of the device. The ability to control the flow of fluid from the device may provide certain advantages over a device not so equipped. These advantages include reducing the amount of fluid at the tissue treatment site and the likelihood of having to apply suction to the treatment site to remove fluid.

For device 5s in FIGS. 74-79, a single multi-positional, multi-functional switch and valve assembly 190 comprises a switch button 192. Button 192 protrudes through an aperture 194 formed in handle portions 20a, 20b. Button 192 is preferably integrally connected via a single piece polymer molding to a proximally extending switch arm 196 which provides a portion of a fluid flow control mechanism, preferably formed when interacting with handle portion 20a to turn the flow of fluid 24 to the tissue treating portion of the device on (full flow, i.e. unregulated flow at full flow rate through the tubing) and off (no flow).

More specifically, the fluid flow control mechanism of switch/valve assembly 190 is provided with the changing the separation distance between the proximal end portion 198 of switch arm 196 and wall section 200 of handle portion 20a as switch arm 196 is moved proximally and distally along track 206 formed and defined by apertures 208 of ribs 210 of handle portion 20a in response to button 192 being moved proximally and distally in switch button aperture 194.

Figure 76:
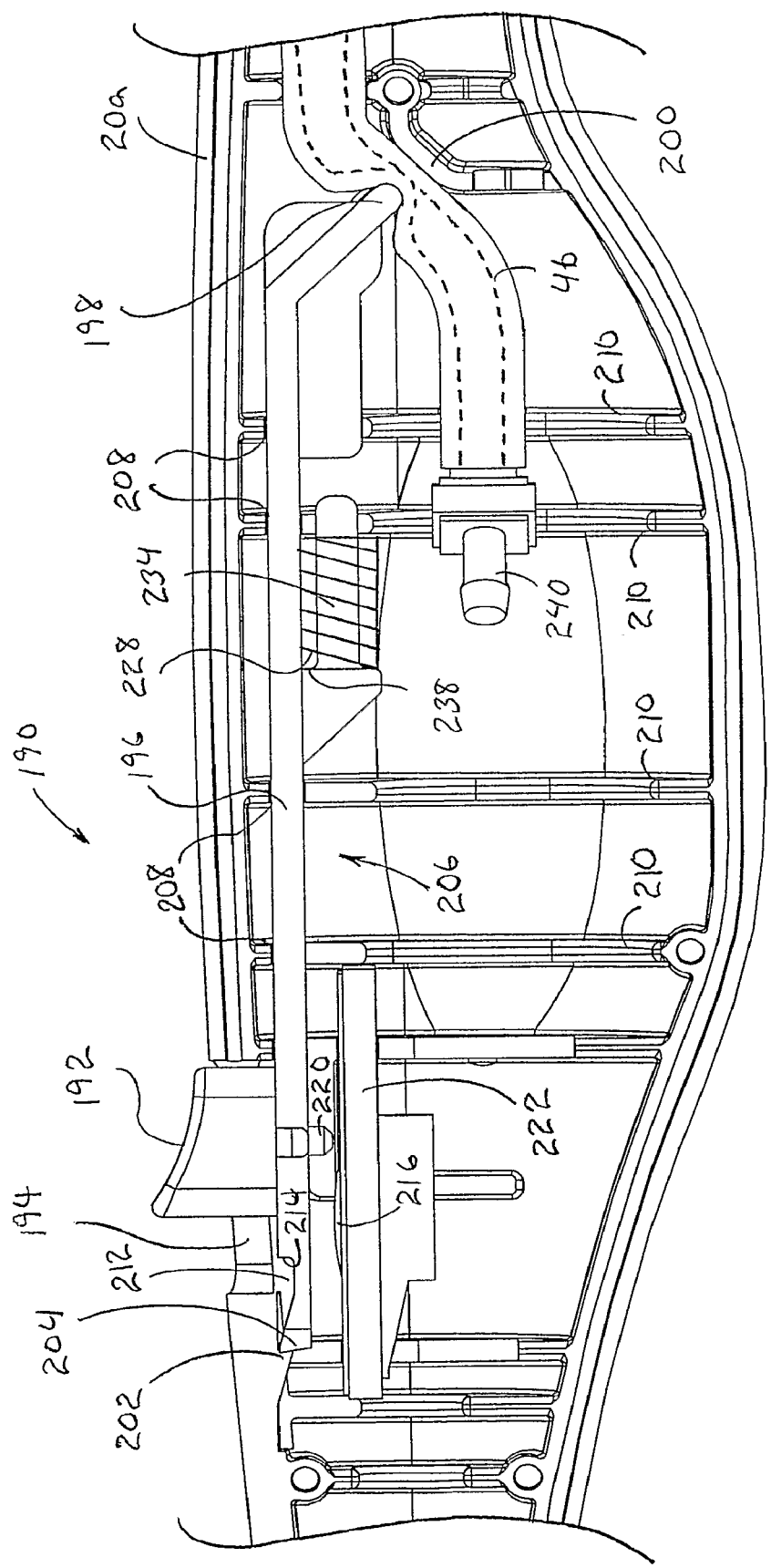
FIG. 76 is a schematic close-up side view of a portion of the assembly of FIG. 75.

As shown in FIG. 76, fluid line 4b is located between proximal end portion 198 of switch arm 196 and wall section 200 of handle portion 20a. As button 192 and switch arm 196 are moved proximally by hand force, thus decreasing separation distance between proximal end portion 198 of switch arm 196 and wall section 200 of handle portion 20a, fluid line 4b is externally squeezed and compressed therebetween and its lumen correspondingly occluded to decrease, and preferably completely stop, the fluid flow rate. As exhibited by the above fluid flow control mechanism, preferably the mechanism does not make contact with fluid 24, thus reducing the likelihood of inadvertent contamination.

Continuing with FIG. 76, preferably the fluid flow control mechanism of switch/valve assembly 190 comprises a mechanism which holds the arm 196 in a fixed, locked position while compressing and occluding fluid line 4b. As shown, preferably the locking mechanism comprises a locking tab 202 of handle portion 20a which holds arm 196 in its locked rearward position by engaging a distal end portion 204 of switch arm 196.

Figure 77:
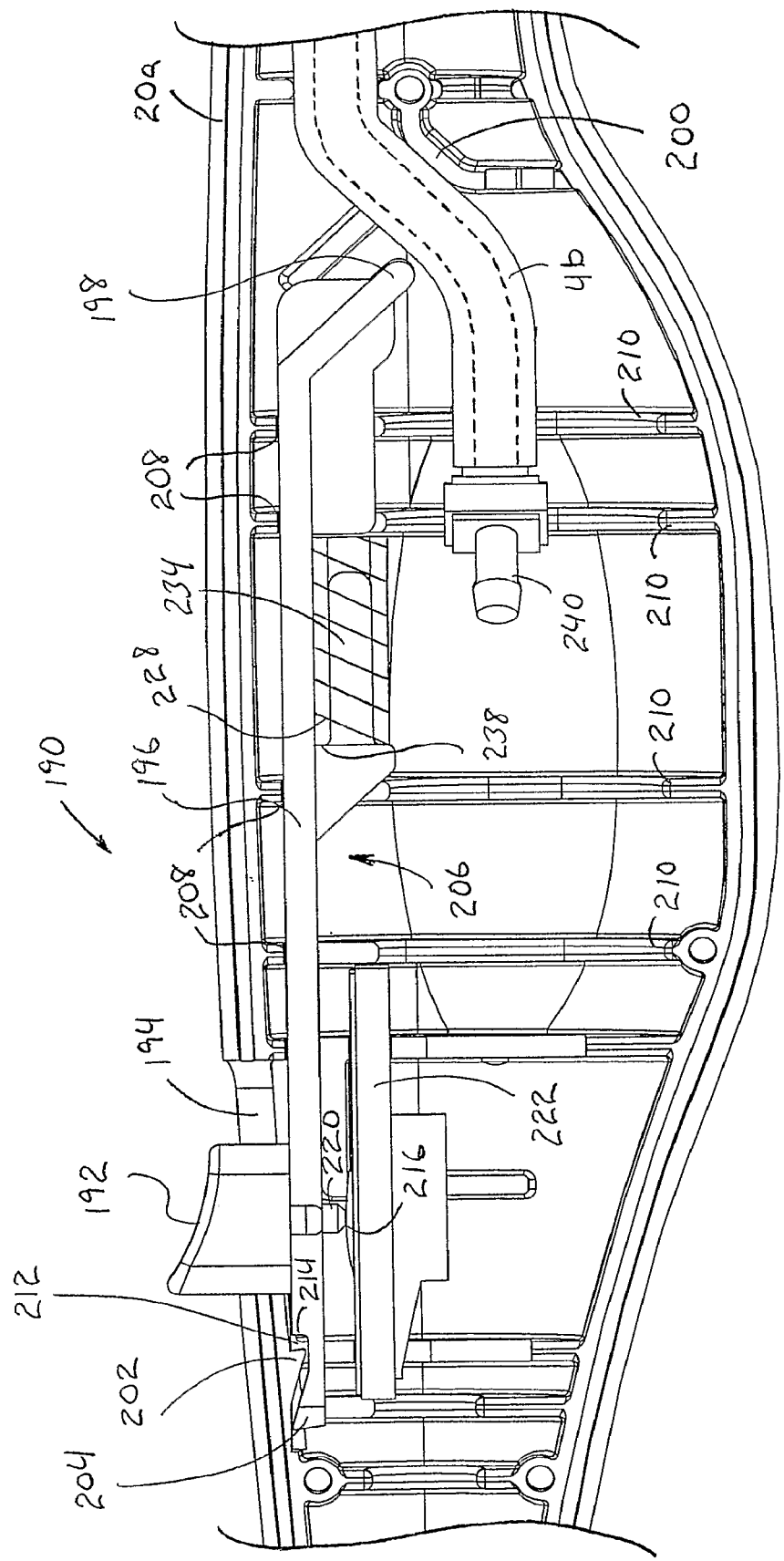
FIG. 77 is a schematic close-up side view of a portion of the assembly of FIG. 75.

Locking tab 202 is disengaged from distal end portion 204 of switch arm 196 by depressing button 192. Upon depressing button 192, the distal end portion 204 of switch arm also separates from tab 202 and tab 202 disengages from distal end portion 204. As best shown in FIG. 77, simultaneously switch arm 196 is forced distally by the decompression of resilient fluid line 4b such that tab 202 enters detent 212. Preferably switch arm 196 is also forced distally by decompression of a linear spring 228 which biases proximal movement of arm 196 to the switch's off position against fluid line 4b with compression thereof, and, with decompression thereof, helps return the switch 192 to its on position upon arm 196 being disengaged from tab 202. As shown, spring 228 is supported on arm 196 by circular post 234 and is compressed between a flange 238 located at the base of post 234 and one of ribs 210. Upon distal end portion 204 of arm 196 disengaging from tab 202, button 192 and switch arm 196 may travel distally until tab 202 engages the proximal end 214 of detent 212.

Once the flow of fluid 24 has resumed, switch button 192 of switch/valve assembly 190 may now be depressed to activate the flow of electric current to electrodes 25a, 25b. As discussed above, electrodes 25a, 25b are preferably coupled to the generator 6 via wire conductors 38a, 38b of insulated wires 21a, 21b. Here, for example, the active and return electrodes comprise electrodes 25a, 25b.

Figure 78:
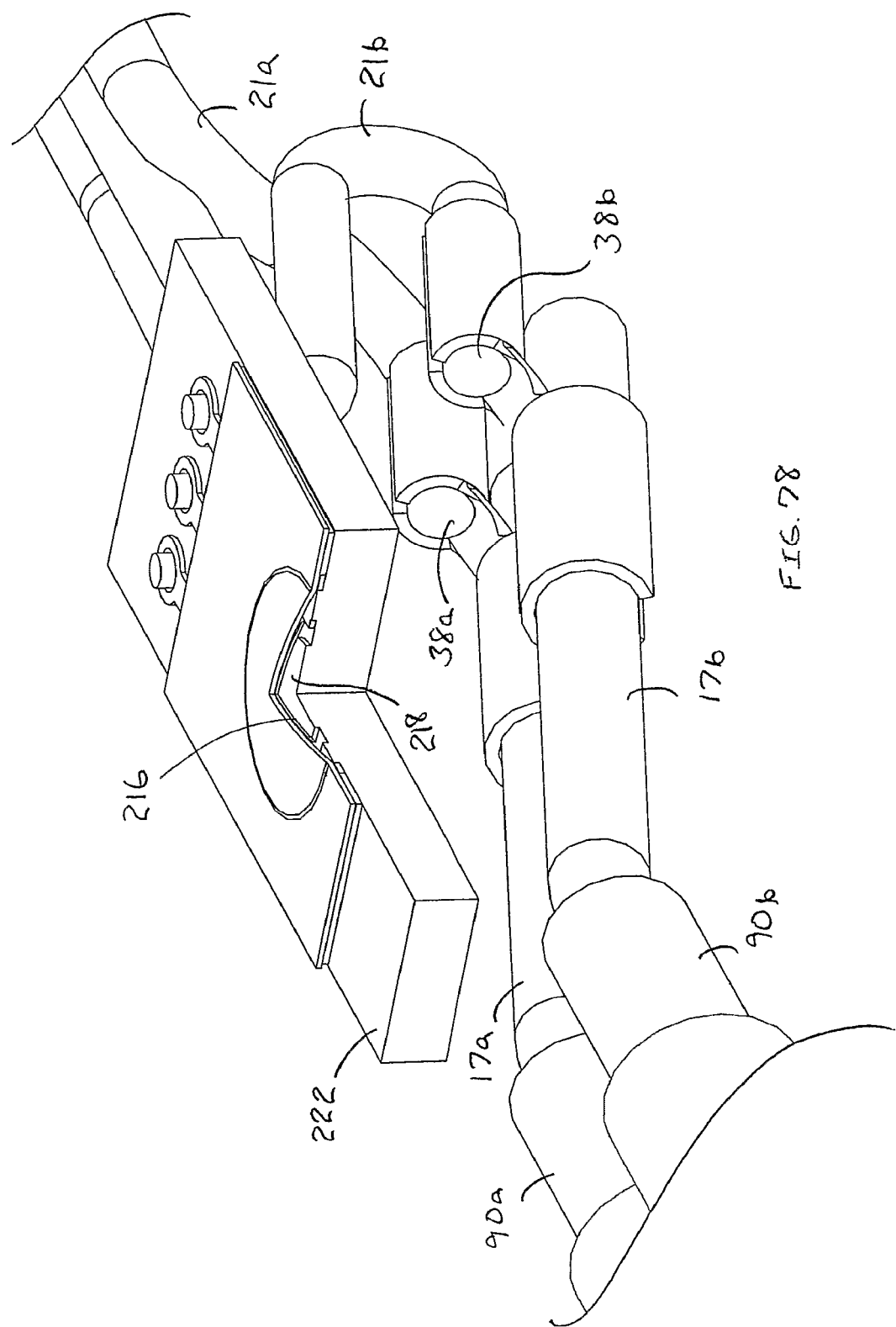
FIG. 78 is a schematic partial cross-sectional front perspective view of the electrical connections for the device of FIG. 74.
Figure 79:
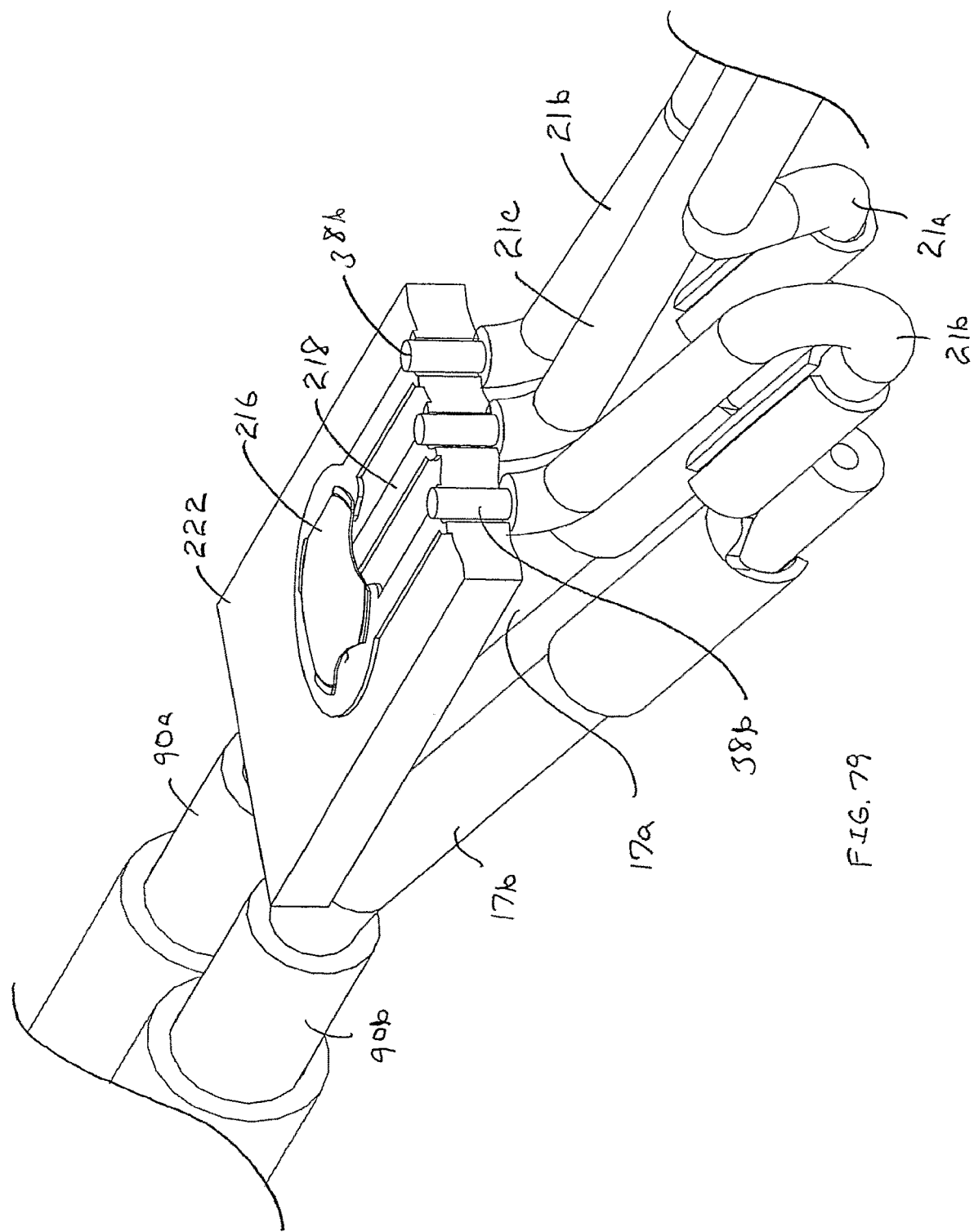
FIG. 79 is schematic partial cross-sectional rear perspective view of the electrical connections for the device of FIG. 74.

As shown in FIGS. 78-79, electrode 25a is directly coupled to generator 6 without any additional inclusion of an on/off switch with an associated control circuit therebetween. However, in addition to being directly coupled to generator 6, the electrical coupling of electrode 25b to generator 6 now includes the presence of two separated electrical contacts 216 and 218 which, in the open position, create an open control circuit between electrode 25b and generator 6. The wiring of this electrical control circuit with the generator 6 is known in the art and discussed briefly below.

As best shown in FIGS. 77-79, contacts 216 and 218 are disposed on a platform 222 partially underling switch button 192 and arm 196. As best shown in FIG. 78, contact 216 comprises a domed contact which overlies contact 218. In the open, or undepressed, position, contact 216 remains separated from underlying contact 218 by virtue of the domed configuration of contact 216, thus resulting in an open control circuit between electrode 25b and generator 6. However, when switch button 192 of switch/valve assembly 190 is in its depressed position, post 220 in turn depresses dome contact 216 into contact with contact 218, thus closing the control circuit between electrode 25b and generator 6. The presence of the closed control circuit formed with wire 21c is then sensed by generator 6 through a low voltage sensor which then provides the set power to electrodes 25a, 25b.

When a depression force is removed from switch button 192, contact 216 returns to its pre-depression domed position as a result of its resiliency or elastic memory, thus returning switch button 192 to its undepressed position and reopening the control circuit between electrode 25b and generator 6. The presence of the open control circuit is then sensed by the generator which then stops providing power to electrodes 25a, 25b. Alternatively, where switch button 192 is not used and the physician chooses to activate electrodes 25a, 25b with a foot pedal switch, the set electrical power to the electrodes 25a, 25b only flows directly through contact 218 to complete the electrical circuit.

It should be understood that switch/valve assembly 190 is configured such that electrical current cannot be provided to electrodes 25a, 25b while the flow of fluid 24 is off. As shown in FIG. 77, when switch button 192 and switch arm 196 are in their proximal position, post 220 does not overlie domed contact 216. Consequently, if switch button 192 is depressed, post 220 merely makes contact with platform 222 and the electrical circuit between electrodes 25a, 25b and generator 6 remains opened.

It should also be understood that in the case of a single main fluid passage which may branch into multiple secondary passages, preferably switch/valve assembly 190 acts on the main fluid passage to reduce complexity. As shown in FIGS. 76-77, preferably switch/valve assembly 190 is located proximal of splitter 240.

Figure 80:
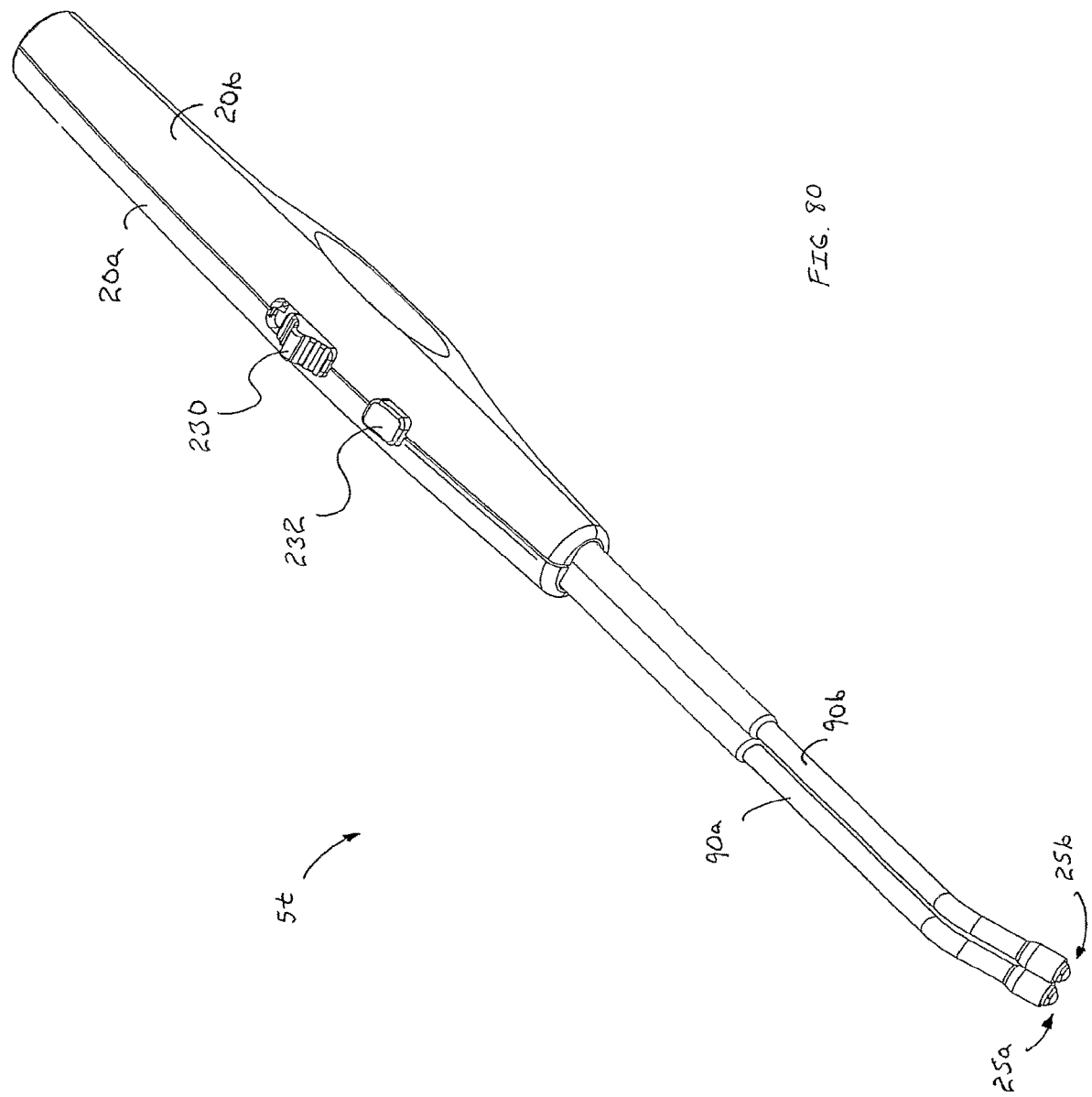
FIG. 80 is a schematic perspective view of an alternative electrosurgical device according to the present invention.
Figure 81:
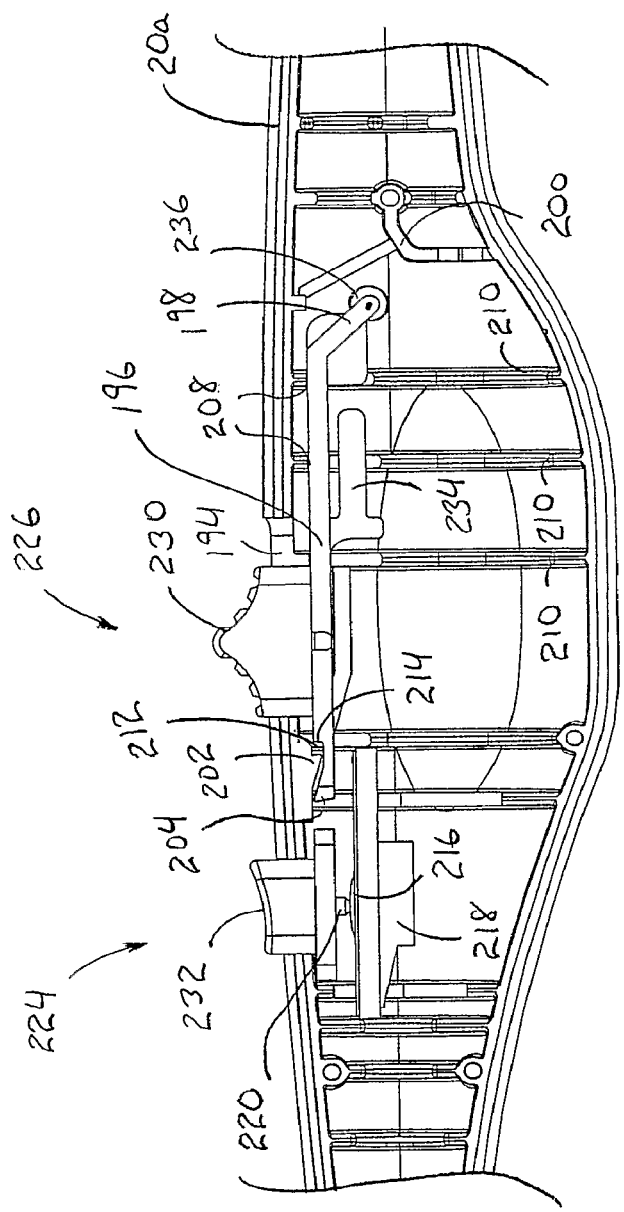
FIG. 81 is a schematic side view of a handle portion of the device of FIG. 80 assembled with various components.
Figure 82:
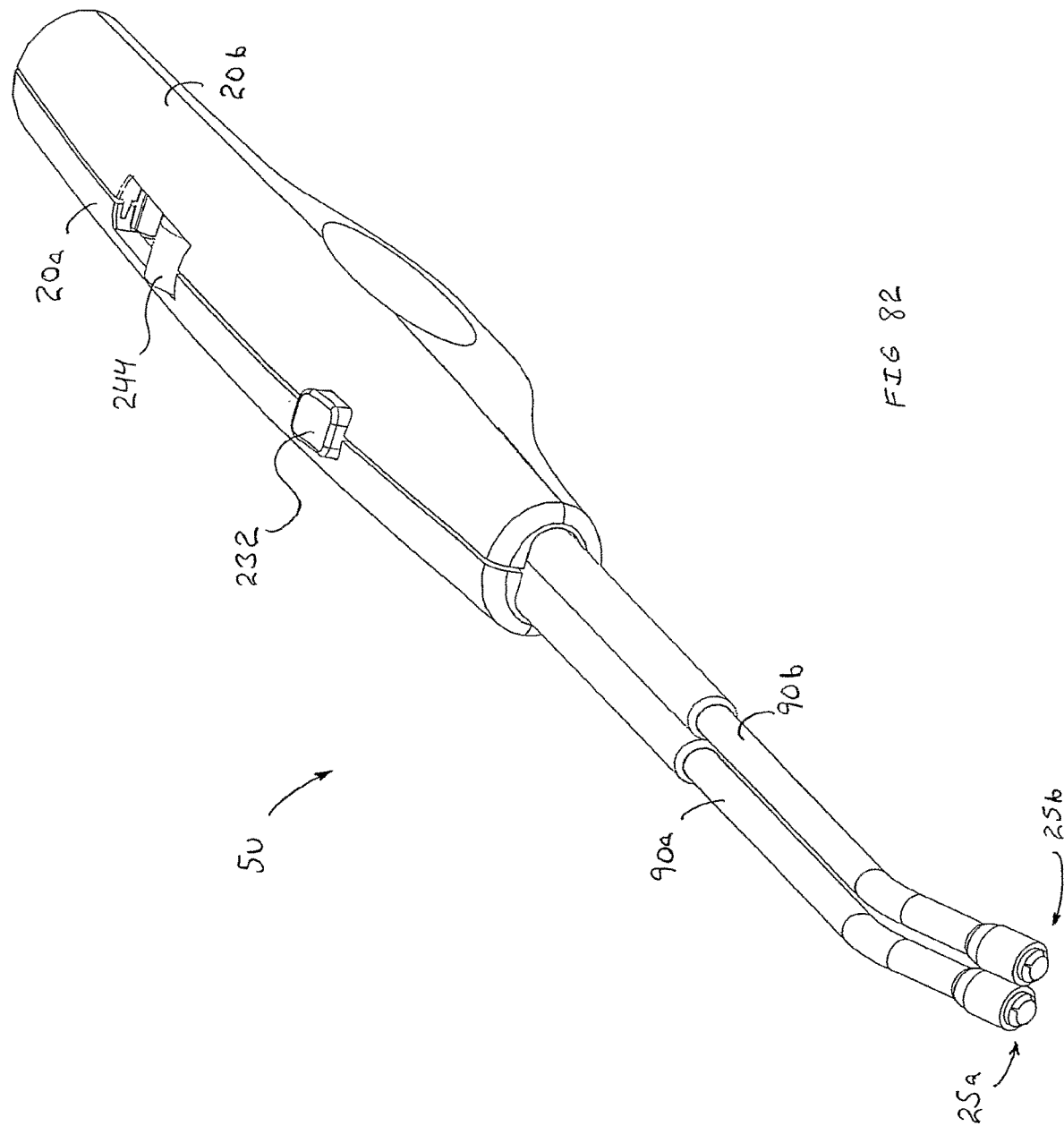
FIG. 82 is a schematic perspective view of an alternative electrosurgical device according to the present invention.
Figure 83:
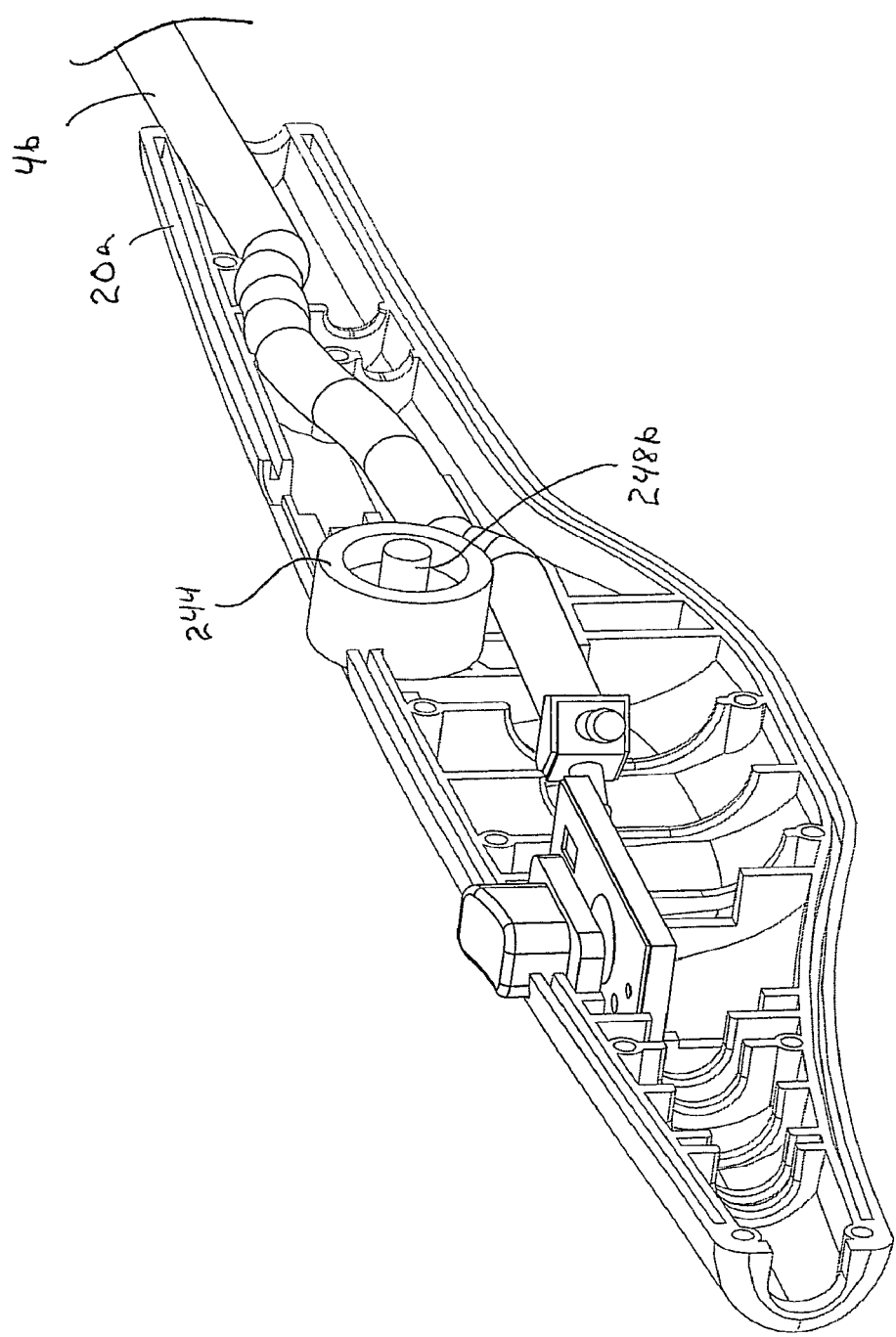
FIG. 83 is a schematic perspective view of a handle portion of the device of FIG. 82 assembled with various components.

In other embodiments one or more of the devices of the present invention may include a separate power switch and fluid flow valve assembles rather than part of a single multi-positional switch/valve assembly. As shown in FIGS. 80-81, device 5t comprises a switch assembly 224 for turning power on and off to the tissue treating portion of the device and a valve assembly 226 for turning fluid flow on (full flow) and off (no flow) to the tissue treating portion of the device.

As best shown in FIG. 81, switch button 230 of switch assembly 224 turns fluid flow on and off in substantially the same manner as switch button 192 of switch/valve assembly 190 (i.e. with distal and proximal movement). However, unlike device 5s, proximal end portion 198 of switch arm 196 of device 5t includes a roller wheel 236 to aid with compression and decompression of fluid line 4b.

With regards to power, switch button 232 of valve assembly 226 turns power on and off in substantially the same manner as switch button 192 of switch/valve assembly 190 (i.e. in depressed and unpressed positions). However, unlike switch/valve assembly 190, with valve assembly 226 power can be turned on and off independently of fluid flow. In other words, switch button 232 of valve assembly 226 can be in the power "on" position while switch button 230 of switch assembly 224 is in the fluid flow "off" position. Thus, the device 5t can be configured to operate as dry electrosurgical device without fluid 24 being provided simultaneously from the tissue treating portion of the device.

In yet another embodiment, as shown in FIGS. 82-86, the second valve assembly for turning fluid flow on and off to the tissue treating portion of the device may comprise a roller pinch clamp assembly. As best shown in FIGS. 83-86, device 5u includes a roller pinch clamp assembly 242 and, more specifically, an inclined ramp roller pinch clamp assembly (as opposed to a parallel acting clamp).

Figure 84:
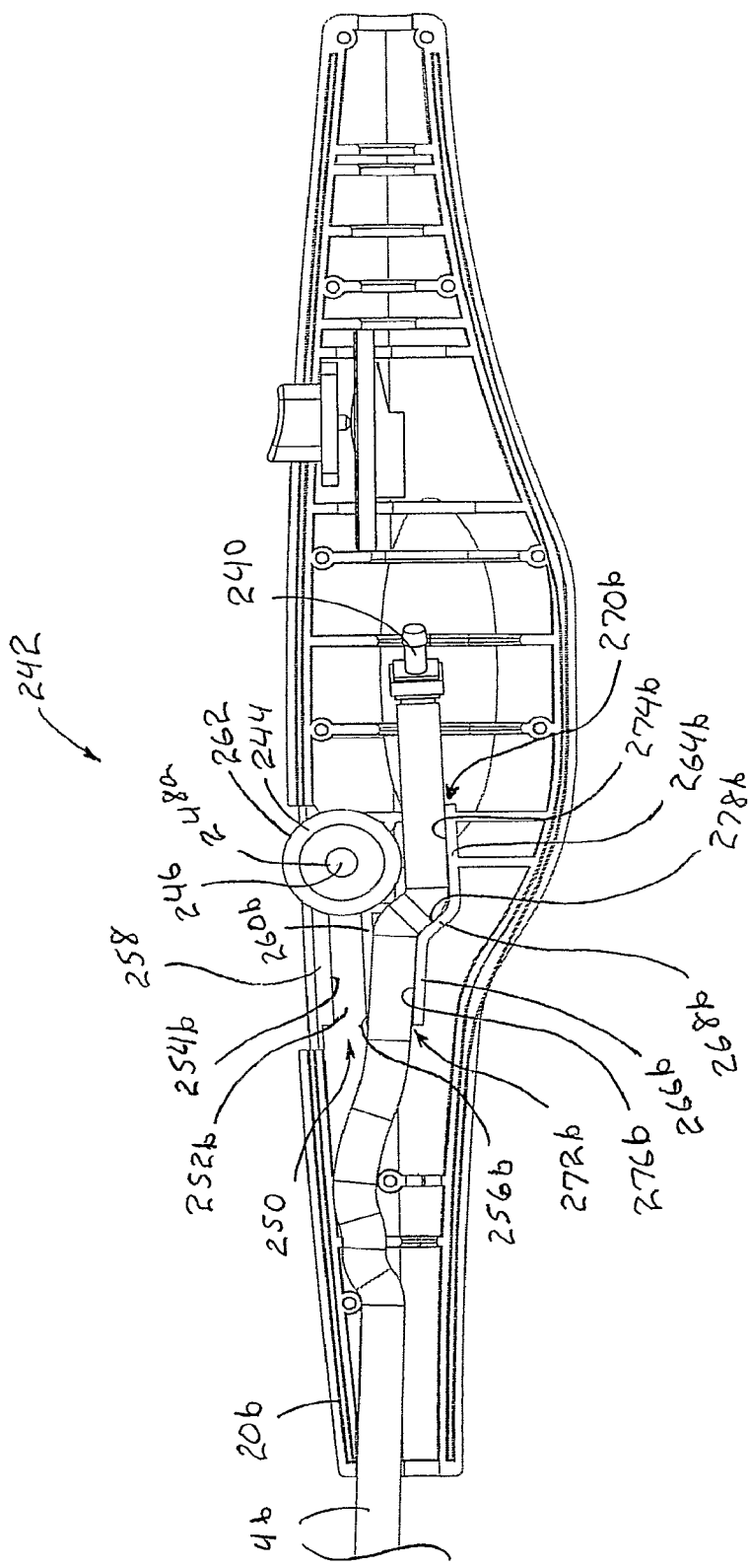
FIG. 84 is a schematic side view of a handle portion of the device of FIG. 82 assembled with various components.
Figure 85:
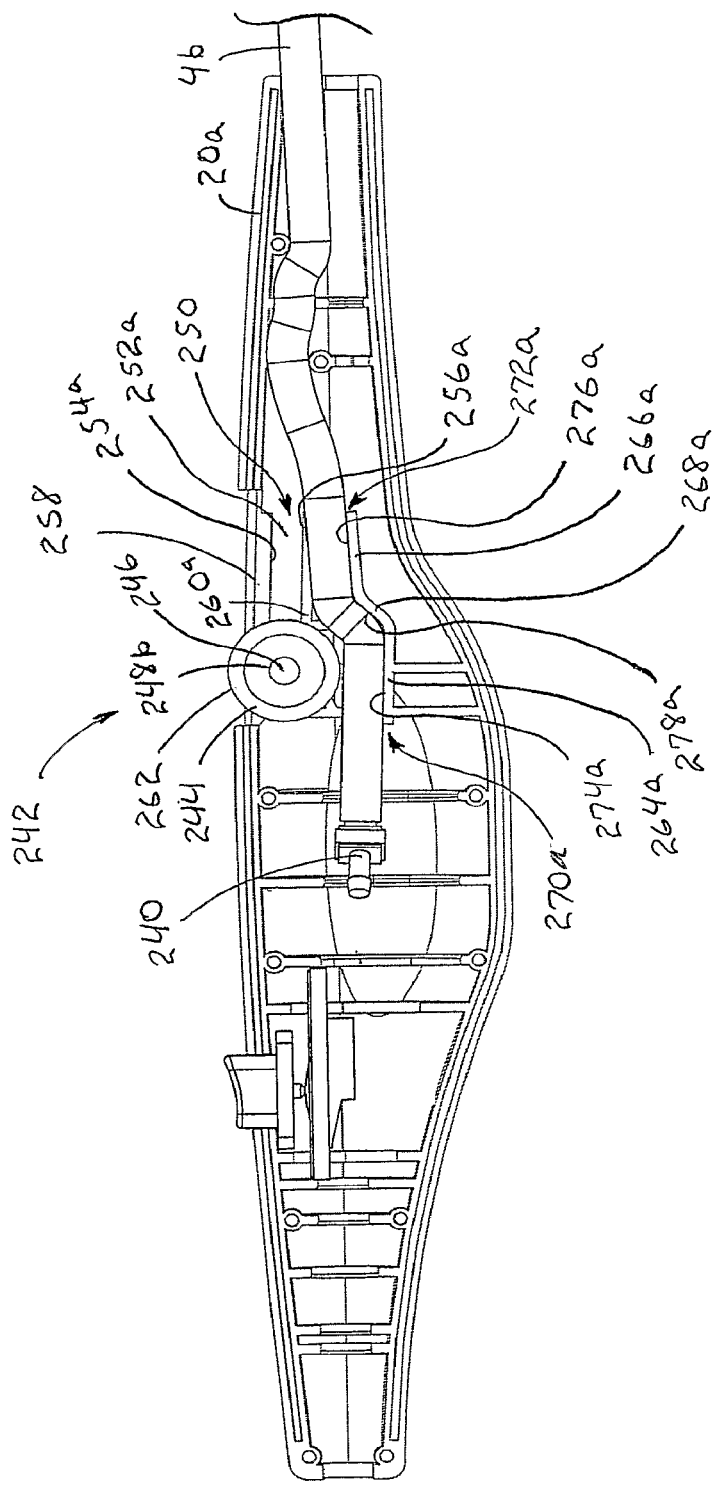
FIG. 85 is a schematic side view of a handle portion of the device of FIG. 82 assembled with various components.

As best shown in FIGS. 84-85, the clamp includes a housing provided by handles 20a, 20b, a roller wheel 244 having a wheel center axis 246 and a guide pin hub. As shown, the guide pin hub is provided by pair of opposing, integrally formed, cylindrical trunnions 248a, 248b, but may also be provided by a separately formed pin. Trunnions 248a, 248b are contained within and move along a track 250 preferably provided and defined by opposing trunnion channels 252a, 252b formed between wheel upper guide surfaces 254a, 254b and wheel lower guide surfaces 256a, 256b extending longitudinally and parallel inward from the side wall portions of the handles 20a, 20b. As shown, wheel upper guide surfaces 254a, 254b are provided by a lip portion of the handles 20a, 20b which partially define aperture 258 through which roller wheel partially extends while wheel lower guide surfaces 256a, 256b are provided by ribs 260a, 260b.

Handles 20a, 20b also preferably provide tubing guide surfaces 272a, 272b which at least a portion of which provide a clamping surface against which plastic tubing 4b is clamped by roller 244. As best shown in FIGS. 84-85, tubing guide surfaces 272a, 272b are provided by ribs 270a, 270b. In use, fluid line 4b is externally squeezed and compressed between the outer perimeter surface 262 of roller wheel 244 and at least a portion of tubing guide surfaces 272a, 272b. In this embodiment, preferably surface 262 is serrated.

Figure 86:
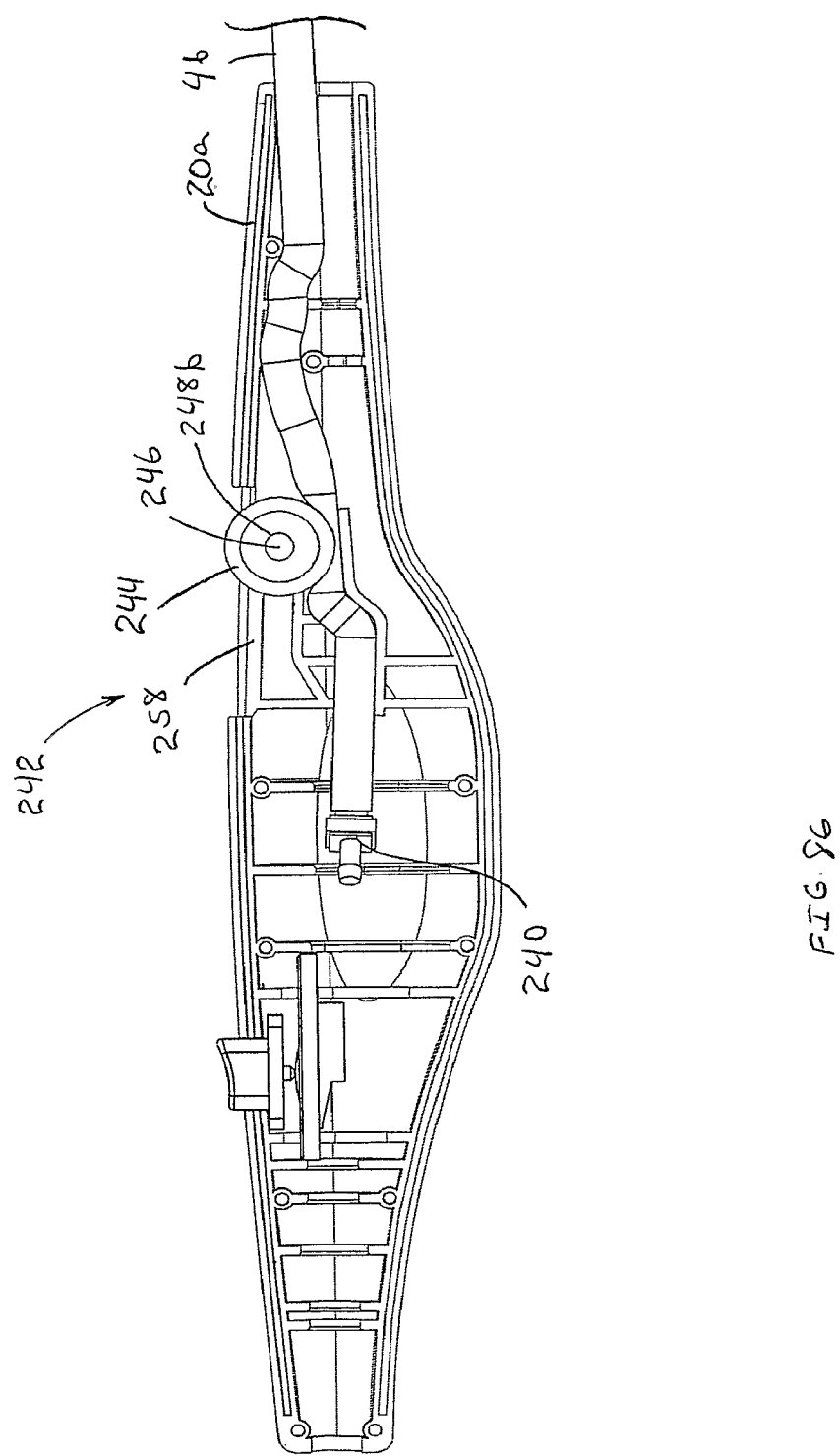
FIG. 86 is a schematic side view of a handle portion of the device of FIG. 82 assembled with various components.

Trunnions 248a, 248b support the movement of roller wheel 244 in two opposing directions, here proximally and distally, along track 250. As best shown in FIGS. 85-86, the separation distance between the outer perimeter surface 262 of roller wheel 244 and tubing guide surfaces 272a, 272b changes throughout the proximal and distal travel of roller wheel 244 along track 250. More specifically, the separation distance between the outer perimeter surface 262 of roller wheel 244 and tubing guide surfaces 272a, 272b is greater between the outer perimeter surface 262 of roller wheel 244 and distal end portions 274a, 274b of tubing guide surfaces 272a, 272b provided by distal end portions 264a, 264b of ribs 270a, 270b than between the outer perimeter surface 262 of roller wheel 244 and proximal end portions 276a, 276b of tubing guide surfaces 272a, 272b provided by proximal end portions 266a, 266b of ribs 270a, 270b.

As shown in FIGS. 84-85, when axis 246 of roller wheel 244 is opposing distal end portions 274a, 274b of tubing guide surfaces 272a, 272b, preferably the separation distance is configured such that the tubing 4b may be uncompressed and the lumen of tubing 4b completely open for full flow therethrough. Conversely, as shown in FIG. 86, when axis 246 of roller wheel 244 is opposing proximal end portions 276a, 276b of tubing guide surfaces 272a, 272b preferably the separation distance is configured such that the tubing 4b is compressed and the lumen of tubing 4b is completely blocked so that the flow of fluid through tubing 4b is prevented.

Distal end portions 274a, 274b of tubing guide surfaces 272a, 272b are separated from proximal end portions 276a, 276b of tubing guide surfaces 272a, 272b by transition surfaces 278a, 278b which are provided by transition rib portion 268a, 268b of ribs 270a, 270b. Preferably compression of tubing initially begins between transition surfaces 278a, 278b and the outer perimeter surface 262 of roller wheel 244 and increases as wheel 244 moves proximally along proximal end portions 276a, 276b of tubing guide surfaces 272a, 272b. With this configuration, consideration may be given to eliminating at least that portion of distal end portions 274a, 274b of tubing guide surfaces 272a, 272b that do not contribute to compression of the tubing 4b. However, given that of distal end portions 274a, 274b of tubing guide surfaces 272a, 272b guide tubing 4b to splitter 240, such may not be desirable.

As shown in FIGS. 84-86, both transition surfaces 278a, 278b and proximal end portions 276a, 276b of tubing guide surfaces 272a, 272b provide sloped inclining surfaces proximally along their respective lengths which decreases the separation distance between the outer perimeter surface 262 of roller wheel 244 and the tubing guide surfaces 272a, 272b as the wheel 244 moves proximally. As shown, preferably the transition surfaces 278a, 278b and proximal end portions 276a, 276b of tubing guide surfaces 272a, 272b have different slopes such that the separation distance decreases at a faster rate along transition surfaces 278a, 278b as compared to proximal end portions 276a, 276b of tubing guide surfaces 272a, 272b. In this manner, compression of tubing 4b is non-linear along the length of travel of wheel 244 with a majority of the compression occurring between roller wheel 244 and transition surfaces 278a, 278b. More preferably, the lumen of tubing 4b is completely blocked when roller wheel 244 is compressing the tubing 4b against the proximal portion of transition surfaces 278a, 278b, and the added compression of the tubing 4b along proximal end portions 276a, 276b of tubing guide surfaces 272a, 272b provides an additional safety to assure complete blocking of the lumen even where there are variations in the tubing, such as the size of the lumen.

It should be realized that, due to the slope of the transition rib portion 268a, 268b, as the roller wheel 244 moves proximally relative to transition surfaces 278a, 278b the lumen of tubing 4b is blocked incrementally. Thus, in addition to providing an on/off mechanism, the roller pinch clamp assembly 242 can also be used to regulate the fluid flow rate between two non-zero flow values. It should also be realized that the roller pinch clamp assembly 242 of the device may be used in series conjunction with another roller pinch clamp assembly which is typically provided as part of an IV set (i.e. IV bag, IV bag spike, drip chamber, connecting tubing, roller clamp, slide clamp, luer connector). When used in this manner, the roller pinch clamp assembly of the IV set may be used to achieve a primary (major) adjustment for fluid flow rate, while the roller pinch clamp assembly 242 of the device may be used to achieve a secondary (more precise minor) adjustment for the fluid flow rate.

Figure 87:
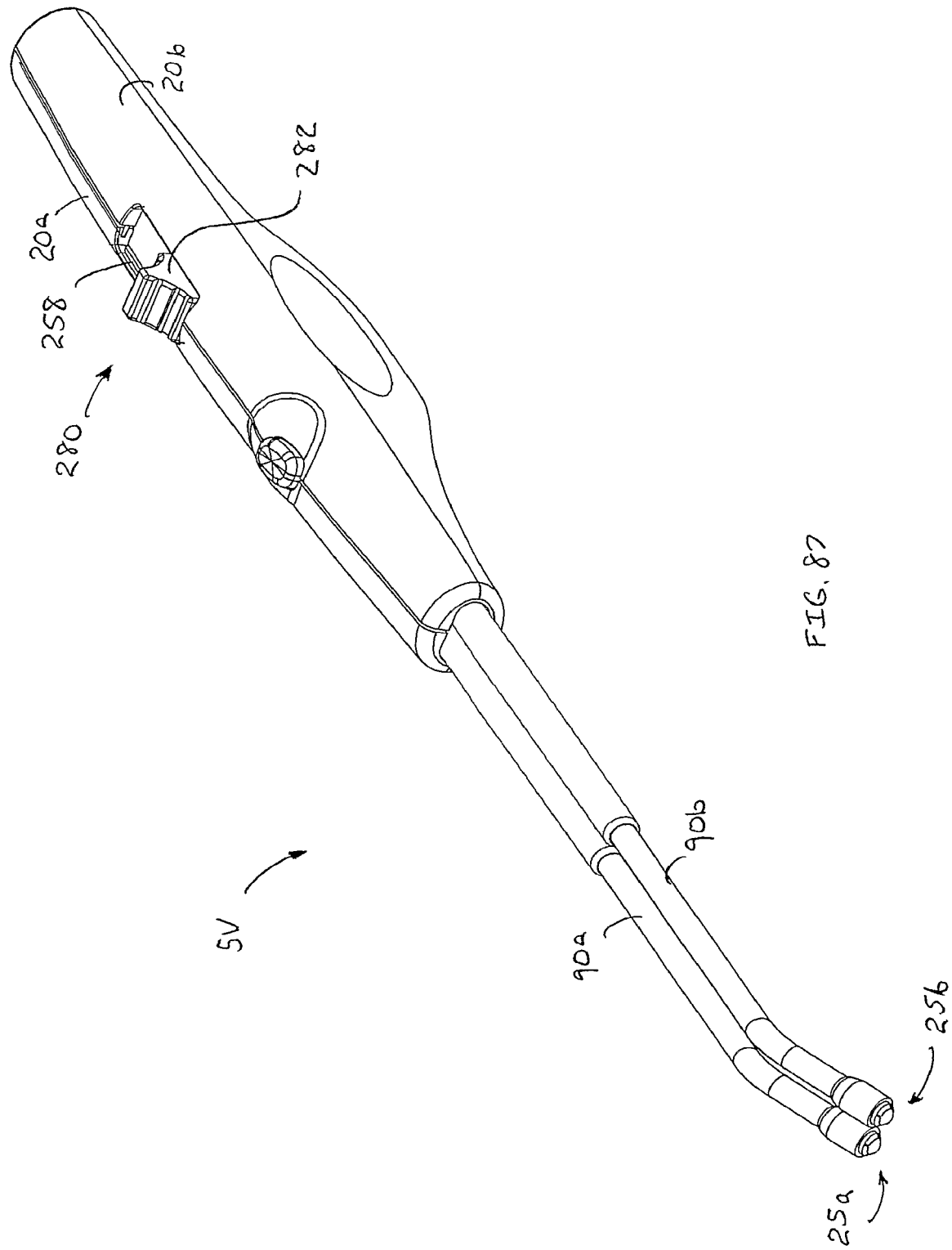
FIG. 87 is a schematic perspective view of an alternative electrosurgical device according to the present invention.
Figure 88:
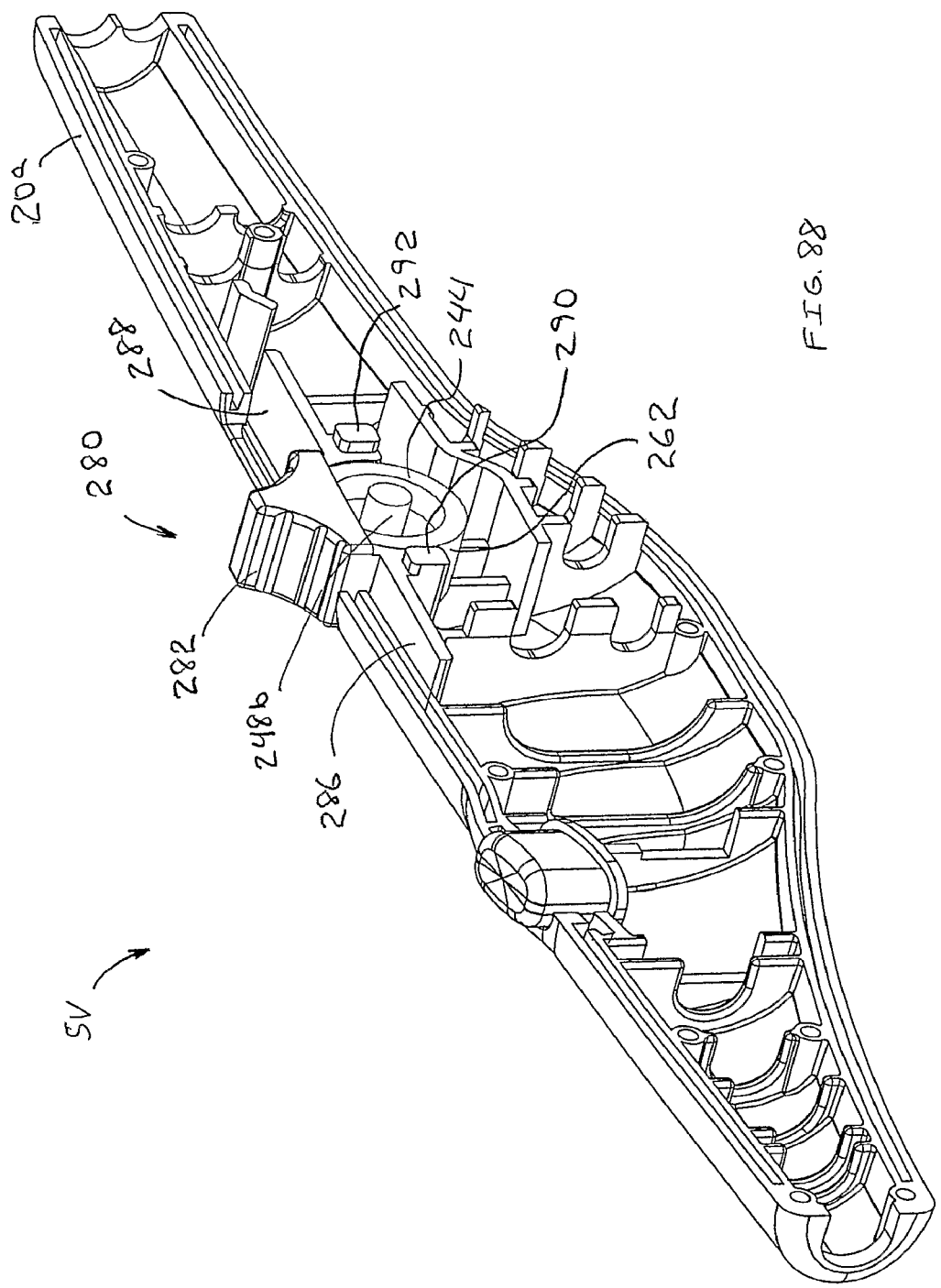
FIG. 88 is a schematic perspective view of a handle portion of the device of FIG. 87.
Figure 89:
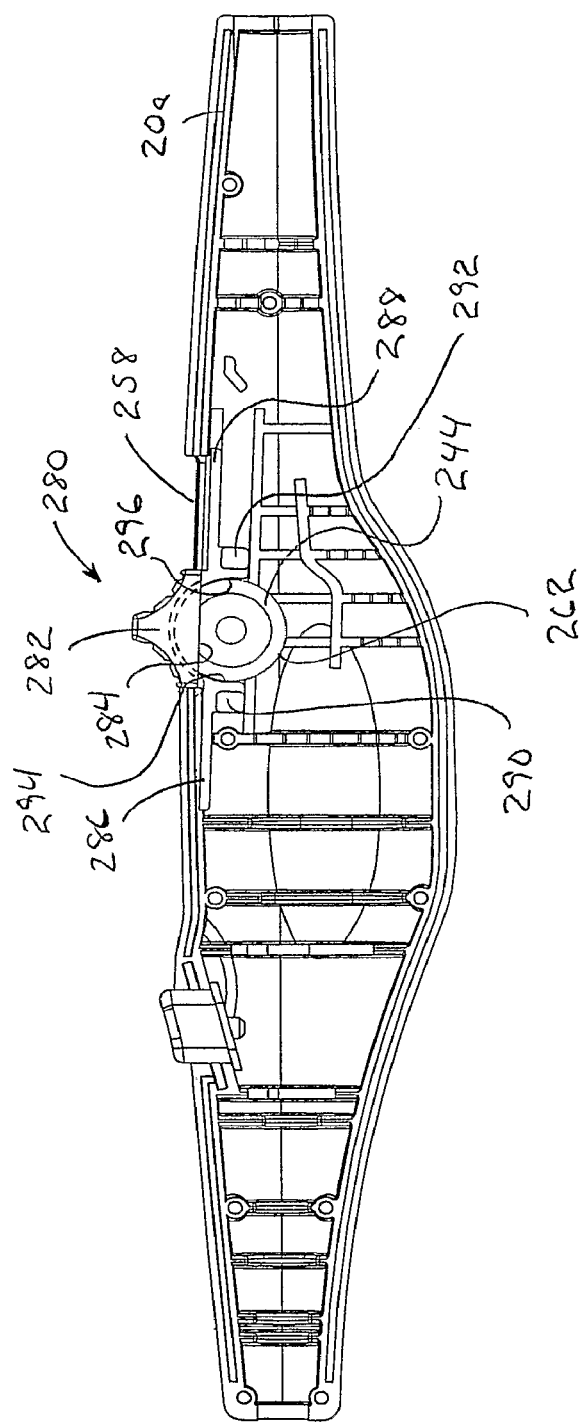
FIG. 89 is a schematic side view of a handle portion of the device of FIG. 87.

In another embodiment, as shown in FIGS. 87-89 for device 5v, the roller pinch clamp assembly 242 may include a cover 280 which at least partially closes aperture 258 and/or conceals roller wheel 244. Among other things, cover 280 reduces the possibility of undesirable foreign fluid (e.g. blood and other bodily fluids) from entering into the confines of handle 20a, 20b through aperture 258. Furthermore, cover 280 reduces the exposure of the internal mechanics of the roller pinch clamp assembly 242. In this manner, cover 280 reduces the possibility of foreign objects (e.g. practitioner's rubber gloves) from entering into the confines of handle 20a, 20b through aperture 258 and getting snagged, for example, between the trunnions 248a, 248b and track 250.

As shown in FIGS. 88-89, preferably cover 280 overlies and moves distally and proximally with roller wheel 244, and is configured to provide a switch button portion 282 when wheel 244 is covered within semi-circular receptacle 284 and inaccessible to direct manipulation. Preferably cover 280 is configured to substantially close aperture 258 regardless of the position of the wheel 244, preferably by means of a distal shield portion 286 and a proximal shield portion 288. Preferably, distal shield portion 286 and a proximal shield portion 288 each have a length equal to or greater than the length of aperture 258 minus the length of switch button portion 282.

Also as shown, preferably cover 280 comprises a distal guide portion 290 and a proximal guide portion 292 located beneath distal shield portion 286 and a proximal shield portion 288 on opposing sides of wheel 244. As shown proximal guide portion 292 and distal shield portion 286 both comprise rectangular guide pins and preferably move along a track 250 similarly to wheel 244. Wheel 244 partially extends into receptacle 284 which has a slightly larger diameter than wheel 244.

With movement of switch button portion 282 proximally by a proximal directed force apply by, for example, a finger, the inner surface 294 of distal guide portion 290 makes contact with surface 262 of wheel 244 and pushes wheel proximally. Conversely, with movement of switch button portion 282 distally by a distally directed force apply by, for example, a finger, the inner surface 296 of proximal guide portion 292 makes contact with outer surface 262 of wheel 244 and pushes wheel distally. In this embodiment, the surface 262 of wheel 244 is preferably smooth and wheel 244 preferably comprises a self-lubricating polymer material such as polyacetal.

Figure 90:
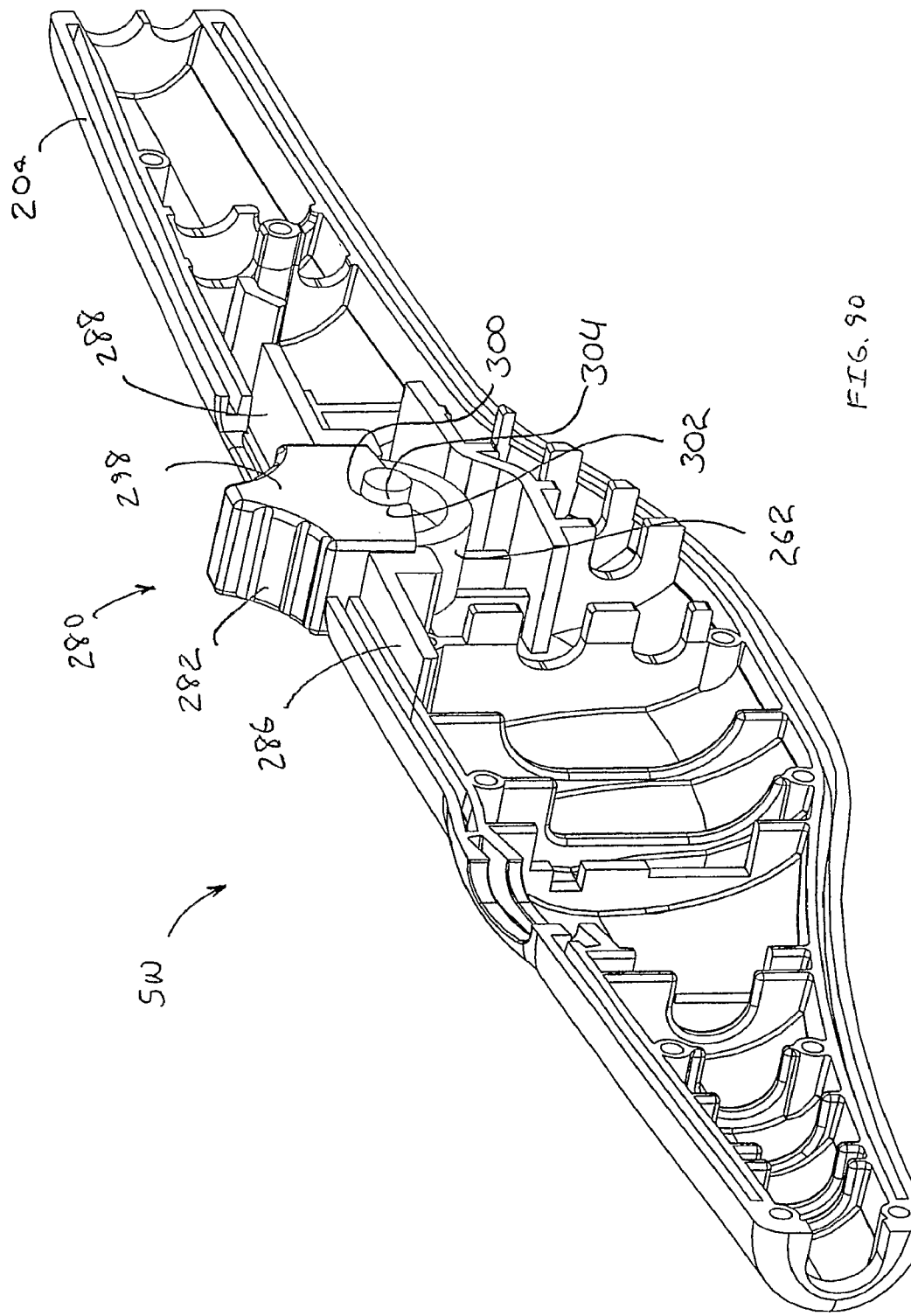
FIG. 90 is a schematic perspective view of a handle portion an alternative electrosurgical device according to the present invention.
Figure 91:
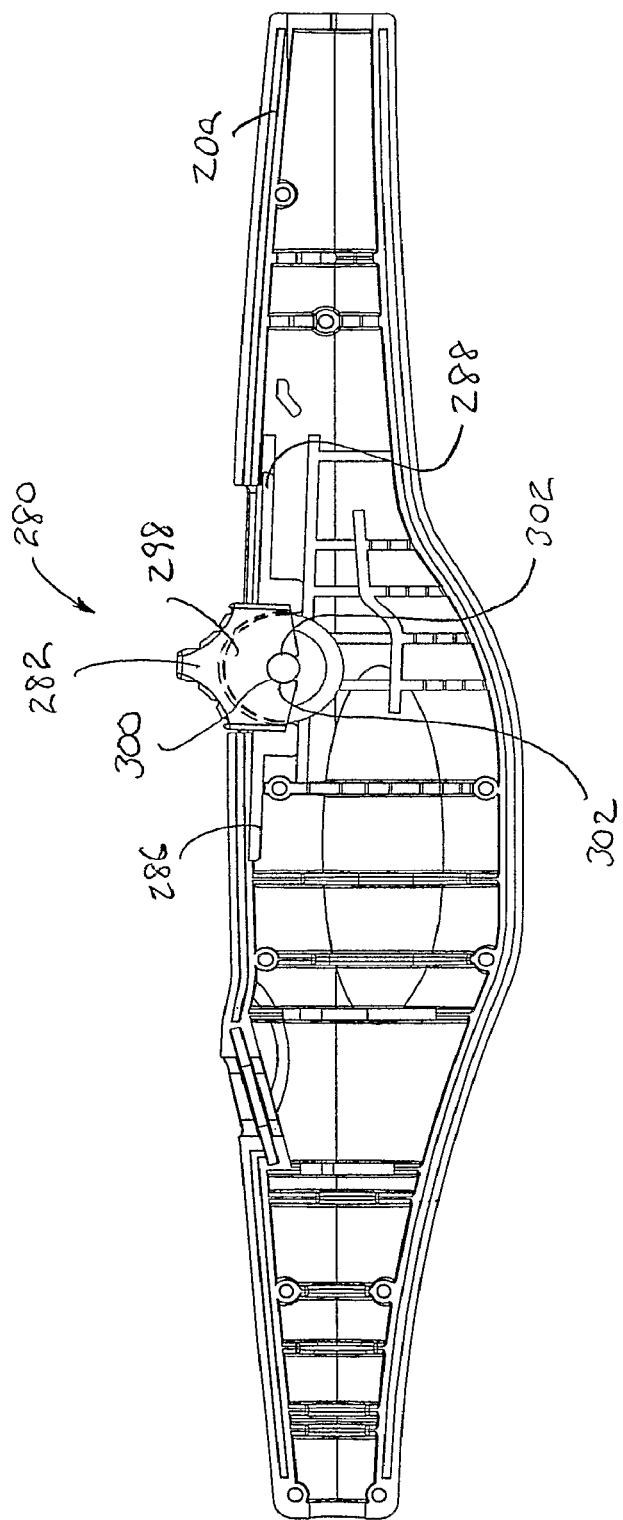
FIG. 91 is a schematic side view of the handle portion of FIG. 90.

In another embodiment, as shown in FIGS. 90-91 for device 5w, the switch button portion 282 of cover 280 may include side portions 298 which cover the opposing sides of wheel 244. However, unlike embodiment 5v, a portion of the cover 280 for device 5w is not contained in or directly guided by track 250 as distal guide portion 290 and proximal guide portion 292 have been eliminated. While the cover 280 for embodiment 5w still applies directional force to wheel 244 to move wheel 244, cover 280 now is joined to wheel 244 and conveyed along track 250 by trunnions 248a, 248b of wheel 244. As shown, cover 280 includes two opposing C-shaped apertures 300 which provided wheel hub receptacles for trunnions 248a, 248b. As shown, trunnions 248a, 248b are located in apertures 300.

Thus, with movement of switch button portion 282 proximally by a proximal directed force, the inner surface 302 of cover 280 defining apertures 300 makes contact with cylindrical side surface 304 of trunnions 248a, 248b and pushes wheel proximally. Conversely, with movement of switch button portion 282 distally by a distally directed force, the inner surface 302 of cover 280 defining apertures 300 also makes contact with cylindrical side surface 304 of trunnions 248a, 248b and pushes wheel distally.

Figure 92:
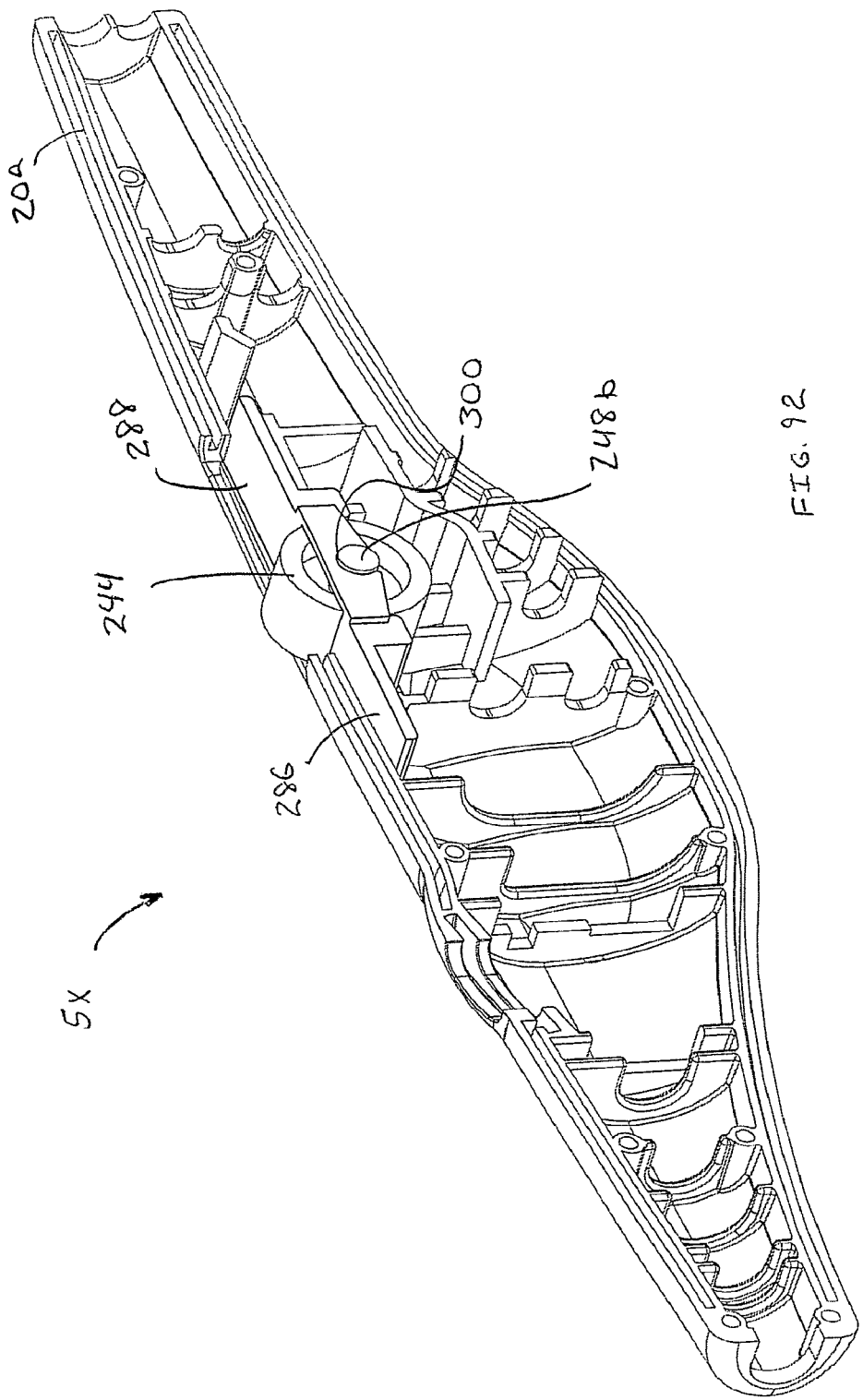
FIG. 92 is a schematic perspective view of a handle portion an alternative electrosurgical device according to the present invention.
Figure 93:
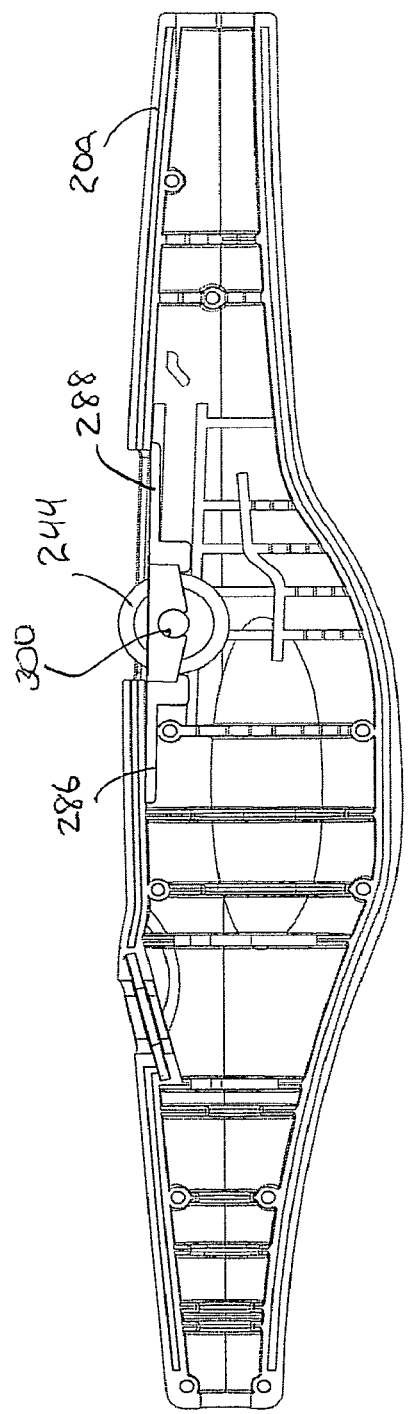
FIG. 93 is a schematic side view of the handle portion of FIG. 92.

In another embodiment, as shown in FIGS. 92-93 for device 5x, the switch button portion 282 of cover 280 has been eliminated. Thus, roller wheel 244 is now exposed and may be acted on directly rather than through switch button portion 282.

While the various embodiments of switch assembles described above have predominately been described with reference to bipolar devices, it should be understood that the various switch assemblies may be equally adaptable to other fluid-assisted medical devices such as the monopolar devices of the present invention.

Bipolar devices 5i-5x are particularly useful as non-coaptive tissue sealers given they do not grasp tissue. Devices 5i-5x are particularly useful to surgeons to achieve hemostasis after dissecting through soft tissue as part of hip or knee arthroplasty. The tissue treating portions can be painted over the raw, oozing, surface 22 of tissue 32 to seal the tissue 32 against bleeding, or focused on individual larger bleeding vessels to stop vessel bleeding.

Devices 5i-5x are also useful to stop bleeding from the surface of cut bone tissue as part of any orthopaedic procedure that requires bone to be cut. Bipolar devices 5i-5x are particularly useful for these applications over a monopolar device 5a as a much greater surface area 22 of tissue 32 may be treated in an equivalent period of time and with better controlled depth of the treatment.

As is well known, bone, or osseous tissue, is a particular form of dense connective tissue consisting of bone cells (osteocytes) embedded in a matrix of calcified intercellular substance. Bone matrix mainly contains collagen fibers and the minerals calcium carbonate, calcium phosphate and hydroxyapatite. Among the many types of bone within the human body are compact bone and cancellous bone. Compact bone is hard, dense bone that forms the surface layers of bones and also the shafts of long bones. It is primarily made of haversian systems which are covered by the periosteum. Compact bone contains discrete nutrient canals through which blood vessels gain access to the haversian systems and the marrow cavity of long bones. For example, Volkmann's canals which are small canals found in compact bone through which blood vessels pass from the periosteum and connect with the blood vessels of haversian canals or the marrow cavity. Bipolar devices as disclosed herein may be particularly useful to treat compact bone and to provide hemostasis and seal bleeding vessels (e.g. by shrinking to complete close) and other structures associated with Volkmann's canals and Haversian systems.

In contrast to compact bone, cancellous bone is spongy bone and forms the bulk of the short, flat, and irregular bones and the ends of long bones. The network of osseous tissue that makes up the cancellous bone structure comprises many small trabeculae, partially enclosing many intercommunicating spaces filled with bone marrow. Consequently, due to their trabecular structure, cancellous bones are more amorphous than compact bones, and have many more channels with various blood cell precursors mixed with capillaries, venules and arterioles. Bipolar devices as disclosed herein may be particularly useful to treat cancellous bone and to provide hemostasis and seal bleeding structures such as the above micro-vessels (i.e. capillaries, venules and arterioles) in addition to veins and arteries. Such devices may be particularly useful for use during orthopaedic knee, hip, shoulder and spine procedures (e.g. arthroplasty).

During a knee replacement procedure, the condyle at the distal epiphysis of the femur and the tibial plateau at the proximal epiphysis of the tibia are often cut and made more planer with saw devices to ultimately provide a more suitable support structure for the femoral condylar prosthesis and tibial prosthesis attached thereto, respectively. The cutting of these long bones results in bleeding from the cancellous bone at each location. In order to seal and arrest the bleeding from the cancellous bone which has been exposed with the cutting of epiphysis of each long bone, the bipolar devices disclosed herein may be utilized. Thereafter, the respective prostheses may be attached.

Turning to a hip replacement procedure, the head and neck of the femur at the proximal epiphysis of the femur is removed, typically by cutting with a saw device, and the intertrochantic region of the femur is made more planer to provide a more suitable support structure for the femoral stem prosthesis subsequently attached thereto. With respect to the hip, a ball reamer is often used to ream and enlarge the acetabulum of the innominate (hip) bone to accommodate the insertion of an acetabular cup prosthesis therein, which will provide the socket into which the head of the femoral stem prosthesis fits. The cutting of the femur and reaming of the hip bone results in bleeding from the cancellous bone at each location. In order to seal and arrest the bleeding from the cancellous bone which has been cut and exposed, the bipolar devices disclosed herein may be utilized. Thereafter, as with the knee replacement, the respective prostheses may be attached.

The bipolar devices disclosed herein may be utilized for treatment of connective tissues, such as for shrinking intervertebral discs during spine surgery. Intervertebral discs are flexible pads of fibrocartilaginous tissue tightly fixed between the vertebrae of the spine. The discs comprise a flat, circular capsule roughly an inch in diameter and about 0.25 inch thick, made of a tough, fibrous outer membrane called the annulus fibrosus, surrounding an elastic core called the nucleus pulposus.

Under stress, it is possible for the nucleus pulposus to swell and herniate, pushing through a weak spot in the annulus fibrosus membrane of the disc and into the spinal canel. Consequently, all or part of the nucleus pulposus material may protrude through the weak spot, causing pressure against surrounding nerves which results in pain and immobility.

The bipolar devices disclosed herein may be utilized to shrink protruding and herniated intervertebral discs which, upon shrinking towards normal size, reduces the pressure on the surrounding nerves and relieves the pain and immobility. The devices disclosed herein may be applied via posterior spinal access under surgeon control for either focal shrinking of the annulus fibrosus membrane.

Where a intervertebral disc cannot be repaired and must be removed as part of a discectomy, the devices disclosed herein may be particularly useful to seal and arrest bleeding from the cancellous bone of opposing upper and lower vertebra surfaces (e.g. the cephalad surface of the vertebral body of a superior vertebra and the caudad surface of an inferior vertebra). Where the disc is removed from the front of the patient, for example, as part of an anterior, thoracic spine procedure, the devices disclosed herein may also be particularly useful to seal and arrest bleeding from segmental vessels over the vertebral body.

The bipolar devices disclosed herein may be utilized to seal and arrest bleeding of epidural veins which bleed as a result of the removal of tissue around the dural membrane during, for example a laminectomy or other neurosurgical surgery. The epidural veins may start bleeding when the dura is retracted off of them as part of a decompression. Also during a laminectomy, the devices disclosed herein, may be used to seal and arrest bleeding from the vertebral arch and, in particular the lamina of the vertebral arch.

One or more of the features of the previously described system can be built into a custom RF generator. This embodiment can provide one or more advantages. For example, this type of system can save space and reduce overall complexity for the user. This system can also enable the manufacturer to increase the power delivered into low impedance loads, thereby further reducing the time to achieve the desired tissue effects. This changes the curve of FIG. 5, by eliminating or reducing the slope of the low impedance ramp 28a of power versus impedance.

Alternatively, for situations where the high impedance ramp 28b may be exceeded with use of the devices of the present invention, it may be desirable to provide an impedance transformer 224 in a series circuit configuration between the electrode(s) of the device 5 and the power output of generator 6. Consequently, the impedance transformer 224 may be provided with the device 5, the generator 6 or any of the wire connectors (e.g. wire 21) connecting device 5 and generator 6. Impedance transformer 224 is configured to match the load impedance provided to generator 6 such that it is within the working range of the generator 6 and, more preferably in the working range between the low and high cut-offs.

To effectively treat thick tissues, it can be advantageous to have the ability to pulse the RF power on and off. Under some circumstances, the temperature deep in tissue can rise quickly past the 100° C. desiccation point even though the electrode/tissue interface is boiling at 100° C. This manifests itself as "popping," as steam generated deep in the tissue boils too fast and erupts toward the surface. In one embodiment of the invention, a switch is provided on the control device or custom generator to allow the user to select a "pulse" mode of the RF power. Preferably, the RF power system in this embodiment is further controlled by software.

In some embodiments, it can be desirable to control the temperature of the conductive fluid before it is released from the electrosurgical device. In one embodiment, a heat exchanger is provided for the outgoing saline flow to either heat or chill the saline. The heat exchanger may be provided as part of the electrosurgical device or as part of another part of the system, such as within the enclosure 14. Pre-heating the saline to a predetermined level below boiling reduces the transient warm-up time of the device as RF is initially turned on, thereby reducing the time to cause coagulation of tissue. Alternatively, pre-chilling the saline is useful when the surgeon desires to protect certain tissues at the electrode/tissue interface and treat only deeper tissue. One exemplary application of this embodiment is the treatment of varicose veins, where it is desirable to avoid thermal damage to the surface of the skin. At the same time, treatment is provided to shrink underlying blood vessels using thermal coagulation. The temperature of the conductive fluid prior to release from the surgical device can therefore be controlled, to provide the desired treatment effect.

In another embodiment, the flow rate controller is modified to provide for a saline flow rate that results in greater than 100% boiling at the tissue treatment site. For example, the selection switch 12 of the flow rate controller 11 (shown in FIG. 1) can include settings that correspond to 110%, 120% and greater percentages of boiling. These higher settings can be of value to a surgeon in such situations as when encountering thick tissue, wherein the thickness of the tissue can increase conduction away from the electrode jaws. Since the basic control strategy neglects heat conduction, setting for 100% boiling can result in 80% of 90% boiling, depending upon the amount of conduction. Given the teachings herein, the switch of the flow rate controller can accommodate any desirable flow rate settings, to achieve the desired saline boiling at the tissue treatment site.

Some embodiments of the invention can provide one or more advantages over current electrosurgical techniques and devices. For example, the invention preferably achieves the desired tissue effect (for example, coagulation, cutting, and the like) in a fast manner. In a preferred embodiment, by actively controlling the flow rate of saline, both in quantity (Q vs. P) and location (for example, using gutters to direct fluid distally to tissue, using holes to direct flow of fluid, or other similar methods) the electrosurgical device can create a hot non-desiccating electrode/tissue interface and thus a fast thermally induced tissue coagulation effect.

The use of the disclosed devices can result in significantly lower blood loss during surgical procedures such as liver resections. Typical blood loss for a right hepatectomy can be in the range of 500-1,000 cubic centimeters. Use of the devices disclosed herein to perform pre-transection coagulation of the liver can result in blood loss in the range of 50-300 cubic centimeters. Such a reduction in blood loss can reduce or eliminate the need for blood transfusions, and thus the cost and negative clinical consequences associated with blood transfusions, such as prolonged hospitalization and a greater likelihood of cancer recurrence. Use of the device can also provide improved sealing of bile ducts, and reduce the incidence of post-operative bile leakage, which is considered a major surgical complication.

The invention can, in some embodiments, deliver fast treatment of tissue without using a temperature sensor built into the device or a custom special-purpose generator. In a preferred embodiment, there is no built-in temperature sensor or other type of tissue sensor, nor is there any custom generator. Preferably, the invention provides a means for controlling the flow rate to the device such that the device and flow rate controller can be used with a wide variety of general-purpose generators. Any general-purpose generator is useable in connection with the fluid delivery system and flow rate controller to provide the desired power; the flow rate controller will accept the power and constantly adjust the saline flow rate according to the control strategy. Preferably, the generator is not actively controlled by the invention, so that standard generators are useable according to the invention. Preferably, there is no active feedback from the device and the control of the saline flow rate is "open loop." Thus, in this embodiment, the control of saline flow rate is not dependent on feedback, but rather the measurement of the RF power going out to the device.

For purposes of the appended claims, the term "tissue" includes, but is not limited to, organs (e.g. liver, lung, spleen, gallbladder), highly vascular tissues (e.g. liver, spleen), soft and hard tissues (e.g. adipose, areolar, bone, bronchus-associated lymphoid, cancellous, chondroid, chordal, chromaffin, cicatricial, connective, elastic, embryonic, endothelial, epithelial, erectile, fatty, fibrous, gelatiginous, glandular, granulation, homologous, indifferent, interstitial, lymphadenoid, lymphoid, mesenchymal, mucosa-associated lymphoid, mucous, muscular, myeloid, nerve, osseous, reticular, scar, sclerous, skeletal, splenic, subcutaneous) and tissue masses (e.g. tumors).

While preferred embodiments of the present invention have been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes.

The invention claimed is:

1. A medical device, comprising:
a first shaft defining a first fluid perfusion lumen there through;
a second shaft defining a second fluid perfusion lumen there through, a distal end of the second shaft being inhibited from separating relative to a distal end of the first shaft;
the first shaft including a first electrode defining a rounded tip and a first fluid outlet in fluid communication with the first fluid perfusion lumen, the first electrode extending a distance away from the distal end of the first shaft and in fluid communication with the first fluid perfusion lumen;
the second shaft including a second electrode defining a rounded tip and a second fluid outlet in fluid communication with the second fluid perfusion lumen, the second electrode extending a distance away from the distal end of the second shaft and in fluid communication with the second fluid perfusion lumen, the distal end of second electrode defining a substantially co-planar surface with the distal end of the first electrode; and
the first electrode and the second electrode are engageable with a radiofrequency energy source and are configured to transmit bipolar radiofrequency energy between each other to coagulate a target tissue region.

2. The medical device of claim 1, further comprising a handle, and wherein the handle is configured to engage a portion of the first shaft and a portion of the second shaft.

3. The medical device of claim 2, wherein the handle is configured to be coupled to the radiofrequency source.

4. The medical device of claim 1, wherein the first shaft defines a first major longitudinal axis and the second shaft defines a second major longitudinal axis, and the substantially co-planar surface is substantially orthogonal to the first major longitudinal axis and the second major longitudinal axis.

5. A medical device, comprising:
an elongate first shaft defining a first fluid perfusion lumen there through and a first outer diameter;
an elongate second shaft defining a second fluid perfusion lumen there through and a second outer diameter, the first and second shafts defining a longitudinal direction and having distal ends;
the distal end of the second shaft being retained in a position relative to the distal end of the first shaft, and the first shaft and the second shaft are longitudinally immovable with respect to each other, the first outer diameter being substantially the same as the second outer diameter;
the first shaft including a first electrode defining a rounded tip and a first fluid outlet proximal to the rounded tip in fluid communication with the first fluid perfusion lumen, the first electrode extending a distance away from the distal end of the first shaft and in fluid communication with the first fluid perfusion lumen;
the second shaft including a second electrode defining a rounded tip and a second fluid outlet proximal to the rounded tip in fluid communication with the second fluid perfusion lumen, the second electrode extending a distance away from the distal end of the second shaft and in fluid communication with the second fluid perfusion lumen, the distal end of second electrode defining a substantially co-planar surface with the distal end of the first electrode; and
during use of the medical device, the first electrode and the second electrode are in fluid communication with each other and the first electrode and the second electrode each release a conductive fluid and transmit bipolar radiofrequency energy between each other energizing the conductive fluid.

6. A medical device, comprising:
a first malleable shaft defining a first fluid perfusion lumen there through and a first outer diameter;
a second malleable shaft defining a second fluid perfusion lumen there through and a second outer diameter, the second shaft being immovable with respect to an entirety of the first shaft, the first outer diameter being substantially the same as the second outer diameter;

the first shaft including a first electrode defining a rounded tip and a first fluid outlet proximal to the rounded tip in fluid communication with the first fluid perfusion lumen, the first electrode extending a distance away from the distal end of the first shaft and in fluid communication with the first fluid perfusion lumen;

the second shaft including a second electrode defining a rounded tip and a second fluid outlet proximal to the rounded tip in fluid communication with the second fluid perfusion lumen, the second electrode extending a distance away from the distal end of the second shaft and in fluid communication with the second fluid perfusion lumen, the distal end of second electrode defining a substantially co-planar surface with the distal end of the first electrode; and during use of the medical device, the first electrode and the second electrode are in fluid communication with each other and release a conductive fluid and the first electrode and the second electrode transmit bipolar radiofrequency energy between each other energizing the conductive fluid to coagulate a target tissue region.

* * * * *